US006284796B1

(12) United States Patent
Geyer et al.

(10) Patent No.: US 6,284,796 B1
(45) Date of Patent: Sep. 4, 2001

(54) UKOKINASE INHIBITORS

(75) Inventors: Andrew G. Geyer, Chicago; William J. McClellan, Waukegan; Todd W. Rockway, Grayslake; Kent D. Stewart, Gurnee; Moshe Weitzberg, Highland Park; Michael D. Wendt, Deerfield, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/236,254

(22) Filed: Jan. 25, 1999

Related U.S. Application Data

(63) Continuation-in-part of application No. 09/129,989, filed on Aug. 6, 1998.

(51) Int. Cl.$^7$ ....................... A61K 31/165; C07C 233/65
(52) U.S. Cl. ............................. 514/620; 564/164
(58) Field of Search .............................. 514/620; 564/164

(56) References Cited

U.S. PATENT DOCUMENTS 5,541,343 * 7/1996 Himmelsbach et al. ............. 514/424

FOREIGN PATENT DOCUMENTS

| 7730198 | 4/1999 | (AU) . |
| 0540051 | 5/1993 | (EP) . |
| 0568289 | 11/1993 | (EP) . |
| 6227971 | 8/1994 | (JP) . |
| 9616940 | 6/1996 | (WO) . |
| 9905124 | 4/1999 | (WO) . |

OTHER PUBLICATIONS

S.J. Teague et al., "The Synthesis of Highly Functionalized Naphthalene Derivatives", *Synthesis*, vol. 5, (1986), pp. 427–429.

H.J.J. Loozen et al, "A Short Route to Functionalized Naphthalene", *Journal Of Organic Chemistry*, vol. 40, No. 4 (1975), pp. 520–521.

O. Saksela, "Plasminogen Activation and Regulation of Pericellular Proteolysis", *Biochimica Et Biophysica Acta*, vol. 823, (1985), pp. 35–36.

F. Blasti et al., "Urokinase–Type Plasminogen Activator: Proenzyme, Receptor, and Inhibitors", *Journal Of Cell Biology*, vol. 104, (1987), pp. 801–804.

M.A. Alliegro et al., "Inhibition of In Vitro Angiogenesis by Amiloride", *Journal Of Cell Biology*, vol. 155 [3 pt 2], (1991), p. 402a.

S.M. Berge et al., "Pharmaceutical Salts", *Journal Of Pharmaceutical Sciences*, vol. 66, (1997), pp. 1–19.

T. Aoyama et al., "Synthesis and Structure—Activity Study of Protease Inhibitors. IV. Amidinonaphthols and Related Acyl Derivatives", *Chemical And Pharmaceutical Bulletin*, vol. 33, No. 4 (1985), pp. 1458–1471.

B.A. Littlefield, "Plasminogen Activators in Endometrial Physiology and Embryo Implantaion: A Review", *Annals Of The New York Academy Of Sciences*, vol. 622 (1991), pp. 167–175.

J.E. Testa et al., "The Role of Urokinase–Type Plasminogen Activator in Aggressive Tumor Cell Behavior", *Cancer Metastasis Reviews*, vol. 9, (1990), pp. 353–367.

J.A. Kellen et al., "Antimetastatic Effecy of Amiloride in an Animal Tumour Model", *Anticancer Research*, vol. 8 (1988), pp. 1373–1376.

E.B. Roche ed., *Bioreversible Carriers In Drug Design: Theory And Application*, American Pharmaceutical Association and Pergamon Press (1987).

K. Dano et al., *Advances In Cancer Research*, vol. 44, (1985), pp. 139–266.

Prescot, ed., *Methods In Cell Biology*, vol. XIV, Academic Press, New York, NY (1976), p. 33 et seq.

J. Sturzebecher, et al. "Chemical Abstracts", *Synthetische Inhibitoren der Serinproteinasen*, vol. 90 (1979), pp. 16–20.

T. Nagahara, et al., "Dibasic (Amidinoaryl) propanoic Acid Derivatives as Novel Blood Coagulation Factor Xa Inhibitors", *Journal Of Medicinal Chemistry*, vol. 37, No. 8 (15–04–94), pp. 1200–1207, 1994.

S. Katakura et al, "Molecular Model of an interaction between factor Xa and DX–9065a, a novel factor Xa inhibitor: contribution of the acetimidoylpyrrolidine moiety of the inhibitor to potency and selectivity for serine proteases", *Eur. J. Med. Chem.*, vol. 30, No. 5 (1995), pp. 387–394.

* cited by examiner

*Primary Examiner*—Shailendra Kumar
(74) *Attorney, Agent, or Firm*—B. Gregory Donner; Gregory W. Steele

(57) ABSTRACT

Compounds having the formula are inhibitors of urokinase and are useful in the treatment of diseases in which urokinase plays a role. Also disclosed are urokinase-inhibiting compositions and a method of inhibiting urokinase in a mammal.

14 Claims, No Drawings

UKOKINASE INHIBITORS

CROSS REFERENCE TO RELATED APPLICATIONS

This application is a continuation-in-part of U.S. application Ser. No. 09/129,989, filed Aug. 6, 1998, pending.

BACKGROUND OF THE INVENTION

The present invention provides naphthamidine compounds which inhibit the urokinase enzyme, pharmaceutical compositions containing these compounds and medical methods of treatment using these compounds.

TECHNICAL FIELD

Urokinase (urinary-type plasminogen activator or uPA (International Union of Biochemistry classification number: EC3.4.21.31)) is a proteolytic enzyme which is highly specific for a single peptide bond in plasminogen. Plasminogen activation (cleavage of this bond by the urokinase enzyme) results in formation of plasmin, a potent general protease.

Many cell types use urokinase as a key initiator of plasmin-mediated proteolytic degradation or modification of extracellular support structures such as extracellular matrix (ECM) and basement membrane (BM). Cells exist, move and interact with each other in tissues and organs within the physical framework provided by ECM and BM. Movement of cells within ECM or across BM requires local proteolytic degradation or modification of the structures and allows cells to invade adjacent areas previously unavailable prior to the degradation or modification.

Cellular invasiveness intiated by urokinase is central to a variety of normal and disease-state physiological processes (Blasi, F., Vassalli, J. D., and Dano, K. J. Cell Biol. 104:801–804, 1987; Dano, K., Anderson, P. A., Grondahl-Hansen, J., Kristensen, P., Nielsen, L. S., and Skriver, L Adv. Cancer Res. 44:139–266, 1985; Littlefield, B. A. Ann. N. Y. Acad. Sci. 622: 167–175, 1991; Saksela, O., Biochim. Biophys. Acta 823: 35–65, 1985; Testa, J. E. and Quigley, J. P. Cancer Metast. Rev. 9:353–367, 1990). Such processes include, but are not limited to, angiogenesis (neovascularization), bone restructuring, embryo implantation in the uterus, infiltration of immune cells into inflammatory sites, ovulation, spermatogenesis, tissue remodelling during wound repair and organ differentiation, fibrosis, tumor invasion, metastatic spread of tumor cells from primary to secondary sites and tissue destruction in arthritis. Amiloride, for example, a known urokinase inhibitor of only moderate potency, has been reported to inhibit tumor metastasis in vivo (Kellen, J. A., Mirakian, A. Kolin, A. Anticancer Res. 8:1373–1376, 1988) and angiogenesis/capillary network formation in vitro (Alliegro, M. C. and Glaser, B. M. J. Cell Biol. 115[3 Pt 2]: 402a, 1991).

Inhibitors of urokinase, therefore, have mechanism-based anti-angiogenic, anti-arthritic, anti-inflammatory, anti-retinopathic (for angiogenesis-dependent retinopathies), contraceptive and tumoristatic uses.

SUMMARY OF THE INVENTION

In its principle embodiment, the present invention provides a compound or a pharmaceutically acceptable salt, ester or prodrug thereof, of formula (I)

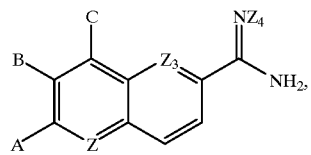

(I)

wherein Z is seleted from the group consisting of
(1) nitrogen;
(2) methine; and
(3) methine substituted with —$NR_1R_2$;
$Z_3$ is selected from the group consisting of
(1) methine and
(2) nitrogen;
Z4 is selected from the group consisting of
(1) hydrogen and
(2) hydroxy;
A is selected from the group consisting of
(1) hydrogen and
(2) -$L_AR_A$;
B is selected from the group consisting of
(1) hydrogen and
(2) -$L_BR_B$ and
C is selected from the group consisting of
(1) hydrogen and
(2) -$L_CR_C$,
with the proviso that at least one of A, B or C is other than hydrogen; and with the proviso that when A is other than hydrogen, at least one of B or C is other than hydrogen, wherein for A, B, and C, $L_A$, $L_B$ and $L_C$ are independently selected from the group consisting of
(1) a covalent bond,
(2) —$(CH_2)m$—,
(3) —$NR_1$—,
(4) —$NR_2C(X)NR_3$—,
(5) —C(X)—,
(6) —$NR_2C(X)$—,
(7) —$C(X)NR_2$—,
(8) —CH=CH—,
(9) —C≡C—,
(10) —O—,
(11) —$S(O)_t$—,
(12) —C≡C$(CH_2)_n NR_2C(X)$—,
(13) —$C(X)NR_2(CH_2)_n$C≡C—,
(14) —$(CH_2)_n NSO_2$—,
(15) —$NR_2SO_2(CH_2)_n$C—≡C—,
(16) —C≡C$(CH_2)_n NR_2SO_2NR_3$—,
(17) —$NR_2SO_2NR_3(CH_2)_n$C≡C—,
(18) —$SO_2NR_2$—,
(19) —$NR_2SO_2$—,
(20) —$NR_2SO_2NR_3$—,
(21) —N=N—,
(22) —$C(X)N(OR_2)$—,
(23) —$N(OR_2)C(X)$—,
(24) —HC=CH$(CH_2)_n NR_2C(X)$—,
(25) —$(CH_2)_n NR_2C(X)$CH=CH—,
(26) —CH=CH$(CH_2)_n NSO_2$—,

(27) —NR$_2$SO$_2$(CH$_2$)$_n$CH=CH—,
(28) —(CH$_2$)$_n$NR$_2$SO$_2$NR$_3$—,
(29) —NR$_2$SO$_2$NR$_3$(CH$_2$)$_n$CH=CH—,
(30) —NR$_2$C(O)O—,
(31) —OC(O)NR$_2$—,
(32) —CH=NO—,
(33) —ON=CH— and

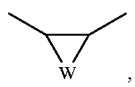

(34) wherein W is selected from the group consisting of
(a) —O—,
(b) —S—,
(c) —NR$_1$—,
(d) —(CH$_2$)m—,
(35) —(CZ$_1$=CZ$_2$)—, wherein Z$_1$ and Z$_2$ are independently selected from the group consisting of
(a) hydrogen,
(b) halogen, and
(c) alkyl of one to ten carbon atoms,
(36) —NR$_2$CH$_2$—,
(37) —S(O)$_t$CH=CH—, and
(38) —NR$_1$—(CH$_2$)m—,
wherein each functional group is depicted with its right-hand end being the end which is attached to the naphthyl or quinolyl ring and its left-hand end being the end which is attached to R$_A$, R$_B$ or R$_C$;

R$_A$, R$_B$ and R$_C$ are independently selected from the group consisting of
(1) aryl;
(2) arylalkoxy, wherein the alkylene group is of one to six carbon atoms;
(3) alkyl of one to ten carbon atoms;
(4) alkenyl of two to ten carbon atoms;
(5) alkoxycarbonyl of one to six carbon atoms;
(6) alkynyl of two to ten carbon atoms;
(7) halogen;
(8) —NR$_1$R$_2$;
(9) heterocycle;
(10) cycloalkenyl of four to twelve carbon atoms;
(11) cycloalkyl of three to twelve carbon atoms;
(12) —NR$_1$C(O)NR$_2$R$_3$; and
(13) —NR$_1$C(O)R$_{50}$, wherein R$_{50}$ is alkyl of one to six carbon atoms;
wherein, at each occurence, R$_1$ is selected from the group consisting of
(1) hydrogen;
(2) an N-protecting group;
(3) alkyl of one to six carbon atoms;
(4) alkenyl of two to six carbon atoms;
(5) alkynyl of two to six carbon atoms;
(6) aryl;
(7) arylalkyl, wherein the alkylene group is of one to six carbon atoms;
(8) cycloalkyl of three to eight carbon atoms and
(9) cycloalkylalkyl, wherein the cycloalkyl group is of three to eight carbon atoms, and the alkylene group is of one to ten carbon atoms; and wherein, at each occurence, R$_2$ and R$_3$ are independently selected from the group consisting of
(1) hydrogen;
(2) alkyl of one to six carbon atoms;
(3) alkenyl of two to six carbon atoms;
(4) alkynyl of two to six carbon atoms;
(5) aryl;
(6) arylalkyl, wherein the alkylene group is of one to six carbon atoms
(7) cycloalkyl of three to eight carbon atoms and
(8) cycloalkylalkyl, wherein the cycloalkyl group is of three to eight carbon atoms, and the alkylene group is of one to ten carbon atoms; and
wherein, at each occurence, X is selected from the group consisting of
(1) O and
(2) S; and
wherein, at each occurence,
m is one to five,
n is zero to four and
t is zero to two; and
wherein, at each occurence, the alkyl, alkenyl, alkynyl, aryl, heterocycle, cycloalkyl, and cycloalkenyl groups are optionally substituted.

The present invention also relates to a method of inhibiting urokinase in a mammal, particularly humans, by administering a therapeutically effective amount of a composition comprising a compound of formula (I).

The present invention also relates to pharmaceutical compositions which comprise a therapeutically effective amount of a compound of formula (I) in combination with a pharmaceutically acceptable carrier.

DETAILED DESCRIPTION OF THE INVENTION

As used throughout this specification and the appended claims, the following terms have the meanings specified:

The term "alkyl," as used herein, represents a monovalent group derived from a straight or branched chain saturated hydrocarbon by the removal of a single hydrogen atom and is exemplified by methyl, ethyl, n- and iso-propyl, n-, sec-, iso- and tert-butyl, neopentyl and the like and may be optionally substituted with one, two, three or four substituents independenfly selected from the group consisting of (1) alkoxy of one to six carbon atoms; (2) alkylsulfinyl of one to six carbon atoms; (3) alkylsulfonyl of one to six carbon atoms; (4) amino; (5) aryl; (6) arylalkoxy, wherein the alkylene group is of one to six carbon atoms; (7) aryloyl; (8) azido; (9) carboxaldehyde; (10) cycloalkyl of three to eight carbon atoms; (11) halo; (12) heterocycle; (13) (heterocycle)oxy; (14) (heterocycle)oyl; (15) hydroxy; (16) N-protected amino; (17) nitro; (18) oxo; (19) spiroalkyl of three to eight carbon atoms; (20) thioalkoxy of one to six carbon atoms; (21) —CO$_2$R$_2$; (22) —C(O)NR$_2$R$_3$; (23) —SO$_2$R$_4$, wherein R$_4$ is selected from the group consisting of (a) alkyl, (b) aryl and (c) arylalkyl, wherein the alkylene group is of one to six carbon atoms; (24) —SO$_2$NR$_5$R$_6$, wherein R$_5$ and R$_6$ are independently selected from the group consisting of (a) hydrogen, (b) alkyl, (c) aryl and (d) arylalkyl, wherein the alkylene group is of one to six carbon atoms; (25) —NR$_7$R$_8$, wherein R$_7$ and R$_8$ are independently selected from the group consisting of (a) hydrogen; (b) an N-protecting group; (c) allyl of one to six carbon atoms; (d) alkenyl of two to six carbon atoms; (e) alkynyl of two to six carbon atoms; (f)

aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group.

The term "alkanoyl," as used herein, represents an alkyl group, as defined herein, attached to the parent molecular group through a carbonyl group, as defined herein, and is exemplified by formyl, acetyl, propionyl, butanoyl and the like.

The term "alkenyl," as used herein, represents monovalent straight or branched chain groups containing a carbon—carbon double bond derived from an alkene by the removal of one hydrogen atom and is exemplified by ethenyl, 1-propenyl, 2-propenyl, 2-methyl-1-propenyl, 1-butenyl, 2-butenyl and the like and may be optionally substituted with one, two, three or four substituents independently selected from the group consisting of (1) alkoxy of one to six carbon atoms; (2) alkylsulfinyl of one to six carbon atoms; (3) alkylsulfonyl of one to six carbon atoms; (4) amino; (5) aryl; (6) arylalkoxy, wherein the alkylene group is of one to six carbon atoms; (7) aryloyl; (8) azido; (9) carboxaldehyde; (10) cycloalkyl of three to eight carbon aioms; (11) halo; (12) heterocycle; (13) (heterocycle)oyl; (15) hydroxy; (16) N-protected amino; (17) nitro; (18) oxo; (19) spiroalkyl of three to eight carbon atoms; (20) thioalkoxy of one to six carbon atoms; (21) —$CO_2R_2$; (22) —$C(O)NR_2R_3$; (23) —$SO_2R_4$, wherein $R_4$ is selected from the group consisting of (a) alkyl, (b) aryl and (c) arylalkyl, wherein the alkylene group is of one to six carbon atoms; (24) —$SO_2NR_5R_6$, wherein $R_5$ and $R_6$ are independendy selected from the group consisting of (a) hydrogen, (b) alkyl, (c) aryl and (d) arylalkyl, wherein the alkylene group is of one to six carbon atoms; (25) —$NR_7R_8$, wherein $R_7$ and $R_8$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group.

The term "alkoxy," as used herein, represents an alkyl group attached to the parent molecular group through an oxygen atom.

The term "alkoxyalkyl" as used herein, represents an alkyl group to which is attached an alkoxy group.

The term "alkoxycarbonyl," as used herein, represents an ester group; i.e. an alkoxy group, attached to the parent molecular group through a carbonyl group and is exemplified by methoxycarbonyl, ethoxycarbonyl and the like.

The term "alkylene," as used herein, represents a saturated divalent hydrocarbon group derived from a straight or branched chain saturated hydrocarbon by the removal of two hydrogen atoms, and is exemplified by methylene, ethylene, isopropylene and the like.

The term "alkylsulfinyl," as used herein, represents an alkyl group attached to the parent molecular group through an —S(O)— group.

The term "alkylsulfinylalkyl," as used herein, represents an alkyl group, as defined herein, substituted by a sulfinyl group.

The term "alkylsulfonyl," as used herein, represents an alkyl group attached to the parent molecular group through an —$SO_2$— group.

The term "alkylsulfonylalkyl," as used herein, represents an alkyl group, as defined herein, substituted by a sulfonyl group.

The term "alkynyl," as used herein, represents monovalent straight or branched chain groups of two to six carbon atoms containing a carbon—carbon triple bond derived from an aLkyne by the removal of one hydrogen atom and is exemplified by ethynyl, 1-propynyl, and the like and may be optionally substituted with one, two, three or four substituents independently selected from the group consisting of (1) alkoxy of one to six carbon atoms; (2) alkylsulfinyl of one to six carbon atoms; (3) alkylsulfonyl of one to six carbon atoms; (4) amino; (5) aryl; (6) arylalkoxy, wherein the alkylene group is of one to six carbon atoms; (7) aryloyl; (8) azido; (9) carboxaldehyde; (10) cycloalkyl of three to eight carbon atoms; (11) halo; (12) heterocycle; (13) (heterocycle) oxy; (14) (heterocycle)oyl; (15) hydroxy; (16) N-protected amino; (17) nitro; (18) oxo; (19) spiroalkyl of three to eight carbon atoms; (20) thioalkoxy of one to six carbon atoms; (21) —$CO_2R_2$; (22) —$C(O)NR_2R_3$; (23) —$SO_2R_4$, wherein $R_4$ is selected from the group consisting of (a) alkyl, (b) aryl and (c) arylalkyl, wherein the alkylene group is of one to six carbon atoms; (24) —$SO_2NR_5R_6$, wherein $R_5$ and $R_6$ are independently selected from the group consisting of (a) hydrogen, (b) alkyl, (c) aryl and (d) arylalkyl, wherein the alkylene group is of one to six carbon atoms; (25) —$NR_7R_8$, wherein $R_7$ and $R_8$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group.

The term "amino," as used herein, represents an —$NH_2$ group.

The term "aminocarbonyl," as used herein, represents an amino group attached to the parent molecular group through a carbonyl group and is exemplified by —$C(O)NH_2$.

The term "aminoalkyl," as used herein, represents an alkyl group, as defined herein, substituted by an amino group.

The term "aryl," as used herein, represents a mono- or bicyclic carbocyclic ring system having one or two aromatic rings and is exemplified by phenyl, naphthyl, 1,2-dihydronaphthyl, 1,2,3,4tetrahydronaphthyl, fluorenyl, indanyl, indenyl and the like and may be optionally substituted with one, two, three, four or five substituents independently selected from the group consisting of (1) alkanoyl of one to six carbon atoms; (2) alkyl of one to six carbon atoms; (3) alkoxy of one to six carbon atoms; (4) alkoxyalkyl, wherein the alkyl and alkylene goups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfinylalkyl, wherein the alkyl and alkylene groups are independently of one to six carbon atoms; (9) aryl; (10) arylalkyl, wherein the alkyl group is of one to six carbon atoms; (11) amino; (12) aminoalkyl of one to six carbon atoms; (13) aryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde)alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocycle; (25) (heterocycle)oxy; (26) (heterocycle)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —$(CH_2)_qCO_2R_2$, wherein q is zero to four; (37) —$(CH_2)_qC(O)NR_2R_3$; (38) —$(CH_2)_q SO_2R_4$, wherein $R_4$ is selected from the group consisting of (a) alkyl, (b) aryl and (c) arylalkyl, wherein the alkylene group is of one to six carbon atoms; (39) —$(CH_2)_q SO_2NR_5R_6$, wherein $R_5$ and $R_6$ are independently selected from the group consisting of(a) hydrogen, (b) alkyl, (c) aryl and(d) arylalkyl, wherein the alkylene group is of one to six carbon atoms; (40) —$(CH_2)_qNR_7R_8$, wherein $R_7$ and $R_8$ are independendy selected from the group consisting of (a) hydrogen, (b) an N-protecting group, (c) alkyl of one to six carbon atoms, (d) alkenyl of two to six carbon atoms, (e) alkynyl of two to six carbon atoms, (f) aryl, (g) arylalkyl, wherein the alkylene group is of one to six carbon atoms, (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) perfluoroalkyl; (43) perfluoroalkoxy; (44) aryloxy; (45) cycloalkoxy; (46) cycloalkylalkoxy; (47) arylalkoxy; (48) aminocarbonyl; and (49) alkenyl.

The term "arylalkyl," as used herein, represents an aryl group attached to the parent molecular group through an alkyl group.

The term "arylalkoxy," as used herein, represents an arylalkyl group attached to the parent molecular group through an oxygen atom.

The term "aryloxy," as used herein, represents an aryl group which is attached to the parent molecular group through an oxygen atom.

The term "aryloyl," as used herein, represents an aryl group which is attached to the parent molecular group through a carbonyl group.

The term "azido," as used herein, represents an —$N_3$ group.

The term "azidoalkyl," as used herein, represents an alkyl group, as defined herein, substituted by an azido group.

The termn "carbonyl," as used herein, represents a C=O group.

The term "carboxaldehyde," as used herein, represents a —CHO group.

The term "(carboxaldehyde)alkyl," as used herein, represents an alkyl group, as defined herein, substituted by a carboxaldehyde group.

The term "carboxy," as used herein, represents a —$CO_2H$ group.

The term "carboxyalkyl," as used herein, represents an alkyl group, as defined herein, substituted by a carboxy group.

The term "cycloalkyl," as used herein represents a monovalent saturated cyclic hydrocarbon group and is exemplified by cyclopropyl, cyclobutyl, cyclopentyl, cyclohexyl, cycloheptyl, bicyclo[2.2.1]heptyl and the like. The cycloalkyl groups of this invention can be optionally substituted with (1) alkanoyl of one to six carbon atoms; (2) alkyl of one to six carbon atoms; (3) alkoxy of one to six carbon atoms; (4) alkoxyalkyl, wherein the alkyl and alkylene goups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfonylalkyl, wherein the alkyl and alkylene groups are independently of one to six carbon atoms; (9) aryl; (10) arylalkyl, wherein the alkyl group is of one to six carbon atoms; (11) amino; (12) aminoalkyl of one to six carbon atoms; (13) aryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde) alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocycle; (25) (heterocycle)oxy; (26) (heterocycle)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —$(CH_2)_qCO_2R_2$, wherein q is zero to four; (37) —$(CH_2)_q C(O)NR_2R_3$; (38) —$(CH_2)_qSO_2R_4$, wherein $R_4$ is selected from the group consisting of (a) alkyl, (b) aryl and (c) arylalkyl, wherein the alkylene group is of one to six carbon atoms; (39) —$(CH_2)_qSO_2NR_5R_6$, wherein $R_5$ and $R_6$ are independently selected from the group consisting of(a) hydrogen, (b) alkyl, (c) aryl and (d) arylalkyl, wherein the alkylene group is of one to six carbon atoms; (40) —$(CH_2)_q NR_7R_8$, wherein $R_7$ and $R_8$ are independently selected from the group consisting of (a) hydrogen, (b) an N-protecting group, (c) alkyl of one to six carbon atoms, (d) alkenyl of two to six carbon atoms, (e) alkynyl of two to six carbon atoms, (f) aryl, (g) arylalkyl, wherein the alkylene group is of one to six carbon atoms, (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) perfluoroalkyl; (43) perfluoroalkoxy; (44) aryloxy; (45) cycloalkoxy; (46) cycloalkylalkoxy; and (47) arylalkoxy.

The term "cycloalkenyl," as used herein represents a monovalent cyclic hydrocarbon having at least one carbon—carbon double bond. The cycloalkenyl groups of this invention can be optionally substituted with (1) alkanoyl of one to six carbon atoms; (2) alkyl of one to six carbon atoms; (3) alkoxy of one to six carbon atoms; (4) alkoxyalkyl, wherein the alkyl and alkylene goups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfonylalkyl, wherein the alkyl and alkylene groups are independently of one to six carbon atoms; (9) aryl; (10) arylalkyl, wherein the alkyl group is of one to six carbon atoms; (11) amino; (12) aminoalkyl of one to six carbon atoms; (13) aryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde) alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocycle; (25) (heterocycle)oxy; (26) (heterocycle)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —$(CH_2)_qCO_2R_2$, wherein q is zero to four; (37) —$(CH_2)_qC(O)NR_2R_3$; (38) —$(CH_2)_qSO_2R_4$, wherein $R_4$ is selected from the group consisting of (a) alkyl, (b) aryl and (c) arylalkyl, wherein the alkylene group is of one to six carbon atoms; (39) —$(CH_2)_qSO_2NR_5R_6$, wherein $R_5$ and $R_6$ are independently selected from the group consisting of (a) hydrogen, (b) alkyl, (c) aryl and (d) arylalkyl, wherein the alkylene group is of one to six carbon atoms; (40) —$(CH_2)_qNR_7R_8$, wherein $R_7$ and $R_8$ are independently selected from the group consisting of (a) hydrogen, (b) an N-protecting group, (c) alkyl of one to six carbon atoms, (d) alkenyl of two to six carbon atoms, (e) alkynyl of two to six carbon atoms, (f) aryl, (g) arylalkyl, wherein the alkylene group is of one to six carbon atoms, (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) perfluoroalkyl; (43) perfluoroalkoxy; (44) aryloxy; (45) cycloalkoxy; (46) cycloalkylalkoxy; and (47) arylalkoxy.

The term "cycloalkoxy," as used herein represents a cycloalkyl group, as defined herein, attached to the parent molecular group through an oxygen atom.

The term "cycloalkylalkoxy," as used herein, represents an alkoxy group, as defined herein, to which is attached a cycloalkyl group.

The term "cycloalkylalkyl," as used herein, represents a cycloalkyl group, as defined herein, attached to the parent molecular group through an alkyl group.

The term "haloalkyl," as used herein, represents an alkyl group, as defined herein, substituted by one, two, or three halogen atoms and is exemplified by chloromethyl, bromoethyl, trifluoromethyl and the like.

The term "halogen," as used herein, represents F, Cl, Br and I.

The term "heterocycle," as used herein, represents a 5-, 6- or 7-membered ring containing one, two or three heteroatoms independently selected from the group consisting of nitrogen, oxygen and sulfur. The 5-membered ring has zero to two double bonds and the 6- and 7-membered rings have zero to three double bonds. The term "heterocycle" also includes bicyclic, tricyclic and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring such as indolyl, quinolyl, isoquinolyl, tetrahydroquinolyl, benzofuryl, benzothienyl and the like. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

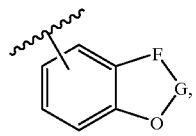

wherein F is selected from the group consisting of —$CH_2$—, —$CH_2O$— and —O—, and G is selected from the group consisting of —C(O)— and —$(C(R')(R''))_v$—, wherein R' and R'' are independently selected from the group consisting of hydrogen or alkyl of one to four carbon atoms, and v is one to three and includes groups such as 1,3-benzodioxolyl, 1,4-benzodioxanyl and the like. Any of the heterocycle groups mentioned herein may be optionally substituted with one, two, three, four or five substituents independently selected from the group consisting of (1) alkanoyl of one to six carbon atoms; (2) alkyl of one to six carbon atoms; (3) alkoxy of one to six carbon atoms; (4) alkoxyalkyl, wherein the alkyl and alkylene goups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfonylalkyl, wherein the alkyl and alkylene groups are independently of one to six carbon atoms; (9) aryl; (10) arylalkyl, wherein the alkyl group is of one to six carbon atoms; (11) amino; (12) aminoalkyl of one to six carbon atoms; (13) aryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde) alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocycle; (25) (heterocycle)oxy; (26) (heterocycle)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —$(CH_2)_qCO_2R_2$, wherein q is zero to four; (37) —$(CH_2)_qC(O)NR_2R_3$; (38) —$(CH_2)_qSO_2R_4$, wherein $R_4$ is selected from the group consisting of (a) alkyl, (b) aryl and (c) arylalkyl, wherein the alkylene group is of one to six carbon atoms; (39) —$(CH_2)_qSO_2NR_5R_6$, wherein $R_5$ and R6 are independently selected from the group consisting of (a)

hydrogen, (b) alkyl, (c) aryl and(d) arylalkyl, wherein the alkylene group is of one to six carbon atoms; (40) —$(CH_2)_q$NR$_7$R$_8$, wherein R$_7$ and R$_8$ are independently selected from the group consisting of (a) hydrogen, (b) an N-protecting group, (c) alkyl of one to six carbon atoms, (d) alkenyl of two to six carbon atoms, (e) alkynyl of two to six carbon atoms, (f) aryl, (g) arylalkyl, wherein the alkylene group is of one to six carbon atoms, (h) cycloalkyl of three to eight carbon atoms and (i) cycloalkylallyl, wherein the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) perfluoroalkyl; (43) perfluoroalkoxy; (44) aryloxy; (45) cycloalkoxy; (46) cycloalkylalkoxy; (47) arylalkoxy; and (48) alkoxycarbonyl.

The term "(heterocycle)oxy," as used herein, represents a heterocycle group, as defined herein, attached to the parent molecular group through oxygen.

The term "(heterocycle)oyl," as used herein, represents a heterocycle group, as defined herein, attached to the parent molecular group through a carbonyl group.

The term "hydroxy" as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group and is exemplified by hydroxymethyl, dihydroxypropyl and the like.

The term "methine" as used herein, represents a =C(H)— group.

The term "N-protected amino," as used herein, refers to an amino group, as defined herein, to which is attached an N-protecting or nitrogen-protecting group, as defined herein.

The term "N-protected aminoalkyl," as used herein, refers to an alkyl group, as defined herein, which is substituted by an N-protecting or nitrogen-protecting group, as defined herein.

The term "nitro," as used herein, represents an —NO$_2$ group.

The term "nitroalkyl," as used herein, represents an alkyl group substituted by an —NO$_2$ group.

The terms "N-protecting group" or "nitrogen protecting group" as used herein, represent those groups intended to protect an amino group against undersirable reactions during synthetic procedures. Commonly used N-protecting groups are disclosed in Greene, "Protective Groups In Organic Synthesis," (John Wiley & Sons, New York (1981)), which is incorporated herein by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "oxo," as used herein, represents =O.

The term "perfluoroalkyl," as used herein, represents an alkyl group, as defined herein, wherein each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, refers to a perfluoroalkyl group, as defined herein, attached to the parent molecular group through an oxygen atom.

The term "pharmaceutically acceptable salt," as use herein, represents those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well known in the art For example, S. M Berge, et al. describe pharmaceutically acceptable salts in detail in J3 Pharmaceutical Sciences, 1977, 66:1–19. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like. The term "pharmaceutically acceptable ester," as used herein, represents esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl group preferably has not more than 6 carbon atoms. Examples of particular esters includes formates, acetates, propionates, butyates, acrylates and ethylsuccinates.

The term "pharmaceutically acceptable prodrugs" as used herein, represents those prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins, et al.Synthetic Communications, 26(23), 4351–4367 (1996), each of which is incorporated herein by reference.

The term "spiroalkyl," as used herein, represents an alkylene diradical, both ends of which are bonded to the same carbon atom of the parent group to form a spirocyclic group.

The term "sulfonyl," as used herein, represents an —$SO_2$- group.

The term "thioalkoxy," as used herein, represents represents an alkyl group attached to the parent molecular group through a sulfur atom.

The term "thioalkoxyalkyl," as used herein, represents an alkyl group substituted by a thioalkoxy group.

Asymmetric or chiral centers may exist in the compounds of the present invention. The present invention contemplates the various stereoisomers and mixtures thereof. Individual stereoisomers of compounds of the present invention are prepared synthetically from commercially available starting materials which contain asymmetric or chiral centers or by preparation of mixtures of enantiomeric compounds followed by resolution well-known to those of ordinary skill in the art. These methods of resolution are exemplified by (1) attachment of a racemic mixture of enantiomers, designated (±), to a chiral auxiliary, separation of the resulting diastereomers by recrystallization or chromatography and liberation of the optically pure product from the auxiliary or (2) direct separation of the mixture of optical enantiomers on chiral chromatographic columns. Enantiomers are designated herein by the symbols "R" or "S," depending on the configuration of subsitiuents around the chiral carbon atom.

Geometric isomers may also exist in the compounds of the present invention. The present invention contemplates the various geometric isomers and mixtures thereof resulting from the arrangement of substituents around a carbon—carbon double bond and designates such isomers as of the Z or E configuration, wherein the term "Z" represents substituents on the same side of the carbon—carbon double bond and the term "E" represents substituents on opposite sides of the carbon—carbon double bond.

PREFERRED EMBODIMENTS

Preferred compounds of the present invention have formula (I), wherein
A and C are hydrogen and B is -$L_B R_B$, wherein
-$L_B$- is —O—, and
$R_B$ is alkyl of two to six carbon atoms, and
wherein the alkyl group is substituted.

More preferred embodiments of the present invention have formula (I), wherein

A is -$L_A R_A$ and B and C are hydrogen,
wherein -$L_A$- is selected from the group consisting of
(1) a covalent bond,
(2) —$(CH_2)_m$—,
(3) —$NR_2C(X)$—,
(4) —$C(X)NR_2$—,
(5) —$NR_2C(X)NR_3$—,
(6) —C≡C—,
(7) —CH=CH—,
(8) —$C(X)NR_2(CH_2)_n$C≡C—
(9) —C(X)—,
(10) —O—,
(11) —$OC(O)NR_2$— and
(12)

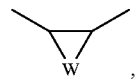

and wherein
$R_A$ is selected from the group consisting of
(1) amino;
(2) aryl;
(3) alkyl of one to ten carbon atoms;
(4) arylalkyl, wherein the alkylene group is of one to ten carbon atoms;
(5) cycloalkyl of three to eight carbon atoms;
(6) arylalkoxy, wherein the alkylene group is of one to ten carbon atoms and
(7) heterocycle, wherein the heterocycle is selected from the group consisting of
(1) furanyl,
(2) thienyl and
(3) imidazolyl; and
wherein, at each occurence, $R_2$ is selected from the group consisting of
(1) hydrogen and
(2) alkyl of one to six carbon atoms; and
wherein, at each occurence,
m is two,
n is one,
$R_1$ and $R_3$ are hydrogen,
W and X are O,
aryl is phenyl,
the alkyl group and the aryl group are optionally substituted and the alkenyl group is substituted.

Still more preferred compounds of the present invention have formula (I), wherein
A and B are hydrogen;
C is -$L_C R_C$;
-$L_C$- is selected from the group consisting of
(1) a covalent bond,
(2) —$OC(O)NR_2$—,
(3) —$SO_2NR_2$—,
(4) —$C(X)NR_2$—,
(5) —$NR_1$— and
(6) —O—;
RC is selected from the group consisting of
(1) alkyl of one to six carbon atoms;
(2) aryl;

(3) arylalkyl, wherein the alkylene group is of one to six carbon atoms and
(4) hererocycle, wherein the heterocycle is selected from the group consisting of
(1) furanyl;
(2) pyriridinyl; and
(3)

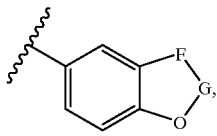

wherein F is —O—, G is —(C(R')(R"))$_v$—, R' and R" are hydrogen and v is one;
X is O; and
wherein, at each occurence,
R$_1$ and R$_2$ are H,
aryl is phenyl and the alkyl is optionally substituted.
Still more preferred compounds of the present invention have formula (I) wherein
A is -L$_A$R$_A$,
B is -L$_B$R$_B$,
C is hydrogen,
-L$_A$- and -L$_B$- are —O—, and
R$_A$ and R$_B$ are alkyl of one to six carbon atoms.
Still more preferred compounds of the present invention have formula (1) wherein
A is -L$_A$R$_A$,
B is -L$_B$R$_B$,
C is -L$_C$R$_C$,
-L$_A$-, -L$_B$-, and -L$_C$- are —O— and R$_A$, R$_B$, and R$_C$ are alkyl of one to six carbon atoms.
Still more preferred compounds of the present invention have formula (I) wherein
A is hydrogen;
B is -L$_B$R$_B$;
C is -L$_C$R$_C$;
-L$_B$- is —O—;
-L$_C$- is selected from the group consisting of
(1) a covalent bond,
(2) —O—,
(3) —CH=CH—,
(4) —NR$_2$— and
(5) —NR$_2$C(O)O—;
RB is selected from the group consisting of
(1) alkyl and
(2) arylalkyl, wherein the alkylene group is of one to six carbon atoms;
RC is selected from the group consisting of
(1) alkyl of one to six carbon atoms;
(2) alkenyl of one to six carbon atoms;
(3) halogen;
(4) aryl and
(5) heterocycle, wherein
the heterocycle is selected from the group consisting of
(1) benzofuranyl;
(2) tetrahydrofuranyl;
(3) pyrimidinyl;
(4) pyrazolyl;
(5) furanyl;
(6) pyrimidinyl;
(7) thiazolyl and
(8)

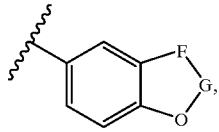

wherein F is —O—, G is —(C(R')(R"))$_v$—, R' and R" are hydrogen and v is one; and
wherein, at each occurence, aryl is phenyl and alkyl, aryl and heterocycle are optionally substituted.
Preferred compounds falling within the scope of formula (I) include:
7,8-dimethoxy-2-naphthalenecarboximidamide mono (trifluoroacetate) salt;
6,7,8-trimethoxy-2-naphthalenecarboximidamide mono (trifluoroacetate) salt;
6,7-dimethoxy-2-naphthalenecarboximidamide mono (trifluoroacetate) salt;
2-[(7-aminoiminomethyl-2-methoxy- 1-naphthalenyl)oxy]acetamide mono(trifluoroacetate) salt;
7-benzyloxy-8-iodo-2-naphthalenecarboximidamide mono (trifluoroacetate) salt;
methyl [(7-aminoiminomethyl-2-methoxy-1-naphthalenyl)oxy]acetate mono(trifluoroacetate) salt;
2-[(7-aminoiminomethyl-2-methoxy-1-naphthalenyl)oxy]-yl-acetic acid mono(trifluoroacetate) salt;
N-[4(aminomethyl)phenyl]-6-aminoiminomethyl-2-naphthalenecarboxamide bis(trifluoroacetate) salt;
N-[4(amino)phenyl]-6-aminoiminomethyl-2-naphthalenecarboxamide bis(trifluoroacetate) salt;
1-[(7-aminoiminomethyl-2-methoxy-1-naphthalenyl)oxy]-3-hydroxypropane mono(trifluoroacetate) salt;
phenylmethyl [7-(aminoiminomethyl)-1-naphthalenyl)carbamate mono(trifluoroacetate) salt;
N-[7-(aminoiminomethyl)-1-naphthalenyl)acetamide mono (trifluoroacetate) salt;
methyl [7-(aminoiminomethyl)-1-naphthalenyl)carbamate mono(trifluoroacetate) salt;
methyl 3-[[7-(aminoiminomethyl)-1-naphthalenyl]amino]-3-oxopropanoate mono(trifluoroacetate) salt;
N-[7-(aminoiminomethyl)-1-naphthalenyl]-2-(phenylmethoxy)acetamide mono(trifluoroacetate) salt;
N-[7-(aminoiminomethyl)-1-naphthalenyl]-1,3-benzodioxole-5-carboxamide mono(tifluoroacetate) salt;
N-[7-(aminoiminomethyl)- 1-naphthalenyl] benzenemethanesulfonamide mono(trifluoroacetate) salt;
1-[(7-aminoiminomethyl-2-methoxy-1-naphthalenyl)oxy]-3-bromopropane mono(hydrochloride) salt;
3-[(7-aminoimiomethyl-2-methoxy-1-naphthalenyl)oxy] propene mono(trifluoroacetate) salt;
1-[(7-aminoiminomethyl-2-methoxy-1-naphthalenyl)oxy]-3-phenylpropane mono(hydrochloride) salt;
1-[(7-aminoiminomethyl-2-methoxy-1-naphthalenyl)oxy]-3-[1-(3,4-dimethoxy)phenyl]-propane mono (hydrochloride) salt;
7-methoxy-8-(2-furanyl)-2-naphthalenecarboximidamide mono(trifluoroacetate) salt;
methyl 6-(aminoiminomethyl)-4[(methoxycarbonyl) amino]-2-naphthalenecarboxylate mono(trifluoroacetate) salt;

(E)-(7-methoxy-8-[2-(Phenyl)ethenyl])-2-naphthaleneimidamide mono(trifluoroacetate) salt
6-(4phenylbutynyl)-2-naphthalenecarboximidamide mono(trifluoroacetate) salt;
7-(2-hydroxyethoxy)-8-iodo-2-naphthalenecarboximidamide mono(trifluoroacetate) salt;
7-(2-hydroxyethoxy)-2-naphthalenecarboximidamide mono(trifluoroacetate) salt;
6-(4-methyl-1-pentynyl)-2-naphthalenecarboximidamide mono(trifluoroacetate) salt;
6-(5-phenylpentynyl)-2-naphthalenecarboximidamide mono(trifluoroacetate) salt;
6-(3-phenyl-1-propynyl)-2-naphthalenecarboximidamide mono(trifluoroacetate) salt;
6-(phenylethynyl)-2-naphthalenecarboximidamide mono(trifluoroacetate) salt;
3-amino-N-[3-[6-(aminoiminomethyl)-2-naphthalenyl]-2-propynyl]benzamide mono(trifluoroacetate) salt;
4-amino-N-[3-(6-aminoiminomethyl-2-naphthalenyl)-2-propynyl]benzamide mono(trifluoroacetate) salt;
(S)-2-amino-N-[1-[(6-aminoiminomethyl-2-naphthalenyl)carbonyl]cyclohexyl]propionamide bis(trifluoroacetate) salt;
6-methoxy-8-benzyloxy-2-naphthalenecarboximidamide mono(trifluoroacetate) salt;
2-[(7-aminoiminomethyl-3-methoxy-1-naphthalenyl)oxy]acetamide mono(trifluoroacetate) salt;
N-(6-aminoiminomethyl-2-naphthalenyl)-N'-phenylurea mono(trifluoroacetate) salt;
(E)-6-[2-(phenyl)ethenyl]-2-naphthalenecarboximidamide mono(trifluoroacetate) salt;
6-[2-(phenyl)ethyl]-2-naphthalenecarboximidamide mono(trifluoroacetate) salt;
7-propoxy-8-iodo-2-naphthalenecarboximidamide mono(trifluoroacetate) salt;
(±)- 6-(3-phenyloxiranyl)-2-naphthalenecarboximidamide mono(trifluoroacetate) salt;
(E)-6-[2-(2-thienyl)ethenyl]-2-naphthalenecarboximidamide mono(trifluoroacetate) salt;
6-(3-oxobutyl)-2-naphthalenecarboximidamide mono(trifluoroacetate) salt;
6-(3-methoxyphenyl)-2-naphthalenecarboximidamide mono(trifluoroacetate) salt;
N-[3-(methyl)phenyl]-6-aminoiminomethyl-2-naphthalenecarboxamide mono(trifluoroacetate) salt;
6-(2-formylphenoxy)-2-naphthalenecarboximidamide mono(trifluoroacetate) salt;
6-(2-formylphenyl)-2-naphthalenecarboximidamide mono(trifluoroacetate) salt;
6-[2-(hydroxymethyl)phenyl]-2-naphthalenecarboximidamide mono(trifluoroacetate ) salt;
6-(3-oxo-1-butenyl)-2-naphthalenecarboximidamide mono(trifluoroacetate) salt;
7-methoxy-8-(1H-pyrazol4yl)-2-naphthalenecarboximidamide mono(trifluoroacetate) salt;
7-methoxy-8-iodo2-naphthalenecarboximidamide mono(trifluoroacetate) salt;
N-phenyl-6-aminoiminomethyl-2-naphthalenecarboxamide mono(methanesulfonate) salt;
4[(6aminoiminomethyl-2-naphthalenyl)oxy]-N-methylbenzeneacetamide mono(trifluoroacetate) salt;
6-[2-(methylthio)phenyl]-2-naphthalenecarboximidamide mono(methanesulfonate) salt;
6-[2-(2-thiomethoxyethyl)phenyl]naphthalene-2-carboximidamide mono(methanesulfonate) salt;
7-methoxy-8-(3furanyl)-2-naphthalenecarboximidamide mono(methanesulfonate) salt;
7-methoxy-8-(2-benzofuranyl)naphthalene-2-carboximidamide mono(methanesulfonate) salt;
(E)-8-[2-(1,3-benzodioxol-5-yl)ethenyl]-2-naphthalenecarboximidamide mono(methanesulfonate) salt;
(±)-7-methoxy-8-(tetrahydro-3-furanyl)-2-naphthalenecarboximidamide mono(methanesulfonate) salt;
6-[[4(2-aminoethyl)phenyl]ethynyl]-2-naphthalenecarboximidamide mono(trifluoroacetate) salt;
7-methoxy-8-[2-pyrimidinyl(oxy)]-2-naphthalenecarboximidamide mono(trifluoroacetate) salt;
5 7-methoxy-8-[2-thiazoyl(oxy)]naphthalene-2-carboximidamide mono(trifluoroacetate) salt;
7-methoxy-8-(4nitrophenoxy)-2-naphthalenecarboximidamide mono(trifluoroacetate) salt;
7-methoxy-8-pentafluorophenoxy-2-naphthalenecarboximidamide mono(trifluoroacetate) salt;
7-methoxy-8-[N-2-pyrimidinyl(amino)]-2-naphthalenecarboximidamide mono(trifluoroacetate) salt;
N-(6-aminoiminomethyl-2-naphthalenyl)-N'-benzylurea mono(trifluoroacetate) salt;
N-(6-aminoiminomethyl-2-naphthalenyl)-N'-methylurea mono(trifluoroacetate) salt;
N-(6-aminoiminomethyl-2-naphthalenyl)-N'isopropylurea mono(trifluoroacetate) salt;
N-(6-aminoiminomethyl-2-naphthalenyl)-N'-phenyl-N'-methylurea mono(trifluoroacetate) salt;
6-aminonaphthalene-2-carboximidamide mono (trifluoroacetate) salt;
N-(6-aminoiminomethyl-2-naphthalenyl)-N'-cyclohexylurea mono(trifluoroacetate) salt;
N-(6-aminoiminomethyl-2-naphthalenyl)-N'-benzyloxyurea mono(trifluoroacetate) salt;
1,1-dimethylethyl [4-[[(6-cyano-2-naphthalenyl)amino]carbonyl]phenyl]carbamate mono(trifluoroacetate) salt
N-[6-(aminoiminomethyl)-2-naphthalenyl]-4(aminomethyl)benzamide mono(trifluoroacetate) salt;
ethyl [6-(aminoiminomethyl)-2-naphthalenyl]carbamate mono(trifluoroacetate) salt;
1,1-dimethylethyl[4[[[6-aminoiminomethyl)-2-naphthalenyl)amino]carbonyl]amino]-phenyl]carbamate mono(trifluoroacetate) salt;
(E)-6-[2-(phenylthio)ethenyl]-2-naphthalenecarboxiinidamide mono(trifluoroacetate) salt;
(E)-6-[2-(2-furanyl)ethenyl]-2-naphthalenecarboximidamide mono(trifluoroacetate) salt;
(E)-6-[2-(1H-imidazol-1-yl)ethenyl]-2-naphthalenecarboximidamide mono(trifluoroacetate) salt;
(E)-4-[2-(6-aminoiminomethyl-2-naphthalenyl)ethenyl]benzenesulfonamide mono(trifluoroacetate) salt;
(E)-4-[2-(6-aminoiminomethyl-2-naphthalenyl)ethenyl]benzoic acid mono(trifluoroacetate) salt;
4-[7-(aminoiminomethyl)-2-methoxy- 1 -naphthalenyl]dihydro-2(3H)-furanone mono(trifluoroacetate) salt;
7-methoxy-8-(1-acetyl-1H-pyrazolyl)-2-naphthalenecarboximidamide mono(trifluoroacetate) salt;
7-methoxy-8-[1-(methylsulfonyl)- 1H-4-pyrazoly]-2-naphthalenecarboximidamide mono(trifluoroacetate) salt;
(E)4-[2-(6-aminoiminomethyl-2-naphthalenyl)ethenyl]benzamide mono(trifluoroacetate) salt;
6-[2-(4-aminophenyl)ethoxy]-2-naphthalenecarboximidamide mono(trifluoroacetate) salt;
methyl [3-methoxy-6-(aminoiminomethyl)4naphthalenyl]carbamate mono(trifluoroacetate) salt;
7-methoxy-8-[2-pyrimidinyl(amino)]-2-naphthalenecarboximidamide bis(trifluoroacetate) salt;

phthalenecarboxamide, mono(trifluoroacetate) salt;
6-(4aminophenyl)2-naphthalenecarboximidamide, bis(trifluoroacetate) salt;
methyl 2-[4-[[[6-(aminoiminomethyl)-2-naphthalenyl]carbonyl]amino]-phenoxy]acetate,mono(trifluoroacetate) salt;
(E)-6-[2-[(3-hydroxymethyl)phenyl]ethenyl]-2-naphthalenecarboximidamide, mono(trifluoroacetate) salt;
6-(2-phenyl-1-cyclopropyl)-2-naphthalenecarboximidamide, mono(trifluoroacetate) salt;
(E)-6-[2-[4(aminomethyl)phenyl]ethenyl]-2-naphthalenecarboximidamide, bis(trifluoroacetate) salt;
(E6-[2-[4-(1,2-dihdyroxyethyl)phenyl]ethenyl]-2-naphthalenecarboximidamide, mono(trifluoroacetate) salt;
(E)-6-[2-[4-(1R-amino-2-hydroxyethyl)phenyl]ethenyl]-2-naphthalenecarboximidamide, bis(trifluoroacetate) salt;
7-methoxy-8-(2-pyrimidinylamino)-2-naphthalenecarboximidamide, bis(trifluoroacetate) salt;
(E)-6-[2-[[4-(dimethylamino)methyl]phenyl]ethenyl]-2-naphthalenecarboxinidamide, bis(trifluoroacetate) salt;
(E)-6-[2-[4-(hydroxymethyl)phenyl]ethenyl]-2-naphthalenecarboximidamide, mono(trifluoroacetate) salt;
4-[[6-(aminoiminomethyl)-2-naphthalenyl]ethynyl]-L-phenylalanine, mono(trifluoroacetate) salt;
6-(3-formylphenyl)-2-naphthalenecarboximidamide, mono(trifluoroacetate) salt;
(E)-6-[2-(1,2,3,4tetrahydro-6-isoquinolinyl)ethenyl]-2-naphthalenecarboximidamide, bis(trifluoroacetate) salt;
(E)- 6-[2-[3-(2-hydroxyethyl)phenyl]ethenyl]-2-naphthalenecarboximidamide, mono(trifluoroacetate) salt;
6-(aminoiminomethyl)-N-(2,3-dihydro-1H-inden-5-yl)-2-naphthalenecarboxamide, mono(tiifluoroacetate) salt;
6-[(4-aminophenyl)ethynyl]-2-naphthalenecarboximidamide, bis(trifluoroacetate) salt;
1,1-dimethylethyl [2-[3-[[6-(aminoiminomethyl)-2-naphathalenyl]ethynyl]-6-methoxyphenyl]ethyl]carbamate, mono(trifluoroacetate) salt;
1,1-dimethylethyl [[4-[[6-(aminoiminomethyl)-2-naphathalenyl]ethynyl]- phenyl]methyl]carbamate, mono(trifluoroacetate) salt;
6-[[4(aminomethyl)phenyl]ethynyl]-2-naphthalenecarboximidamide, bis(trifluoroacetate) salt;
6-[[3-(2-aminoethyl)-4-methoxyphenyl]ethynyl]-2-naphthalenecarboximidamide, bis(trifluoroacetate) salt;
6-[[4(hydroxymethyl)phenyl]ethynyl]-2-naphthalenecarboximidamide, mono(trifluoroacetate) salt;
6-[(1,2,3,4-tetrahydro-6-isoquinolinyl)ethynyl]-2-naphthalenecarboximidamide, bis(trifluoroacetate) salt;
6-(aminoiminomethyl)-N-(4methylphenyl)-2-naphthalenecarboxamide, mono(trifluoroacetate) salt;
1,1-dimethylethyl [[4-[[[6-(aminoiminomethyl)-2-naphathalenyl]amino]-carbonyl]phenyl]methyl]carbamate, mono(trifluoroacetate) salt;
N-[6-(aminoiminomethyl)-2-naphthalenyl)benzamide, mono(trifluoroacetate) salt;
1,1-dimethylethyl [[4-[[[6-(aminoiminomethyl)-2-naphathalenyl]amino]carbonyl]-cyclohexyll]methyl]carbamate, mono(trifluoroacetate) salt;
N-[6-(aminoiminomethyl)-2-naphthalenyl]-N'-(4-aminophenyl)urea, bis(trifluoroacetate) salt;
N-[6-(aminoiminomethyl)-2-naphthalenyl]-4-4-(aminomethyl)cyclohexanecarboxamide, bis(trifluoroacetate) salt;
N-[6-(aminoiminomethyl)-2-naphthalenyl]-N'-[(4-aminomethyl)phenyl]urea, bis(tifluoroacetate) salt;
6-(aminoiminomethyl)-N-(4-ethylphenyl)-2-naphthalenecarboxamide, acetate salt;
6-(aminoiminomethyl)-N-(2-naphthalenyl)-2-naphthalenecarboxamide, mono(trifluoroacetate) salt;
6-(5-phenyl-2-oxazolyl)-2-naphthalenecarboximidamide, mono(trifluoroacetate) salt;
6-(5-phenyl-2-thiazolyl)-2-naphthalenecarboximidamide, mono(trifluoroacetate) salt;
6-(aminoiminomethyl)-N-(1 ,2,3,4tetrahydro-6-quinolinyl)-2-naphthalenecarboxamide, bis(trifluoroacetate) salt;
6-[amino(hydroxyimino)metyhl]-N-phenyl-2-naphthalenecarboxamide;
6-[4-(hydroxymethyl)phenyl]methoxy]-2-naphthalenecarboximidamide, methanesulfonate salt;
6-(2-pyridinylethynyl)-2-naphthalenecarboximidamide, mono(trifluoroacetate) salt;
N-[4(aminocarbonyl)phenyl]-6-(aminoiminomethyl)-2-naphthalenecarboxamide, mono(trifluoroacetate) salt;
6-(aminoiminomethyl)-N-(2-thiazolyl)-2-naphthalenecarboxamide, monohydrochloride
6-(aminoiminomethyl)N-(6methoxy-3-pyridinyl)-2-naphthalenecarboxamide, monohydrochloride
6-(aminoiminomethyl)-N-(1,3-benzodioxol-5-yl)-2-naphthalenecarboxamide, mono(trifluoroacetate) salt;
6-(aminoiminomethyl)-N-(1,2,3,4-tetrahydro-2,4dioxo5-pyrimidinyl)-2-naphthalenecarboxamide, monohydrochloride
6-(aminoiminomethyl)-N-(3,5difluorophenyl)-2-naphthalenecarboxamide, mono(trifluoroacetate) salt;
6-(aminoiminomethyl)-N-(1H-pyrazol-3-yl)-2-naphthalenecarboxamide, mono(trifluoroacetate) salt;
6-(aminoiminomethyl)-N-(5-methyl-3-isoxazolyll)-2-naphthalenecarboxamide, mono(trifluoroacetate) salt;
6-(aminoiminomethyl)-N-(pyrazinyl)-2-naphthalenecarboxamide, mono(trifuoroacetate) salt;
6-(aminoiminomethyl)-N-(6-methyl-2-pyridinyl)-2-naphthalenecarboxamide, mono(trifluoroacetate) salt;
6-(aminoiminomethyl)-N-(3,4,5-trimethoxyphenyl)-2-naphthalenecarboxamide, monohydrochloride
6-(aminoiminomethyl)-N-(3-methyl-2-pyridinyl)-2-naphthalenecarboxamide, bis(trifluoroacetate) salt;
6-(aminoiminomethyl)-N-(5-bromo-2-thiazolyll)-2-naphthalenecarboxamide, mono(tdifluoroacetate) salt;
6-(aminoiminomethyl)-N-(5-methyl-2-pyridinyl)-2-naphthalenecarboxamide, mono(trifluoroacetate) salt;
6-(aminoiminomethyl)-N-(4-methyl-2-thiazolyl)2-naphthalenecarboxamide, mono(trifluoroacetate) salt;
6-(aminoiminomethyl)-N-(6-quinolinyl)-2-naphthalenecarboxamide, bis(trifiuoroacetate) salt;
6-(aminoiminomethyl)-N-(1H-indazol-6-yl)-2-naphthalenecarboxamide, bis(trifluoroacetate) salt;
6(aminoiminomethyl)-N-(1H-indazol-5-yl)-2-naphthalenecarboxamide, bis(trifiuoroacetate) salt;
6-(aminoiminomethyl)-N-(1H-indol-5-yl)-2-naphthalenecarboxamide, mono(trifiuoroacetate) salt;
6-(aminoiminomethyl)-N-(5-pyrimidinyl)-2-naphthalenecarboxamide, mono(trifluoroacetate) salt;
6-(aminoiminomethyl)-N-(3-pyridazinyl)-2-naphthalenecarboxamide, mono(trifluoroacetate) salt;
5 6-(aminoiminomethyl)-N-(5-bromo-2-pyridinyl)-2-naphthalenecarboxamide, mono(trifluoroacetate) salt;
6-(aminoiminomethyl)-N-[3-(1-methylethoxy)phenyl]-2-naphthalenecarboxamide, mono(trifluoroacetate) salt;
6-(aminoiminomethyl)-N-(1H-imidazolyl)-2-naphthalenecarboxamide, bis(trifluoroacetate) salt;

6-[2-[4-(hydroxymethyl)phenyl]-1-cyclopropyl]-2-naphthalenecarboximidamide, mono(trifluoroacetate) salt;
N-(ethoxycarbonyl)-6-(2-phenyl-1-cyclopropyl)2-naphthalenecarboximidamide 6-(aminoiminomethyl)-N-(2-methyl-6quinolinyl)-2-naphthalenecarboxamide, bis (trifluoroacetate) salt;
6-(aminoiminomethyl)-N-(3-propoxyphenyl)-2-naphthalenecarboxamide, mono(trifluoroacetate) salt;
6-(aminoiminomethyl)-N-[3-(1-ethylpropoxy)phenyl]-2-naphthalenecarboxamide, mono(trifluoroacetate) salt;
6-(aminoiminomethyl)-N-[3-(cyclopentyloxy)phenyl]-2-naphthalenecarboxamide, mono(trifluoroacetate) salt;
6-(aminoiminomethyl)-N-(3-phenoxyphenyl)-2-naphthalenecarboxamide, mono(trifluoroacetate) salt;
6-(aminoiminomethyl)-N-[3-(phenylmethoxy)phenyl]-2-naphthalenecarboxamide, mono(trifluoroacetate) salt;
6-(aminoiminomethyl)-N-(3-ethoxyphenyl)-2-naphthalenecarboxamide, mono(tifluoroacetate) salt;
6-(aminoiminomethyl)-N-(4-nitrophenyl)-2-naphthalenecarboxamide, mono(trifluoroacetate) salt;
6-(aminoiminomethyl)-N-[3-(cyclobutylmetboxy)phenyl]-2-naphthalenecarboxamide, mono(trifluoroacetate) salt;
6-[amino(ethoxycarbonyl)imino]-N-[3-(1-methylethoxy)phenyl]-2-naphthalenecarboxamide;
6-(aminoiminomethyl)-4-[5-(ethylsulfonyl)-3-furanyl]-N-phenyl-2-naphthalenecarboxamide, monohydrochloride;
methyl [7-(aminoiminomethyl)-2-methoxy-1-naphthalenyl) carbamate, mono(trifluoroacetate) salt;
7-methoxy-8-(2-pyrimidinylamino)-2-naphthalenecarboximidamide, bis(trifluoroacetate) salt,
7-methoxy-8-1(phenylmethyl)amino]-2-naphthalenecarboximidamide, mono(trifluoroacetate) salt;
7-methoxy-8-(phenylamino)-2-naphthalenecarboximidamide, mono(trifluoroacetate) salt;
7-methoxy-8-[(4methoxyphenyl)amino]-2-naphthalenecarboximidamide, mono(trifluoroacetate) salt;
(E)-3-[7-(aminoiminomethyl)-2-methoxy- 1-naphthalenyl)-2-propenamide, mono(trifluoroacetate) salt;
7-methoxy-8-(3-oxo-1-cyclopenten-1-yl)-2-naphthalenecarboximidamide, mono(trifluoroacetate) salt;
methyl 4-[[[7-(aminoiminomethyl)-1-(2-pyrimidinylamino)-2-naphthalenyl]oxy]methyl]benzoate, mono(trifluoroacetate) salt;
4-[[[7-(aminoiminomethyl)-1-(2-pyrimidinylamino)-2-naphthalenyl]oxy]methyl]benzoic acid, mono (trifluoroacetate) salt;
7-methoxy-8-(pyrazinyloxy)-2-naphthalenecarboximidamide, dimethanesulfonate salt;
7-methoxy-8-(phenylthio)-2-naphthalenecarboximidamide, methanesulfonate;
7-methoxy-8-(pyrazinylamino)-2-naphthalenecarboximidamide, bis(trifluoroacetate) salt;
methyl 5-[7-[(aminoiminomethyl)-2-naphthalenyl]oxy] pentanoate, mono(trifluoroacetate) salt;
5-[[6-(aminoiminomethyl)-2-naphthalenyl]oxy]pentanoic acid, mono(trifluoroacetate) salt;
methyl 4-[[[7-amino(hydroxyimino)methyl]-2-naphthalenyl]oxy]methyl]benzoate;
methyl 2-[[6-(aminoiminomethyl)-2-naphthalenyl]oxy] acetate, mono(trifluoroacetate) salt;
7-[2-(4morpholinyl)ethoxy]-2-naphthalenecarboximidamide, bis(trifluoroacetate) salt;
2-[[6-(aminoiminomethyl)-2-naphthalenyl]oxy]acetic acid, mono(trifluoroacetate) salt;
methyl 4-[6-(aminoiminomethyl)-2-naphthalenyl]oxy] methyl]benzoate, mono(trifluoroacetate) salt;
methyl [7-(aminoiminomethyl)-1-naphthalenyl] methylcarbamate, mono(trifluoroacetate) salt;
propyl [7-(aminoiminomethyl)-1-naphthalenyl]carbamate, mono(trifluoroacetate) salt;
N-[7-(aminoiminomethyl)-1-naphthalenyl]-N'-methylurea, mono(trifluoroacetate) salt;
ethyl [7-(aminoiminomethyl)-1-naphthalenyl)carbamate, mono(trifluoroacetate) salt;
N-[7-(aminoiminomethyl)-1-naphthalenyl)propanamide, mono(trifluoroacetate) salt,
N-[7-(aminoiminomethyl)-1-naphthalenyl)-2-methoxyacetamide, mono(trifluoroacetate) salt;
N-[7-(aminoiminomethyl)-1-naphthalenyl]urea, mono (trifluoroacetate) salt;
N-[7-(aminoiminomethyl)-1-naphthalenyl]-2-hydroxyacetamide, mono(trifluoroacetate) salt;
8-(2-pyrimidinylamino)-2-naphthalenecarboximidamide, bis(trifluoroacetate) salt;
8-amino-2-naphthalenecarboximidamide, bis (trifiuoroacetate) salt;
8-(2-pyridinylamino)-2-naphthalenecarboximidanide, bis (trifluoroacetate) salt;
N-hydroxy-8-(2-pyrimidinylamino)-2-naphthalenecarboximidamide, mono(trifluoroacetate) salt;
6-(aminoiminomethyl)-4-(3-furanyl)-N-[4-(trifluoromethyl) phenyl]-2-naphthalenecarboxamide, mono (trifluoroacetate) salt;
6-(aminoiminomethyl)-4-(3-furanyl)-N-(4pyndinyl)-2-naphthalenecarboxamide, dihydrochloride;
6-(aminoiminomethyl)-4-(3-furanyl)-N-(1H-pyrazol-3-yl)-2-naphthalenecarboxamide, dihydrochloride;
6-(aminoiminomethyl)-4-(3-furanyl)-N-(3-pyridinyl)-2-naphthalenecarboxamide, dihydrochloride;
methyl [7-(aminoiminomethyl)-3-[[[4-(aminomethyl) phenyl]amino]carbonyl]-1-naphathalenyl]carbamate, bis (triuoroacetate) salt;
6-(aminoiminomethyl)-4(3-furanyl)-N-(2-pyridinyl)-2-naphthalenecarboxamide, dihydrochloride;
6-(aminoiminomethyl)-4-(3-furanyl)-N-phenyl-2-naphthalenecarboxamide, monohydrochloride
6-(aminoiminomethyl)-4[1-(methylsulfonyl)-1H-pyrazol-4yl]-N-phenyl-2-naphthalenecarboxamide, monohydrochloride;
6-(aminoiminomethyl)-4-[5-(methylthio)-3-furanyl)]-N-phenyl-2-naphthalenecarboxamide, monohydrochloride;
6-(aminoiminomethyl)-N-[4-(aminomethyl)phenyl]-4-(2-pyrimidinylamino)-2-naphthalenecarboxamide, tris (trifluoroacetate) salt;
6-(aminoiminomethyl)-N-phenyl-4-(2-pyrimidinylamino)-2naphthalenecarboxamide, mono(trifluoroacetate) salt;
N-[(4-aminomethyl)phenyl]-6-[amino(hydroxyimino) methyl]-4(2-pyrimidinylamino)-2-naphthalenecarboxamide, bis(trifluoroacetate) salt;
6-(aminoiminomethyl)-N-[4-(hydroxymethyl)phenyl]-4-(2-pyrimidinylamino)-2-naphthalenecarboxamide, mono (trifluoroacetate) salt;
methyl [3-[[[4-(aminomethyl)phenyl]amino]carbonyl]-7-(4-amino(hydroxyimino)methyl]-l1naphthalenyl]carbamate, bis(trifluoroacetate) salt;
6-(aminoiminomethyl)-N-phenyl-4(tetrahydro-3-furanyl)-2-naphthalenecarboxamide, monohydrochloride;
6-[amino(hydroxyimino)methyl]-N-phenyl-4(2-pyrimidinylamino)-2-naphthalenecarboxamide 6-(aminoiminomethyl)-4-[5-(ethylthio)-3-furanyl]-N-phenyl-2-naphthalenecarboxamide, monohydrochloride;
6-(aminoiminomethyl)-4-[5-(propylthio)-3-furanyl]-N-phenyl-2-naphthalenecarboxamide, monohydrochloride;
6-(aminoiminomethyl)-N-phenyl-4-(2-pyrrolidinyl)-2-naphthalenecarboxamide, mono(trifluoroacetate) salt;
6-(aminoiminomethyl)4-[5-(propylsulfonyl)3-furanyl]-N-phenyl-2-naphthalenecarboxamide, monohydrochloride;
6-(aminoiminomethyl)-4-[5-[methylthio)methyl]-3-furanyl]-N-phenyl-2-naphthalenecarboxamide, monohydrochloride;
6-(aminoiminomethyl)-4-[5-(methoxymethyl)-3-furanyl]-N-phenyl-2-naphthalenecarboxamide, monohydrochloride;
6-(aminoiminomethyl)-4-[5-(methylsulfonyl)-3-furanyl]-N-phenyl-2-naphthalenecarboxamide, mono(trifluoroacetate) salt;
6-(aminoiminomethyl)4-[5-(ethythio)tetrahydro-3-furanyl]-N-phenyl-2-naphthalenecarboxamide, monohydrochloride;
ethyl 7-[[[6-(aminoiminomethyl)-2-naphthalenyl]carbonyl]amino]- 1,2,3,4-tetrahydro-1-(hydroxymethyl)-2-isoquinolinecarboxylate mono(trifluoroacetate) (salt));
6-(aminoiminomethyl)-N-[3,4-dihydro- 1-(2-methylpropyl)-6-isoquinolinyl]-2-naphthalenecarboxamide bis(trifluoroacetate) (salt);
1,1-dimethylethyl 6-[[[6-(aminoiminomethyl)-2-naphthalenyl]carbonyl]amino]-1,2,3,4-tetrahydro-1-(2-methylpropyl)-2-isoquinolinecarboxylate mono(trifluoroacetate) (salt);
6-(aminoiminomethyl)-N-[1,2,3,4-tetrahydro-1 -(2-methylpropyl)-6-isoquinolinyl]-2-naphthalenecarboxamide bis(trifluoroacetate) (salt);
6-(aminoimninomethyl)N-[1,2,3,4-tetrahydro-2-[(4-methylphenyl)mehtyl]-6-isoquinolinyl]-2-naphthalenecarboxamide bis(trifluoroacetate) (salt);
6-(aminoiminomethyl)-N-[1,2,3,4-tetrahydro-2-[(3-methylphenyl)mehtyl]-6-isoquinolinyl]-2-naphthalenecarboxamide bis(trifluoroacetate) (salt);
phenylmethyl 6-[[[6-(aminoiminomethyl)-2-naphthalenyl] carbonyl]amino]-1,2,3,4-tetrahydro-2-isoquinolinecarboxylate mono(trifluoroacetate) (salt);
6-(aminoiminomethyl)-N-[4-ethyl- 1,2,3,4-tetrahydro-2-(2-propenyl)-6-isoquinolinyl)-2-naphthalenecarboxamide bis(trifluoroacetate) (salt);
6-(aminoiminomethyl)-N-(4-ethyl- 1,2,3,4-tetrahydro-6-isoquinolinyl)-2-naphthalenecarboxamide bis(trifluoroacetate) (salt);
6-(aminoiminomethyl)-N-(3,5-dimethoxyphenyl)-2-naphthalenecarboxamide;
6-(aminoiminomethyl)-N-[3-(2-methylpropylphenyl]-6-isoquinolinyl]-2-naphthalene-carboxamide monohydrochloride mono(trifluoroacetate) (salt);
6-(aminoiminomethyl)-N-[3-(cyclopentylmethyl)phenyl]-6-isoquinolinyl]-2-naphthalenecarboxamide, monohydrochloride mono(trifluoroacetate) (salt);
6-(aminoiminomethyl)-N-[1,2,3,4-tetrahydro-1-[4-methyl-2-(2-propenyl)-6-isoquinolinyl]-2-naphthalenecarboxamide bis(triuoroacetate) (salt);
6-(aminoixninomethyl)-N-(4-methyl- 1,2,3, 4tetrahydroisoquinolin-6-yl)-2-naphthalenecarboxaride;
6-(amninoiminomethyl)-N-(2,4-difluorophenyl)-2-naphthalenecarboxamide;
6-(6-fluoro-1,3-benzoxazol-2-yl)-2-naphthalenecarboximidamide;
6-(amino(hydroxyimino)methyl)-N-(2,4-difluorophenyl)-2-naphthalenecarboxamide;
4-[[6-(aminoiminomethyl)-2-naphthalenyl]ethynyl]-N-[(1,1-dimethylethoxy)carbonyl]-L-phenylalanine mono(trifluoroacetate) (salt);
6-phenyl-2-naphthalenecarboximidamide;
(Z)-6-[2-chloro-2-phenylethenyl]naphthalene-2-carboximidamide;
(Z)-6-(2-chloro-2-(3-(2-methyl-1-propenyl)phenyl)ethenyl)-2-naphthalenecarboximidamide;
(Z)-6-(2-chloro-2-(3-(1-methylethoxy)phenyl)thenyl)-2-naphthalene-carboximidamide;
(Z)-6-[1-chloro-2-phenylethenyl]-2-naphthalenecarboximidamide mono(trifluoroacetate) (salt);
(Z)-6-(1-chloro-2-(3-(1-methylethoxy)phenyl)ethenyl)-2-naphthalene-carboximidamide monohydrochloride;
(Z)-6-(1-chloro-2-(2-(1-methylethoxy)phenyl)ethenyl)-2-naphthalenecarboximidamide monohydrochloride;
(Z)-6-(1-chloro-2-(4(1methylethoxy)phenyl)ethenyl)-2-naphthalenecarboximidamide;
(E)-6-[2-[3,4-dihydro-1-(1-methyethyl)-7-isoquinolinyl]ethenyl]-2-naphthalenecarboximidamide bis(trifluoroacetate) (salt);
6-((3-(cyclopentyloxy)phenyl)ethynyl)-2-naphthalenecarboximidamide;
(Z)-6-[1-bromo-2-[3-(cyclopentyloxy)phenyl]ethenyl]-2-naphthalenecarboximidamide mono(trifluoroacetate) (salt);
(Z)-6-[1-fluoro-2-[3-(cyclopentyloxy)phenyl]ethenyl]-2-naphthalenecarboximidamide mono(trifluoroacetate) (salt);
(Z)-6-[2-bromo2-[3-(cyclopentyloxy)phenyl]ethenyl]-2-naphthalenecarboximidamide mono(trifiuoroacetate) (salt);
6-((methylphenylamino)methyl)-2-naphthalenecarboximidamide;
N-(6-(aminoiminomethyl)-2-naphthaleny)lurea;
6-(2-(4methoxyphenyl)cyclopropyl)-2-naphthalenecarboximidamide;
6-(2-(4-(1-methylethyl)phenyl)-1-cyclopropyl)-2-naphthalenecarboximidamide monohydrochloride;
6-Aminonaphthalene-2-carboximidamide mono(trifluoroacetate) salt;
(E)-6-(2-(phenylsulfinyl)ethenyl)-2-naphthalenecarboximidamide;
6-((3-propoxyphenyl)amino)methyl)-2-naphthalenecarboximidamide;
2-(aminoiminomethyl)-N-((1-methylethoxy)phenyl)-6-quinolinecarboxamide; and
2-(aminoiminomethyl)-N-(3,5-bis(trifluoromethyl)phenyl)-6-quinolinecarboxamide.

Determination of Urokinase inhibition

The efficacy of the compounds of this invention as urokinase inhibitors was determined by measuring the inhibition of the urokinase enzyme Abbokinase (Abbott Laboratories, Abbott Park, Ill.) on substrate S-2444, of formula pyroGlu-Arg-pNA-HCl (DiaPharma Group, Inc. Distributor of Chromogenix) at 200 μM.

The assay was performed in a 96 well polystyrene, flat bottom plate in a 50 mM Tris/0.15 M NaCl+0.5% Pluronic F-68 (Sigma P-5556), pH 7.4 (with HCl) buffer. The compounds of this invention, 10 mM in DMSO, were diluted with DMSO to eight half log concentrations, for example: 1200 μM, 400 μM, 120 μM, 40 μM, 12 μM, 4 μM, 1 μM and 0.4 μM. Four concentrations were chosen, then 5 μl of each were diluted to a total assay volume of 200 μl. The final compound concentrations in the assay, according to the above example, were 30 µM, 10 µM, 3 µM, 1 µM, 0.3 µM, 0.1 µM, 0.03 µM and 0.01 µM, respectively. The substrate S-2444 was used at 200 µM in the assay. Several vials were reconstituted as directed on the vial, aliquoted and stored frozen. The enzyme was further diluted in assay buffer and 10 µl was used in the assay. Enzyme concentration in the assay was 2–3 nM. The assay was performed as follows: 175 µL of buffer was pipetted into the polystyrene plate, 5 µL solution of a compound of this invention in DMSO was added, the mixture was vortexed, 10 µL of enzyme in buffer was added, the mixture was vortexed, 10 µL of substrate in water was added, the mixture was vortexed, and the plate was placed in a Spectromax ® (Molecular Devices Corporation, Sunnyvale, Calif.) plate reader to follow the course of the reaction for 15 min at 405 nm. The Spectromax ® calculated the reaction rates which were used to calculate percent inhibition of the compounds of this invention versus the reaction rate of the enzyme in the absence of any inhibitor. The Ki's of the inhibitors were calculated from the percent inhibition and previously established Km. The compounds of this invention inhibit urokinase as shown by the data for representative examples in Table 1.

TABLE 1

Inhibitory Potency of Representative Compounds Against Urokinase

| Example | $IC_{50}$ (µM) |
|---|---|
| 1 | 6.6 |
| 2 | 9.8 |
| 3 | 36 |
| 4 | 0.5 |
| 5 | 2.5 |
| 6 | 2.3 |
| 7 | 3.5 |
| 8 | 0.1 |
| 9 | 1.1 |
| 10 | 3.2 |
| 14 | 0.33 |
| 15 | 2.5 |
| 16 | 0.03 |
| 17 | 4.26 |
| 18 | 0.42 |
| 19 | 2.21 |
| 20 | 0.803 |
| 21 | 1.7 |
| 22 | 1.7 |
| 23 | 4.0 |
| 24 | 4.9 |
| 25 | 2.1 |
| 26 | 0.04 |
| 27 | 0.93 |
| 28 | 2.1 |
| 29 | 2.5 |
| 30 | 3.6 |
| 31 | 2.93 |
| 32 | 4.6 |
| 33 | 2.4 |
| 34 | 3.5 |
| 35 | 3.97 |
| 36 | 1.75 |
| 37 | 2.34 |
| 38 | 6.35 |
| 39 | 12.2 |
| 40 | 0.31 |
| 41 | 2.38 |
| 42 | 2.08 |
| 43 | 2.2 |
| 44 | 0.35 |
| 45 | 2.94 |
| 46 | 2.4 |
| 47 | 4.8 |
| 48 | 1.3 |
| 49 | 3.3 |
| 50 | 6.13 |

TABLE 1-continued

Inhibitory Potency of Representative Compounds Against Urokinase

| Example | $IC_{50}$ (µM) |
|---|---|
| 51 | 4.7 |
| 52 | 4.7 |
| 53 | 2.96 |
| 54 | 2.7 |
| 55 | 0.9 |
| 56 | 2.9 |
| 57 | 3.4 |
| 58 | 2.53 |
| 59 | 0.41 |
| 60 | 0.72 |
| 61 | 0.73 |
| 62 | 0.64 |
| 63 | 0.37 |
| 64 | 0.56 |
| 65 | 0.54 |
| 66 | 3.13 |
| 67 | 2.78 |
| 68 | 1.74 |
| 69 | 1.38 |
| 70 | 2.57 |
| 71 | 2.39 |
| 72 | 4.30 |
| 73 | 3.3 |
| 74 | 1.61 |
| 75 | 2.09 |
| 76 | 0.96 |
| 77 | 0.23 |
| 78 | 3.57 |
| 79 | 0.96 |
| 80 | 1.93 |
| 81 | 3.21 |
| 82 | 3.08 |
| 83 | 2.24 |
| 84 | 10.0 |
| 85 | 1.38 |
| 86 | 3.6 |
| 87 | 0.63 |
| 88 | 2.73 |
| 89 | 6.5 |
| 90 | 0.07 |
| 91 | 0.05 |
| 92 | 0.04 |
| 93 | 2.36 |
| 95 | 1.73 |
| 96 | 0.86 |
| 97 | 1.31 |
| 98 | 0.24 |
| 99 | 3.02 |
| 100 | 3.16 |
| 101 | 0.8 |
| 102 | 0.34 |
| 103 | 0.57 |
| 104 | 1.2 |
| 105 | 0.84 |
| 106 | 0.76 |
| 107 | 2.34 |
| 108 | 0.996 |
| 109 | 2.85 |
| 110 |  |
| 111 | 4.17 |
| 112 | 0.45 |
| 113 | 0.403 |
| 114 | 0.344 |
| 115 | 0.063 |
| 116 | 0.045 |
| 117 | 0.278 |
| 118 | 0.121 |
| 119 | 4.41 |
| 120 | 0.93 |
| 121 | 0.89 |
| 122 | 0.33 |
| 123 | 1.24 |
| 124 | 0.12 |
| 125 | 0.23 |
| 126 | 0.87 |

TABLE 1-continued

Inhibitory Potency of Representative Compounds Against Urokinase

| Example | IC$_{50}$ ($\mu$M) |
|---|---|
| 127 | 0.085 |
| 129 | 4.84 |
| 131 | 4.18 |
| 132 | 0.96 |
| 133 | 0.044 |
| 134 | 0.064 |
| 135 | 1.91 |
| 136 | 1.67 |
| 137 | 0.82 |
| 138 | 0.46 |
| 139 | 2.64 |
| 140 | 0.46 |
| 141 | 0.00117 |
| 142 | 0.54 |
| 143 | 0.36 |
| 144 | 1.26 |
| 145 | 2.59 |
| 146 | 0.372 |
| 147 | 0.213 |
| 148 | 0.81 |
| 149 | 3.8 |
| 150 | 0.16 |
| 152 | 0.083 |
| 153 | 0.877 |
| 154 | 0.035 |
| 155 | 2.33 |
| 156 | 0.18 |
| 157 | 3.12 |
| 158 | 0.09 |
| 159 | 2.23 |
| 160 | 2.62 |
| 161 | 1.59 |
| 162 | 1.33 |
| 163 | 0.03 |
| 164 | 0.45 |
| 165 | 0.00068 |
| 166 | 0.002 |
| 167 | 0.052 |
| 168 | 0.003 |
| 170 | 0.695 |
| 171 | >30 |
| 174 | 0.17 |
| 176 | 5.011 |
| 177 | 14.9 |
| 179 | 1.61 |
| 180 | 0.097 |
| 181 | 8.92 |
| 182 | >30 |
| 184 | 0.375 |
| 185 | 3.19 |
| 186 | 2.98 |
| 187 | 0.613 |
| 188 | 0.22 |
| 189 | 1.3 |
| 190 | 0.565 |
| 191 | 0.887 |
| 192 | 1.6 |
| 193 | 0.85 |
| 194 | 0.56 |
| 195 | 1.3 |
| 196 | 0.62 |
| 197 | 2.03 |
| 198 | 0.504 |
| 199 | 2.3 |
| 200 | 0.037 |
| 201 | 0.077 |
| 202 | 0.792 |
| 203 | 0.624 |
| 204 | 0.331 |
| 205 | 0.337 |
| 206 | 5.73 |
| 207 | 4.12 |
| 208 | 0.96 |
| 209 | 0.82 |
| 210 | 0.78 |
| 211 | 0.072 |
| 212 | 5.09 |
| 213 | 4.58 |
| 214 | 2.559 |
| 215 | 1.1 |
| 216 | >30 |
| 217 | 0.67 |
| 218 | 0.086 |
| 219 | 0.103 |
| 220 | 0.03 |
| 221 | 0.52 |
| 222 | 0.346 |
| 223 | 0.07 |
| 224 | 1.773 |
| 225 | 0.104 |
| 226 | >30 |
| 227 | 0.015 |
| 228 | 0.025 |
| 229 | 0.117 |
| 230 | 0.103 |
| 231 | 0.015 |
| 232 | 0.123 |

Pharmaceutical Compositions

The present invention also provides phannaceutical compositions which comprise compounds of the present invention formulated together with one or more non-toxic pharmaceutically acceptable carriers. The pharmaceutical compositions may be specially formulated for oral administration in solid or liquid form, for parenteral injection or for rectal administration.

The pharmaceutical compositions of this invention can be administered to humans and other animals orally, parenterally, intracisternally, intravaginally, intraperitoneally or topically (such as powders, ointments or drops), bucally or as an oral or nasal spray. The term "parenteral" administration, as used herein, refers to modes of administration wich include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents (such as aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art They may optionally contain opacifying agents and may also be of a composition such that they release the active ingredient(s) only, or preferentially, in a certain part of the intestinal tract, optionally or in delayed fashion. Examples of embedding compositions which can be used include polymeric substances and waxes.

The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved. Generally dosage levels of about 1 to about 50, more preferably of about 5 to about 20 mg, of active compound per kilogram of body weight per day when administered orally to a mammalian patient If desired, the effective daily dose may be divided into multiple doses for purposes of administration, e.g. two to four separate doses per day.

Preparation of Compounds of this Invention

The compounds of this invention may be prepared by a variety of synthetic routes. Representative procedures are outlined in the following Schemes 1–6.

Abbreviations

Abbreviations which have been used in the descriptions of the schemes and the examples that follow are: CBZ-Cl for carbobenzyloxy chloride; DPPB for 1,4-bis(diphenylphosphino)butane; THF for tetrahydrofuran; DMF for N,N-dimethylformamide; $OEt_2$ for diethyl ether; EDC for 1-(3-dimethylaminopropyl)-3-ethylcarbodiimide hydrochloride; NMM for N-methylmorpholine; HMPT for hexamethylphosphorous triamide; LDA for lithium diisopropylamide; MsCl for methane-sulfonyl chloride TEA for triethylamine; TFA for trifluoroacetic acid; DMSO for dimethylsulfoxide; DMAP for 4-(N,N-dimethylamino)-pyridine; HATU for O-(azabenzotriazole-1-yl)-N,N,N',N'-tetramethyluroniumhexafluorophosphate; Boc for tert-butylcarbonyloxy; DDQ for 2,3-dichloro-5,6-dicyano-1,4-benzoquinone; Bn for benzyl; DPPA for diphenylphosphoryl azide; DCC for dicyclohexylcarbodimide; EDC for 1-(3-dimethylaminopropyl)-3-ethylcarbodiimide hydrochloride; RP for reverse phase; MPLC for medium pressure liquid chromatography; SEM for 2-(trimethylsilyl)ethoxymethyl; dppf for 1,1'-bis(diphenylphosphino)ferrocene; DIEA for diisopropylethylamine; and dba for dibenzyl-ideneacetone. Starting materials, reagents and solvents were purchased from Aldrich Chemical Company (Milwaukee, Wis).

As shown in Scheme 1, naphthalenecarbonitriles 4.5 and 6 were prepared by treating 3-cyanopropionaldehyde diethyl acetal 2 with a strong base such as lithium diisopropylamide then treating the resulting anion with the appropriately substituted benzaldehyde 1 followed by cyclization and aromatization of the corresponding cyanohydrins 3 with a Lewis acid such as sulfuric acid.

Scheme 1

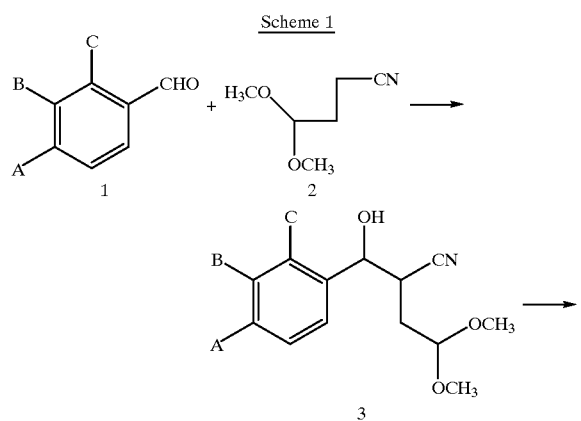

A, B and C are hydrogen and $-L_A R_A$, $-L_B R_B$, $-L_C R_C$
$-L_A-$, $-L_B-$ and $-L_C-$ are —O—
$R_A$, $R_B$ and $R_C$ are alkyl

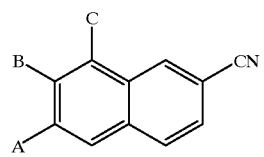

4: A is hydrogen; B and C are $OCH_3$
5: A, B and C are $OCH_3$
6: A and B are $OCH_3$, and C is hydrogen As shown in Scheme 2, selective demethylation of 4 with a Lewis acid such as $AlCl_3$ or $BBr_3$, preferably $AlCl_3$, provided 7. 7 was treated with a base such as potassium carbonate, sodium hydride or cesium fluoride followed by $R_C$—X, wherein X is a leaving group, to provide 8 ($-L_C-$ is —O—). Alternatively, treatment of 7 with trifluoromethanesulfonic anhydride or 1,1,1-trifluoro-N-phenyl-N-[(triuoromethyl)sulfonyl]methanesulfonamide provided 9 which may be treated with $R_C$—$B(OH)_2$,

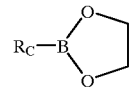

$R_C$—I, or

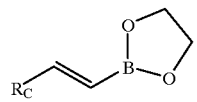

wherein $R_C$ is unsubstituted or substituted aryl or heterocycle, in the presence of a palladium catalyst, preferably $Pd(II)Cl_2(dba)$ or $Pd(Ph_3P)_4$, and base, preferably cesium fluoride or potassium carbonate, to provide 10. Alternatively, 9 may be treated with $R_C$—$NR_1 R_2$, wherein $R_C$ is unsubstituted or substituted aryl or heterocycle, and at least one of $R_1$ or $R_2$ is hydrogen, in the presence of a strong base, such as potassium t-butoxide, and a catalyst, such as $Pd(II)Cl_2(dba)$, to provide 11.

Scheme 2

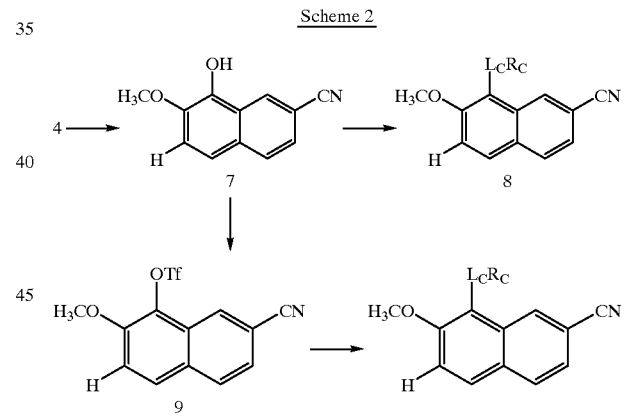

$R_C$ is unsubstituted or substituted aryl or heterocycle
10: ——$L_C$—— is a covalent bond
11: ——$L_C$—— is ——$NR_1$——

As shown in Scheme 3, selective O-triflation of 12 followed by protection of the amino group of the resulting 13 with acid-labile carbobenzlyoxy provided 14. Conversion of 14 to 15 was achieved with KCN in the presence of a palladium catalyst, preferably tris(dibenzylideneacetone)dipalladium(0)-chloroform adduct, and deprotection of 15 to provide 16 was accomplished with acid, preferably 30% HBr in acetic acid. Treatment of 15 with acylating agents $R_C C(O)Cl$ and base, preferably triethylamine, diisopropyletnylamine or potassium carbonate provided intermediate 17.

Scheme 3

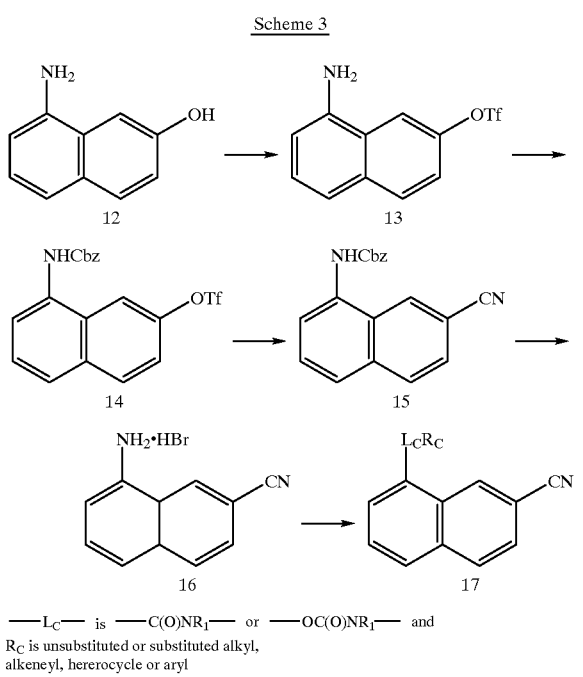

—L$_C$— is —C(O)NR$_1$— or —OC(O)NR$_1$— and
R$_C$ is unsubstituted or substituted alkyl, alkeneyl, hererocycle or aryl As shown in Scheme 4, selective demethylation of the 8-methoxy group of 18 with a Lewis acid such as AlCl$_3$ or BBr$_3$, preferably AlCl$_3$, was followed by reprotection of phenol 19 by alkylation with Bn-X, wherein X is Cl, Br or I, in the presence of a base such as potassium carbonate, sodium hydride or cesium fluoride. 20 was prepared by deprotonation of this intermediate with a strong, non-nucleophilic base such as lithium, sodium or potassium diisopropylamide or alkoxide followed by treatment with an alkyl formate, preferably ethyl formate to provide enol 20. Treatment of 20 with hydroxylamine provided isoxazole 21 which may be opened with lithium, sodium or potassium alkoxide, preferably sodium methoxide, to provide 22. Carbonyl reduction with concomitant alkene formation with achieved with sodium borohydride to provide 23; and aromatization with DDQ and catalytic debenzylation with hydrogen and a palladium catalyst, preferably palladium on carbon, provided 24. 24 was alkylated by treatment with a base such as potassium carbonate, sodium hydride or cesium fluoride followed by treatment R$_C$—X.

Scheme 4

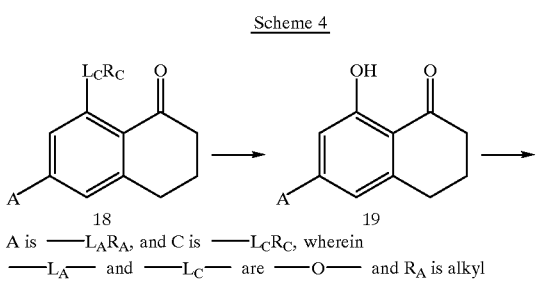

A is —L$_A$R$_A$, and C is —L$_C$R$_C$, wherein
—L$_A$— and —L$_C$— are —O— and R$_A$ is alkyl

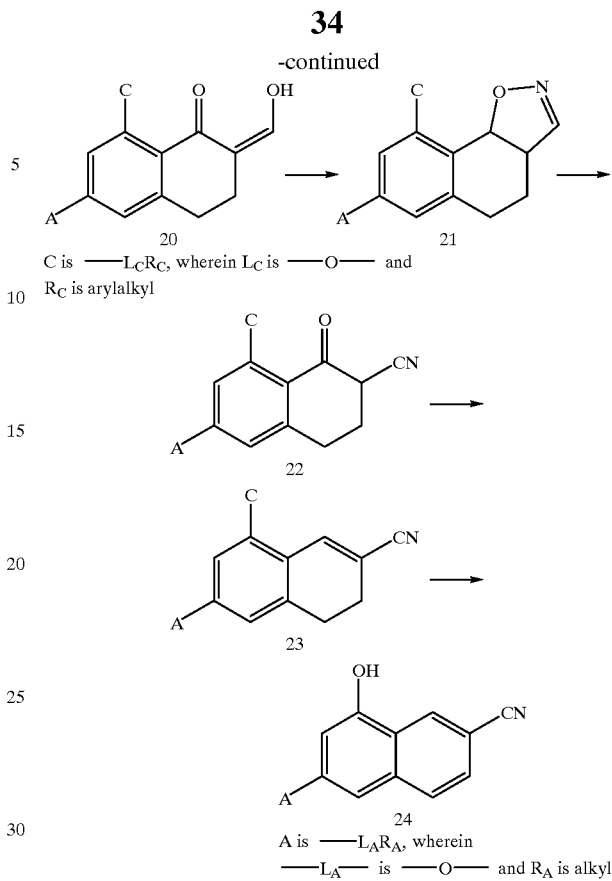

C is —L$_C$R$_C$, wherein L$_C$ is —O— and R$_C$ is arylalkyl

A is —L$_A$R$_A$, wherein
—L$_A$— is —O— and R$_A$ is alkyl

As shown in Scheme 5, monohydrolysis of 25 with one equivalent of base such as lithium, sodium or potassium hydroxide provided the acid-ester 26. Treatment of 26 with thionyl chloride or oxalyl chloride/DMF followed by treatment with ammonia provided amide 27. Treatment of 27 with a dehydrating agent such as thionyl chloride or phosphorus oxychloride provided nitrile 28.

Regioselective nitration of 28 with nitric acid/potassium nitrate followed by reduction of the nitro group with a palladium catalyst, preferably palladium on carbon, provided intermediate 31, which was treated with R$_C$C(O)Cl or R$_C$OC(O)Cl and base, preferably diisopropylethylamine or potassium carbonate, to provide 37.

Hydrolysis of 28 with one equivalent of lithium, sodium or potassium hydroxide to form carboxylic acid 29 followed by treatment with DPPA or thionyl chloride then sodium azide and hydrolysis of the intermediate isocyanate 32 with acid, preferably sulfuric acid, provided amine 33. Alternatively, treatment of 32 with a primary or secondary amine provided urea 34

(-L$_A$-=—NR$_1$C(X)R$_2$—, wherein X is O).

29 may be coupled to primary or secondary amines, and 33 may be coupled to carboxylic acids to form amides 35 and 36, respectively. In either case, the amines and carboxylic acids are coupled using a dehydrating agent such as DCC, EDC or HATU.

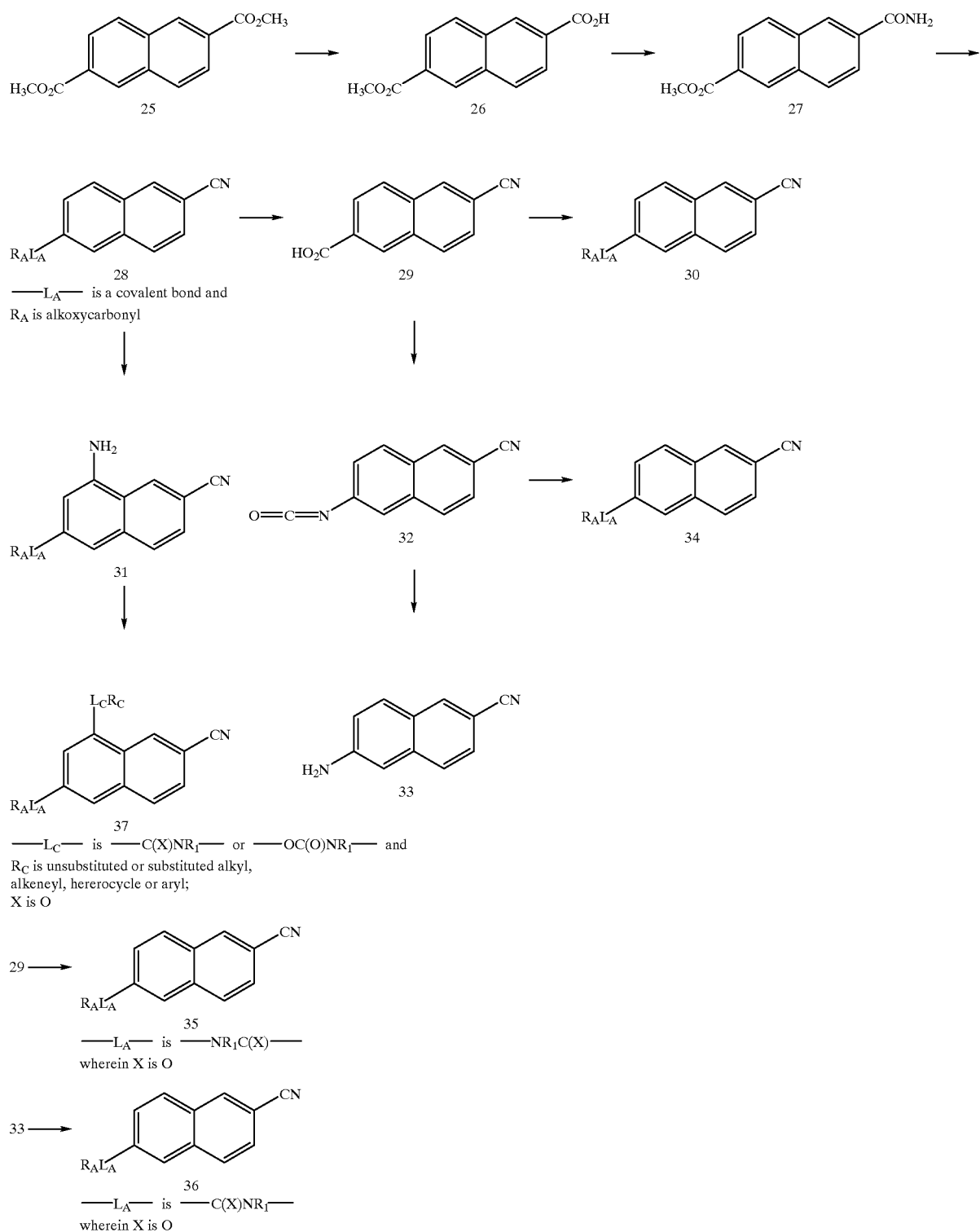

As shown in Scheme 6, intermediates wherein -L$_A$- is —C≡C— or —C=C— were prepared by treatment of of 38 with a triflating agent, preferably trifluoromethanesulfonyl anhydride, to form 39, followed by coupling of the appropriate substituted alkenes or unsubstituted or substituted alkynes using a palladium catalyst, preferably palladium (II) acetate, to form 40.

Scheme 6

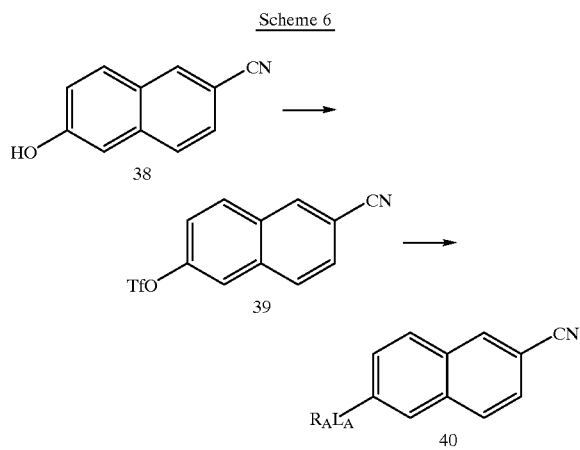

As shown in Scheme 7, conversion of the nitrile intermediates to the carboximidamide urokinase inhibitors 41 was achieved by three methods: (1) treatment of the intermediate carbonitriles with a non-nucleophilic base such as lithium, sodium or potassium bis(trimethylsilylamide), preferably lithium bis(trimethylsilylamide) followed by hydrolysis with acid, preferably HCl; (2) treatment of the nitrile with acid, preferably HCl, followed by treatment with ammonium acetate; and (3) treatment of the nitrile with H$_2$S followed by treatment with ammonia gas in methanol. Of the three methods, the H$_2$S/NH$_3$/methanol method is preferred. The compounds of the invention were precipitated as hydrochloride or methane sulfonate salts or were purified by reversed phase medium pressure chromatography to form mono- or bis- trifluoroacetate salts.

Scheme 7

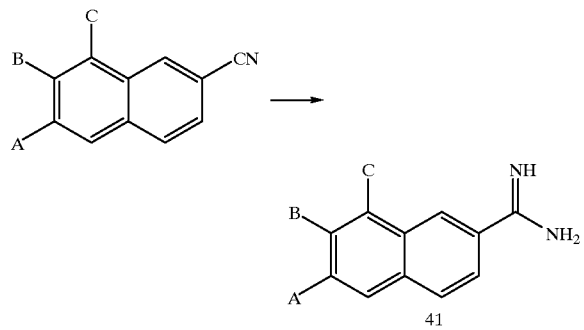

Synthetic Methods

The foregoing may be better understood by reference to the following examples which illustrate the methods by which the compounds of the invention may be prepared and are not intended to limit the scope of the invention as defined in the appended claims.

EXAMPLE 1

7,8-Dimethoxy-2-naphthalenecarboximidamide mono(trifluoroacetate) salt

EXAMPLE 1A 7,8-Dimethoxy-2-naphthalenecarbonitrile

A solution of freshly prepared LDA in THF at −78° C. was treated dropwise with 3-cyanopropionaldehyde diethyl acetal (3.0 g) in THF (5 mL), stirred for 1 h, treated with 2,3-dimethoxybenzaldehyde (3.2 g) in THF (5 mL), warmed to room temperature over 90 min, treated with water (40 mL), concentrated and extracted with chloroform. The organic layer was washed with brine, dried (MgSO$_4$) and concentrated to provide 1.5 g of a yellow oil.

MS (DCI/NH$_3$) m/e 341 (M+H$_2$O)$^+$.

A solution of the oil in methanol (5 mL) was added dropwise to 20% aqueous sulfuric acid (100 mL) at 90° C. The solution was heated for 90 min, cooled to room temperature and extracted with chloroform. The combined organic extracts are washed with brine, dried (MgSO$_4$) and concentrated to provide 1.0 g of a brown solid which was purified by flash chromatography on silica gel with 3:1 hexane/ethyl acetate to provide 800 mg of the title compound.

MS (DCI/NH$_3$) m/e 231 (M+H$_2$O)$^+$.

EXAMPLE 1B 7,8-Dimethoxy-2-naphthalenecarboximidamide mono(trifluoroacetate) salt A solution of Example 1 (200 mg) in THF (5 mL) at 0° C. was treated with lithium bis(trimethylsilylamide) (1.0 M in hexane, 1.1 mL), stirred for 18 h at room temperature, treated with 10% HCl (10 mL), stirred for 24 h at room temperature, concentrated and purified by medium pressure liquid chromatography on a 30 cm×2 cm C-18 column (40 micron, J. T Baker) with UV detection at 250 nM with solvent mixtures in a gradient ranging from 90%A (0.1% aq TFA)/10%B (methanol) to 10%A/90%B over 160 min at a flow rate of 5 mL/min (fractions were collected every 2 min for 100 min and analyzed by TLC (10:1:1 acetonitriile/water/acetic acid) for product) to provide 100 mg of the title compound.

$^1$H NMR (300 MHz, DMSO-d$_6$) δ 4.41 (s, 3H), 4.62 (s, 3H), 7.41 (d, 1H), 7.43 (dd, 1H), 7.60 (d, 1H), 7.80 (d, 1H), 8.49 (d, 1H), 9.31 (bs, 2H), 9.48 (bs, 2H);

MS (DCI/NH$_3$) m/e 231 (M+H)$^+$.

Anal. calcd for C$_{13}$H$_{14}$N$_2$O$_2$•TFA: C, 52.33; H, 4.39; N, 8.14. Found: C, 51.91; H, 4.35; N, 8.05.

EXAMPLE 2

6,7,8-trimethoxy-2-naphthalenecarboximidamide mono(trifluoroacetate) salt

EXAMPLE 2A 6,7,8-trimethoxy-2-naphthalenecarbonitrile

The title compound was prepared as described in Example 1A but substituting 2,3,4-trimetlioxybenzaldehyde for 2,3-trimethoxybenzaldehyde.

MS (DCI/NH$_3$) m/e 261 (M+H$_2$O)$^+$.

EXAMPLE 2B 6,7,8-trimethoxy-2-naphthalenecarboximidamide mono(trifluoroacetate) salt The title compound was prepared and purified as described in Example 1B to provide 100 mg of the title compound.

¹H NMR (DMSO-d₆, 300 MHz) δ 3.91 (s, 3H), 3.98 (s, 3H), 4.06 (s, 3H), 7.36 (s, 1H), 7.75 (dd, 1H) 7.99 (d, 1H), 8.49 (d, 1H), 9.18 (bs, 2H), 9.38 (bs, 2H);

MS (DCI/NH₃) m/e 261 (M+H)⁺.

Anal. calcd for $C_{14}H_{16}N_2O_3 \cdot TFA$: C, 51.34; H, 4.58; N, 7.48. Found: C, 50.91; H, 4.25; N, 7.35.

EXAMPLE 3

6,7-dimethoxy-2-naphthalenecarboximidamide mono(trifluoroacetate) salt

EXAMPLE 3A 6,7-dimethoxy-2-naphthalenecarbonitrile

The title compound was prepared as described in Example 1A but substituting 3,4-dimethoxybenzaldehyde for 2,3-dimethoxy-benzaldehyde to provide 1.3 g of the title compound.

MS (DCI/NH₃) m/e 231 (M+H₂O)⁺.

EXAMPLE 3B 6,7-dimethoxy-2-naphthalenecarboximidamide mono(trifluoroacetate) salt The title compound was prepared and purified as described in Example 1B to provide 100 mg of the title compound.

¹H NMR (DMSO-d₆, 300 MHz) δ 3.92 (s, 3H), 3.94 (s, 3H), 7.41 (s, 1H), 7.44 (s, 1H), 7.69 (dd, 1H), 7.93 (d, 1H), 8.49 (d, 1H), 9.18 (bs, 2H), 9.38 (bs, 2H);

MS (DCI/NH₃) m/e 231 (M+H)⁺.

Anal. calcd for $C_{13}H_{14}N_2O_2 \cdot TFA$: C, 52.33; H, 4.39; N 8.14. Found: C, 52.15; H, 4.20; N 8.10.

EXAMPLE 4

2-[(7-Aminoiminomethyl-2-metioxy-1-naphthalenyl)oxy]acetamide mono(trifluoroacetate salt

EXAMPLE 4A

7-Methoxy-8-hydroxynaphthalene-2-carbonitrile

A solution of Example 1A (1 g) in methylene chloride (100 mL) at 0° C. was treated with AlCl₃, stirred for 4 h at 0 ° C. and at room temperature for 18 h, poured into water (200 mL) containing 6N HCl (20 mL), stirred for 1 h and diluted with methylene chloride (100 mL). The layers were separated, and the organic layer was washed with brine and dried (MgSO₄) to provide 810 mg of the title compound as an off-white solid.

MS (DCI/NH₃) m/e 217 (M+H₂O)⁺.

EXAMPLE 4B 1.1-Dimethylethyl 2-[(7-Cyano-2-methoxy-1-naphthalenyl)oxy]acetate A slurry Example 4A (100 mg), K₂CO₃ (70 mg), t-butyl bromoacetate (120 mg) and tetrabutylammonium iodide (25 mg) in DMF (3 mL) was stirred for 18 h at room temperature, diluted with water (20 mL) and extracted with ethyl acetate. The organic extract was washed with saturated NaHCO₃ and brine, dried (Na₂SO₄) and concentrated to provide 200 mg of the title compound as a clear oil.

MS (DCI/NH₃) m/e 331 (M+H₂O)⁺.

EXAMPLE 4C

2-[(7-Aminoiminomethyl-2-methoxy-1-naphthalenyfl)oxy]acetamide mono(trifluoroacetate) salt Example 4B (100 mg) in methanol (5 mL) at 0° C. was treated with HCl(g), stirred for 18 h at room temperature and concentrated to provide an off-white solid. The solid was treated with 2N NH₃ in methanol (10 mL), heated at 50° C. for 3.5 h, cooled and concentrated to a yellow solid which was purified as described in Example 1B to provide 10 mg of the title compound.

¹H NMR (300 MHz, DMSO-d₆) δ 3.93 (s, 3H), 4.79 (s, 2H), 7.55 (d, 2H), 7.65 (dd, 1H), 7.72 (d, 1H), 7.85 (d, 1H), 8.09 (d, 1H), 8.7 (d, 1H), 9.03 (bs, 2H), 9.45 (bs, 2H);

MS (DCI/NH₃) m/e 274 (M+H)⁺.

Anal. calcd for $C_{14}H_{15}N_3O_3 \cdot TFA$: C, 49.62; H, 4.16; N, 10.85. Found: C, 49.33; H, 4.03; N, 10.50.

EXAMPLE 5

7-Benzyloxy-8-iodo-2-naphthalenecarboximidamide mono(trifluoroacetate) salt

EXAMPLE 5A

7-Benzyloxy-8-iodo-2-naphthalenecarbonitrile

The title compound was prepared as described in Example 43A but substituting benzyl bromide for propyl iodide.

MS (DCI/NH₃) m/e 403 (M+NH₄)⁺.

EXAMPLE 5B

7-Benzyloxy-8-iodo-2-naphthalenecarboximidamide mono(trifluoroacetate) salt

The title compound was prepared from Example 5A according to the procedure of Example 1B.

¹H NMR (300 MHz, DMSO-d₆) δ 9.30 (br, 4H), 8.44 (s, 1H), 8.12 (d, 1H), 7.71 (d, 2H), 7.67 (dd, 1H), 7.57 (d, 2H), 7.45–7.34 (m, 3H), 5.45 (s, 2H);

MS (DCI/NH3) m/e 403 (M+H)⁺.

Anal. calcd for $C_{18}H_{15}N_2OI \cdot TFA$: C, 46.53; H, 3.12; N, 5.43. Found: C; 46.55; H, 3.10; N, 5.19.

EXAMPLE 6

Methyl [(7-aminoiminomethyl-2-methoxy-1-naphthalenyl)oxylacetate mono(trifluoroacetate)

EXAMPLE 6A

Methyl [(7-cyano-2-methoxy-1-naphthalenyl)oxy]acetate

A solution of Example 4A (600 mg), Cs₂CO₃ (500 mg), t-butyl bromoacetate (120 mg) and tetrabutylammonium iodide (25 mg) in DMF (15 mL) was stirred for 18 h at room temperature, diluted with water (20 mL) and extracted with ethyl acetate. The organic extract was washed with saturated NaHCO₃ and brine, dried (Na₂SO₄) and concentrated to provide 800 mg of the title compound as a clear oil.

MS (DCI/NH₃) m/e 331 (M+H₂O)⁺.

EXAMPLE 6B

Methyl [(7-aminoiminomethvl-2-methoxy-1-naphthalenyl)oxy]acetate mono(trifluoroacetate Example 6A (100 mg) in methanol (30 mL) at 0° C. was treated with HCl(g), stirred for 18 h at room temperature and concentrated to provide an off-white solid. The solid was treated with ammonium acetate (100 mg) in methanol (10 mL), heated at 40° C. for 15 h, cooled and concentrated to a yellow solid which was purified as described in Example 1B to provide 10 mg of the title compound.

$^1$H NMR (300 MHz, DMSO-$d_6$) δ 3.65 (s, 3H), 3.93 (s, 3H), 4.79 (s, 2H), 7.65 (dd, 1H), 7.72 (d, 1H), 7.85 (d, 1H), 8.09 (d, 1H), 8.7 (d, 1H), 9.03 (bs, 2H), 9.45 (bs, 2H); MS(DCI/NH$_3$) m/e 289 (M+H)$^+$.

Anal. calcd for $C_{15}H_{16}N_2O_4$•TFA: C, 50.75; H, 4.26; N, 6.96. Found: C, 50.42; H, 4.03; N, 6.77.

EXAMPLE 7

[(7-aminoiminomethyl-2-methoxy-1-naphthalenyloxylacetic acid mono(trifluoroacetate) salt A solution of Example 6B (100 mg) and LiOH•H$_2$O (150 mg) in 1:1 THF/H$_2$O (10 mL) at 5° C. was stirred 45 min and concentrated to provide an off-white solid. The solid was dissolved in 1N HCl (20 mL), stirred 48 h at room temperature and filtered. The resulting white solid was purified as described in Example 1B to provide 20 mg of the title compound.

$^1$H NMR (300 MHz, DMSO-$d_6$) δ 3.93 (s, 3H), 4.79 (s, 2H), 7.65 (dd, 1H), 7.72 (d, 1H), 7.85 (d, 1H), 8.09 (d, 1H), 8.7 (d, 1H), 9.23 (bs, 2H), 9.45 (bs, 2H); MS (DCI/NH$_3$) m/e 275 (M+H)$^+$.

Anal. calcd for $C_{14}H_{14}N_2O_4$•TFA: C, 49.49; H, 3.89; N, 7.21. Found: C, 47.53; H, 3.71; N, 6.83.

EXAMPLE 8

N-[4-(Aminometyl)phenyl]-6-aminoiminomethyl-2-naphthalenecarboxamide bis(trifluoroacetate) salt

EXAMPLE 8A 2,6Napthalenedicarboxylic acid, monomethyl ester

A suspension of dimethyl 2,6-naphthalenedicarboxylic acid (39.6 g, 162 mmole) in dioxane (1.20 L) was heated at 70–80° C. until all solid dissolved, slowly treated with 1 equivalent of KOH in methanol, stirred for additional 30 minutes at 70° C., cooled to room temperature, filtered and washed with dioxane and diethyl ether, dissolved in water, treated with 1N HCl until the aqueous layer was acidic to pH paper, filtered, washed with water and dried under vacuum to provide 33 g of a white powder.

MS (DCI/NH$_3$) m/e 231 (M+H)$^+$.

EXAMPLE 8B 6-(Chlorocarbonyl)-2-naphthalenecarboxylic acid, methyl ester

A suspension of Example 8A (15 g, 65 mmole) in toluene (190 mL) was treated with thionyl chloride (20 mL, 276 mmole) then DMAP (15 mg), heated at reflux for 1 h and heated at 85° C. for an additional 35 min. The condenser was replaced with a distilling head and 60 mL of solvent was removed. The thick precipitate which formed while cooling to room temperature was triturated with hexane and filtered to provide 14.8 g of white solid.

MS (DCI/NH$_3$) m/e 249 (M+H)$^+$.

EXAMPLE 8C 6-(Aminocarbonyl)-2-naphthalenecarboxlic acid, methyl ester

A solution of Example 8B (15 g, 60.3 mmole) in methylene chloride (400 mL) at room temperature was treated with dry ammonia gas to precipitate the product. The mixture was stirred for an additional 15 min and filtered. The solid was washed with water and dried under vacuum to yield 13.3 g of a white powder.

MS (DCI/NH$_3$) m/e 230 (M+H)$^+$.

EXAMPLE 8D

6-Cyano-2-naphthalenecarboxylic acid,methyl ester

A suspension of Example 8C (31 g, 135 mmole) in trimethyl phosphate (450 mL) was treated with triphosgene (27 g, 136 mmole), stirred for 20 min at room temperature and heated in an oil bath at 80° C. for 1 h. The product precipated from the solution while cooling to room temperature. The thick slurry was treated with water and filtered, and the white solid was thoroughly washed with water and dried under vacuum to provide 26.3 g of the title compound.

MS (DCI/NH$_3$) m/e 212 (M+H)$^+$.

EXAMPLE 8E

6-Cyano-2-naphthalenecarboxylic acid

Example 8D (1.9 g, 9 mmole) in 1:1 THF/H$_2$O (40 mL) was treated with LiOH•H$_2$O (1.9 g, 45 mmole), stirred 90 min at room temperature and concentrated to a thick slurry. The slurry was dissolved in water (20 mL), acidified to pH 2 with solid citric acid and extracted with ethyl acetate. The combined organic extracts were washed with brine, dried (Na$_2$SO$_4$) and concentrated to provide 1.6 g of the title compound as a white solid.

MS (DCI/NH$_3$) m/e 197 (M+H)$^+$.

EXAMPLE 8F tert-Butoxycarbonylamino-4-aminomethylaniline

4-Aminomethylaniline (2 g) in 2:1 THF/H$_2$O(30 mL) was treated with Boc anhydride (3.93 g), stirred at room temperature for 18 h, diluted with water and concentrated to white slurry. The slurry was dissolved in ethyl acetate, washed with water and brine, dried (Na$_2$SO$_4$) and concentrated to provide 2.4 g of a yellow solid.

MS (DCI/NH$_3$) m/e 223 (M+H)$^+$.

EXAMPLE 8G

N-[4-(aminomethyl)phenyl]-6-cyano-2-naphthalenecarboxamide

A solution of Example 8E (200 mg) and hunig's base (180 μL) in DMF (5 mL) at 5 ° C. was treated with HATU (193 mg), stirred for 1 h at 5° C., treated with Example 8F (120 mg) and disopropylethylamine (100 μL ) in DMF (5 mL), stirred for 8 h at room temperature, diluted with ethyl acetate (100 mL), washed sequentially with 1N H$_3$PO$_4$, saturated sodium bicarbonate and brine, dried (Na$_2$SO$_4$) and concentrated to provide a yellow oil which was purified on silica gel with 1% methanol/methylene chloride to provide 200 mg of the title compound.

MS (DCI/NH3) m/e 419 (M+H$_2$O )$^+$.

EXAMPLE 8H

N-[4-(aminomethyl)phenyl]-6-aminoininomethyl-2-naphthalenecarboxamide bis(trifluoroacetate) salt The title compound was prepared from Example 8G (200 mg) by the procedure and purification from Example 5B to provide 37 mg of the title compound.

$^1$H NMR (300 MHz, DMSO-d$_6$) δ 4.08 (m, 2H), 7.45 (d, 2H), 7.88 (d, 2H), 7.95 (dd, 1H), 8.18 (dd,1H), 8.20 (bs, 3H), 8.23 (d,1H), 8.35 (d,1H), 8.58 (s,1H), 8.70 (s, 1H), 9.39 (s, 2H), 9.55 (s, 2H), 10.68 (s, 1H);

MS (DCI/NH$_3$) m/e 319 (M+H)$^+$.

Anal. calcd for C$_{19}$H$_{17}$N$_4$O•TFA: C, 50.56; H, 3.69; N, 10.25; Found: C, 50.18; H, 3.59; N, 10.11.

EXAMPLE 9

N-[4=(amino)phenyl]-6-aminoiminomethyl-2-naphthalenecarboxamide bis(trifluoroacetate)

EXAMPLE 9A

N-[4-(amino)phenyl]-6-cyano-2-naphthalenecarboxamide

The title compound was prepared according to the procedure described for Example 8G but substituting 1,4-diaminobenzene for Example 8F. MS (DCINH$_3$) m/e 288 (M+H)$^+$.

EXAMPLE 9B

N-[4(amino)phenyl]-6-aminoiminomethyl-2-naphthalenecarboxamide bis(trifluoroacetate) salt The title compound was prepared with Example 9A (100 mg) following the procedure and purification from Example 6B.

$^1$H NMR (300 MHz, DMSO-d$_6$) δ7.15 (d, 2H), 7.75 (d, 2H), 7.95 (dd, 1H), 8.18 (dd, 1H), 8.23 (d, 1H), 8.35 (d, 1H), 8.58 (s, 1H), 8.70 (s, 1H), 9.25 (s, 2H), 9.48 (s, 2H), 10.58 (s, 1H);

MS (DCI/NH$_3$) m/e 305 (M+H)$^+$.

Anal. calcd for C$_{18}$H$_{16}$N$_4$O•02TFA: C, 49.63; H, 3.41; N, 10.52; Found: C, 46.57; H, 3.62; N, 10.66.

EXAMPLE 10

1-[(7-Aminoiminomethyl-2-methoxy-1-naphthalenyl)oxy]-3-hydroxypropane mono (trifluoroacetate) salt

EXAMPLE 10A

1-[(7-Cyano-2-methoxy-1-naphthalenyl)oxy]-3-[(2-tetrahydro-2H-pyranyl]oxy)propane mono (trifluoroacetate) salt A suspension of Example 4A (200 mg) and Cs$_2$CO$_3$ (0.32 g) in DMF (15 mL) was treated with 2-(3-bromopropyl)-tetrahydro-2H-pyran (0.25 g), stirred at room temperature for 18 h then diluted with water (100 mL) and ethyl acetate (50 mL). The organic layer was separated, washed with 10% citric acid, water and brine, dried (MgSO$_4$) and concentrated to provide 320 mg of an oil.

MS (DCI/NH$_3$) m/e 323 (M+H)$^+$.

EXAMPLE 10B

1-[(7-Aminoiminomethyl-2-methoxy-1-naphthalenyl)oxyl-3-hydroxypropane mono (trifluoroacetate) salt Example 10A (0.3 g) was processed and purified according to the procedure of Example 1B to provide 110 mg of an off-white solid.

$^1$H NMR (300 MHz, DMSO-d$_6$) δ 1.97 (q, 2H), 3.67 (t, 2H), 4.20 (t, 2H), 7.61–7.70 (m, 3H), 7.84 (d,1H), 8.08 (d, 1H), 8.50 (d, 1H);

MS (DCI/NH$_3$) m/e 275 (M+H)$^+$.

Anal. calcd for C$_{13}$H$_{13}$N$_3$O$_2$•TFA0.75H$_2$O: C, 50.81; H, 5.14; N, 6.97. Found: C, 51.23; H, 5.28; N, 6.97.

EXAMPLE 11

8-amino-2-naphthalenecarbonitrile hydrobromide

EXAMPLE 11A

2-Trifluoromethanesulfonyloxy-8-aminonaphthelene

A solution of 8-amino-2-naphthol (10 g) and triethylamine (12 mL) in dioxane (200 mL) was treated with N-phenyltrifluoromethane sulfonimide (25 g) in dioxane (80 mL), stirred for 4 h and concentrated. The resulting dark brown solid was triturated with hexane and filtered to provide 12 g of the title compound as a brown solid.

MS (DCI/NH$_3$) m/e 292 (M+H)$^+$.

EXAMPLE 11B

2-Trifluoromethanesulfonyloxy-8-carbonylbenzyloxyaminonaphthelene

A solution of Example 11A (2 g) in 10% aq Na$_2$CO$_3$ (20 mL) and dioxane (250 mL) was treated with benzylchloroformate (2 mL) in dioxane (20 mL), stirred at room temperature for 5 h then extracted with ethyl acetate. The organic layer was dried (MgSO$_4$) and concentrated, and the crude product was chromatographed on silica gel with 7:1 hexane/ethyl acetate to provide 2.5 g (86%) of the title compound.

MS (DCI/NH$_3$) m/e 443 (M+NH$_4$)$^+$.

EXAMPLE 11C 8-(N-carbonylbenzyloxy)-2-naphthalenecarbontrile

Tris(dibenzylideneacetone)dipalladium(0)-chloroform adduct (120 mg), 1,1'-bis(diphenylphosphino)-ferrocene (260 mg), potassium cyanide (766 mg), Example 11B (2.5 g) and N-methyl-2-pyrrolidione (5 mL) were combined sequentially, stirred at room temperature until a yellow reaction complex formed then warmed to 80° C. for 40 min. The dark brown reaction mixture was cooled to room temperature and chromatographed on silica gel with 9:1 hexane/ethyl acetate to provide 1.5 g of the title compound as a colorless solid.

MS (DCI/NH$_3$) m/e 292 (M+NH$_4$)$^+$.

EXAMPLE 11D

8-Amino-2-naphthalenecarbonitrile hydrobromide

Example 11C (1.4 g) was treated with a solution of 30% HBr in acetic acid (5 mL) and stirred at room temperature for 6 h. The reaction mixture was treated with diethyl ether and filtered to provide 1.1 g of the title compound as a yellow solid.

MS (DCI/NH$_3$) m/e186 M+NH$_4$)$^+$.

EXAMPLE 12

General Acylation Procedure

A suspension of Example 10D (1equivalent), triethylamine (1 equivalent) and DMAP (0.25 equivalents) in methylene chloride (0.3M) was treated dropwise with the appropriate acid chloride (1.1 equivalents) in methylene chloride (0.3 M), stirred at room temperature for 30 min and treated with water (50 mL). The organic layer was dried (MgSO$_4$), concentrated and used in following reactions without further purification.

EXAMPLE 13

General Amidine Synthesis Procedure

A solution of crude acylation products from Example 12 (ca. 100 mg) at room temperature in 10:1 pyridine:triethylamine (10 mL) was treated with hydrogen sulfide for 5 min, stirred at room temperature for 18 h, diluted with water (50 mL) and extracted with ethyl acetate. The ethyl acetate was dried (MgSO$_4$) and concentrated. The residue was dissolved in acetone (30 mL), treated with methyl iodide (2 mL), refluxed for 1 hour, evaporated to dryness, redissolved in methanol (25 mL), treated with ammonium acetate (100 mg), stirred for 18 h at room temperature, concentrated and purified as described in Example 1B to provide Examples 14–20 as white solids.

EXAMPLE 14

8-(carbonylbenzyloxy)amino-2-naphthalenecarboximidamide mono(trifluoroacetate) salt $^1$H NMR (DMSO-d$_6$, 300 MHz) δ 5.14 (s, 2H), 7.36–7.50 (m, 5H), 7.67–7.90 (m, 4H), 8.14 (d, 1H), 8.67 (s, 1H), 9.08 (s, 2H), 9.37 (s, 2H), 9.78 (s, 1H);

MS (DCI/NH$_3$) m/e 320 (M+H)$^+$.

Anal. calcd for C$_{19}$H$_{15}$N$_3$O$_2$•1.5•TFA0.5H$_2$O: C, 52.91; H, 3.94; N, 8.41. Found: C, 52.86; H. 4.07; N, 8.18.

EXAMPLE 15

N-[7-(aminoiminomethyl)-1-naphthalenyl)acetamide mono(trifluoroacetate) salt $^1$H NMR (DMSO-d$_6$, 300 MHz) δ 4.19 (s, 3H), 7.66–7.88 (m, 3H), 8.12–8.16 (m, 2H), 8.69 (s, 1H), 8.98 (d, 1H), 9.16 (s, 2H), 9.47 (s, 2H), 10.14 (s, 1H);

MS (DCI/NH$_3$) m/e 228 (M+H)$^+$.

Anal. calcd for C$_{14}$H$_{12}$N$_3$O•1.2TFA•0.25H$_2$O: C, 50.18; H, 4.02; N, 11.40. Found: C, 50.62; H, 4.47; N, 10.90.

EXAMPLE 16

Methyl [7-(aminoiminomethyl)-1-naphthalenyl) carbamate mono(trifluoroacetate) salt $^1$H NMR (DMSO-d$_6$, 300 MHz) δ 3.88 (s, 3H), 7.67–7.85 (m, 4H), 8.14 (d, 1H), 8.6 (s, 1H), 8.28 (s, 3H), 9.67 (s, 1H);

MS (DCI/NH$_3$) m/e 244 (M+H)$^+$.

Anal. calcd for C$_{13}$H$_{13}$N$_3$O$_2$•TFA: C,50.43; H, 3.95; N, 11.76. Found: C, 50.12; H, 4.05; N, 11.61.

EXAMPLE 17

Methyl 3[[7-(aminoiminomethyl)-1-naphthalenyl] amino]-3-oxopropionate mono(trifluoroacetate) salt $^1$H NMR (DMSO-d$_6$, 300 MHz) δ 3.69 (s, 2H), 3.71 (s, 3H), 7.69 (m, 4H), 8.18 (d, 1H), 8.58 (s, 1H), 9.11 (s, 2H), 9.48 (s, 2H);

MS (DCI/NH$_3$) m/e 286 (M+H)$^+$.

Anal. calcd for C$_{15}$H$_{14}$N$_3$O$_3$•1.1TFA•H$_2$O: C, 48.18; H, 4.26; N, 9.80. Found: C, 48.30; H, 4.09; N, 9.58.

EXAMPLE 18

N-[7-(aminoiminomethyl)-1-naphthalenyl]-2-(phenylmethoxy)acetamide mono(trifluoroacetate) salt $^1$H NMR (DMSO-d$_6$, 300 MHz) δ 4.29 (s, 2H), 4.73 (s, 2H), 7.33–7.48 (m, 5H), 7.69 (m, 4H), 8.17 (d, 1H), 8.47 (s, 1H), 9.21 (br, 4H), 10.0 (s, 1H);

MS (DCI/NH$_3$) m/e 334 (M+H)$^+$.

Anal. calcd for C$_{20}$H$_{18}$N$_3$O$_2$•1TFA•H$_2$C, 56.77; H, 4.76; N, 9.03. Found: C, 56.84; H, 4.49; N, 8.93.

EXAMPLE 19

N-[7-(aminoiminomethyl)-1-naphthalenyl]-1,3-benzodioxole-5-carboxamide mono(trifluoroacetate) salt $^1$H NMR (DMSO-d$_6$, 300 MHz) δ 6.19 (1H, 2H), 7.12 (d, 1H), 7.65–7.79 (m, 5H), 7.97 (d, 1H), 8.20 (s, 1H), 8.53 (s, 1H), 9.2 (br s, 3H), 10.35 (s, 2H);

MS (DCI/NH$_3$) m/e 334 (M+H)$^+$. Anal. calcd for C$_{18}$H$_{14}$N$_3$O$_2$•TFA: C, 55.82; H, 3.68; N, 9.30. Found: C, 55.69; H, 33.61; N, 9.23.

EXAMPLE 20

N-[7-(aminoiminomethyl)-1-naphthalenyl] benzenemethanesulfonamide mono(trifluoroacetate) salt $^1$H NMR (DMSO-d$_6$, 300 MHz) δ 4.60 (s, 2H), 7.32–7.33 (m, 5H), 7.67–7.70 (m, 2H), 7.82 (d,1H), 7.92 (d,1H), 8.17 (s, 1H), 8.70 (s, 1H), 9.14 (s, 2H), 9.35 (s, 2H), 9.19 (s, 1H);

MS (DCI/NH$_3$) m/e 340 (M+H)$^+$.

Anal. calcd for C$_{18}$H$_{17}$N$_3$O$_2$S•TFA•H$_2$O: C, 50.95; H, 4.28; N, 8.91; Found: C, 50.76; H, 3.70; N, 8.65.

EXAMPLE 21

1[(7-aminoiminomethyl-2-methoxy-1-naphthalenyl) oxy]-3-bromopropane mono(hydrochloride) salt

EXAMPLE 21A

1[(7-Cyano-2-methoxy-1-naphthalenyl)oxy]-3-bromopropane mono(hydrochloride) salt The title compound was prepared from Example 4A, 1,3-dibromopropane and the procedure of Example 10A.

MS (DCI/NH$_3$) m/e 337 (M+NH$_4$)$^+$.

EXAMPLE 21B

1-[(7-Aminoiminomethyl-2-methoxy-1-naphthalenyl)oxy]-3-bromopropane mono (hydrochloride) salt The title compound was prepared from Example 21A and the procedure of Example 1B. After HCl hydrolysis, the solution was cooled to 0° C., and the white solid which precipitated was filtered and dried to provide the title compound.

$^1$H NMR (300 MHz, DMSO-d6) δ 2.35 (m, 2H), 3.86 (t, 2H), 4.00 (s, 3H), 4.25 (t, 2H), 7.65 (dd, 1H), 7.70 (d, 1H), 7.90 (d, 1H), 8.10 (d, 1H), 8.55 (s, 1H), 9.15 (br s, 2H), 9.42 (br s, 2H);

MS (DCI/NH$_3$) m/e 337 (M+H)$^+$.

Anal. calcd for C$_{15}$H$_{17}$BrN$_2$O$_2$HCl·0.75H$_2$O: C, 46.53; H, 5.08; N, 7.23. Found: C, 46.65; H, 5.11; N, 7.16.

EXAMPLE 22

3-[(7-Aminoiminomethyl-2-methoxy-1-naphthalenyl)oxy]propene mono(trifluoroacetate)

EXAMPLE 22A

3-[(7-Cyano-2-methoxy-1-napbthalenyl)oxylpropene

The title compound was obtained as a biproduct from the procedure of Example 21A. MS (DCI/NH$_3$) m/e 257 (M+NH4)$^+$.

EXAMPLE 22B 3-8(7-Aminoiminomethyl-2-methoxy-1-naphthalenyl)oxylpropene mono(trifluoroacetate)

The title compound was prepared from Example 22A and the procedure and purification in Example 1B.

$^1$H NMR (300 MHz, DMSO-d$_6$) δ 4.00 (s, 3H), 4.70 (d, 2H), 5.22 (d, 1H), 5.42 (d, 1H), 6.18 (m, 1H), 7.62 (dd, 1H), 7.85 (d, 1H), 8.10 (d, 1H), 8.50 (s, 1H), 9.12 (br s, 2H), 9.45 (br s, 2H);

MS (DCI/NH$_3$) m/e 257 (M+H)$^+$.

Anal. calcd for C$_{15}$H$_{16}$N$_2$O$_2$·TFA·0.25H$_2$O: C, 54.47; H, 4.71; N, 7.47. Found: C, 54.61; H, 4.38; N, 7.40.

EXAMPLE 23

1-[(7-Aminoiminomethyl-2-methoxy-1-naphthalen)oxy]-3-phenylpropane mono(hydrochloride) salt

EXAMPLE 23A

1-[(7-Cyano-2-methoxy-1-naphthalenyl)oxy]-3-phenylpropane

The title compound was prepared from Example 4A, 1-bromo-3-phenylpropane, and the procedure of Example 10A.

MS (DCI/NH$_3$) m/e 335 (M+NH$_4$)$^+$.

EXAMPLE 23B

1-[(7-Aminoiminomethyl-2-methoxy-1-naphthalenyl)oxy]-3-phenylpropane mono (hydrochloride) salt The title compound was prepared from Example 23A and the procedure of Example 21B.

$^1$H NMR (300 MHz, CD$_3$OD) δ 2.21 (m, 2H), 2.94 (t, 2H), 4.00 (s, 3H), 4.22 (t, 2H), 7.18 (m, 1H), 7.28 (m, 4H), 7.62 (m, 2H), 7.79 (d, 1H), 8.02 (d, 1H), 8.62 (s, 1H);

MS (DCI/NH$_3$) m/e 335 (M+H)$^+$.

HRMS (FAB) calcd m/e for C$_{21}$H$_{23}$N$_2$O$_2$·HCl: 335.1760 (M+H)$^+$. Found m/e 335.1762.

EXAMPLE 24

1-[(7-Aminoiminomethyl-2-methoxy-1-naphthalenyl)oxy]-3-[1-(3,4- dimethoxy) phenyl] propane mono(hydrochloride) salt

EXAMPLE 24A

1-Bromo-3-(3,4-dimethoxyphenyl)propane

The title compound was prepared from 3-(3,4-dimethoxyphenyl)-1-propanol as described in Journal of the American Chemical Society, 95, 8749 (1973), which is incorporated herein by reference, to provide the title compound.

MS (DCI/NH$_3$) m/e 276 (M+NH$_4$)$^+$.

EXAMPLE 24B

1-[(7-Cyano-2-methoxy-1-naphthalenyl)oxy]-3-[1-(3,4-dimethoxy)phenyl]propane

The title compound was prepared from Examples 4A and 24A and the procedure of Example 10A.

MS (DCI/NH$_3$) m/e 395 (M+NH$_4$)$^+$.

EXAMPLE 24C

1-[(7-Aminoiminomethyl-2-methoxy-1-naphthalenyl)oxy]-3-[1-(3,4-dimethoxy) phenyl] propane mono(hydrochloride) salt The title compound was prepared from Example 24B and the procedure of Example 21B.

$^1$H NMR (300 MHz, DMSO-d$_6$) δ 2.11 (m, 2H), 2.80 (t, 2H), 3.74 (s, 6H), 3.98 (s, 3H), 4.15 (t, 2H), 6.75–6.92 (m, 3H), 7.65 (dd, 1H), 7.70 (d, 1H), 7.86 (d, 1H), 8.10 (d, 1H), 8.55 (s, 1H), 9.15 (br s, 2H), 9.53 (br s, 2H);

MS (DCI/NH$_3$) m/e 395 (M+H)$^+$.

Anal. calcd for C$_{23}$H$_{26}$N$_2$O$_4$·HCl·0.5H$_2$O: C, 62.79; H, 6.42; N, 6.37. Found: C, 63.08; H, 6.38; N, 6.17.

EXAMPLE 25

7-Methoxy-8-(2-furanyl)-2-naphthalenecarboximidamide mono(trifluoroacetate) salt

EXAMPLE 25A

7-Methoxy-8-trifluoromethanesulfonyloxy-2-naphthalenecarbonitrile

A solution of Example 4A (310 mg) in methylene chloride (5 mL) at 0° C. was treated with 1,1,1-trifluoro-N-phenyl-N-[(trifluoromethyl)sulfonyl]methanesulfonamide (614 mg) and triethylamine (240 mL), stirred for 18 h at room temperature, diluted with methylene chloride (100 mL), washed with water and 20% aq NaOH, dried (MgSO$_4$) and concentrated to provide 560 mg of the title compound as a white solid.

MS (DCI) m/e 349 (M+H$_2$O)$^+$.

EXAMPLE 25B

Furan-2-boronic acid

A solution of furan (5.3 mL, 73 mmole) in diethyl ether (67 mL) at −20° C. was treated with n-butyllithium (2.5 M in hexanes, 26 mL, 65 mmole), stirred for 2 hours at −20° C. and transferred by cannula to a −20° C. solution of triisopropyl borate (33 mL, 147 mmole) in diethyl ether (17 mL). The thick mixture was warmed to room temperature, treated with 3N HCl (200 mL) and extracted with diethyl ether. The extracts were washed with 1N KOH, and the KOH layer was cooled to 0° C. and acidified with 6N HCl. The acidic solution was extracted with diethyl ether, and the acidic ether extracts were washed with brine, dried (MgSO$_4$) and concentrated to provide the title compound.

$^1$H NMR (300 MHz, DMSO-d$_6$) δ 6.45 (dd, 1H), 7.05 (t, 1H), 7.80 (dd, 1H), 8.19 (s, 2H).

EXAMPLE 25C

7-Methoxy-8-(2-furanyl)-2-naphthalenecarbonitrile

Example 25A (1.10 mmol) was combined with Pd(OAc)$_2$ (0.11 mmol) and 1,1'-bis(diphenylphosphino) ferrocene (0.22 mmol) in DMF (5 mL), stirred for 10 min, treated with Example 25B (1.32 mmol) and Cs$_2$CO$_3$ (3.3 mmol), heated at 85° C. for 6 h, cooled to room temperature and chromatographed on silica gel with 10% ethyl acetate/hexane to provide the title compound.

MS (DCI/NH$_3$) m/e 250 (M+H)$^+$.

EXAMPLE 25D

8-(2-Furanyl)-7-methoxy-2-naphthalenecarboximidamide mono(trifluoroacetate) salt The title compound was prepared from Example 25C and the procedure and purification in Example 1B.

$^1$H NMR (300 MHz, DMSO-d$_6$) δ 3.97 (s, 3H), 6.73 (m, 1H), 6.80 (m, 1H), 7.64 (dd, 1H), 7.78 (d, 1H), 7.91 (m, 1H), 8.16 (d, 1H), 8.20 (d, 1H), 8.30 (s, 1H), 9.08 (br s, 2H), 9.40 (br s, 2H);

MS (DCI/NH$_3$) m/e 267 (M+H)$^+$.

Anal. calcd for C$_{16}$H$_{14}$N$_2$O$_2$•TFA: C, 56.85; H, 3.98; N, 7.37. Found: C, 56.68; H, 3.67; N, 7.35.

EXAMPLE 26 methyl 6-(aminoiminomethyl)-4-[(methoxycarbonyl)amino]-2-naphthalenecarboxylate mono(trifluoroacetate) salt

EXAMPLE 26A

2-Cyano-1-nitro-6-carboxynaphthalene methyl ester

A solution of 2-cyano-6-methylnaphthoate (5.2 g) in concentrated sufuric acid (75 mL) at 0° C. was treated with potassium nitrate (1.03 eq) in one portion, stirred for 10 min, poured onto ice (500 g) and extracted with ethyl acetate. The ethyl acetate layer was washed with water, 1N NaOH and brine, dried (MgSO$_4$), treated with silica gel and filtered. Concentration of the ethyl acetate to ca. 200 mL precipitated the product. The mixture was heated until all solid dissolved, treated with MeOH (20 mL) and ether (20 mL) and stirred overnight. The resulting solid was filtered and washed with methanol to provide 2.31 g of the title compound as a cream-colored solid. The mother liqueuor was evaporated, treated with methylene chloride (250 mL) then solid silica gel, filtered and concentrated. Crystalization from ethyl acetate/methanol afforded an additional 1.6 g of product for a total yield: 3.91 g (62%).

MS (DCI/NH$_3$) m/e 257 (M+H)$^+$.

EXAMPLE 26B

2-Cyano-1-amino-6-carboxynaphthalene methyl ester

A solution of Example 26A (1g, 3.9mmole) and 10% Pd on carbon (112 mg) in ethyl acetate (80 mL) was stirred under 1 atm of hydrogen for 9 h, purged with nitrogen for 1 h, filtered and evaporated to provide 810 mg (92%) of the title compound as a yellow solid.

MS (DCI/NH$_3$) m/e 227 (M+NH$_4$)$^+$.

EXAMPLE 26C

6-Cyano-4-[(methoxycarbonyl)amino]-2-naphthalenecarboxylic acid,methyl ester A solution of Example 26B (2.50 mmol) in methylene chloride (40 mL) was treated sequentially with diisopropylethylamine (2 mL) and methylchloroformate (195 μL, 2.52 mmole), stirred for 2 h, treated with methanol (10 mL), stirred for an additional 10 minutes, diluted with methylene chloride (60 mL), washed with water and brine, dried (MgSO$_4$) and evaporated. The residue was purified on silica gel using 10% ethyl acetateihexane to provide 280 mg (59%) of light yellow solid.

MS (DCI/NH$_3$) m/e 285 (M+H)$^+$.

EXAMPLE 26D

Methyl 6-(aminoiminomethyl)-4-[(methoxycarbonyl)amino]-2-naphthalenecarboxylate mono(trifluoroacetate) salt The title compound was prepared using Example 26C (125 mg, 0.44 mmol) and the procedure in Example 40D to provide 35mg of a white solid.

$^1$H NMR (DMSO-d$_6$) δ 3.78 (s, 3H), 3.95 (s, 3H), 7.89 (dd, 1H), 8.37–8.40 (m, 3H), 8.53 (s, 1H), 8.740 (s, 1H) 9.18 (br s, 2H), 9.45 (br s, 2H), 9.90 (s, 1H), 8.42 (s, 1H), 8.63 (d, 1H), 9.18 (br s, 4H), 10.58 (s, 1H);

MS (DCI/NH$_3$) m/e 302 (M+H)$^+$.

Anal. calcd for C$_{15}$H$_{15}$N$_3$O$_4$•TFA•1.5H$_2$O: C, 46.16; H, 4.33; N, 9.50. Found: C, 45.96; 46.16; H, 4.06; N, 9.12.

EXAMPLE 27

(E)-{7-Methoxy-8-[2-(Phenyl)ethenyl]}-2-naphthaleneimidamide mono(trifluoroacetate) salt

EXAMPLE 27A

(E)-{7-Methoxy-8-[2-(Phenyl)ethenyl]}-2-naphthalenecarbonitrile

Example 25A and styrene boronic ester, prepared according to the procedure of Journal of the American Chemical Society, 97 5249 (1975), which is incorporated herein by reference, was processed according to the procedure described in Example 26B to provide the title compound.

MS (DCI/NH$_3$) m/e 303 (M+NH$_4$)$^+$.

EXAMPLE 27B

(E)-{7-Methoxy-8-[2-(Phenyl)ethenyl]}-2-naphthaleneimidamide mono(trifluoroacetate) salt The title compound was prepared from Example 27A and the procedure of Example 1B.

$^1$H NMR (300 MHz, DMSO-d$_6$) δ 3.98 (s, 3H), 7.28 (t, 2H), 7.39 (t, 2H), 7.64 (m, 5H), 8.00 (d, 1H), 8.10 (d, 1H), 8.62 (s, 1H), 9.22 (br s, 2H), 9.42 (br s, 2H);

MS (DCI/NH$_3$) m/e 303 (M+H)$^+$.

Anal. calcd for C$_{20}$H$_{18}$N$_2$O•TFA: C, 63.46; H, 4.60; N, 6.73. Found: C, 63.10; H, 4.73; N, 6.43.

EXAMPLE 28

6-(4-Phenylbutynyl)-2-naphthalenecarboximidamide mono(trifluoroacetate) salt

EXAMPLE 28A

6-Hydroxy-2-naphthalenecarbonitrile

A solution of 6-bromo-2-naphthol (25.0 g, 112 mmol) and copper(I) cyanide (11 g, 123 mmol) in DMF (30 mL) was heated at 135° C. for 18 h, cooled, diluted with ethyl acetate (50 mL), triturated with 10% aq sodium hydroxide and filtered through Celite®. The filtrate was acidified to pH 2 and extracted with ethyl acetate. The combined extracts were concentrated, dissolved in ethanol (150 mL) and triturated with water to precipitate 14.01 g of the title compound.

MS (DCI/NH$_3$) m/e 170 (M+H)$^+$.

EXAMPLE 28B 6-(Trifluoromethanesulfonyloxy)-2-naphthalenecarbonitrile

A solution of Example 28A (14.01 g, 82.8 mmol) and triethylamine (9.2 g, 91.1 mmol) in methylene chloride (40 mL) at 0° C. was treated dropwise with trifluoromethylsulfonic anhydride (28 g, 99.4 mmol), warmed to 25° C. for 48 h, concentrated, redissolved in ethanol (50 mL) and triturated with water to precipitate 8.4 g of the title compound.

MS (DCI/NH$_3$) m/e 319 (M+NH$_4$)$^+$.

EXAMPLE 28C 6-(4-Phenylbutynyl)-2-naphthalenecarbonitrile

The title compound was prepared from Example 28B, 4-phenyl-1-butyne and the procedure of Example 57B.

MS (DCI/NH$_3$) m/e 299 (M+NH$_4$)$^+$.

EXAMPLE 28D

6(4Phenylbulynyl)-2-naphthalenecarboximidamide mono(trifluoroacetate) salt

The title compound was prepared from Example 28C and the procedure of Example 1B.

$^1$H NMR (300 MHz, DMSO-d$_6$) δ 2.80 (t, 2H), 2.95 (t, 2H), 7.22 (m, 1H), 7.36 (m, 4H), 7.58 (d, 1H), 7.82 (d, 1H), 8.05 (d, 1H), 8.10 (d, 2H), 8.45 (s, 1H), 9.10 (br s, 2H), 9.42 (br s, 2H);

MS (DCI/H$_3$) m/e 299 (M+H)$^+$.

Anal. calcd for C$_{21}$H$_{18}$N$_2$•TFA•0.75H$_2$O: C, 64.86; H, 4.85; N, 6.58. Found: C, 64.78; H, 4.64; N, 6.03.

EXAMPLE 29

7-(2-Hydroxyethoxy)-8-iodo-2-napthalenecarboximidamide mono(trifluoroacetate) salt

EXAMPLE 29A

3-[[(1,1-Dimethylethyl)dimethylsilyl]oxy]-1-propanol,4nitrobenzenesulfonate

A solution of 3-t-butyldimethylsiloxy-1-propanol, prepared by the method of McDougal, et al. JOC, 1986, 51, 3388, which is incorporated herein by reference, (7.6 g, 40 mmol) and diisopropylethylamine (10.4 mL, 60 mmol) in methylene chloride (200 mL) at 0° C. was treated with p-nitrophenylsulfonyl chloride (9.7 g, 44 mmol), stirred for 3 h, poured into saturated NaHCO$_3$ and extracted with diethyl ether. The extracts were washed with brine, dried (Na$_2$SO$_4$), and concentrated. The residue was chromatographed on silica gel with 5% ethyl acetate/hexanes to provide 6.00 g of the title compound.

MS (DCI/NH$_3$) m/e 395 (M+NH4)$^+$.

EXAMPLE 29B

7-[2-[[(1,1-Dimethylethyl)dimethylsilyl]oxy]ethoxy]-8-iodo-2-napbthalenecarbonitrile The title compound was prepared in a manner analogous to that of Example 43A but substituting Example 29A for propyl iodide.

MS (DCI/NH$_3$) m/e 468 (M+H)$^+$.

EXAMPLE 29C 7-(2-Hydroxyethoxy)-8-iodo-2-naphthalenecarbonitrile

The title compound was prepared in a manner analogous to that of Example 53F but substituting Example 29B for Example 53E.

MS (DCI/NH$_3$) m/e 357 (M+H)$^+$.

EXAMPLE 29D 7-(2-Hydroxyethoxy)-8-iodo-2-naphthalenecarboximidamide mono(trifluoroacetate) salt The title compound was prepared from Example 29B according to the procedure of Example 1B.

$^1$H NMR (300 MHz, DMSO-d$_6$) δ 1.96 (m, 2H), 3.69 (t, 2H), 4.33 (t, 2H), 4.58 (br, 1H), 7.63 (d, 1H), 7.66 (dd, 1H), 8.12 (dd, 2H), 8.42 (s, 1H), 9.20 (s, 2H), 9.53 (s, 2H);

MS (DCI/NH3) m/e 245 (M+H)$^+$;

Anal. calcd for C$_{13}$H$_{12}$N$_2$O$_2$I•TFA•0.21H$_2$O: C, 53.07; H, 4.85; N, 7.74. Found: C, 53.07; H, 4.75; N, 7.65.

EXAMPLE 30

7-(2-Hydroxyethoxy)-2-naphthalenecarboximidamide mono(trifluoroacetate) salt

EXAMPLE 30A 7-(2-Hydroxyethoxy)-2-naphthalenecarbonitrile

Example 29B (120 mg, 0.26 mmol), palladium(II)Cl$_2$dppf (46 mg, 0.03 mmol) and diisopropylamine (263 mg, 2.6 mmol) were heated in a sealed tube for 2 h at 100° C., cooled to room temperature, diluted with ethyl acetate, washed with water, dried (Na$_2$SO$_4$), and concentrated. The residue was purified on silica gel with 15% ethyl acetatelhexanes to provide 85 mg of the title compound.

MS (DCI/NH$_3$) m/e 342 (M+H)$^+$.

EXAMPLE 30B 7-(2-Hydroxyethoxy)-2-naphthalenecarboximidamide mono(tiifluoroacetate) salt The title compound was prepared from Example 29B according to the procedure of Example 1B.

$^1$H NMR (300 MHz, DMSO-d$_6$) δ 1.96 (m, 2H), 3.69 (t, 2H), 4.33 (t, 2H), 4.58 (br, 1H), 7.63 (d, 1H), 7.66 (dd, 1H), 8.12 (dd, 2H), 8.42 (s, 1H), 9.20 (s, 2H), 9.53 (s, 2H);

MS (DCI/NH$_3$)m/e 228 (M+H)$^+$;

Anal. calcd for C$_{14}$H$_{15}$N$_2$O$_2$•TFA: C, 53.78; H, 4.51; N, 7.84. Found: C, 53.60; H, 4.30; N, 7.81.

EXAMPLE 31

6-(4-Methyl-1-pentynyl)-2-napbthalenecarboximidamide mono(trifluoroacetate) salt

EXAMPLE 31A 6-(4-Methyl-1-pentynyl)-2-naphthalenecarbonitrile

The title compound was obtained from Example 28B, 4-methyl-1-pentyne and the procedure of Example 57B.

MS (DCI/NH$_3$) m/e 251 (M+NH4)$^+$.

EXAMPLE 31B 6-(4-Methyl-1-pentynyl)-2-naphthalenecarboximidamide mono(tiifluoroacetate) salt The title compound was prepared from Example 31A and the procedure of Example 1B.

$^1$H NMR (300 MHz, DMSO-d$_6$) δ 1.05 (d, 6H), 1.90 (m, 1H), 2.20 (d, 2H), 7.62 (dd, 1H), 7.82 (dd, 1H), 8.09 (d, 1H), 8.12 (d, 1H), 8.18 (s, 1H), 8.48 (s, 1H), 9.12 (br s, 2H), 9.42 (br s, 2H);

MS (DCI/NH$_3$) m/e 251 (M+H)$^+$.

Anal. calcd for C$_{17}$H$_{18}$N$_2$•TFA: C, 62.63; H, 5.26; N, 7.69. Found: C, 64.85; H, 5.32; N, 7.46.

EXAMPLE 32

6-(5-Phenylpentynyl)-2-naphthalenecarboximidamide mono(trifluoroacetate) salt

EXAMPLE 32A 6-(5-Phenylpentynyl)-2-naphthalenecarbonitrile

The title compound was obtained from Example 28B, 5-phenyl-1-pentyne and the procedure of Example 57B.

MS (DCI/NH$_3$) m/e 313 (M+NH4)$^+$.

EXAMPLE 32B 6-(5-Phenylpentynyl)-2-naphthalenecarboximidamide mono(trifluoroacetate) salt The title compound was prepared from Example 32A and the procedure of Example 1B.

$^1$H NMR (300 MHz, DMSOd$_6$) δ 1.90 (m, 2H), 2.80 (t, 2H), 3.39 (t, 2H), 7.19–7.37 (m, SH), 7.62 (dd, 1H), 7.82 (dd, 1H),.8.08 (d, 1H), 8.15 (d, 1H), 8.18 (s, 1H), 8.48 (s, 1H), 9.15–9.45 (br d, 4H);

MS (DCI/NH$_3$) m/e 313 (M+H)$^+$.

Anal. calcd for C$_{22}$H$_{20}$N$_2$•TFA: C, 67.60; H, 4.96; N, 6.57. Found: C, 67.32; H, 5.21; N, 6.27.

EXAMPLE 33

6-(3-Phenyl-1-propynyl)-2-naphthalenecarboximidamide mono(trifluoroacetate) salt

EXAMPLE 33A 6-(3-Phenyl-1-propynyl)-2-naphthalenecarbonitrile

The title compound was obtained from Example 28B, 3-phenyl-1-propyne and the procedure of Example 57B.

MS (DCI/NH$_3$) m/e 285 (M+NH4)$^+$.

EXAMPLE 33B

6(3-Phenyl-1-propynyl)-2-naphthalenecarboximidamide mono(trifluoroacetate) salt

The title compound was prepared from Example 33A and the procedure of Example 5B.

$^1$H NMR (300 MHz, DMSOd$_6$) δ 4.00 (s, 2H), 7.28–7.50 (m, 5H), 7.70 (dd, 1H), 7.85 (dd, 1H), 8.09 (d, 1H), 8.15 (d, 1H), 8.21 (s, 1H), 8.49 (s, 1H), 9.21 (br s, 2H), 9.45 (br s, 2H);

MS (DCI/NH3) m/e 285 (M+H)$^+$.

Anal. calcd for C$_{20}$H$_{16}$N$_2$•TFA•0.25H$_2$O: C, 65.59; H, 4.38; N, 6.95. Found: C, 65.43; H, 3.95; N, 6.70.

EXAMPLE 34

6-Phenylethynyl)-2-naphthalenecarboximidamide mono(trifluoroacetate) salt

EXAMPLE 34A 6-(Phenylethynyl)-2-naphthalenecarbonitrile

The title compound was obtained from Example 28B, phenylacetylene and the procedure of Example 57B. MS (DCI/NH$_3$) m/e 271 (M+NH$_4$)$^+$.

EXAMPLE 34B

6-Phenylethynyl-2-napbthalenecarboximidamide mono(trifluoroacetala) salt

The title compound was prepared from Example 34A and the procedure of Example 1B.

$^1$H NMR (300 MHz, DMSO-d$_6$) δ 7.49 (t, 3H), 7.62 (m, 2H), 7.80 (dd, 1H), 7.86 (dd, 1H), 8.15 (d, 1H), 8.19 (d, 1H), 8.38 (s, 1H), 8.52 (s, 1H), 9.38 (br s, 4H);

MS (DCI/NH$_3$) m/e 271 (M+H)$^+$.

Anal. calcd for C$_{19}$H$_{14}$N$_2$•TFA: C, 65.62; H, 3.93; N, 7.29. Found: C, 65.64; H, 4.11; N, 7.21.

EXAMPLE 35

3-Amino-N-[3-[6-(aminoiminomethyl)-2-naphthalenyl]-2-propynyl]benzamide mono (trifluoroacetate) salt

EXAMPLE 35A 6-(3-Amino-1-propynyl)-2-naphthalenecarbonitrile

The title compound was obtained from Example 28B, propargyl amine and the procedure of Example 41A.

MS (DCI/NH$_3$) m/e 207 (M+NH4)$^+$.

EXAMPLE 35B

3-Amino-N-[3-(6-cyano-2-naphthalenyl)2-propynyl]benzamide

A solution of Example 35A (100 mg, 0.49 mmole), 3-aminobenzoic acid (73 mg, 0.53 mmole), EDC (141 mg, 0.74 mmole) and DMAP (89 mg, 0.74 mmole), in THF (5.5 mL) was stirred at room temperature for 2.5 h and concentrated. The residue was dissolved in methylene chloride, washed with 1N HCl, water, saturated NaHCO$_3$, and brine, dried (MgSO$_4$), concentrated and purified by flash chromatography on silica gel with 2% ethanol/methylene chloride to provide the title compound.

MS (DCI/NH$_3$) m/e 326 (M+H)$^+$.

EXAMPLE 35C

3-Amino-N-[3-[6-(aminoiminomethyl)-2-naphthalenyl]-2-propynyl]benzamide mono (trifluoroacetate) salt The title compound was prepared from Example 35B and the procedure of Example 1B.

¹H NMR (300 MHz, DMSO-d$_6$) δ 4.32 (d, 2H), 5.69 (br s, 2H), 6.58 (d, 2H), 7.62 (m, 3H), 7.82 (d, 1H), 8.08 (d, IH), 8.14 (d, 1H), 8.20 (s, 1H), 8.43 (s, 1H), 8.60 (t, 1H), 9.19 (br s, 2H), 9.42 (br s, 2H);

MS (DCI/NH$_3$) m/e 343 (M+H)$^+$.

Anal. calcd for C$_{21}$H$_{18}$N$_4$O•TFA•0.25H$_2$O: C, 59.93; H, 4.26; N, 12.16. Found: C, 59.86; H, 3.97; N, 11.93.

EXAMPLE 36

4-Amino-N-[3-(6-aminoiminomethyl-2-naphthalenyl)-2-propynyl]benzamide mono (trifluoroacetate) salt

EXAMPLE 36A

4-Amino-N-[3-(6-cyano-2-naphthalenyl)2-propynyl] benzamide

Example 35A and 4-aminobenzoic acid were subjected to the conditions described in Example 35B to afford the title compound.

MS (DCI/NH$_3$) m/e 326 (M+H)$^+$.

EXAMPLE 36B

4-Amino-N-[3-(6-aminoiminomethyl-2-naphthalenyl)-2-propynyl]benzamide mono (trifluoroacetate) salt The title compound was prepared from Example 36A and the procedure of Example 5B.

¹H NMR (300 MHz, DMSO-d$_6$) δ 4.38 (d, 2H), 6.89 (m, 1H), 7.20 (m, 2H), 7.22 (s, 1H), 7.63 (dd, 1H), 7.82 (dd, 1H), 8.09 (d, 1H), 8.12 (d, IH), 8.20 (s, 1H), 8.46 (s, 1H), 8.95 (t, 1H), 9.19 (br s, 2H), 9.42 (br s, 2H);

MS (DCI/NH$_3$) m/e 343 (M+H)$^+$.

Anal. calcd for C$_{21}$H$_{16}$N$_4$O•2.5TFA: C, 49.27; H, 3.19; N, 8.54. Found: C, 49.27; H, 3.33; N, 8.89.

EXAMPLE 37

(S)-2-Amino-N-[1-[(6-aminoiminomethyl-2-naphthalenyl)carbonyl]cyclohexyl]propionamide bis (toifluoroacetate) salt

EXAMPLE 37A

6-[(1-Aminocyclohexyl)ethynyl]-2-napbtbalenecarbonitrile

The title compound was obtained from Example 28B, 1-ethynylcyclohexylamine and the procedure of Example 41A.

MS (DCI/NH$_3$) m/e 275 (M+NH$_4$)$^+$.

EXAMPLE 37B (S)-2-Amino-N-[1-[(6-cyano-2-naphthaleny)carbonyl]cyclohexyl]propionamide Example 37A and N-(t-butoxycarbonyl)-L-alanine were subjected to the conditions described in Example 35B to provide the title compound.

MS (DCI/NH$_3$) m/e 446 (M+H)$^+$.

EXAMPLE 37C (S)-2-Amino-N-[1-[(6-aminoiminomethyl-2-naphthalenyl)carbonyl ]cyclohexyl]propionamide bis(trifluoroacetate) salt The title compound was a rearrangement product of Example 37B resulting from the procedure of Example 5B.

¹H NMR (300 MHz, DMSO-d$_6$) δ 1.24 (d, 3H), 1.40–1.62 (m, 8H), 2.15–2.26 (s, 1H), 2.29–2.38 (s, 1H), 3.51 (d, 1H), 3.78 (d, 1H), 3.82 (s, IH), 7.90 (dd, 2H), 8.09 (dd, 1H), 8.18 (d, 1H), 8.37 (d, 1H), 8.55 (s, 1H), 8.78 (s, 1H), 9.31 (s, 2H), 9.50 (s, 2H);

MS (DCI/NH$_3$) m/e 381 (M+H)$^+$.

Anal. calcd for C$_{23}$H$_{28}$N$_4$O$_2$•2TFA•2H$_2$O: C, 49.39; H, 5.22; N, 8.53. Found: C, 49.15; H, 4.79; N, 8.70.

EXAMPLE 38

6-methoxy-8-benzyloxy-2-naphthalenecarboximidamide mono(trifluoroacetate) salt

EXAMPLE 38A

8-Hydroxy-6-methoxy-3,4-dihydro-2H-naphthalen-1-one

A solution of 6,8-dimethoxy-3,4-dihydro-2H-naphthalen-1-one (15 g, 72.8 mmole), prepared according to the procedure of J. Chem. Soc., London 2782 (1955), which is incorporated herein by reference, in methylene chloride (150 mL) at 0° C. was treated portionwise with AlCl$_3$ (14.3 g, 107 mmole), stirred for 20 h at room temperature, poured onto ice with stirring and extracted with methylene chloride when the ice melted. The extracts were washed with water and brine, dried (MgSO$_4$) and concentrated to provide 13.8 g of the title compound.

MS (DCI/NH$_3$) m/e 193 (M+H)$^+$.

EXAMPLE 38B

8-Benzyloxy-6-methoxy-3,4-dihydro-2H-naphthalen-1-one

A mixture of Example 38A (2.5 g, 13 mmole), benzyl bromide (2.1 mL, 17.8 mmole), K$_2$CO$_3$ powder (14.3 g, 100 mmole), and 2-butanone (88 mL) was stirred at reflux for 4 h, treated with additional benzyl bromide (1.0 mL, 8.5 mmole), stirred at reflux for an additional 3 h, cooled to room temperature, filtered and concentrated. The residue was dissolved in methylene chloride, washed with 1N HCl, water and brine, dried (MgSO$_4$) and concentrated. The crude product was purified on silica gel with 30% ethyl acetate/hexanes to provide the title compound.

MS (DCI/NH$_3$) m/e 283 (M+H)$^+$.

EXAMPLE 38C 3,4-Diydro-2-(hydroxymethylene)6-methoxy-8-(phenylmethoxy)-1(2H)-naphthalenone Sodium metal (1.29 g, 55.9 mmole) was added portionwise to a mixture of ethanol (4.2 mL) and benzene (15 mL). The mixture was stirred at reflux for 1.5 h, cooled to 0° C. and treated dropwise with ethyl formate (5.6 mL, 70 mmole) then dropwise with of a solution of Example 38B (6.7g, 23.8 mmole) in benzene (20 mL), stirred at room temperature for 2 h, cooled to 0° C., treated sequentially with ice/water and 6N HCl (75 mL) and extracted with ethyl acetate. The extracts were washed with brine, dried (MgSO$_4$) and concentrated to provide the title compound.

MS (DCI/NH$_3$) m/e 311 (M+H)$^+$.

EXAMPLE 38D 4,5-Dihydro-7-methoxy-9-(phenylmethoxy)naphth [2,1-d]isoxazole [2,1-d]isoxazole A suspension of Example 38C (7.5 g, 24.3 mmole), hydroxylamine hydrochloride (4.0 g, 57.6 mmole) and acetic acid (63 mL) was stirred at 110° C. for 7 min, cooled to room temperature, diluted with water and extracted with methylene chloride. The extracts were washed with water and brine, dried (MgSO$_4$), and concentrated. The crude product was purified by flash chromatography on silica gel with 30% ethyl acetate/hexanes to provide the title compound.

MS (DCI/NH$_3$) m/e 308 (M+H)$^+$.

EXAMPLE 38E

8-Benzyloxy-2-cyano-6-methoxy-3, 4dihydronaphthalen-1-one

Sodium methoxide, prepared from sodium metal (0.17 g, 7.35 mmol) in methanol (3.9 mL), was treated dropwise with a solution of Example 38D (1.5 g, 4.9 mmole) in benzene (50 mL), stirred at room temperature for 4.5 h, treated sequentially with water and 1N HCl and extracted with ethyl acetate. The extracts were washed with brine, dried (MgSO$_4$) and concentrated to provide the title compound.

MS (DCI/NH$_3$) m/e 308 (M+H)$^+$.

EXAMPLE 38F

2-Cyano-6-methoxy-8-Benzyloxy-3, 4dihydronaphthalene

A suspension of Example 38E (2.6 g, 8.6 mmole) in absolute ethanol (25 mL) at room temperature was treated portionwise with NaBH$_4$ (1.6 g), stirred for 20 min at room temperature and for 20 min at reflux, cooled to room temperature, treated with water (20 mL) and concentrated. The residue was dissolved in methylene chloride, washed with water and brine, dried (MgSO$_4$), filtered and concentrated to provide 2.6 g of an orange foam. The foam was stirred at reflux for 20 min with p-toluenesulfonic acid monohydrate (0.52 g, 2.7 mmole) in benzene (52 mL), cooled to room temperature, diluted with ethyl acetate, washed with water and brine, dried (MgSO$_4$) and concentrated to provide the title compound.

MS (DCI/NH$_3$) m/e 309 (M+NH$_4$)$^+$.

EXAMPLE 38G

2-Cyano-6-methoxy-8-benzyloxynaphthalene

A solution of Example 38F (0.4 g, 1.4 mmole), 2,3-dichloro-5,6-dicyano-1,4-benzoquinone (0.79 g, 3.5 mmole) in benzene (40 mL) was stirred at reflux for 4 hours, treated with additional 2,3-dichloro-5,6-dicyano-1,4-benzoquinone (0.4 g, 1.8 mmole), stirred at reflux for an additional 5 h, cooled to room temperature, diluted with ethyl acetate, washed with saturated NaHCO$_3$ and brine, dried (MgSO$_4$) and concentrated to provide the title compound.

MS (DCI/NH$_3$) m/e 290 (M+H)$^+$.

EXAMPLE 38H

8-Benzyloxy-6-methoxy-2-naphthalenecarboximidamide mono(trifluoroacetate) salt

The title compound was prepared from Example 38G and the procedure of Example 1B.

$^1$H NMR (300 MHz, DMSO-d$_6$)67 4.38 (d, 2H), 6.89 (m, 1H), 7.20 (m, 2H), 7.22 (s, 1H), 7.63 (dd, 1H), 7.82 (dd, 1H), 8.09 (d, 1H), 8.12 (d, 1H), 8.20 (s, 1H), 8.46 (s, 35 1H), 8.95 (t, 1H), 9.19 (br s, 2H), 9.42 (br s, 2H);

MS (DCI/NH$_3$) m/e 307 (M+H)$^+$.

Anal. calcd for C$_{19}$H$_{18}$N$_2$O$_2$•TFA: C, 60.00; H, 4.56; N, 6.66. Found: C, 59.93; H, 4.46; N, 6.51.

EXAMPLE 39

2-[(7-Aminoiminomethyl-3-methoxy-1-naphthalenyl)oxy]acetamide mono(trifluoroacetate) salt

EXAMPLE 39A

6-Methoxy-8-hydroxy-2-naphthalenecarbonitrile

A mixture of Example 38G (1.62 g, 5.6 mmole) and 10% dry Pd/C (0.50 g) in methanol (150 mL) was hydrogenated in a Parr shaker at room temperature under 4 atm for 30 h. The mixture was filtered and concentrated to provide the title compound.

MS (DCI/NH$_3$) m/e 217 (M+NH$_4$)$^+$.

EXAMPLE 39B

2-[(7-Cyano-3-methoxy-1-naphthalenyl)oxy] acetamide

Example 39A and 2-bromoacetamide were subjected to the conditions described in Example 5A to provide the title compound.

MS (DCI/NH$_3$) m/e 274 (M+NH$_4$)$^+$.

EXAMPLE 39C

2-[(7-Aminoiminomethyl-3-methoxy-1-naphthalenyl)oxy]acetamide mono(trifluoroacetate) salt The title compound was prepared from Example 39B and the procedure of Example 1B.

$^1$H NMR (300 MHz, DMSO-d$_6$) δ 3.93 (s, 3H), 4.70 (s, 2H), 6.70 (d, 1H), 7.09 (d, 1H), 7.65 (s, 2H), 7.82 (dd, 1H), 7.99 (d, 1H), 8.70 (s, 1H), 9.05 (s, 2H), 9.38 (s, 2H);

MS (DCI/NH3) m/e 274 (M+H)$^+$.

Anal. calcd for C$_{14}$H$_{15}$N$_3$O$_3$•TFA: C, 49.62; H, 4.16; N, 10.85. Found: C, 49.68; H, 30 4.24; N, 10.61.

EXAMPLE 40

N-(6-aminoiminomethyl-2-naphthalenyl)-N'-phenylurea mono(trifluoroacetate) salt

EXAMPLE 40A

6-Cyano2-naphthalenecarbonyl chloride

A suspension Example 8E (4.4 g, 22.3 mmol) in toluene (100 mL) was treated with thionyl chloride (6.0 mL) and DMAP (5 mg), heated at 55° C. for 1 h, treated with additional thionyl chloride (3 mL), warmed to 95° C. for 1 h, cooled to room temperature, stirred in hexane (75 mL) for 2.5 h and fltered to provide 3.62 of the title compound as a white powder. The filtrate was concentrated and triturated with ether to provide an additional 1.02 g of the title compound.

MS (DCI/NH$_3$) m/e 215 (M+H)$^+$.

EXAMPLE 40B

2-Cyano4-naphthoyl azide

A solution of Example 40A (1.65 g, 7.65 mmole) in acetone (600 mL) at room temperature was treated with a solution of sodium azide (3 g, 46 mmole) in water (10 mL), stirred for 1.5 h and diluted with water (60 mL). The resulting solid was filtered, washed with water and dried to provide 4.24 g of the title compound as a white powder.

MS (DCI/NH$_3$) m/e 240 (M+NH$_4$)$^+$.

EXAMPLE 40C

N-(6-cyano-2-naphthalenyl)-N'-phenylurea

A solution of Example 40B (221.2 mg, 1 mmole) in toluene (18 mL) was heated at 85° C. for 1 h then at 95° C. for 1.5 h, cooled to room temperature, treated with aniline (240 μL, 2.63 mmole), stirred for 25 min and treated with ether (10 mL). The resulting solid was collected, washed with ether and dried under vacuum to yield 230 mg of white powder.

MS (DCI/NH$_3$) m/e 305 (M+NH$_4$)$^+$.

EXAMPLE 40D

N-(6aminoiminomethyl-2-naphthalenyl)-N'-phenylurea mono(trifluoroacetate) salt

A solution of Example 40C (148 mg, 0.5 mmole) in 10:1 pyridine:triethylamine (10 mL) was treated with H$_2$S for 5 min, stirred at room temperature for 18 h and concentrated. The resulting solid was dissolved in acetone (15 mL), treated with iodomethane (0.8 mL, 12.8 mmole), stirred for 2 h, diluted with ether (10 mL), filtered, washed with ether and dried under vacuum. Ihe resulting solid was dissolved in methanol, treated with 2N NH$_3$ in methanol (2 mL), warmed to 50° C. for 4 h and concentrated. The product was purified according to the procedure described in Example 1B to provide 62 mg of the title compound.

$^1$H NMR (300 MHz, DMSO-d$_6$) δ 7.00 (t, 1H), 7.31 (dd , 2H), 7.52 (d, 1H), 7.65 (dd, 1H), 7.76 (dd, 1H, 8.02 (d, 2H), 8.30 (s, 1H), 8.39 (s, 1H), 9.05 (br s, 2H), 9.11 (s, 1H), 9.33 (br s, 2H), 9.42 (s, 1H);

MS (DCI/NH$_3$) m/e 305 (M+H)$^+$;

Anal. calcd for C$_{18}$H$_{16}$N$_4$O•TFA: C, 57.42; H, 4.10; N, 13.39. Found: C, 57.50; H, 05; N, 13.08.

EXAMPLE 41

(E)-6-[2-(Phenyl)ethenyl]-2-naphthalenecarboximidamide mono(trifluoroacetate) salt

EXAMPLE 41A (E)-6-[2-(Phenyl)ethenyl]-2-naphthalenecarbonitrile

A solution of Example 28B (350 mg, 1.16 mmol), styrene (157 mg, 1.51 mmol), palladium (II) acetate (26 mg, 0.12 mmol), triphenylphosphine (61 mg, 0.23 mmol), triethylamine (2 mL) and acetonitrile (1 mL) in a sealed tube with minimal head volume was heated at 100° C. for 19 h, diluted with ethyl acetate (20 mL), washed with water, dried (MgSO$_4$) and concentrated with silica gel (4 g). The mixture was chromatographed on silica gel with 10% ethyl acetatel-hexane to provide 160 mg of the title compound.

MS (DCI/NH$_3$) m/e 273 (M+NH$_4$)$^+$.

EXAMPLE 41B (E)-6-[2-(Phenyl)ethenyl]-2-napbthalenecarboximidamide mono(trifluoroacetate) salt The title compound was prepared from Example 41A from the procedure of Example 1B.

$^1$H NMR (300 MHz, DMSO-d$_6$) δ 7.33 (t, 1H), 7.4 (t, 2H), 7.5 (d, 2H), 7.69 (d, 1H), 7.70 (d, 1H), 7.81 (dd, 1H), 8.03 (dd, 1H), 8.10 (d, 1H), 8.13 (d, 1H), 8.17 (s, 1H), 8.44 (s, 1H), 8.97 (s, 2H), 9.41 (s, 2H);

MS (DCI/NH$_3$) m/e 273 (M+H)$^+$;

Anal. calcd for C$_{19}$H$_{16}$N$_2$•TFA: C, 65.28; H, 4.43; N, 7.25. Found: C; 64.95; H, 4.60; N, 6.42.

EXAMPLE 42

6-[2-(Phenyl)ethyl]-2-naphthalenecarboximidamide mono(trifluoroacetate) salt

EXAMPLE 42A

6-[2-(Phenyl)ethyl]-2-naphthalenecarbonitrile

A mixture of Example 57B (80 mg, 0.31 mmol) and palladium on carbon (20% water, 50 mg) in methanol (5 mL) was stirred under 1 atm of hydrogen for 0.5 h, filtered and concentrated to provide 72 mg of the title compound.

MS (DCI/NH$_3$) m/e 275 (M+NH4)$^+$.

EXAMPLE 42B

6-[2-(Phenyl)ethyl]-2-naphthalenecarboximidamide mono(trifluoroacetate) salt

The title compound was prepared from Example 42A and the procedure of Example 1B.

$^1$H NMR (300 MHz, DMSO-d$_6$) δ 3.03 (m, 2H), 7.23 (m, 5H), 7.60 (dd, 1H), 7.76 (dd, 1H), 7.85 (s, 1H), 8.03 (t, 2H), 8.42 (s, 1H), 8.99 (s, 2H), 9.39 (s, 2H);

MS (DCI/NH$_3$) m/e 275 (M+H)$^+$.

Anal. calcd for C$_{19}$H$_{18}$N$_2$O.1O8 1.33TFA: C, 61.29; H, 4.59; N, 6.61. Found: C; 61.56; H, 4.62; N, 5.21.

EXAMPLE 43

7-Propoxy-8-iodo-2-naphthalenecarboximidamide mono(trifluoroacetate) salt

EXAMPLE 43A 7-propoxy-8 iodo-2-naphthalenecarbonitrile

Example 53A (65 mg, 0.25 mmol) in DMF (2 mL) was treated with propyl iodide (40 mL), stirred at 65° C. for 1 h, diluted with water and extracted with diethyl ether. The organic extracts were dried (MgSO$_4$) and concentrated, and the residue was purified on silica gel with 10% ethyl acetate/hexanes to provide 160 mg of the title compound.

MS (DCI/NH$_3$) m/e 355 (M+H)$^+$.

EXAMPLE 43B

7-Propxy-8-iodo-2-naphthalenecarboximidamide mono(trifluoroacetate) salt

The title compound was prepared from the product in Example 43A according to the procedure of Example 1B.

$^1$H NMR (300 MHz, DMSO-d$_6$) δ 1.09 (t, 3H), 1.82 (m, 2H), 4.23 (t, 2H), 7.62 (d, 1H), 7.65 (dd, 1H), 8.12 (dd, 2H), 9.15 (s, 2H), 9.42 (s, 1H), 9.53 (s, 2H);

MS (D)CI/NH$_3$) m/e 355 (M+H)$^+$.

Anal. calcd. for C$_{14}$H$_{15}$N$_2$OI•TFA•0.26C$_7$H$_8$: C, 43.49; H, 3.70; N, 5.69. Found: C; 43.50; H, 3.59; N, 5.75.

EXAMPLE 44

(±)-6-(3-Phenyloxiranyl)-2-naphthalenecarboximidamide mono(trifluoroacetate) salt

EXAMPLE 44A (±)-6-(3-Phenyloxiranyl)-2-naphthalenecarbonitile

A solution of Example 41A (69 mg, 0.27 mmol) and m-chloroperbenzoic acid (70 mg, 0.41 mmol) in methylene chloride (3 mL) was stirred at 25° C. for 3 days, concentrated, loaded on a silica gel column (pretreated with 0.1% triethylamine in ethyl acetate) and eluted with 10% ethyl acetatethexane) to provide 72 mg of the title compound.

MS (DCI/NH$_3$) m/e 289 (M+NH$_4$)$^+$.

EXAMPLE 44B (±)6-(3-Phenyloxiranyl)-2-naphthalenecarboximidamide mono(trifluoroacetate) salt The title compound was prepared with Example 44A from the procedure of Example 1B.

$^1$H NMR (300 MHz, DMSO-d$_6$) δ 4.24 (d, 1H), 4.35 (d, 1H), 7.43 (m, 5H), 7.67 (dd, 1H), 7.83 (dd, 1H), 8.12 (s, 1H), 8.13 (d, 1H), 8.16 (d, 1H), 8.50 (s, 1H), 9.03 (s, 2 H), 9.44 (s, 2H);

MS (DCI/NH$_3$) m/e 289 (M+H)$^+$.

Anal. calcd for C$_{19}$H$_{16}$N$_2$O•1.3 TFA: C, 64.52; H, 4.55; N, 6.51. Found: C; 64.35; H, 4.60; N, 5.87.

EXAMPLE 45

(E)-6-[2-(2-Thienyl)ethenyl]-2-naphthalenecarboximidamide mono(trifluoroacetate) salt

EXAMPLE 45A

2-Vinylthiophene

A suspension of methyltriphenylphosphonium bromide (19.13 g, 53.5 mmol) in THF (100 mL) was treated dropwise with 2M butyllithium in THF (17.8 mL) then dropwise with 2-carboxythiophene (5 g, 44.6 mmol), stirred for 30 min then distilled at 74–78° C. to provide the title compound.

MS (DCI/NH$_3$) m/e 111 (M+H)$^+$.

EXAMPLE 45B (E)-6-[2-(2-Thienyl)ethenyl]-2-naphthalenecarbonitrile

The title compound was prepared from the product of Example 45A and the procedure of Example 41 A.

MS (DCI/NH$_3$) m/e 279 (M+NH$_3$)$^+$.

EXAMPLE 45C (E)-6-[2-(2-Thienyl)ethenyl]-2-naphthalenecarboximidamide mono(trifluoroacetate) salt The title compound was prepared from Example 45B and the procedure of Example 1B.

$^1$H-NMR (300 MHz, DMSO-d$_6$) δ 7.12 (dd, 2H), 7.15 (d, 1H), 7.32 (d, 1H), 7.6 (d, 1H), 7.74 (d, 1H), 7.80 (dd, 1H), 7.9-8.1 (m, 3H), 8.14 (s, 1H), 8.43 (s, 1H), 9.03 (s, 2H), 9.42 (s, 2H);

MS (DCI/NH$_3$) m/e 279 (M+H)$^+$;

Anal. calcd. for C$_{17}$H$_{14}$N$_2$O$_2$S•TFA: C, 53.77; H, 3.56; N, 6.60. Found: C; 54.88; H, 3.66; N, 6.45.

EXAMPLE 46

6-(3-Oxobutyl)-2-naphthalenecarboximidamide mono(trifluoroacetate) salt

EXAMPLE 46A 6-(3-Oxobutyl)-2-naphthalenecarbonitrile

The title compound was prepared from Example 28B, 1-buten-3-ol and the procedure of Example 41A.

MS (DCI/NH$_3$) m/e 241 (M+NH$_4$)$^+$.

EXAMPLE 46B 6-(3-Oxobutyl)-2-naphthalenecarboximidamide mono(trifluoroacetate) salt The title compound was prepared from Example 46A and the procedure of Example 1B.

$^1$H NMR (300 MHz, DMSO-d$_6$) δ 2.13 (s, 1H), 2.94 (m, 4H), 7.57 (dd, 1H) 7.78 (dd, 1H), 7.85 (s, 1H), 8.01 (d, 1H), 8.05 (d, 1H), 8.43 (s, 1H), 8.48 (m, 2H), 9.06 (s, 2H), 9.40 (s, 2H);

MS (DCI/NH$_3$) m/e 241 (M+H)$^+$;

Anal. calcd. for C$_{15}$H$_{16}$N$_2$O•1.3TFA: C, 54.31; H, 4.48; N, 7.19. Found: C; 54.33; H, 4.35; N, 7.27.

EXAMPLE 47

6(3-Methoxyphenyl)-2-naphthalenecarboximidamide mono(trifluoroacetate) salt

EXAMPLE 47A 6-(3-Methoxyphenyl)-2-naphthalenecarbonitrile

A solution of Example 28B (300 mg, 1 mmol), palladium (II) acetate (22 mg, 0.1 mmol) and 1-1'-bis (diphenyphosphino)ferrocene (111 mg, 0.2 mmol) was stirred in DMF (3 mL) for 15 min, treated with Cs$_2$CO$_3$ (813 mg, 2.5 mmol) and 3-methoxyphenylboronic acid (228 mg, 1.5 mmol), stirred for 20 min at 80° C., cooled, treated with pH 7 buffer (10 mL) and extracted with diethyl ether. The ether extracts were dried (MgSO$_4$), concentrated and purified on silica gel with 10% ethyl acetate/haexane to provide 140 mg of the title compound as a white solid.

MS (DCI/NH$_3$) m/e 277 (M+NH$_4$)$^+$.

EXAMPLE 47B 6-(3-Methoxyphenyl)-2-naphthalenecarboximidamide mono(trifluoroacetate) salt The title compound was prepared from Example 47A and the procedure of Example 1B.

$^1$H NMR (300 MHz, DMSO-d$_6$) δ 3.88 (s, 3H), 7.03 (m, 1H), 7.44 (m, 3H), 7.84 (dd, 1H), 8.05 (dd, 1H), 8.19 (d, 1H), 8.21 (d, 1H), .41 (s, 1H), 8.51 (s, 1H), 9.11 (s, 2H), 9.45 (s, 2H);

MS (DCI/NH$_3$) m/e 277 (M+H)$^+$;

Anal. calcd for C$_{18}$H$_{16}$N$_2$O•TFA•0.2H$_2$O: C, 61.03; H, 4.45; N, 7.12. Found: C; 61.03; H, 4.11; N, 6.86.

EXAMPLE 48

N-[3-(methyl)phenyl]-6-aminoiminomethyl-2-naphthalenecarboxamide mono(trifluoroacetate) salt

EXAMPLE 48A

N-[3-(methyl)phenyl]-6-cyano-2-naphthalenecarboxamide

The title compound was prepared from 3-methyl phenylisocyanate, Example 55C and the procedure from Example 55C.

MS (DCI/NH$_3$) m/e 287 (M+H)$^+$.

EXAMPLE 48B

N-[3-(methyl)phenyl]-6-aminoiminomethyl-2-naphthalenecarboxamide mono(trifluoroacetate) salt The title compound was prepared from Example 48A and the procedure of Example 1B. $^1$H NMR (300 MHz, DMSO-d$_6$) δ 2.34 (s, 3H), 6.96 (d, 1H), 7.27 (t, 1H), 7.62 (d, 1H), 7.66 (s, 1H), 7.91 (dd, 1H), 8.15 (dd, 1H), 8.29 (d, 1H), 8.31 (d, 1H), 8.54 (s, 1H), 8.68 (s, 1H), 9.15 (s, 2H), 9.49 (s, 2H), 10.46 (s, 1H);

MS (DCI/NH$_3$) m/e 304 (M+H)$^+$;

Anal. calcd for C$_{19}$H$_{17}$N$_3$O•TFA•0.12C$_7$H$_8$: C, 61.23; H, 4.46; N, 9.81. Found: C; 61.12; H, 4.42; N, 9.43.

EXAMPLE 49

6-(2-Formylphenoxy)-2-naphthalenecarboximidamide mono(trifluoroacetate) salt

EXAMPLE 49A 6-(2-Formylphenoxy)-2-naphthalenecarbonitrile

A solution of 2-hydroxybenzaldehyde (72 mg, 0.59 mmol), 6-bromo-1cyanonaphthalene (150 mg, 0.65 mmol), and Cs$_2$CO$_3$ (248 mg, 15 0.76 mmol) in DMF (10 mL) was heated at 90° C. for 2 days, treated with water and extracted with ethyl acetate. The combined organic extracts were dried (MgSO$_4$) and concentrated, and the crude product was purified by column chromatography with 10% ethyl acetate/hexane to provide 40 mg of the title compound.

MS (DCI/NH$_3$) m/e 291 (M+NH$^4$)$^+$.

EXAMPLE 49B 6-(2-Formylphenoxy)-2-naphthalenecarboximidamide mono(trifluoroacetate) salt The title compound was prepared with Example 49A and the procedure of Example 1B.

$^1$H-NMR (300 MHz, DMSO-d$_6$) δ 7.19 (d, 1H), 7.44 (t, 1H), 7.56 (s, 1H), 7.60 (d, 1H), 7.79 (m, 2H), 7.94 (dd, 1H), 8.01 (d, 1H), 8.2 (d, 1H), 8.51 (s, 1H), 9.03 (s, 2H), 9.41 (s, 2H), 10.35 (s, 1H);

MS (DCI/NH$_3$) m/e 291 (M+H)$^+$.

Anal. calcd for C$_{18}$H$_{14}$N$_2$O$_2$•TFA•1.7H$_2$O: C, 55.16; H, 4.27; N, 6.43. Found: C; 55.17; H, 3.92; N, 5.94.

EXAMPLE 50

6-(2-Formylphenyl)-2-naphthalenecarboximidamide mono(tifluoroacetate) salt

EXAMPLE 50A 6-(2-Formylphenyl)-2-naphthalenecarbonitrile

The title compound was prepared from Example 28B, 2-formylphenylboronic acid and the procedure of Example 47A.

MS (DCI/NH$_3$) m/e 275 (M+NH$_4$)$^+$.

EXAMPLE 50B 6-(2-Formylphenyl)-2-naphthalenecarboximidamide mono(trifluoroacetate) salt The title compound was prepared from Example 50A and the procedure of Example 1B.

$^1$H NMR (300 MHz, DMSO-d$_6$) δ 7.71–7.64 (m, 2H), 7.79 (d, 1H), 7.81 (s, 1H), 7.88 (dd, 1H),7.9 (d, 1H), 8.16 (d, 1H), 8.23 (t, 2H), 8.56 (s, 1H), 9.05 (s, 2H), 9.48 (s, 2H), 9.92 (s, 1H);

MS (DCI/NH$_3$) m/e 275 (M+H)$^+$;

Anal. calcd for C$_{18}$H$_{14}$N$_2$O•TFA: C, 61.86; H, 3.89; N, 7.21. Found: C; 61.98; H, 3.59; N, 6.88.

EXAMPLE 51

6-[2-(Hydroxymethyl)phenyl]-2-naphthalenecarboximidamide mono(trifluoroacetate salt

EXAMPLE 51A

6-[2-(Hydroxymethyl)]-2-naphthalenecarbonitrile

Example 50A (98 mg, 0.38 mmol) and sodium borohydride (15 mg, 0.80 mmol) were dissolved in methanol (10 mL) and stirred for 0.5 h. The solution was concentrated, and the residue was purified on silica gel with 30% ethyl acetate/hexane to provide 90 mg of the title compound.

MS (DCI/NH$_3$) m/e 277 (M+NH$_4$)$^+$.

EXAMPLE 51B

6-[2-(Hydroxymethyl)phenyl]-2-naphthalenecarboximidamide mono(trifluoroacetate) salt The title compound was prepared from Example 51A and the procedure of Example 1B.

$^1$H NMR (300 MHz, DMSO-d$_6$) δ 9.46 (s, 2H), 9.06 (s, 2H), 8.54 (s, 1H), 8.16 (t, 2H), 8.07 (s, 1H), 7.85 (dd, 1H), 7.74 (dd, 1H), 7.63 (d, 1H), 7.49-7.34 (m, 3H), 4.46 (s, 2H);

MS (DCI/NH$_3$) m/e 277 (M+H)$^+$;

Anal. calcd. for C$_{18}$H$_{16}$N$_2$O•1.44TFA: C, 56.93; H, 3.99; N, 6.36. Found: C; 56.94; H, 3.88; N, 6.46.

EXAMPLE 52

6-(3-Oxo-1-butenyl)-2-naphthalenecarboximidamide mono(trifluoroacetate) salt

EXAMPLE 52A 6-(3-Oxo-1-butenyl)-2-naphthalenecarbonitrile

The title compound was prepared from methyl acrylate, Example 28B and the procedure of Example 41A. MS (DCI/NH$_3$) m/e 222 (M+H)$^+$.

EXAMPLE 52B 6-(3-Oxo-1-butenyl)-2-naphthalenecarboximidamide mono(trifluoroacetate) salt The title compound was prepared from Example 52A and the procedure of Example 1B.

$^1$H NMR (300 MHz, DMSO-d$_6$) δ 9.46 (s, 2H), 9.13 (s, 2H), 8.48 (s, 1H), 8.38 (s, 1H), 8.18 (d, 1H), 8.15 (d, 1H), 8.01 (dd, 1H), 7.85 (dd, 1H), 7.82 (d, 1H), 7.03 (d, 1H), 2.40 (s, 1H);

MS (DCI/NH$_3$) m/e 239 (M+H)$^+$.

Anal. calcd for C$_{15}$H$_{14}$N$_2$O•1.58TFA: C, 52.13; H, 3.75; N, 6.69. Found: C; 52.09; H, 3.63; N, 6.64.

EXAMPLE 53

7-Methoxy-8-(1H-pyrazol-4-yl)-2-naphthalenecarboximidamide bis(trifluoroacetate) salt

EXAMPLE 53A 7-hydroxy-8-iodo-2-naphthalenecarbonitrile

A mixture of 7-cyano-2-naphthol (22.3 g, 131.8 mmol), sodium carbonate (29.3 g, 277 mmol) and I$_2$ (31.8 g, 125.2 mmol) in water (500 mL) and THF (80 mL) at 0 ° C was stirred at room temperature for 3 h, acidified with 1M HCl and extracted with ethyl acetate. The extracts were washed with saturated Na$_2$S$_2$O$_3$ and brine, dried (Na$_2$SO$_4$) and concentrated. The product was recrystallized from ethyl acetate to yield 33 g of the title compound.

MS (DCI/NH$_3$) m/e 313 (M+NH$_4$)$^+$.

EXAMPLE 53B

7-Methoxy-8-iodo-2-naphthalenecarbonitrile

Example 53A (36.7 g, 124.2 mmol) in methanol (500 mL) and ethyl acetate (300 mL) was treated over 3 h with 2M trimethylsilyldiazomethane in hexane (260 mL), stirred for 24 h, concentrated and recrystallized from ethyl acetate to provide 36.4 g of the title compound MS (DCI/NH$_3$) m/e 327 (M+NH$_4$)$^+$.

EXAMPLE 53C

4-Iodo-1-[[2-(trimethylsilyl)ethoxy]methyl]-1H-pyrazole

A slurry of NaH (1.94 g, 48.5 mmol) in THF (40 mL) at 0° C. was treated with a solution of 4-iodopyrazole (8.97 g, 46.2 mmol) in THF (20 mL), stirred for 1 h, treated with SEM chloride (9.00 mL, 50.8 mmol), stirred at room temperature for 1 h, poured into water and extracted with ethyl acetate. The extracts were washed with brine, dried (MgSO$_4$) and concentrated. The residue was chromatographed on silica gel with 10% ethyl acetate/hexanes to provide 14.4 g of the title compound.

MS (DCI/NH$_3$) m/e 325 (M+H)$^+$.

EXAMPLE 53D

[1-[[2-(Trimethylsilyl)ethoxy]methyl]-1H-pyrazol4-yl]boronic acid

Example 53C (12.97 g, 40 mmol) in THF (250 mL) at −78° C. was treated with 2.5 M butyllithium in hexanes (17.6 mL, 44 mmol), stirred at −78° C. for 10 min, treated with trimethyl borate (11.36 mL, 100 mmol), warmed to room temperature, treated with 3M HCl (400 mL) and extracted with ethyl acetate. The extracts were concentrated, and the residue was dissolved in 1M NaOH (500 mL), extracted with diethyl ether, acidified with concentrated HCl and extracted with ethyl acetate. The extracts were washed with brine, dried (Na$_2$SO$_4$), and concentrated. The residue was chromatographed on silica gel with ethyl acetate to provide 2.20 g of the title compound.

MS (DCI/NH$_3$) m/e 199 (M-B(OH)$_2$)$^+$.

EXAMPLE 53E

7-Methoxy-8-[1-[[2-(trimethylsilyl)ethoxy]methyl]-1H-pyrazol-4-yl]-2-naphthalenecarbonitrile Examples 53B (1.55 g, 5 mmol) and 53D (1.45 g, 6 mmol) were subjected to the procedure described in Example 47A to provide 1.64 g of the title compound. MS (DCI/NH$_3$) m/e 380 (M+H)$^+$.

EXAMPLE 53F

7-Methoxy-8-(1H-pyrazol-4-yl)-2-naphthalenecarbonitrile

A solution of Example 53E (1.84 g, 4.85 mmol) in THF (10 mL) was treated with 1M tetrabutylammonium fluoride in THF (24 mL), refluxed for 6 h and concentrated. The residue was chromatographed on silica gel with 1:1 ethyl acetate/hexanes to provide 0.88 g of the title compound. MS (DCI/NH$_3$) m/e 267 (M+NH$_4$)$^+$.

EXAMPLE 53G

7-Methoxy-8-(1H-pyrazol-4-yl)-2-naphthalenecarboximidamide bis(trifluoroacetate) salt The title compound was prepared from Example 53F and the procedure of Example 1B.

$^1$H NMR (300 MHz, DMSO-d$_6$) δ 3.89 (s, 3H), 7.60 (dd, 2H), 7.71 (d, 1H), 7.92 (s, 2H), 8.05 (d, H), 8.12 (d, 1H), 8.29 (s, 1H), 9.33 (s, 2H), 9.34 (s, 2H); MS (DCI/NH$_3$) m/e 267 (M+H)$^+$; Anal. calcd. for C$_{15}$H$_{14}$N$_4$O.2.8TFA: C, 42.30; H, 2.90; N, 9.59. Found: C; 42.54; H, 3.11; N, 9.03.

EXAMPLE 54

7-Methoxy-8-iodo-2-naphthalenecarboximidamide mono(trifluoroacetate) salt

The title compound was prepared from Example 53B and the procedure of Example 1B.

$^1$H NMR (300 MHz, DMSO-d$_6$) δ 4.01 (s, 3H), 7.65 (m, 2H), 8.12 (d, 1H), 8.15 (d, 1H), 8.42 (s, 1H), 9.14 (s, 2H), 9.52 (s, 2H); MS (DCI/NH$_3$) m/e 327 (M+H)$^+$. Anal. calcd for C$_{12}$H$_{12}$N$_2$OI.1.2TFA: C, 37.28; H, 2.87; N, 6.04. Found: C; 37.35; H, 2.47; N, 5.93.

EXAMPLE 55

N-phenyl-6-aminoiminomethyl-2-naphthalenecarboxamide mono(methanesulfone) salt

EXAMPLE 55A

2-Trifluoromethanesulfonyloxy-6-bromonaphthalene

A solution of 6-bromo-2-naphthol (4.96 g, 22.25 mmol), N-phenyltrifluoromethanesulfonate (7.95 g, 22.25 mmol), and diisopropylethylamine (7.75 mL, 44.5 mmol) in methylene chloride (25 mL) were stirred for 3 h at room temperature, poured into water and extracted with diethyl ether. The extracts were washed with brine, dried (MgSO$_4$), and concentrated. The residue was chromatographed on silica gel with 3% ethyl acetate/hexane to provide 7.89 g of the title compound.

MS (DCI/NH$_3$) m/e 354 and 356 (M+H)$^+$.

EXAMPLE 55B

6-Bromo-2-naphthalenecarbonitrile

Example 55A (7.89 g, 22.2 mmol) was combined with Zn(CN)$_2$ (1.33 g, 11.33 mmol) and Pd(PPh$_3$)$_4$ (256 mg, 0.22 mmol) in DMF (50 mL), heated at 90° C. for 3 h, cooled to room temperature, treated with saturated NaHCO$_3$ and extracted with diethyl ether. The extracts were washed with brine, dried over (MgSO$_4$), and condensed. The residue was chromatographed on silica gel with 5% ethyl acetate/hexanes to provide 2.67 g of the title compound.

MS (DCI/NH$_3$) m/e 231 and 233 (M+H)$^+$.

EXAMPLE 55C

N-phenyl-6-cyano-2-naphthalenecarboxamide

A solution of Example 55B (224 mg, 0.965 mmol) in THF (3 mL) and hexanes (1 mL) at −100° C. was treated with 2.5 M butyllithium in hexanes (0.386 mL, 0.965 mmol), stirred at −100° C. for 5 min, treated with phenyl isocyanate (0.115 mL, 1.06 mmol), warmed to room temperature, treated with pH 7 buffer (0.5 mL) and concentrated. The residue was chromatographed on silica gel with 20% ethyl acetate/hexanes as eluent, to provide 54 mg of the title compound:

MS (DCI/NH$_3$) m/e 273 (M+H)$^+$.

EXAMPLE 55D

N-phenyl-6-aminoiminomethyl-2-naphthalenecarboxamide mono(methanesulfonate) salt A solution of Example 55C (52 mg, 0.191 mmol) in THF (2 mL) was treated with 1M lithium bis(trimethylsilyl)amide in THF (0.6 mL), stirred for 18 h, treated with 2M HCl (4 mL), stirred for another 24 h, made basic with saturated Na$_2$CO$_3$ and extracted with ethyl acetate. The extracts were washed with brine, dried (Na$_2$SO$_4$) and concentrated. The crude product was dissoved into a minimal amount of methanol (ca. 1 mL), treated with methanesulfonic acid (1 drop), diluted with diethyl ether (400 mL) and filtered to provide 15 mg of the title compound.

$^1$H NMR (300 MHz, DMSO-d$_6$) δ 2.32 (s, 3H), 7.15 (dd, 1H), 7.40 (dd, 2H), 7.83 (d, 2H), 7.90 (dd, 1H), 8.17 (dd, 1H), 8.25 (d, 1H), 8.34 (d, 1H), 8.57 (s, 1H), 8.70 (s, 1H), 9.09 (br s, 2H), 9.51 (br s, 2H); MS (DCI/NH$_3$) m/e 290 (M+H)$^+$. Anal. calcd for C$_{18}$H$_{16}$N$_3$O.1.1 CH$_3$SO$_3$H: C, 57.96; H, 4.95; N, 10.61. Found: C, 58.03; H, 4.48; N, 10.36.

EXAMPLE 56

4-[(6-Aminoiminomethyl-2-naphthalenyl)oxy]-N-methylbenzeneacetamide mono(trifluoroacetate) salt

EXAMPLE 56A

N-methyl-3-hydroxyphenylacetamide

A solution of 3-hydroxyphenylacetic acid (1.00 g, 6.57 mmol) and oxalyl chloride (0.63 mL, 7.22 mmol) in methylene chloride (20 mL) was treated dropwise with pyridine (0.6 mL, 7.37 mmol), stirred for 90 min, poured into 40% aqueous methylamine (30 mL), stirred for 15 min, concentrated, dissolved into 1M HCl and extracted with ethyl acetate. The extracts were washed with brine, dried (MgSO$_4$) and concentrated. The residue was chromatographed on silica gel with ethyl acetate to provide 260 mg of the title compound. MS (DCI/NH$_3$) m/e 166 (M+H)$^+$.

EXAMPLE 56B

4-[(6-Cyano-2-naphthalenyl)oxy]-N-methylbenzeneacetamide

A mixture of Example 56A (245 mg, 1.48 mmol), Example 55B (344 mg, 1.48 mmol) and Cs$_2$CO$_3$ (530 mg, 1.63 mmol) in DMF (3 mL) was stirred for 72 h at 120° C., cooled and chromatographed on silica gel with 1:1 ethyl acetate/hexanes to provide 54 mg of the title compound.

MS (DCI/NH$_3$) m/e 317 (M+H)$^+$.

EXAMPLE 56C

4-[(6-Aminoiminomethyl-2-naphthalenyl)oxy]-N-methylbenzeneacetamide mono(trifluoroacetate) salt The title compound was prepared from Example 56B and the procedure of Example 55D.

$^1$H NMR (300 MHz, DMSO-d$_6$) δ 2.33 (s, 3H), 2.58 (d, 3H), 3.42 (s, 2H), 7.05 (m, 2H),7.12 (d, 1H), 7.40 (dd, 1H), 7.45 (m, 2H), 7.79 (dd, 1H), 7.98 (q, 1H), 8.02 (d, 1H), 8.15 (d, 1H), 8.49 (s, 1H), 8.99 (br s, 2H), 9.39 (br s, 2H);

MS (DCI/NH$_3$) m/e 334 (M+H)$^+$. Anal. calcd for C$_{19}$H$_{17}$N$_3$O$_2$.1.5CH$_3$SO$_3$H: C, 54.08; H, 5.28; N, 8.80. Found: C, 53.80; H, 5.37; N, 8.52.

EXAMPLE 57

6-[2-(Methylthio)phenyl]-2-naphthalenecarboximidamide mono (methanesulfonate) salt

EXAMPLE 57A

2-Cyanonaphthalene-6-boronic acid

A solution of Example 55B (6.37 g, 27.45 mmol) in THF (220 mL) and hexanes (50 mL) at −100° C. was treated with 2.5 M butyllithium in hexanes (11.0 mL, 27.5 mmol), stirred at −100° C. for 10 min, treated with trimethyl borate (7.8 mL, 68.6 mmol), warmed to room temperature, treated with 3M HCl (400 mL) and extracted with ethyl acetate. The extracts were concentrated and the residue was dissolved into 1M NaOH (500 mL), extracted with diethyl ether, acidified with 12M HCl and extracted with ethyl acetate. The extracts were washed with brine, dried (Na$_2$SO$_4$), and concentrated. The residue was dissolved into minimal methanol and ethyl acetate and triturated with hexanes to yield 2.74 g of the title compound.

MS (DCI/NH$_3$) m/e 215 (M+NH$_4$)$^+$.

EXAMPLE 57B

6-[2-(Methylthio)phenyl]-2-naphthalenecarbonitrile

A solution of 2-bromothioanisole (0.147 mL, 1.10 mmol), Pd(OAc)$_2$ (24 mg, 0.11 mmol) and 1,1'-bis (diphenylphosphinoferrocene) (120 mg, 0.22 mmol) in DMF (5 mL) was stirred for 10 min, treated with Example 57A (260 mg, 1.32 mmol) and Cs$_2$CO$_3$ (1.07 g, 3.3 mmol), heated at 85° C. for 6 h, cooled to room temperature and chromatographed on silica gel with 10% ethyl acetate/hexanes to provide 155 mg of the title compound.

MS (DCI/NH$_3$) m/e 231 (M+NH$_4$)$^+$.

EXAMPLE 57C

6-[2-(Methylthio)phenyl]-2-naphthalenecarboximidamide mono (methanesulfonate) salt The title compound was prepared from Example 57B and the procedure of Example 55D.

$^1$H NMR (300 MHz, DMSO-d$_6$) δ 2.32 (s, 3H), 2.40 (s, 3H), 7.34 (m, 2H), 7.45 (m, 2H), 7.82 (dd, 2H), 7.95 (dd, 1H), 8.06 (s, 1H), 8.15 (d, 1H), 8.20 (d, 1H), 8.55 (s, 1H), 9.03 (br s, 2H), 9.56 (br s, 2H); MS (DCI/NH$_3$) m/e 293 (M+H)$^+$. Anal. calcd for C$_{18}$H$_{17}$N$_2$S.CH$_3$SO$_3$H: C, 58.18; H, 5.18; N, 7.12. Found: C, 57.97; H, 5.31; N, 6.97.

EXAMPLE 58

6-[2-(2-Thiomethoxoxyethyl)phenyl]naphthalene-2-carboximidamide mono(methanesulfonate) salt

EXAMPLE 58A 2-(2-Bromoethyl)bromobenzene

A solution of 2-bromophenethyl alcohol (5.05 g, 25.1 mmol) and pyridine (3.65 mL, 45.2 mmol) in acetonitrile (60 mL) was treated with Ph$_3$PBr$_2$ (13.8 g, 32.65 mmol), stirred at 0° C. for 2 h, diluted with hexanes and filtered through a plug of silica gel with 25% diethyl ether/hexanes to provide 6.0 g of the title compound.

MS (DCI/NH$_3$) m/e 263 (M+H)$^+$.

EXAMPLE 58B 2-(2-Thiomethoxyethyl)bromobenzene

A solution of Example 58A (990 mg, 3.75 mmol) and sodium thiomethoxide (290 mg, 4.12 mmol) in DMF (5 mL) was heated at 90° C. for 5 h, cooled and chromatographed on silica gel with 1% ethyl acetate/hexanes to provide 646 mg of the title compound. MS (DCI/NH$_3$) m/e 231, 233 (M+H)$^+$.

EXAMPLE 58C

6-[2-(2-Thiomethoxyethyl)phenyl]-2-naphthalenecarbonitrile

The title compound was prepared from Example 58B (300 mg, 1.30 mmol), Example 57A (260 mg, 1.32 mmol) and the procedure described in Example 57B. MS (DCI/NH$_3$) m/e 321 (M+NH$_4$)$^+$.

EXAMPLE 58D

6-[2-(2-Thiomethoxoxyethyl)phenyl]naphthalene-2-carboximidamide mono(methanesulfonate) salt The title compound was prepared from Example 58C and the procedure from Example 55D.

$^1$H NMR (300 MHz, DMSO-d$_6$) δ 1.78 (s, 3H), 2.31 (s, 3H), 2.55 (m, 2H), 2.85 (m, 2H), 7.30–7.48 (m, 4H), 7.66 (dd, 1H), 7.85 (dd, 1H), 8.04 (s, 1H), 8.18 (d, 1H), 8.20 (d, 1H), 8.55 (s, 1H), 9.01 (br s, 2H), 9.43 (br s, 2H); MS (DCI/NH$_3$) m/e 321 (M+H)$^+$. Anal. calcd for C$_{20}$H$_{20}$N$_2$S$_2$.1.35CH$_3$SO$_3$H: C, 56.96; H, 5.69; N, 6.22. Found: C, 57.08; H, 5.49; N, 6.14.

EXAMPLE 59

7-Methoxy-8-(3-furanyl)-2-naphthalenecarboximidamide mono (methanesulfonate) salt

EXAMPLE 59A

7-Methoxy-8-(3-furanyl)-2-naphthalenecarbonitrile

The title compound was prepared from Example 53B, furan-3-boronic acid (873 mg, 7.80 mmol) and the procedure of Example 57B.

MS (DCI/NH$_3$) m/e 267 (M+NH$_4$)$^+$.

EXAMPLE 59B

7-Methoxy-8-(3-furanyl)-2-naphthalenecarboximidamide mono (methanesulfonate) salt The title compound was prepared from Example 58C and the procedure from Example 55D.

$^1$H NMR (300 MHz, DMSO-d$_6$) δ 2.34 (s, 3H), 3.91 (s, 3H), 6.76 (s, 2H), 7.62 (dd, 1H), 7.74 (d, 1H), 7.87 (dd, 1H), 7.96 (s, 1H), 8.12 (d, 1H), 8.15 (d, 1H), 8.25 (s, 1H), 8.96 (br s, 2H), 9.35 (br s, 2H); MS (DCI/NH$_3$) m/e 267 (M+H)$^+$. Anal. calcd for C$_{16}$H$_{14}$N$_2$O$_2$.CH$_3$SO$_3$H: C, 55.77; H, 5.00; N, 7.63. Found: C, 55.73; H, 4.61; N, 7.48.

EXAMPLE 60

7-Methoxy-8-(2-benzofuranyl)naphthalene-2-carboximidamide mono(methanesulfonate) salt

EXAMPLE 60A

7-Methoxy-8-(2-benzofuranyl)-2-naphthalenecarbonitrile

The title compound was prepared from Example 53B (166 mg, 0.50 mmol), benzofuran-2-boronic acid (113 mg, 0.70 mmol) and the procedure of Example 57B.

MS (DCI/NH$_3$) m/e 317 (M+NH$_4$)$^+$.

EXAMPLE 60B

7-Methoxy-8-(2-benzofuranyl)naphthalene-2-carboximidamide mono(methanesulfonate) salt The title compound was prepared from Example 60A (72 mg, 0.240 mmol) and the procedure from Example 55D.

$^1$H NMR (300 MHz, DMSO-d$_6$) δ 2.30 (s, 3H), 3.98 (s, 3H), 7.24 (s, 1H), 7.36 (m, 2H), 7.67 (m, 2H), 7.75 (m, 1H), 7.84 (d, 1H), 8.21 (d, 1H), 8.30 (d, 1H), 8.32 (s, 1H), 8.88 (br s, 2H), 9.39 (br s, 2H); MS (DCI/NH$_3$) m/e 317 (M+H)$^+$. Anal. calcd for C$_{20}$H$_{16}$N$_2$O$_2$.1.3CH$_3$SO$_3$H: C, 57.98; H, 4.84; N, 6.35. Found: C, 57.79; H, 4.78; N, 6.22.

EXAMPLE 61

(E)-8-[2-(1,3-Benzodioxol-5-yl)ethenyl]-2-naphthalenecarboximidamide mono (methanesulfonate) salt

EXAMPLE 61A (E)-8-[2-(1,3-Benzodioxol-5-yl)ethenyl]-2-naphthalenecarbonitrile Example 53B (75 mg, 0.243 mmol), PdCl$_2$(dppf) (20 mg, 0.024 mmol), 3,4-methylenedioxystyrene (43 mg, 0.291 mmol) and diisopropylethylamine (0.170 mL, 0.97 mmol) in N-methylpyrrolidinone (2 mL) were stirred at 90° C. for 18 h, cooled to room temperature and chromatographed on silica gel with 20% ethyl acetate/hexanes to provide 46 mg of the title compound.

MS (DCI/NH$_3$) m/e 347 (M+NH$_4$)$^+$.

EXAMPLE 61B (E)-8-[2-(1,3-Benzodioxol-5-yl)ethenyl]-2-naphthalenecarboximidamide mono (methanesulfonate) salt The title compound was prepared from Example 61A (43 mg, 0.131 mmol) and the procedure from Example 55D.

$^1$H NMR (300 MHz, DMSO-d$_6$) δ 2.32 (s, 3H), 4.01 (s, 3H), 6.07 (s, 2H), 6.96 (d, 2H), 7.10 (d, 2H), 7.32 (d, 2H), 7.45 (s, 1H), 7.56 (d, 1H), 7.66 (d, 2H), 7.72 (d, 1H), 8.06 (s, 1H), 8.03 (d, 1H), 8.12 (d, 1H), 8.66 (s, 1H), 8.96 (br s, 2H), 9.44 (br s, 2H); MS (DCI/NH$_3$) m/e 347 (M+H)$^+$. Anal. calcd for C$_{21}$H$_{18}$N$_2$O$_3$·1.1CH$_3$SO$_3$H: C, 58.72; H, 4.99; N, 6.20. Found: C, 58.77; H, 5.07; N, 5.99.

EXAMPLE 62

(±)-7-Methoxy-8-(tetrahydro-3-furanyl)-2-naphthalenecarboximidamide mono (methanesulfonate) salt

EXAMPLE 62A (±)-7-methoxy-8-[3-hydroxy-1-(hydroxymethyl)-1-propenyl]-2-naphthalenecarbonitrile A solution of Example 53B (3.09 g, 10 mmol), PdCl$_2$ (120 mg, 1 mmol), cis-2-butene-1,4-diol (1.23 mL, 15 mmol) and NaHCO$_3$ (1.01 g, 12 mmol) in N-methylpyrrolidinone (10 mL) was stirred at 130° C. for 1 h, cooled to room temperature and chromatographed on silica gel with 30% ethyl acetate/hexanes to provide 2.19 g of the title compound as a mixture of diastereomers.

MS (DCI/NH$_3$) m/e 269 (M+H)$^+$.

EXAMPLE 62B (±)-7-Methoxy-8-(tetrahydro-3-furanyl)-2-naphthalenecarbonitrile Example 62A (140 mg, 0.52 mmol) in methylene chloride (3 mL) at 0° C. was treated with triethylsilane (0.166 mL, 1.04 mmol) and BF$_3$·OEt$_2$ (0.096 mL, 0.78 mmol), stirred at room temperature for 4 h, concentrated and chromatographed on silica gel with 25% ethyl acetate/hexanes to provide 100 mg of the title compound.

MS (DCI/NH$_3$) m/e 271 (M+NH$_4$)$^+$.

EXAMPLE 62C (±)-7-Methoxy-8-(tetrahydro-3-furanyl)-2-naphthalenecarboximidamide mono (methanesulfonate) salt The title compound was prepared from Example 62B (96 mg, 0.379 mmol) and the procedure from Example 55D.

$^1$H NMR (300 MHz, DMSO-d$_6$) δ 2.20 (m, 1H), 2.33 (m, 1H), 2.39 (s, 3H), 3.99 (s, 3H), 3.90–4.03 (m, 3H), 4.11 (m, 1H), 4.42 (m, 1H), 7.64 (d, 1H), 7.68 (d, 1H), 8.01 (d, 1H), 8.10 (d, 1H), 8.70 (s, 1H), 9.01 (br s, 2H), 9.41 (br s, 2H), MS (DCI/NH$_3$) m/e 271 (M+H)$^+$. Anal. calcd for C$_{16}$H$_{18}$N$_2$O$_2$·1.2CH$_3$SO$_3$H: C, 53.57; H, 5.96; N, 7.26. Found: C, 53.67; H, 5.78; N, 6.72.

EXAMPLE 63

6-[[4-(2-Aminoethyl)phenyl]ethynyl]-2-naphthalenecarboximidamide mono(trifluoroacetate)

EXAMPLE 63A 6-(Trimethylsilylethynyl)-2-naphthalenecarbonitrile

Example 28B and trimethylsilylacetylene were submitted to the conditions described in Example 42° C. to provide the title compound.

MS (DCI/NH$_3$) m/e 267 (M+NH$_4$)$^+$.

EXAMPLE 63B

6-Ethynyl-2-naphthalenecarbonitrile

A mixture of Example 63A (0.4 g, 1.6 mmole) and K$_2$CO$_3$ (0.4 g, 3.2 mmole) in methanol (16 mL) was stirred at room temperature for 18 h, concentrated, treated with water and extracted with methylene chloride. The organic layer was washed with 0.5 NHCl and brine, dried (MgSO$_4$) and evaporated to provide the title compound.

MS (DCI/NH$_3$) m/e 195 (M+NH$_4$)$^+$.

EXAMPLE 63C

4-Bromo-(N-tert-butoxycarbonyl)phenethylamine

4-Bromophenethylamine and di-t-butyldicarbonate were subjected to the conditions described in Synthesis, 48, 1986 to provide the title compound. MS (DCI/NH$_3$) m/e 319 (M+NH$_4$)$^+$.

EXAMPLE 63D

6-[[4-(2-N-tert-butoxycarbonylaminoethyl)phenyl] ethynyl]-2-naphthalenecarbonitrile The title compound was obtained with Examples 63B and C from the procedure described in Example 57B to provide the title compound.

MS (DCI/NH$_3$) m/e 414 (M+NH$_4$)$^+$.

EXAMPLE 63E

6-[[4-(2-Aminoethyl)phenyl]ethynyl]-2-naphthalenecarboximidamide mono(trifluoroacetate)

The title compound was prepared with Example 63D and the procedure of Example 5B.

$^1$H NMR (300 MHz, DMSO-d$_6$) δ 2.90 (t, 2H), 3.09 (m, 2H) 7.36 (d, 2H), 7.60 (d, 2H), 7.76 (d, 2H), 7.76 (dd, 1H), 7.85 (s, 2H), 7.87 (dd, 1H), 8.13 (d, 1H), 8.18 (d, 1H), 8.31 (s, 1H), 8.50 (s, 1H), 9.18 (s, 2H), 9.45 (s, 2H); MS (DCI/NH$_3$) m/e 314 (M+H)$^+$. Anal. calcd for C$_{21}$H$_{19}$N$_3$·2TFA·H$_2$O: C, 53.67; H, 4.14; N, 7.15. Found: C, 53.37; H, 3.93; N, 7.17.

EXAMPLE 64

7-Methoxy-8-[2-pyrimidinyl(oxy)]-2-naphthalenecarboximidamide mono(trifluoroacetate)

EXAMPLE 64A

7-Methoxy-8-[2-pyrimidinyl(oxy)]-2-naphthalenecarbonitrile

Example 4A (125 mg, 0.627 mmol) and 2-chloropyrimidine (143 mg, 1.25 mmol) were subjected to the procedure described in Example 6A to provide 101 mg of the title compound.

MS (DCI/NH$_3$) m/e 278 (M+H)$^+$.

EXAMPLE 64B

7-Methoxy-8-[2-pyrimidinyl(oxy)]-2-naphthalenecarboximidamide mono(trifluoroacetate)

The title compound was prepared with Example 64A and the procedure of Example 1B.

$^1$H NMR (300 MHz, DMSO-d$_6$) δ 2.51 (s, 3H), 3.83 (s, 3H), 7.18 (t, 1H), 7.70 (dd, 1H), 7.80 (d, 1H), 8.05 (d, 1H), 8.19 (d, 1H), 8.34 (s, 1H), 8.62 (d, 2H), 9.07 (br s, 2H), 9.45 (br s, 2H); MS (DCI/NH$_3$) m/e 295 (M+H)$^+$. Anal. calcd for C$_{20}$H$_{16}$N$_4$O$_4$.1.33TFA: C, 40.48; H, 2.60; N, 8.35. Found: C, 40.25; H, 2.94; N, 8.92.

EXAMPLE 65

7-Methoxy-8-[2-thiazoyl(oxy)]naphthalene-2-carboximidamide mono(trifluoroacetate) salt

EXAMPLE 65A

7-Methoxy-8-[2-thiazoyl(oxy)]-2-naphthalenecarbonitrile

A mixture of Example 4A (250 mg, 1.25 mmol), 2-bromothiazole (225 mL, 2.50 mmol) and CsF (209 mg, 1.38 mmol) in DMSO (4 mL) was stirred at 120° C. for 4 days, cooled and chromatographed on silica gel with 30% ethyl acetate/hexanes to provide 162 mg of the title compound.

MS (DCI/NH$_3$) m/e 283 (M+H)$^+$.

EXAMPLE 65B

7-Methoxy-8-[2-thiazoyl(oxy)]naphthalene-2-carboximidamide mono(trifluoroacetate) salt The title compound was prepared with Example 65A and the procedure of Example 1B. $^1$H NMR (300 MHz, DMSO-d$_6$) δ 3.98 (s, 3H) 7.25 (m, 2H), 7.73 (dd, 1H), 7.86 (d, 1H), 8.12 (d, 1H), 8.22 (d, 1H), 8.35 9.09 (bs, 2H), (s, 1H), 9.48 (bs, 2H). MS (DCI/NH$_3$) m/e 300 (M+H)$^+$. Anal. calcd for C$_{15}$H$_{13}$N$_3$O$_2$S.TFA: C, 49.40; H, 3.41; N, 10.70. Found: C, 49.10; H, 3.40; N, 10.69.

EXAMPLE 66

7-Methoxy-8-(4-nitrophenoxy)-2-naphthalenecarboximidamide mono(trifluoroacetate) salt

EXAMPLE 66A

7-Methoxy-8-(4-nitrophenoxy)-2-naphthalenecarbonitrile

The title compound was prepared from Example 4A (125 mg, 0.627 mmol), 1,4-dinitrobenzene (143 mg, 1.25 mmol) and the procedure described in Example 65A to provide 227 mg of the title compound.

MS (DCI/NH$_3$) m/e 338 (M+NH$_4$)$^+$.

EXAMPLE 66B

7-Methoxy-8-(4-nitrophenoxy)-2-naphthalenecarboximidamide mono(trifluoroacetate) salt The title compound was prepared with Example 66A and the procedure of Example 55D.

$^1$H NMR (300 MHz, DMSO-d$_6$) δ 9.43 (br s, 2H), 8.94 (br s, 2H), 8.25 (m, 4H), 8.15 (d, 1H), 7.88 (d, 1H), 7.72 (dd, 1H), 7.05 (d, 2H), 3.91 (s, 3H), 2.30 (s, 3H); MS (DCI/NH$_3$) m/e 338 (M+H)$^+$. Anal. calcd for C$_{18}$H$_{15}$N$_3$O$_4$.1.75CH$_3$SO$_3$H: C, 46.93; H, 4.39; N, 8.31. Found: C, 47.17; H, 4.32; N, 8.12.

EXAMPLE 67

7-Methoxy-8-pentafluorophenoxy-2-naphthalenecarboximidamide mono(trifluoroacetate) salt

EXAMPLE 67A

7-Methoxy-8-pentafluorophenoxy-2-naphthalenecarbonitrile

Example 4A (100 mg, 0.50 mmol) and hexafluorobenzene (115 mL, 1.00 mmol) were subjected to the procedure described in Example 65A to provide 150 mg of the title compound.

MS (DCI/NH$_3$) m/e 383 (M+NH$_4$)$^+$.

EXAMPLE 67B

7-Methoxy-8-pentafluorophenoxy-2-naphthalenecarboximidamide mono(trifluoroacetate) salt The title compound was prepared with Example 67A and the procedure of Example 55D.

$^1$H NMR (300 MHz, DMSO-d$_6$) δ 2.31 (s, 3H), 3.82 (s, 3H), 7.87 (dd, 1H), 7.88 (d, 1H), 8.02 (d, 1H), 8.20 (d, 1H), 8.65 (s, 1H), 9.04 (br s, 2H), 9.47 (br s, 2H); MS (DCI/NH$_3$) m/e 383 (M+H)$^+$. Anal. calcd for C$_{18}$H$_{11}$N$_2$F$_5$O$_2$.1.2CH$_3$SO$_3$H: C, 46.67; H, 3.19; N, 5.68. Found: C, 46.55; H, 3.00; N, 5.58.

EXAMPLE 68

7-Methoxy-8-[N-2-phenylamino)]-2-naphthalenecarboximidamide mono(trifluoroacetate) salt

EXAMPLE 68A

7-Methoxy-8-[N-2-phenyl(amino)]-2-naphthalenecarbonitrile

A solution of Example 25A (309 mg, 1.00 mmol), aniline (0.109 mL, 1.2 mmol), NaO$^t$Bu (115 mg, 1.2 mmol), Pd$_2$(dba)$_3$ (10 mg, 0.01 mmol) and dppf (17 mg, 0.03 mmol) in toluene (5 mL) was stirred for 3 h at 100° C., cooled and chromatographed on silica gel with 10% ethyl acetate/hexanes to provide 175 mg of the title compound.

MS (DCI/NH$_3$) m/e 275 (M+H)$^+$.

EXAMPLE 68B

7-Methoxy-8-(N-2-phenylamino)-2-naphthalenecarboximidamide mono(trifluoroacetate) salt The title compound was prepared with Example 68A and the procedure of Example 55D.

$^1$H NMR (300 MHz, DMSO-d$_6$) δ 3.95 (s, 3H), 5.92 (bs, 1H), 6.61 (d, 2H), 6.94 (t, 1H), 7.16 (dd, 2H), 7.45 (dd, 1H), 7.48 (d, 1H), 7.76 (d, 1H), 7.88 (d, 1H), 8.13 (d, 1H), 9.08

(bs, 2H), 9.31 (bs, 2H). MS (DCI/NH$_3$) m/e 292 (M+H)$^+$. Anal. Calcd for C$_{18}$H$_{17}$N$_3$O.TFA: C, 59.26; H, 4.48; N, 10.37. Found: C, 59.20; H, 4.32; N, 10.15.

EXAMPLE 69

N-(6-Aminoiminomethyl-2-naphthalenyl)-N'-benzylurea mono(trifluoroacetate) salt

EXAMPLE 69A

N-(6-Cyano-2-naphthalenyl)-N'-benzylurea

The title compound was prepared with Example 40A, benzylamine and the procedure from Example 40B.
MS (DCI/NH$_3$) m/e 302 (M+H)$^+$.

EXAMPLE 69B

N-(6-Aminoiminomethyl-2-naphthalenyl)-N'-benzylurea mono(trifluoroacetate) salt

The title compound was prepared with Example 69A and the procedure from Example 40D.
$^1$H NMR (300 MHz, DMSO-d$_6$) δ 4.35 (d, 2H), 6.91 (t, 1H), 7.35–724 (m, 5H), 7.59 (dd, 1H), 7.72 (dd, 1H), 7.95 (d, 1H), 7.96 (d, 1H), 8.22 (d, 1H), 8.35 (d, 1H), 8.92 (br s, 2H), 9.13 (s, 1H), 9.32 (br s, 2H). MS (DCI/NH$_3$) m/e 319 (M+H)$^+$. Anal. calcd for C$_{19}$H$_{18}$N$_4$O.TFA: C, 50.57; H, 4.24; N, 15.72. Found: C, 50.34; H, 4.15; N, 15.54.

EXAMPLE 70

N-(6-Aminoiminomethyl-2-naphthalenyl)-N'-methylurea mono(trifluoroacetate) salt

EXAMPLE 70A

N-(6-Cyano-2-naphthalenyl)-N'-methylurea

The title compound was prepared with Example 40A (221.2 mg, 1.00 mmole) and methylamine (2.3 mL, 2.34 mmol) in THF (10 mL) according to the procedure from Example 40B.
MS (DCI/NH$_3$) m/e 226 (M+H)$^+$.

EXAMPLE 70B

N-(6-Aminoiminomethyl-2-naphthalenyl)-N'-methylurea mono(trifluoroacetate) salt

The title compound was prepared with Example 70A and the procedure of Example 40D.
$^1$H NMR (300 MHz, DMSO-d$_6$) δ 2.69 (d, 3H), 6.32 (q, 1H), 7.60 (dd, 1H), 7.73 (dd, 1H), 7.93 (d, 1H), 7.95 (d, 1H), 8.19 (d, 1H), 8.49 (d, 1H), 9.09 (s, 1H), 9.15 (br. s, 4H); MS (DCI/NH$_3$) m/e 243 (M+H)$^+$. Anal. calcd for C$_{13}$H$_{14}$N$_4$O.TFA: C, 50.57; H, 4.24; N, 15.72. Found: C, 50.34; H, 4.15; N, 15.54.

EXAMPLE 71

N-(6-Aminoiminomethyl-2-naphthalenyl)-N'-isopropylurea mono(trifluoroacetate) salt

EXAMPLE 71A

N-(6-Cyano-2-naphthalenyl)-N'-isopropylurea

The title compound was prepared with Example 40A, isopropylamine and the procedure from Example 40B.
MS (DCI/NH$_3$) m/e 254 (M+H)$^+$.

EXAMPLE 71B

N-(6-Aminoiminomethyl-2-naphthalenyl)-N'-isopropylurea mono(trifluoroacetate) salt The title compound was prepared with Example 71A and the procedure of Example 5B.
$^1$H NMR (300 MHz, DMSO-d$_6$) δ 1.13 (d, 6H), 3.76–3.84 (m, 1H), 6.28 (d, 1H), 7.55 (dd, 1H), 7.72 (dd, 1H), 7.94 (d, 1H), 7.95 (d, 1H), 8.19 (d, 1H), 8.34 (d, 1H), 8.85 (s, 1H), 9.3 (br s, 2H), 9.0 (br s, 2H); MS (DCI/NH$_3$) m/e 271 (M+H)$^+$. Anal. calcd for C$_{15}$H$_{18}$N$_4$O.TFA: C, 53.12; H, 4.98; N, 14.58. Found: C, 15.13; H, 4.84; N, 14.50.

EXAMPLE 72

N-(6-Aminoiminomethyl-2-naphthalenyl)-N'-phenyl-N'-methylurea mono(trifluoroacetate) salt

EXAMPLE 72A

N-(6-Cyano-2-naphthalenyl)-N'-phenyl-N'-methylurea

The title compound was prepared with Example 40A, N-methyl-N-phenylamine and the procedure from Example 40B.
MS (DCI/NH$_3$) m/e 302 (M+H)$^+$.

EXAMPLE 72B

N-(6-Aminoiminomethyl-2-naphthalenyl)-N'-phenyl-N'-methylurea mono(trifluoroacetate) salt The title compound was prepared with Example 72A and the procedure of Example 40D.
$^1$H NMR (300 MHz, DMSO-d$_6$) δ 3.33 (s, 3H), 7.25–7.47 (m, 5H), 7.71–7.77 (m, 2H), 7.95 (two overlaping doublets, 2H), 8.16 (d, 1H), 8.35 (d, 1H), 8.64 (s, 1H), 8.96 (br s, 2H), 9.34 (br s, 2H); MS (DCI/NH$_3$) m/e 319 (M+H)$^+$. Anal. calcd for C$_{20}$H$_{17}$N$_4$O.TFA: C, 58.33; H, 4.43; N, 11.96. Found: C, 58.38; H, 4.69; N, 11.82.

EXAMPLE 73

6-Aminonaphthalene-2-carboximidamide mono(trifluoroacetate) salt

EXAMPLE 73A

6-Phenylcarbamoyl-2-naphthalenecarbonitrile

The title compound was prepared from Example 40A, phenol and the procedure from Example 40B.
MS (DCI/NH$_3$) m/e 289 (M+H)$^+$.

EXAMPLE 73B

6-Aminonaphthalene-2-carboximidamide mono(trifluoroacetate) salt

The title compound was prepared from Example 73A and the procedure of Example 40D.
$^1$H NMR (300 MHz, DMSO-d$_6$) δ 6.01 (br s, 2H), 6.86 (d, 1H), 7.06 (dd, 1H), 7.58–7.67 (m, 2H), 7.74 (d, 1H), 8.21 (d, 1H), 8.74 (br s, 2H), 9.16 (br s, 2H); MS (DCI/NH$_3$) m/e 196 (M+H)$^+$. Anal. calcd for C$_{12}$H$_{10}$N$_3$.TFA: C, 52.18; H, 4.04; N, 14.04. Found: C, 51.92; H, 3.87; N, 13.80.

EXAMPLE 74

N-(6-aminoiminomethyl-2-naphthalenyl)-N'-cyclohexylurea mono(trifluoroacetate) salt

EXAMPLE 74A

N-(6-Cyano-2-naphthalenyl)-N'-cyclohexylurea

The title compound was prepared with Example 40A, cyclohexylamine and the procedure from Example 40B. MS (DCI/NH$_3$) m/e 294 (M+H)$^+$.

EXAMPLE 74B

N-(6-aminoiminomethyl-2-naphthalenyl)-N'-cyclohexylurea mono(trifluoroacetate) salt The title compound was prepared with Example 74A and the procedure of Example 40D.
$^1$H NMR (300 MHz, DMSO-d$_6$) δ 1.14–1.39 (m, 5H), 1.54–1.58 (m, 1H), 1.65–1.72 (m, 2H), 1.81–1.86 (m, 2H), 3.46–3.52 (m, 1H), 6.36 (d, 1H), 7.55 (dd, 1H), 7.72 (dd, 1H), 7.93 (d, 1H), 7.95 (d, 1H), 8.18 (d, 1H), 8.35 (d, 1H), 8.87 (s, 1H), 9.00 (br s, 2H), 9.28 (br s, 2H); MS (DCI/NH$_3$) m/e 311 (M+H)$^+$. Anal. calcd for C$_{19}$H$_{21}$N$_4$O.TFA: C, 56.60; H, 5.46; N, 13.20. Found: C, 56.61; H, 5.72; N, 13.03.

EXAMPLE 75

N-(6-aminoiminomethyl-2-naphthalenyl)-N'-benzyloxyurea mono(trifluoroacetate) salt

EXAMPLE 75A

N-(6-cyano-2-naphthalenyl)-N'-benzyloxyurea

The title compound was prepared with Example 40A, O-benzylhydroxylamine and the procedure from Example 40B.
MS (DCI/NH$_3$) m/e 318 (M+H)$^+$.

EXAMPLE 75B

N-(6-aminoiminomethyl-2-naphthalenyl)-N'-benzyloxyurea mono(trifluoroacetate) salt The title compound was prepared with Example 75A and the procedure of Example 40D.
$^1$H NMR (300 MHz, DMSO-d$_6$) δ 4.87 (s, 2H), 7.25–7.42 (m, 3H), 7.48–7.51 (m, 2H), 7.75 (dd, 1H), 7.75 (dd, 1H), 7.97 (d, 2H), 8.30 (d, 1H), 8.38 (d, 1H), 8.97 (br s, 2H), 9.21 (s, 1H), 9.35 (br s, 2H), 9.77 (s, 1H); MS (DCI/NH$_3$) m/e 335 (M+H)$^+$. Anal. calcd for C$_{19}$H$_{18}$N$_4$O$_2$.TFA: C, 56.25; H, 4.27; N, 12.49. Found: C, 56.26; H, 4.39; N, 12.30.

EXAMPLE 76

1,1-Dimethylethyl [4-[[(6-aminoiminomethyl-2-naphthalenyl)amino]carbonyl]phenyl]carbamate mono(trifluoroacetate) salt

EXAMPLE 76A

6-Amino-2-naphthalenecarbonitrile

Sulfuric acid (45 mL) was treated with Example 40B (6.5 g), stirred for 30 min, warmed to room temperature for 20 min, poured onto ice, diluted with water to approximately 500 mL, cooled to 0° C. and treated with 50% aq sodium hydroxide such that the temperature did not exceed 35° C. The light solid which precipitated was filtered, washed with water to pH 7, dried under vacuum and purified on silica gel with 20% ethyl acetate/hexanes to provide 3.3 g of the title compound. MS (DCI/NH$_3$) m/e 169 (M+H)$^+$.

EXAMPLE 76B 1,1-Dimethylethyl [4-[[(6-cyano-2-naphthalenyl)amino]carbonyl]phenyl]carbamate mono(trifluoroacetate) salt The title compound was prepared from Example 76A, 4-N-Boc-aminomethylbenzoic acid, the procedure from Example 35B with methylene chloride in place of THF. MS (DCI/NH$_3$) m/e 417 (M+H)$^+$.

EXAMPLE 76C 1,1-Dimethylethyl [4-[[(6-aminoiminomethyl-2-naphthalenyl)amino]carbonyl]phenyl]carbamate mono(trifluoroacetate) salt The title compound was prepared with Example 76B and the procedure of Example 40D.
$^1$H NMR (300 MHz, DMSO-d$_6$) δ 3.30 (s, 9H), 4.22 (d, 2H), 7.42 (d, 2H), 7.49 (t, 1H), 7.79 (dd, 1H), 7.95–8.00 (m, 3H), 8.09 (d, 2H), 8.42 (s, 1H), 8.63 (d, 1H), 9.18 (br s, 4H), 10.58 (s, 1H); MS m/e 434 (M+H)$^+$. Anal. calcd for C$_{24}$H$_{27}$N$_5$O$_3$.TFA: C, 59.56; H, 5.00; N, 10.29. Found: C, 58.55; H, 4.85; N, 10.41.

EXAMPLE 77

N-[6-(Aminoiminomethyl)-2-naphthalenyl]-4-(aminomethyl)benzamide mono(trifluoroacetate) salt

EXAMPLE 77A

N-[6-(Aminoiminomethyl)-2-naphthalenyl]-4-(aminomethyl)benzamide mono(trifluoroacetate) salt A solution of Example 76B (35 mg, 0.07 mmole) in 1:1 TFA/methylene chloride was stirred at room temperature for 1 h then concentrated. The residue was dissolved in water (12 mL), filtered through a 0.45μ filter and concentrated. The solid was suspended in diethyl ether and filtered to yield 27 mg of the title compound as a white solid.
$^1$H NMR (300 MHz, DMSO-d$_6$) δ 4.17 (q, 2H), 7.65 (d, 2H), 7.80 (dd, 1H), 7.99 (dd, 1H), 8.06–8.12 (m, 4H), 8.30 (br s, 2H), 8.44 (d, 1H), 8.64 (d, 1H), 9.13 (br s, 2H), 9.40 (br s, 2H), 10.70 (s, 1H); MS (DCI/NH$_3$) m/e 319 (M+H)$^+$. Anal. calcd for C$_{19}$H$_{18}$N$_4$O.2.25TFA.0.5H$_2$O: C, 48.34; H, 3.67; N, 9.59. Found: C, 48.45; H, 3.74; N, 9.45.

EXAMPLE 78

Ethyl [6-(aminoiminomethyl)-2-naphthalenyl]carbamate mono(trifluoroacetate) salt

EXAMPLE 78A

Ethyl (6-cyano-2-naphthalenyl)carbamate mono(trifluoroacetate) salt

The title compound was prepared with Example 40A, ethanol and the procedure from Example 40B.
MS (DCI/NH$_3$) m/e 241 (M+H)$^+$.

EXAMPLE 78B

Ethyl [6-(aminoiminomethyl)-2-naphthalenyl]carbamate mono(trifluoroacetate) salt The title compound was prepared with Example 78A and the procedure of Example 40D.

¹H NMR (300 MHz, DMSO-$d_6$) δ 1.29 (t, 3H), 4.19 (q, 2H), 7.69 (dd, 1H), 7.76 (dd, 1H), 8.1 (d, 2H), 8.23 (d, 1H), 8.38 (d, 1H), 9.03 (br s, 2H), 9.33 (br s, 2H), 10.11 (s, 1H); MS (DCI/NH$_3$) m/e 258 (M+H)$^+$. Anal. calcd for $C_{14}H_{15}N_3O_2$·TFA: C, 51.76; H, 4.34; N, 11.32. Found: C, 51.32; H, 4.15; N, 10.93.

EXAMPLE 79

1,1-dimethylethyl [4-[[[6-aminoiminomethyl)-2-naphthalenyl)amino]carbonyl]amino]phenyl] carbamate mono(trifluoroacetate) salt

EXAMPLE 79A 1,1-Dimethyl-[4-[[[(6-cyano-2-naphthalenyl)amino]carbonyl]amino]phenyl]carbamate The title compound was prepared with Example 40B, 4-(N-tert-butoxycarbonylamino)-aminobenzene and the procedure from Example 40C.

MS (DCI/NH$_3$) m/e 403 (M+H)$^+$.

EXAMPLE 79B 1,1-dimethylethyl [4-[[[6-aminoiminomethyl)-2-naphthalenyl)amino]carbonyl]amino]phenyl] carbamate mono(trifluoroacetate) salt The title compound was prepared with Example 79A and the procedure of Example 40D.

¹H NMR (300 MHz, DMSO-$d_6$) δ 1.22 (s, 9H), 7.38 (s, 4H), 7.62 (dd, 1H), 7.75 (dd, 1H), 8.00 (d, 2H), 8.27 (d, 1H), 8.38 (d, 1H), 8.77 (s, 1H), 8.90 (br s, 2H), 9.16 (s, 1H), 9.20 (s, 1H), 9.33 (br s, 2H); MS (DCI/NH$_3$) m/e 420 (M+H)$^+$. Anal. calcd for $C_{23}H_{25}N_5O_3$·2TFA: C, 56.28; H, 4.91; N, 13.13. Found: C, 56.18; H, 5.07; N, 12.44.

EXAMPLE 80

(E)-6-[2-(Phenylthio)ethenyl]-2-naphthalenecarboximidamide mono(trifluoroacetate) salt

EXAMPLE 80A (E)-6-[2-(Phenylthio)ethenyl]-2-naphthalenecarbonitrile

The title compound was prepared from Example 55B, phenylvinyl sulfide and the procedure of Example 57B.

MS (DCI/NH$_3$) m/e 305 (M+NH$_4$)$^+$.

EXAMPLE 80B (E)-6-[2-(Phenylthio)ethenyl]-2-naphthalenecarboximidamide mono(trifluoroacetate) salt The title compound was prepared from Example 80A and the procedure of Example 1B.

¹H NMR (300 MHz, DMSO-$d_6$) δ 6.91 (d, 1H), 7.52–7.33 (m, 5H), 7.50 (d, 1H), 7.75–7.83 (m, 1H), 7.98–8.89 (m, 1H), 8.08–8.80 (m, 3H), 8.44 (m, 1H), 9.03 (s, 2H), 9.40 (s, 2H); MS (DCI/NH$_3$) m/e 305 (M+H)$^+$. Anal. calcd for $C_{19}H_{16}N_2S$·1.1TFA: C, 59.55; H, 4.03; N, 6.57. Found: C, 59.53; H, 4.12; N, 6.60.

EXAMPLE 81

(E)-6-[2-(2-Furanyl)ethenyl]-2-naphthalenecarboximidamide mono(trifluoroacetate) salt

EXAMPLE 81A

2-Vinylfuran

A solution of methyl(triphenylphosphonium)bromide (26.78 g, 75 mmol) in toluene (80 mL) was treated with butyllithium in hexanes (27.5 mL, 68.75 mmol) then furfural (6 g, 62.5 mmol), stirred for 0.5 h and distilled at 69–72° C. to provide the title compound as a clear, colorless liquid with some toluene contaminant.

MS (DCI/NH$_3$) m/e 83 (M+H)$^+$.

EXAMPLE 81B (E)-6-[2-(2-Furanyl)ethenyl]-2-naphthalenecarbonitrile

The title compound was prepared from Examples 55B and 81A and the procedure of Example 57B.

MS (DCI/NH$_3$) m/e 263 (M+NH$_4$)$^+$.

EXAMPLE 81C (E)-6-[2-(2-Furanyl)ethenyl]-2-naphthalenecarboximidamide mono(trifluoroacetate) salt The title compound was prepared from Example 81B and the procedure of Example 1B.

¹H NMR (300 MHz, DMSO-$d_6$) δ 6.61 (dd, 1H), 6.66 (d, 1H), 7.19 (d, 1H), 7.38 (d, 1H), 7.77 (d, 1H), 7.80 (dd, 1H), 8.14–7.97 (m, 3H), 8.44 (s, 1H), 9.05 (s, 2H), 9.42 (s, 2H); MS (DCI/NH$_3$) m/e 263 (M+H)$^+$. Anal. calcd for $C_{17}H_{13}N_2O$·1.2TFA: C, 58.49; H, 3.85; N, 7.04. Found: C, 58.45; H, 3.78; N, 7.36.

EXAMPLE 82

(E)-6-[2-(1H-Imidazol-1-yl)ethenyl]-2-naphthalenecarboximidamide mono(trifluoroacetate)

EXAMPLE 82A (E)-6-[2-(1H-Imidazol-1-yl)ethenyl]-2-naphthalenecarbonitrile

The title compound was prepared from Example 55B, 1-vinylimidazole and the procedure of Example 42C.

MS (DCI/NH$_3$) m/e 263 (M+NH$_4$)$^+$.

EXAMPLE 82B (E)-6-[2-(1H-Imidazol-1-yl)ethenyl]-2-naphthalenecarboximidamide mono(trifluoroacetate)

The title compound was prepared from Example 82B and the procedure of Example 40D.

¹H NMR (300 MHz, DMSO-$d_6$) δ 9.44 (s, 2H), 9.14 (s, 2H), 8.15 (d, 1H), 8.17–8.05 (m, 4H), 7.93 (d, 1H), 7.84 (dd, 1H), 7.59 (s, 1H), 7.49 (d, 1H); MS (DCI/NH$_3$) m/e 263 (M+H)$^+$. Anal. calcd for $C_{16}H_{13}N_4$·2.7TFA: C, 45.28; H, 2.97; N, 9.91. Found: C, 45.33; H, 3.52; N, 9.79.

EXAMPLE 83

(E)-4-[2-(6-Aminoiminomethyl-2-naphthalenyl)ethenyl]benzenesulfonamide mono(trifluoroacetate) salt

EXAMPLE 83A 4-vinylsulfonamide

A solution of thionyl chloride (7.5 mL) and 4-t-butylcatachol (45 mg, 0.3 mmol) in DMF (9 mL) at 0° C. was treated with 4-vinylbenzene sulfonic acid sodium salt (3 g, 14.6 mmol), stirred for 6 h, stored at −10° C. for 3 days, poured into ice water and extracted with benzene. The organic layer was washed with water, dried ($Na_2SO_4$), filtered and concentrated to provide 4-vilylsulfonyl chloride as a clear, colorless oil. A portion of the chloride (1 g, 4.95 mmol) was disslolved in THF (10 mL), cooled to 0° C., treated dropwise with concentrated ammonium hydroxide until gas evolution ceased and extracted with ethyl acetate. The combined extracts were dried ($Na_2SO_4$), and concentrated to provide 707 mg of the title compound as a pale yellow solid.

MS ($DCI/NH_3$) m/e 201($M+NH_4$)+.

EXAMPLE 83B (E)-4-[2-(6-Cyano-2-naphthalenyl)ethenyl] benzenesulfonamide

The title compound was prepared from Example 55B, Example 83A and the procedure of Example 57B.

MS ($DCI/NH_3$) m/e 352 ($M+NH_4$)+.

EXAMPLE 83C (E)-4-[2-(6-Aminoiminomethyl-2-naphthalenyl) ethenyl]benzenesulfonamide mono(trifluoroacetate) salt The title compound was prepared from Example 83B and the procedure of Example 40D.

$^1$H NMR (300 MHz, DMSO-$d_6$) δ 9.43 (s, 2H), 9.05 (s, 2H), 8.46 (s, 1H), 8.21 (s, 1H), 8.16–7.95 (m, 3H), 7.86 (s, 2H), 7.84–7.67 (m, 2H), 7.62 (d, 1H), 7.4–7.36 (m, 2H); MS ($DCI/NH_3$) m/e 352 ($M+H$)+. Anal. calcd for $C_{19}H_{17}N_3O_2S.1.5C_2F_3O_2H$: C, 50.84; H, 3.59; N, 8.11. Found: C, 50.83; H, 3.89; N, 7.88.

EXAMPLE 84

(E)-4-[2-(6-Aminoiminomethyl-2-naphthalenyl) ethenyl]benzoic acid mono(trifluoroacetate) salt

EXAMPLE 84A (E)-4-[2-(6-Cyano-2-naphthalenyl)ethenyl]benzoic acid

The title compound was prepared from Example 55B, 4-vinylbenzoic acid and the procedure of Example 57B.

MS ($DCI/NH_3$) m/e 300 ($M+H$)+.

EXAMPLE 84B (E)-4-[2-(6-Aminoiminomethyl-2-naphthalenyl) ethenyl]benzoic acid mono(trifluoroacetate) salt The title compound was prepared with Example 84A and the procedure of Example 40D.

$^1$H NMR (300 MHz, DMSO-$d_6$) δ 7.62–7.58 (m, 2H), 7.90 (d, 2H), 7.98 (d, 1H), 8.12–8.04 (m, 3H), 8.20 (s, 1H), 8.56 (s, 1H), 9.07 (bs, 2H), 9.35 (bs, 2H). MS ($DCI/NH_3$) m/e 317 ($M+H$)+. Anal. calcd for $C_{20}H_{16}N_2O_2.TFA$: C, 61.40; H, 3.98; N, 6.51. Found: C, 61.10; H, 3.63; N, 6.45.

EXAMPLE 85

4-[7-(Aminoiminomethyl)-2-methoxy-1-naphthalenyl]dihydro-2(3H)-furanone mono (trifluoroacetate) salt

EXAMPLE 85A 4-(7-Cyano-2-methoxy-1-naphthalenyl)dihydro-2 (3H)-furanone

Example 62A (269 mg, 1.00 mmol) and pyridinium chlorochromate (360 mg, 1.67 mmol) in methylene chloride (15 mL) were stirred at room temperature for 24 h, filtered through Celite® and concentrated. The residue was chromatographed on silica gel with 20% ethyl acetate/hexanes to provide 170 mg of the title compound.

MS ($DCI/NH_3$) m/e 285 ($M+NH_4$)+.

EXAMPLE 85B

4-[7-(Aminoiminomethyl)-2-methoxy-1-naphthalenyl]dihydro-2(3H)-furanone mono (trifluoroacetate) salt The title compound was prepared from Example 85A and the procedure of Example 40D.

$^1$H NMR (300 MHz, DMSO-$d_6$) δ 2.96–2.75 (m, 2H), 3.96 (s, 3H), 4.33 (m, 1H), 4.66 (t, 1H), 8.85 (m, 1H), 7.68 (dd, 1H), 7.73 (d, 1H), 8.08 (d, 1H), 8.12 (d, 1H), 8.67 (s, 1H), 9.14 (s, 2H), 9.43 (s, 2H); MS ($DCI/NH_3$) m/e 285 ($M+H$)+. Anal. calcd for $C_{16}H_{16}N_2O_3.1.1TFA$: C, 53.72; H, 4.24; N, 6.91. Found: C, 53.75; H, 4.26; N, 6.94.

EXAMPLE 86

7-Methoxy-8-(1-acetyl-1H-pyrazolyl)-2-naphthalenecarboximidamide mono(trifluoroacetate) salt

EXAMPLE 86A

7-Methoxy-8-(1-acetyl-1H-pyrazolyl)-2-naphthalenecarbonitrile

A solution of Example 53F (90 mg, 0.361 mmol) in THF (2 mL) was treated with a 0.5 M solution of potassium bis(trimethylsilyl)amide in toluene (0.866 mL, 0.433 mmol), stirred for 5 min, treated with acetyl chloride (38 mL, 0.542 mmol), stirred for 10 min and concentrated. The crude product was chromatographed on silica gel with 25% ethyl acetate/hexanes to yield 67 mg of the title compound.

MS MS ($DCI/NH_3$) m/e 309 ($M+NH_4$)+.

EXAMPLE 86B

7-Methoxy-8-(1-acetyl-1H-pyrazolyl)-2-naphthalenecarboximidamide mono(trifluoroacetate) salt The title compound was prepared with Example 86A and the procedure of Example 40D.

$^1$H NMR (300 MHz, DMSO-$d_6$) δ 3.89 (s, 3H), 7.59 (d, 1H), 7.92 (s, 2H), 8.06 (d, 1H), 8.12 (d, 1H), 8.28 (s, 1H), 8.94 (s, 2H), 9.34 (s, 2H); MS ($DCI/NH_3$) m/e 309 ($M+H$)+. Anal. calcd for $C_{17}H_{16}N_4O_2.1.9TFA$: C, 47.59; H, 3.44; N, 10.67. Found: C, 54.03; H, 4.06; N, 13.26.

EXAMPLE 87

7-Methoxy-8-[1-(methylsulfonyl)-1H-4-pyrazolyl]-2-naphthalenecarboximidamide mono (trifluoroacetate) salt

EXAMPLE 87A

7-Methoxy-8-[1-(methylsulfonyl)-1H-4-pyrazolyl]-2-naphthalenecarbonitrile

The title compound was prepared from Example 53F (190 mg, 0.762 mmol), methanesulfonyl chloride (0.088 mL, 1.14 mmol) and the procedure of Example 86A to provide 122 mg of the title compound.

MS (DCI/NH$_3$) m/e 345 (M+NH$_4$)$^+$.

EXAMPLE 87B

7-Methoxy-8-[1-(methylsulfonyl)-1H-4-pyrazolyl]-2-naphthalenecarboximidamide mono (trifluoroacetate) salt The title compound was prepared from Example 87A and the procedure of Example 40D.

$^1$H NMR (300 MHz, DMSO-d$_6$) δ 2.75 (s, 3H), 3.98 (s, 3H) 7.64 (dd, 1H), 7.78 (d, 1H), 8.15 (s, 1H), 8.18 (s, 1H), 8.21 (s, 1H), 8.24 (s, 1H), 8.62 (s, 1H), 8.97 (s, 2H), 9.40 (s, 2H); MS (DCI/NH$_3$) m/e 345 (M+H)$^+$. Anal. calcd for C$_{16}$H$_{16}$N$_4$O$_3$S.1.4TFA: C, 44.75; H, 3.47; N, 11.09. Found: C, 44.59; H, 3.86; N, 11.38.

EXAMPLE 88

(E)-4-[2-(6-Aminoiminomethyl-2-naphthalenyl) ethenyl]benzamide mono(trifluoroacetate) salt

EXAMPLE 88A (E)-4-[2-(6-Cyano-2-naphthalenyl)ethenyl] benzamide

Example 85A (160 mg, 0.54 mmol) in thionyl chloride (4 ml) was refluxed for 0.5 h, cooled to 0° C., treated with concentrated aqueous ammonia until gas evolution ceased, diluted with ethyl acetate, heated to dissolve residual solids, washed with water, dried (MgSO$_4$) and concentrated to provide 100 mg of the title compound as an orange solid.

MS (DCI/NH$_3$) m/e 316 (M+NH$_4$)$^+$.

EXAMPLE 88B (E)-4-[2-(6-Aminoininomethyl-2-naphthalenyl) ethenyl]benzamide mono(trifluoroacetate) salt The title compound was prepared with Example 88A and the procedure of Example 1B.

$^1$H NMR (300 MHz, DMSO-d$_6$) δ 7.34 (br, 1H), 7.51 (d, 1H), 7.56 (d, 2H), 7.73 (d, 2H), 7.82 (m, 2H), 7.90 (d, 2H), 7.96 (br, 1H), 8.09 (q, 3H), 8.17 (s, 1H), 8.43 (s, 1H), 9.01 (s, 2H), 9.40 (s, 2H); MS (DCI/NH$_3$) m/e 316 (M+H)$^+$. Anal. calcd for C$_{20}$H$_{17}$N$_3$O.1.1TFA: C, 60.09; H, 4.11; N, 9.44. Found: C, 60.22; H, 4.13; N, 8.79.

EXAMPLE 89

6-[2-(4Aminophenyl)ethoxy]-2-naphthalenecarboximidamide mono(trifluoroacetate) salt

EXAMPLE 89A

6-[2-(4-Aminophenyl)ethoxy]-2-naphthalenecarbonitrile

A solution of Example 4A, (300 mg), Cs$_2$CO$_3$ (1.2 g ), 4-aminophenethylbromide (470 mg) and tetrabutylammonium iodide (10 mg) in DMF (5 ml) was stirred for 18 h at room temperature, diluted with water and extracted with ethyl acetate. The organic extract was washed with saturated aq NaHCO$_3$ and brine, dried (Na$_2$SO$_4$) and concentrated to provide 200 mg of the title compound as a dark brown oil. MS (DCI/NH$_3$) m/e 306 (M+NH$_4$)$^+$.

EXAMPLE 89B

6-[2-(4-Aminophenyl)ethoxy]-2-naphthalenecarboximidamide mono(trifluoroacetate) salt The title compund was prepared with Example 89A according to the procedure of Example 5B.

$^1$H NMR (300 MHz, DMSO-d$_6$) δ 3.15 (t, 2H), 3.6 (bs, 3H), 4.35 (t, 2H), 6.93 (d, 2H), 7.24 (d, 2H) 7.38 (dd, 1H), 7.55 (d, 1H), 7.78 (dd, 1H), 7.98 (dd, 1H), 8.21 (d, 1H), 8.4 (d, 1H), 9.21 (bs, 2H), 9.39 (bs, 2H); MS m/e 306 (M+H)$^+$. Anal. calcd for C$_{19}$H$_{19}$N$_3$O.2TFA: C, 51.79; H, 3.97; N, 7.88; Found: C, 50.99; H, 4.68; N, 7.59.

EXAMPLE 90

Methyl [3-methoxy-6-(aminoiminomethyl)-4-naphthalenyl]carbamate mono(trifluoroacetate) salt

EXAMPLE 90A

7-Methoxy-2-trifluoromethanesulfonyloxy naphthalene

A solution of 7-methoxy-2-naphthol (3.24 g, 18 mmole) in DMF (20 mL) and methylene chloride (20 mL) was treated with N-phenyl trifluoromethanesulfonimide (6.6 g, 18 mmole) and triethylamine (5.2 mL, 37 mmole), stirred 20 h at room temperature, diluted with CH$_2$Cl$_2$ (100 mL), washed sequentially with distilled water, 20% KOH and brine, dried (MgSO$_4$) and concentrated to provide the title compound as a clear oil. MS (DCI/NH$_3$): m/e 272 (M+NH$_4$)$^+$.

EXAMPLE 90B

7-Methoxy-2-naphthalenecarbonitrile

Example 90A (12 mmole), zinc cyanide (12 mmole), Pd(OAc)$_2$ (0.3 mmole) and triphenylphosphine (1.2 mmole) in DMF (40 mL) was heated for 6 h at 85° C., diluted with ethyl acetate (200 mL), washed with saturated NaHCO$_3$, brine, dried (MgSO$_4$) and concentrated to a dark oily residue. Purification of the residue on silica gel with 1:1 hexane: methylene chloride then CH$_2$Cl$_2$ afforded 1.8 g of the title compound as a white solid. MS (DCI/NH$_3$) m/e 201 (M+NH$_4$)$^+$.

EXAMPLE 90C

7-Methoxy-8-nitro-2-naphthalenecarbonitrile

Example 90B (3 g, 16.4 mmole) in acetic anhydride (30 mL) at 0° C. was treated with fuming HNO$_3$ (1.2 mL), and the resulting thick slurry was diluted with water (20 mL), stirred 20 min then filtered and dried in vacuo to provide 3.69 g of the title compound as a yellow solid.

MS (DCI/NH$_3$) m/e 246 (M+NH$_4$)$^+$.

EXAMPLE 90D

7-Methoxy-8-amino-2-naphthonitrile

Example 90C (3.69 g, 16.1 mmole) and 10% Pd/C (0.4 g) in ethyl acetate (100 mL) was stirred under a hydrogen atmosphere for 2 h at room temperature, filtered and concentrated to provide 3 g of the title compound as a yellow solid.

MS (DCI/NH$_3$) m/e 217 (M+NH$_4$)$^+$.

EXAMPLE 90E

Methyl [3-methoxy-6-cyano-4-naphthalenyl] carbamate

Example 90D (81 mg, 0.41 mmol) in dioxane (7 mL) and 10% NaOH (15 mL) was treated with methyl chloroformate (112 mg. 0.98 mmol), stirred for 2 h, diluted with ethyl acetate, washed with water, dried (MgSO$_4$) and concentrated to provide 105 mg of the title compound. MS (DCI/NH$_3$) m/e 274 (M+NH$_3$)$^+$.

EXAMPLE 90F

Methyl [3-methoxy-6-(aminoiminomethyl)-4-naphthalenyl]carbamate mono(trifluoroacetate) salt The title compound was prepared from Example 90E according to the procedure of Example 40D.

$^1$H-NMR (300 MHz, DMSO-d$_6$) δ 9.48 (s, 2H), 8.99 (s, 2H), 8.93 (br, 1H), 8.34 (s, 1H), 8.12 (d, 1H), 8.04 (d, 1H), 7.72 (d, 1H), 7.65 (dd, 1H), 3.95 (s, 3H); MS (DCI/NH$_3$) m/e 274 (M+H)$^+$; Anal. calcd for C$_{14}$H$_{15}$N$_3$O$_3$.1.8TFA: C, 44.07; H, 3.53; N, 8.74. Found: C, 44.14; H, 3.20; N, 8.53.

EXAMPLE 91

7-Methoxy-8-[2-pyrimidinyl(amino)]-2-naphthalenecarboximidamide bis(trifluoroacetate) salt

EXAMPLE 91A

7-Methoxy-8-[2-pyrimidinyl(amino)]-2-naphthalenecarbonitrile

A solution of Example 90D (230 mg, 1.2 mmole), 2-chloropyrimidine (280 mg, 2 mmole), sodium-tert-butoxide (120 mg, 1.2 mmole), Pd(dba)$_3$.CHCl$_3$ and dppf in toluene (5 mL) was heated in a sealed tube for 18 h at 100° C., diluted with ethyl acetate (100 mL), washed with brine, dried (MgSO$_4$) and concentrated to provide 100 mg of a brown oil.

MS (DCI/NH$_3$) m/e 294 (M+NH$_4$)$^+$.

EXAMPLE 91B

7-Methoxy-8-[2-pyrimidinyl(amino)]-2-naphthalenecarboximidamide bis(trifluoroacetate)

The title compound was prepared in a manner analogous to that of Example 40D.

$^1$H-NMR (300 MHz, DMSO-d$_6$) δ 9.43 (s, 2H), 9.11 (s, 2H), 8.46 (s, 1H), 8.16 (br, 3H), 8.15 (d, 1H), 8.04 (d, 1H), 7.82 (dd, 1H), 7.75 (d, 1H), 7.54 (s, 1H) 7.50 (d, 1H), 4.08 (d, 2H); MS (DCI/NH$_3$) m/e 294 (M+H)$^+$. Anal. calcd for C$_{16}$H$_{15}$N$_5$O.3.8TFA: C, 39.01; H, 2.61; N,9.64; Found: C, 39.01; H, 3.06; N, 9.63.

EXAMPLE 92

6-(aminoiminomethyl)-N-[4-(hydroxymethyl)phenyl]-2-naphthalenecarboxamide, mono(trifluoroacetate)(salt)

EXAMPLE 92A 4-amino-benzyloxy-tert-butyldimethylsilyl ether

A solution of 4-aminobenzyl alcohol (1 g, 8.1 mmol) in DMF (20 mL) was treated with imidazole (0.54 g, 8.1 mmol) and tert-butyl dimethylsilyl chloride (1.22 g, 8.12 mmol), stirred overnight at room temperature, diluted with ethyl acetate (100 mL), washed with 1 N H$_3$PO$_4$, saturated NaHCO$_3$ and 10% NaCl, dried (Na$_2$SO$_4$) and concentrated to an oil which was purified on silica gel with 3:1 hexanes-:ethyl acetate to provide 0.5 g of a clear oil.

MS m/z 238 (M+H)$^+$.

EXAMPLE 92B

Example 92A (0.3, 1.1 mmol) and 6-carboxy-2-naphthonitrile, Example 8E (0.2 g, 1 mmol) were processed as described in Example 95C to provide 100 mg of the desired compound.

MS m/z 434 (M+NH$_4$)$^+$.

EXAMPLE 92C

A solution of Example 92B in 1 M tetrabutyl ammonium fluoride THF solution (2 mL) was stirred for 1 hour at room temperature, quenched with 10% NH$_4$Cl solution (50 mL) and diluted with ethyl acetate (100 mL). The layers were separated, and the organic layer was washed with 10% NaCl, dried (MgSO$_4$) and concentrated to provide a light brown oil which was triturated with methylene chloride and filtered to provide 0.1 g of the desired compound as a white solid.

MS m/z 320 (M+NH$_4$)$^+$.

EXAMPLE 92D 6-(aminoiminomethyl)-N-[4-(hydroxymethyl)phenyl]-2-naphthalenecarboxamide, mono(trifluoroacetate)(salt)

Example 92C (0.1 g, 0.33 mmol) was processed and purified according to the procedure in Example 95D to provide 15 mg of the desired compound.

MS m/z 320 (M+H)$^+$; $^1$H NMR 300 MHz, (DMSO-d$_6$): δ 10.45 (s, 1H), 9.45 (bs, 4H), 8.75 (s, 1H), 8.59 (s, 1H), 8.32 (d, 1H), 8.22 (d, 1H), 8.18 (dd, 1H), 7.92 (dd, 1H), 7.85 (d, 2H), 7.45 (d, 2H), 4.20 (s, 2H); Anal. calc'd for C$_{19}$H$_{17}$N$_3$O$_2$.TFA: C, 58.20; H, 4.19; N, 9.70. Found: C, 57.80; H, 3.91; N, 9.35.

EXAMPLE 93

6-(4-aminophenyl)-2-naphthalenecarboximidamide, bis(trifluoroacetate) salt

EXAMPLE 93A 6-cyano-2-naphthalene boronic acid (0.3 g, 1.64 mmol), 4-iodoaniline (0.36 g, 1.64 mmol), Palladium[1,1'-Bis(diphenylphosphino)-ferrocene] dichloride (0.13 g, 0.164 mmol) and CsF (0.75 g, 4.92 mmol) are mixed together in DMF (8 mL) heated 20 hours. at 80° C. The mixture is diluted with ethyl acetate (100 mL) washed with 1 N H$_3$PO$_4$, saturated NaHCO$_3$, 10% NaCl, dried over anhydrous sodium sulfate. The drying agent filtered, solvent removed under vacuum leaving a brown solid. The solid is purified on silica gel eluting with 3:1 hexanes:ethyl acetate. The fractions corresponding to the desired compound are concentrated under vacuum leaving a yellow solid. 0.2 g, 75%.

MS (M+NH$_4$$^+$): 262.

EXAMPLE 93B 6-(4aminophenyl)-2-naphthalenecarboximidamide, bis(trifluoroacetate) salt The desired compound is obtained from the material prepared in Example 93A (0.1 g, 0.41 mmol) using the procedure described in Example 94D Yield: 35 mg, 53% MS (M+H)$^+$262;

¹H NMR 300 MHz, (DMSO-d₆): δ 9.45 (bs, 2H), 9.35 (bs, 2H), 8.45 (d, 1H), 8.22 (s, 1H), 8.15 (d, 1H), 8.10 (d, 1H), 7.99 (dd, 1H), 7.79 (dd, 1H), 7.65 (d, 2H), 6.95 (d, 2H), 4.80 (bs, 3H); Anal. calc'd: $C_{21}H_{17}N_3O_6F_6$: C, 51.54, H, 3.50, N, 8.59, Found: C, 51.95, H, 3.84.

EXAMPLE 95 methyl 2-[4-[[[6-(aminoiminomethyl)-2-naphthalenyl]carbonyl]amino]phenoxy]acetate, mono(trifluoroacetate) salt

EXAMPLE 95A

4-Acetamidophenol (5 g, 33 mmol) is dissolved in THF (100 mL) treated with Cesium carbonate (10.25 g, 33 mmol) and Methyl bromoacetate (3.4 mL, 36 mmol) and stirred 24 hours at room temperature. The reaction mixture is diluted with water (100 mL) and concentrated under vacuum. The residue is dissolved in ethyl acetate (100 mL) washed with 1 N $H_3PO_4$ (20 mL), saturated $NaHCO_3$ (20 mL), 10% NaCl (20 mL) and dried over anhydrous $Na_2SO_4$. The drying agent is filtered and the solvent removed under vacuum leaving the desired compound as a white solid, 6.8 g, (92%). MS (M+NH₄⁺): 241.

EXAMPLE 95B

The material obtained in Example 95A is treated with 2 N HCl (75 mL) and refluxed for 3 hours. The clear mixture is cooled to room temperature then concentrated under vacuum to an off white solid as the desired compound. 6 g, 92%.

MS (M+NH₄⁺): 198.

EXAMPLE 95C 6-carboxy-2-naphthonitrile (0.1 g, 0.51 mmol) is dissolved in DMF (5 mL) cooled in an ice bath to 5° C. To the homogeneous mixture is added Diisopropylethylamine (0.18 mL, 1.05 mmol) and O-(7-Azabenzotriazol-1-yl)-N, N, N', N'-tetramethyluronium hexafluorophosphate (HATU). The resultant slurry is stirred at 5° C. 45 minutes. To this slurry is added the material obtained in Example 95B (0.12 g, 0.56 mmol) and the mixture is stirred at room temperature overnight. The next day, the reaction mixture is diluted with ethyl acetate (100 mL) washed with 1 N $H_3PO_4$ (20 mL), saturated $NaHCO_3$ (20 mL), 10% NaCl, dried over anhydrous $Na_2SO_4$ filtered and solvent removed under vacuum yielding the desired compound as a brown solid. 0.28 g, 65%.

MS (M+NH₄)⁺: 378.

EXAMPLE 95D methyl 2-[4-[[[6-(aminoiminomethyl)-2-naphthalenyl]carbonyl]amino]phenoxy]acetate, mono(trifluoroacetate) salt The material obtained in Example 95C (0.28 g, 0.78 mmol) is dissolved in methanol saturated with HCl (g) (30 mL) stirred 18 hours at room temperature. The solvent removed under vacuum and the resultant yellow solid is treated with 2 M NH₃/methanol (20 mL). This solution is refluxed 6 hours, cooled, solvent removed under vacuum and the resulting brown solid is purified by reverse phase HPLC. The desired compound is obtained from lyophilization. 19.3 mg, 20%.

MS (M+H)⁺: 378 ¹HNMR 300 MHz, (DMSO-d₆): δ 10.45 (s, 1H), 9.45 (bs, 4H), 8.65 (d, 1H), 8.59 (s, 1H), 8.15 (d, 1H), 8.10 (d, 1H), 8.08 (d, 1H), 7.92 (d, 1H), 7.75 (d, 2H), 6.98 (d, 2H), 4.80 (s, 2H), 3.75 (s, 3H), Anal. calc'd: $C_{23}H_{21}N_3O_6F_3$: C, 56.10, H, 4.3, N, 8.53, Found: C, 55.80, H, 3.93, N, 8.33.

EXAMPLE 96

(E)-6-[2-[(3-hydroxymethyl)phenyl]ethenyl]-2-naphthalenecarboximidamide, mono (trifluoroacetate)(salt)

EXAMPLE 96A

The above was prepared from 3-iodobenzyl alcohol using the procedure in Example 41A.

MS (DCI/NH₃) m/z (M+NH₃)⁺303.

EXAMPLE 96B (E)-6-[2-[(3-hydroxymethyl)phenyl]ethenyl]-2-naphthalenecarboximidamide, mono (trifluoroacetate)(salt)

The above was prepared from Example 96A using method from Example 40D.

MS (DCI/NH₃) m/z (M+H)⁺303; ¹H-NMR (300 MHz, DMSO-d₆) δ 9.18 (br, 4H), 8.45 (s, 1H), 8.17 (s, 1H), 8.13–8.04 (m, 3H), 7.81 (dd, 1H), 7.64 (s, 1H), 7.57 (d, 2H), 7.51 (d, 1H) 7.39 (t, 1H), 7.28 (d, 1H), 5.27 (t, 1H), 4.55 (d, 2H); Anal. calc'd for $C_{22}H_{19}N_2O_3F_3$ 3/10 TFA: C, 60.64; H, 4.35; N, 6.28. Found: C, 60.53; H, 4.87; N, 6.57.

EXAMPLE 97

6(2-phenyl-1-cyclopropyl)-2-naphthalenecarboximidamide, mono (trifluoroacetate)(salt)

EXAMPLE 97A

Copper (I) chloride (43 mg, 0.4 mmol), powdered zinc (26 mg, 0.4 mmol) were suspended in 1 mL dioxane for 18 hours. The product from Example 41B (60 mg, 0.2 mmol) was added and stirred and heated at 95° C. for 20 hours. The reaction mixture was concentrated on silica gel and purified by silica gel chromatography to give the desired compound.

MS (DCI/NH₃) m/z (M+NH₃)⁺287.

EXAMPLE 97B 6-(2-phenyl-1-cyclopropyl)-2-naphthalenecarboximidamide, mono (trifluoroacetate)(salt)

The above was prepared from Example 1 using method from Example 1B.

MS (DCI/NH₃) m/z (M+H)⁺287; ¹H-NMR (300 MHz, DMSO-d₆) δ 9.41 (s, 2H), 9.16 (s, 2H), 8.46 (s, 1H), 7.83 (d, 2H), 7.62 (s, 1H), 7.58 (dd, 1H), 7.34 (dd, 1H), 7.35–7.29 (m, 3H), 7.25–7.17 (m, 2H) 2.38–2.28 (m, 2H), 1.61 (t, 2H); Anal. calc'd for $C_{22}H_{19}N_2O_2F_3$ 1/10 TFA: C, 65.00; H, 4.70; N, 6.84. Found: C, 65.22; H, 5.23; N, 5.10.

EXAMPLE 98

(E)-6-[2-[4-(aminomethyl)phenyl]ethenyl]-2-naphthalenecarboximidamide, bis(trifluoroacetate) (salt)

EXAMPLE 98A

The desired compound was prepared using ethene under 500 atm pressure in a manner; Analagous to that of Example 41A.

MS (DCI/NH$_3$) m/z (M+NH$_3$)$^+$197.

EXAMPLE 98B 4-(Aminomethyl)-iodobenzene hydrochloride (1 g, 3.7 mmol) and Boc anhydride (1.22 g, 5.6 mmol) were mixed with 10% NaOH (15 mL), ethyl acetate (20 mL) and stirred 2 hours. The organic layer was washed with 5% sodium bicarbonate (2×, 10 mL), dried (magnesium sulfate), and concentrated to give 1.22 g of desired compound. MS (DCI/NH$_3$) m/z (M+NH$_3$)$^+$351.

EXAMPLE 98C

The desired compound was prepared using the product from Example s 98A and 98B in a manner analagous to that of Example 41A MS (DCI/NH$_3$) m/z (M+NH$_3$)$^+$402.

EXAMPLE 98D (E)-6-[2-[4-(aminomethyl)phenyl]ethenyl]-2-naphthalenecarboximidamide, bis(trifluoroacetate) (salt)

The above product was prepared in a manner analogous to that of Example 40D with the addition of trifluoroacetic acid in methylene chloride to remove the Boc group.

MS (DCI/NH$_3$) m/z (M+H)$^+$302; $^1$H-NMR (300 MHz, DMSO-d$_6$) δ 9.43 (s, 2H), 9.11 (s, 2H), 8.46 (s, 1H), 8.16 (br, 3H), 8.15 (d, 1H), 8.04 (d, 1H), 7.82 (dd, 1H), 7.75 (d, 1H), 7.54 (s, 1H) 7.50 (d, 1H), 4.08 (d, 2H); Anal. calc'd for C$_{24}$H$_{21}$N$_3$O$_4$F$_6$ 2/5 TFA: C, 50.46; H, 3.63; N, 6.99. Found: C; 50.37; H, 3.86; N, 7.05.

EXAMPLE 99 methyl [7-(aminoiminomethyl)-2-methoxy-1-naphthalenyl)carbamate, mono(trifluoroacetate)(salt)

The desired compound was prepared using material prepared as described in Example 90D and utilizing the procedures described in Example 91A and Example 40D.

MS (DCI/NH$_3$) m/z (M+H)$^+$306; $^1$H-NMR (300 MHz, DMSO-d$_6$) δ 9.33 (s, 2H), 8.98 (s, 2H), 8.63 (s, 1H), 7.99 (d, 1H), 7.60 (dd, 1H), 7.58 (s, 1H), 7.54 (d, 1H), 7.35–7.20 (m, 5H), 4.52 (s, 2H); Anal. calc'd for C$_{21}$H$_{20}$N$_3$O$_3$F$_3$ 13/5 TFA: C, 44.03; H, 3.19; N, 5.89. Found: C; 43.97; H, 3.55; N, 6.10.

EXAMPLE 100

7-methoxy-8-(2-pyrimidinylamino)-2-naphthalenecarboximidamide, bis(trifluoroacetate) (salt)

The desired compound was prepared using material prepared as described in Example 90D and utilizing the procedures described in Example 91A and Example 40D.

MS (DCI/NH$_3$) m/z (M+H)$^+$322; $^1$H-NMR (300 MHz, DMSO-d$_6$) δ 9.35 (s, 2H), 8.90 (s, 2H), 8.34 (s, 1H), 8.11 (d, 1H), 7.90 (d, 1H), 7.72 (d, 1H), 7.60 (dd, 1H), 7.47 (s, 2H), 6.70 (d, 2H) 6.49 (d, 2H), 3.88 (s, 3H), 3.64 (s, 3H); Anal. calc'd for C$_{21}$H$_{20}$N$_3$O$_4$F$_3$ 1/10 TFA: C, 56.90; H, 4.53; N, 9.38. Found: C; 56.88; H, 4.41; N, 9.43.

EXAMPLE 101

7-methoxy-8-[(phenylmethyl)amino]-2-naphthalenecarboximidamide, mono (trifluoroacetate)(salt)

EXAMPLE 101A

4-Bromostyrene (4.8 g, 26.2 mmol) was dissolved in 100 mL THF and cooled to −78° C. Butyl lithium (2.5 M in hexanes, 28.8 mmol) was added dropwise and stirred 5 minutes. Iodine in THF was added dropwise until an orange/red color persisted. Concentrated aqueous ammonium chloride (20 mL) was added and the reaction was warmed to room temperature, diluted with ether, washed with 10% Na$_2$S$_2$O$_5$ solution (1×, 50 mL), and brine (1×, 50 mL), dried (magnesium sulfate), and concentrated to give the desired compound.

MS (DCI/NH$_3$) m/z 122.

EXAMPLE 101B

The product from 104A (2.35 g, 10.2 mmol), 1.6 mL 60%, N-methylmorphiline-N-oxide/water solution, 3.75 mL acetone, 0.1 mL water were stirred 1 hour. 20 mL Osmium tetroxide/tert-butanol solution (0.02 mmol/mL) was added and stirred at 0° C. for 20 hours. The reaction was concentrated on silica gel and purified by silica gel chromatography to give the desired compound.

MS (DCI/NH$_3$) m/z (M+NH$_3$)$^+$282.

EXAMPLE 101C

The desired compound from Example 104B is coupled using Method 41A.

MS (DCI/NH$_3$) m/z (M+NH$_3$)$^+$333.

EXAMPLE 101D 7-methoxy-8-[(phenylmethyl)amino]-2-naphthalenecarboximidamide, mono (trifluoroacetate)(salt)

The above was prepared from Example 104C using method described in Example 40D.

MS (DCI/NH$_3$) m/z (M+H)$^+$333; $^1$H-NMR (300 MHz, DMSO-d$_6$) δ 9.42 (s, 2H), 9.12 (s, 2H), 8.45 (s, 1H), 8.15–8.05 (m, 4H), 7.81 (dd, 1H), 7.63 (d, 2H), 7.48 (d, 2H), 7.39 (d, 2H), 4.56 (t, 1H), 3.45 (d, 2H); Anal. calc'd for C$_{23}$H$_{21}$N$_2$O$_4$F$_3$ 2/5 TFA: C, 58.19; H, 4.39; N, 5.71. Found: C, 58.17; H, 4.41; N, 5.87.

EXAMPLE 102

7-methoxy-8-(phenylamino)-2-naphthalenecarboximidamide, mono (trifluoroacetate)(salt)

EXAMPLE 102A

Tert-butylcarbamate (3.62 g, 15.7 mmol) was dissolved in 63 mL propanol. 118 mL NaOH/water solution (0.4 N), tert-butyl hypochlorite (5.5 mL, 47.8 mmol), and $(DHQD)_2$ PHAL (612 mg, 0.61 mmol) in 50 mL propanol were added and stirred 10 minutes. The product from Example 2 (3.62 g, 15.7 mmol), and $K_2OsO_4.2$ water (211 mg, 0.63 mmol) were added and stirred 24 hours. The reaction was concentrated and recrystallized from ethanol/hexanes to give the desired compound.

MS $(DCI/NH_3)$ m/z $(M+NH_3)^+$381.

EXAMPLE 102B

The above was prepared from Example 102 using the method described in Example 41A.

MS $(DCI/NH_3)$ m/z $(M+H)^+$415.

EXAMPLE 102C 7-methoxy-8-(phenylamino)-2-naphthalenecarboximidamide, mono (trifluoroacetate)(salt)

The above was prepared from Example 102B using the method described in Example 94D.

MS $(DCI/NH_3)$ m/z $(M+H)^+$264; $^1$H-NMR (300 MHz, DMSO-$d_6$) δ 9.42 (s, 2H), 9.07 (s, 2H), 8.45 (s, 1H), 8.33 (br, 3H), 8.16–8.03 (m, 4H) 7.75 (d, 2H), 7.56 (s, 2H), 7.49 (d, 2H), 5.49 (br 1 h), 4.28 (br 1H), 3.62 (m, 2H); Anal. calc'd for $C_{25}H_{23}N_3O_5F_6.5$ TFA: C, 37.30; H, 2.51; N, 3.74. Found: C; 37.06; H, 3.12; N, 4.42.

EXAMPLE 103

7-methoxy-8-[(4-methoxyphenyl)amino]-2-naphthalenecarboximidamide, mono (trifluoroacetate)(salt)

EXAMPLE 103A

4-Bromobenzaldehyde (600 mg, 3.24 mmol), 16.2 mL dimethylamine in THF (32.4 mmol), and sodium triacetoxyborohydride (1.24 g, 5.8 mmol) were suspended in dichloroethane (10 mL). The reaction mixture was concentrated, diluted with water acidified to pH=2 and extracted with ether (3×, 20 mL). The aqueous solution was basified with NaOH/water to pH=12 and extracted with methylene chloride (3×, 30 mL, acidified with HCl/methanol and concentrated to give the desired compund.

MS $(DCI/NH_3)$ m/z $(M)^+$214.

EXAMPLE 103B

The above was prepared from Example 107A using method from Example 41A.

MS $(DCI/NH_3)$ m/z $(M+H)^+$313.

EXAMPLE 103C 7-methoxy-8-[(4-methoxyphenyl)amino]-2-naphthalenecarboximidamide, mono (trifluoroacetate)(salt)

The above was prepared from Example 103 using method from Example 40D.

MS $(DCI/NH_3)$ m/z $(M+H)^+$294; $^1$H-NMR (300 MHz, DMSO-$d_6$) δ 9.43 (s, 2H), 9.11 (s, 2H), 8.46 (s, 1H), 8.18–8.06 (m, 4H), 7.84 (d, 4H), 7.60 (s, 2H), 7.56 (s, 1H), 4.53 (s, 2H), 3.05 (s, 6H); Anal. calc'd for $C_{26}H_{25}N_3O_4F_6$7/5 TFA: C, 48.46; H, 3.73; N, 5.91. Found: C, 48.36; H, 4.25; N, 6.19.

EXAMPLE 104

(E)-6-[2-[4-(1,2-dihdyroxyethyl)phenyl]ethenyl]-2-naphthalenecarboximidamide, mono (trifluoroacetate)(salt)

EXAMPLE 104A

The above was prepared from 4-bromobenzyl alcohol and the compound prepared in Example 98A using the method from Example 41A.

MS $(DCI/NH_3)$ m/z $(M+NH_3)^+$303.

EXAMPLE 104B (E)-6-[2-[4-(1,2-dihdyroxyethyl)phenyl]ethenyl]-2-naphthalenecarboximidamide, mono (trifluoroacetate)(salt)

The above was prepared from Example 104A using method from Example 40D.

MS $(DCI/NH_3)$ m/z $(M+H)^+$303; $^1$H-NMR (300 MHz, DMSO-$d_6$) δ 9.00 (br, 4H), 8.44 (s, 1H), 8.15–8.01 (m, 4H), 7.81 (dd, 1H), 7.64 (d, 2H), 7.48 (d, 1H), 7.36 (d, 2H), 5.21 (br, 1H) 4.53 (s, 2H); Anal. calc'd for $C_{22}H_{19}N_2O_3F_3$ 4/5 TFA: C, 55.84; H, 3.93; N, 5.52. Found: C, 55.60; H, 3.93; N, 6.41.

EXAMPLE 105

(E)-6-[2-[4-(1R-amino-2-hydroxyethyl)phenyl]ethenyl]-2-naphthalenecarboximidamide, bis (trifluoroacetate)(salt)

EXAMPLE 105A

Using the procedure described for Example 121A, and substituting N-BOC-p-iodophenylalanine (BACHEM Bioscience Inc.) for 4-iodoaniline, the desired compound was obtained.

MS $(DCI/NH_3)$ m/z 458 $(M+NH_4)^+$; $^1$H NMR (300 MHz, $CDCl_3$) δ 1.35 (s, 9H), 2.90 (t, 1H), 3.09 (dd, 1H), 4.15 (m, 1H), 7.20 (d, 1H), 7.36 (d, 2H), 7.56 (d, 2H), 7.78 (d, 1H), 7.85 (d, 1H), 8.12 (d, 1H), 8.17 (d, 1H), 8.32 (s, 1H), 8.62 (s, 1H).

EXAMPLE 105B

Using the product obtained in Example 105A and the procedure described in Example 40D the desired compound was obtained.

MS (ESI) m/z 458 $(M+H)^+$; $^1$H NMR (300 MHz, DMSO) δ 1.35 (s, 9H), 2.90 (dd, 1H), 3.10 (dd, 1H), 4.13 (m, 1H), 7.10 (d, 1H), 7.36 (d, 2H), 7.55 (d, 2H), 7.78 (dd, 1H), 7.85 (dd, 1H), 8.13 (d, 1H), 8.19 (d, 1H), 8.30 (s, 1H), 8.50 (s, 1H), 9.22 (s, 2H), 9.42 (s, 2H).

EXAMPLE 105C (E)-6-[2-[4-(1R-amino-2-hydroxyethyl)phenyl]ethenyl]-2-naphthalenecarboximidamide, bis (trifluoroacetate)(salt)

Using the product obtained in Example 105B and the procedure described for Example 124D, the desired compound was obtained.

MS (ESI) m/z 358 (M+H)$^+$; $^1$H NMR (300 MHz, DMSO) δ 3.02 (m, 1H), 3.19 (dd, 1H), 3.63 (t, 1H), 7.39 (d, 2H), 7.58 (d, 2H), 7.76 (d, 1H), 7.88 (d, 1H), 8.15 (d, 1H), 8.19 (d, 1H), 8.30 (s, 1H), 8.51 (s, 1H), 9.41 (s, 2H), 9.80 (s, 2H); Anal. calc'd for $C_{24}H_{20}F_3N_3O_4 \cdot H_2O$: C, 58.90; H, 4.53; N, 8.59. Found: C, 58.75; H, 4.22; N, 8.28.

EXAMPLE 106

7-methoxy-8-(2-pyrimidinylamino)-2-naphthalenecarboximidamide, bis(trifluoroacetate) (salt)

EXAMPLE 106A

Sodium borohydride (0.22 g, 5.8 mmol) was added to a suspension of (4-bromobenzoyl)methanol (2.5 g, 11.6 mmol, Maybridge Chem. Co.) and 25 mL abs. ethanol. The reaction mixture was stirred at reflux for 1 hour. After cooling to room temperature, the ethanol was evaporated under vacuum, and water was added to the residue. The mixture was extracted with $CH_2Cl_2$. The extracts were washed with saturated aqueous sodium chloride, dried over $MgSO_4$, filtered, and evaporated under vacuum to afford the desired compound.

MS (DCI/NH$_3$) m/z 234/236 (M+NH$_4$)$^+$; $^1$H NMR (300 MHz, CDCl$_3$) δ 2.10 (t, 1H), 2.62 (d, 1H), 3.63 (m, 1H), 3.78 (m, 1H), 4.81 (m, 1H), 7.25 (d, 2H), 7.50 (d, 2H).

EXAMPLE 106B

Using the product obtained in Example 106A and the procdure described in Example A-226218-A, the desired compound was obtained.

MS (DCI/NH$_3$) m/z 331 (M+NH$_4$)$^+$; $^1$H NMR (300 MHz, CDCl$_3$) d3.45 (t, 1H), 4.59 (q, 1H), 4.76 (t, 1H), 5.36 (d, 1H), 7.42 (d, 2H), 7.59 (d, 2H), 7.78 (dd, 1H), 7.85 (dd, 1H), 8.10 (d, 1H), 8.15 (d, 1H), 8.30 (s, 1H), 8.61 (s, 1H).

EXAMPLE 106C

7-methoxy-8-(2-pyrimidinylamino)-2-naphthalenecarboximidamide, bis(trifluoroacetate) (salt)

Using the product obtained in Example 106B, and the procedure described in Example 40D, the desired compound was obtained.

MS (ESI) m/z 331 (M+H)$^+$; $^1$H NMR (300 MHz, DMSO) δ 3.45 (t, 1H), 4.59 (q, 1H), 4.78 (t, 1H), 5.38 (d, 1H), 7.42 (d, 2H), 7.59 (d, 2H), 7.78 (dd, 1H), 7.84 (dd, 1H), 8.12 (d, 1H), 8.18 (d, 1H), 8.31 (s, 1H), 8.50 (s, 1H), 9.20 (s, 2H), 9.43 (s, 2H); Anal. calc'd for $C_{23}H_{19}F_3N_2O_4 \cdot H_2O$: C, 59.74; H, 4.58; N, 6.06. Found: C, 59.95; H, 4.17; N, 6.13.

EXAMPLE 107

(E)-6-[2-[[4-(dimethylamino)methyl]phenyl]ethenyl]-2-naphthalenecarboximidamide, bis (trifluoroacetate)(salt)

EXAMPLE 107A

Using the procedure described for Example 121A, and substituting 3-benzyloxybromobenzene (*Chem. Ber.*124 (1), 163, 1991) for 4-iodoaniline, the desired compound was obtained.

MS (DCI/NH$_3$) m/z 377 (M+NH$_4$)$^+$; $^1$H NMR (300 MHz, CDCl$_3$) δ 5.11 (s, 2H), 7.02 (d, 1H), 7.20 (m, 2H), 7.29 (d, 1H), 7.31 (d, 1H), 7.42 (m, 3H), 7.60–7.75 (m, 3H), 7.89 (t, 2H), 8.08 (s, 1H), 8.21 (s, 1H).

EXAMPLE 107B

(E)-6-[2-[[4-(dimethylamino)methyl]phenyl] ethenyl]-2-naphthalenecarboximidamide, bis (trifluoroacetate)(salt)

Using the product obtained in Example 108B, and the procedure described in Example 40D, the desired compound was obtained.

MS (ESI) m/z 377 (M+H)$^+$; $^1$H NMR (300 MHz, DMSO) δ 5.18 (S, 2H), 7.12 (dd, 1H), 7.22 (d, 1H), 7.28 (m, 1H), 7.40 (t, 3H), 7.45 (t, 3H), 7.79 (dd, 1H), 7.85 (dd, 1H), 8.16 (d, 1H), 8.20 (d, 1H), 8.35 (s, 1H), 8.50 (s, 1H), 9. 30 (s, 1H); Anal. calc'd for $C_{28}H_{21}F_3N_2O_3 \cdot 0.25\ H_2O$: C, 67.94; H, 4.38; N, 5.66. Found: C, 67.80; H, 4.48; N, 5.43.

EXAMPLE 108

(E)-6-[2-[4-(hydroxymethyl)phenyl]ethenyl]-2-naphthalenecarboximidamide, mono (trifluoroacetate)(salt)

Using the product obtained in Example 108A and the procedure described in Example 94D the desired compound was obtained.

MS (ESI) m/z 287 (M+H)$^+$; $^1$H NMR (300 MHz, DMSO) δ 6.89 (m, 1H), 6.98 (t, 1H), 7.03 (d, 1H), 7.29 (t, 1H), 7.78 (dd, 1H), 7.88 (dd, 1H), 8.13 (d, 1H), 8.17 (d, 1H), 8.32 (s, 1H), 8.50 (s, 1H), 9.40 (s, 5H); Anal. calc'd for $C_{21}H_{15}F_3N_2O_3 \cdot 0.5\ H_2O$: C, 61.62; H, 3.94; N, 6.84. Found: C, 61.29; H, 3.81; N, 6.59.

EXAMPLE 109

4-[[6-(aminoiminomethyl)-2-naphthalenyl]ethynyl]-L-phenylalanine, mono(trifluoroacetate (salt)

EXAMPLE 109A

To a solution of the product from Example 8D (2.13 g, 10.08 mmol) and LiBH$_4$ (121 mg, 5.55 mmol) in THF (5 mL) was added toluene (2 mL), and the THF was boiled off using a short-path distillation apparatus over several hours. The reaction was then heated at 70° C. for 2 hours, cooled, quenched with 1 M HCl, and extracted with 2× ethyl acetate. The extracts were washed with water and brine, dried over Na$_2$SO$_4$, and condensed. The crude product was chromatographed on SiO$_2$ using 50% ethyl acetate/hexanes as eluent, to yield 1.12 g (61%) of the desired compound.

MS (DCI (NH$_3$)) m/z 201 (M+NH$_4$)$^+$; $^1$H NMR (300 MHz, CDCl$_3$) δ 8.22 (s, 1H), 7.90 (m, 3H), 7.61 (m, 2H), 4.92 (d, 2H), 1.84 (t, 1H).

EXAMPLE 109B

To a solution of the product from Example 109A (2.12 g, 11.57 mmol) and LiBr (1.11 g, 12.73 mmol) in DMF (100 mL) was added PBr$_3$ (1.21 mL, 12.73 mmol) at 0° C., and the reaction was warmed to room temperature, and stirred for 1 hours. The reaction was then quenched with pH 7 buffer, and extracted with 3× diethyl ether/hexanes. The extracts were washed with 2× water and 2× brine, dried over Na$_2$SO$_4$, and condensed, to yield 2.72 g (96%) of the desired compound.

MS (DCI (NH$_3$)) m/z 185 (M+NH$_{4-Br}$)$^+$; $^1$H NMR (300 MHz, CDCl$_3$) δ 8.22 (s, 1H), 7.92 (s, 1H), 7.90 (s, 2H), 7.62 (dd, 2H), 4.64 (s, 2H).

EXAMPLE 109C

To a solution of NaH (60% in mineral oil, 44 mg, 1.1 mmol) in DMF (5 mL) was added 4-ethylphenol (122 mg, 1.0 mmol), and the reaction was stirred at room temperature for 20 minutes. The product from Example 109B (270 mg, 1.1 mmol) was then added, and the reaction was stirred for 10 minutes. The crude reaction mixture was chromatographed on $SiO_2$ using hexanes as eluent, to yield 220 mg (77%) of the desired compound. MS (DCI ($NH_3$)) m/z 305 $(M+NH_4)^+$; $^1$H NMR (300 MHz, $CDCl_3$) δ 8.22 (s, 1H), 7.95 (s, 1H), 7.93 (s, 1H), 7.91 (s, 1H), 7.66 (dd, 1H), 7.61 (dd, 1H), 7.15 (d, 2H), 6.94 (d, 2H), 5.22 (d, 2H), 2.60 (q, 2H), 1.21 (t, 3H).

EXAMPLE 109D

4-[[6-(aminoiminomethyl)-2-naphthalenyl]ethynyl]-L-phenylalanine, mono(trifluoroacetate)(salt)

The desired compound was prepared from Example 109C and the procedure of Example 55D.

MS (DCI/$NH_3$) m/z 305 $(M+H)^+$; $^1$H NMR (300 MHz, DMSO-$d_6$) δ 1.15 (t, 3H), 2.14 (s, 3H), 2.56 (q, 2H), 5.30 (s, 2H), 6.98 (d, 2H), 7.14 (d, 2H), 7.74 (dd, 1H), 7.82 (dd, 1H), 8.15 (m, 3H), 8.48 (s, 1H), 9.01 (br s, 2H), 9.62 (br s, 2H); Anal. calc'd for $C_{20}H_{20}N_2O.1.4\ CH_4SO_3$: C, 58.56; H, 5.88; N, 6.38. Found: C, 58.55; H, 5.56; N, 6.39.

EXAMPLE 111

6-(3-formylphenyl)-2-naphthalenecarboximidamide, mono(trifluoroacetate)(salt)

EXAMPLE 111A

The product from Example 28B (334 mg, 1.11 mmol), palladium acetate (25 mg, 0.11 mmol), dppf (123 mg, 0.22 mmol) were dissolved in degassed DMF (5 mL) and stirred at room temperature for ½ hour. Cesium carbonate (902 mg, 2.8 mmol) and 2-formylphenylboronic acid (251 mg, 1.27 mmol) were added and stirred under nitrogen at 80° C. for 1 hour, poured into pH 7 buffer, extrated with diethyl ether (3×, 20 mL), and dried. The desired compound was purified by chromotography eluting with 10% ethyl acetate/hexanes.

MS (DCI/$NH_3$) m/z $(M+NH_3)^+$275.

EXAMPLE 111B 6-(3-formylphenyl)-2-naphthalenecarboximidamide, mono(trifluoroacetate)(salt)

The above product was prepared in a manner analogous to that of Example 1B.

MS (DCI/$NH_3$) m/z $(M+H)^+$274; $^1$H-NMR (300 MHz, DMSO-$d_6$) δ 10.16 (s, 1H), 9.47 (s, 2H), 9.10 (s, 2H), 8.54 (s, 1H), 8.52 (s, 1H), 8.41 (s, 1H), 8.28–8.23 (m, 3H), 8.12 (dd, 1H), 8.00 (dd, 1H), 7.87 (dd, 1H), 7.80 (t, 1H); Anal. calc'd for $C_{20}H_{15}N_2O_3F_3$ 2/5 TFA: C, 59.28; H, 3.70; N, 6.34. Found: C; 59.36;
H, 3.89; N, 7.21.

EXAMPLE 112

(E)-6-[2-(1,2,3,4-tetrahydro-6-isoquinolinyl) ethenyl]-2-naphthalenecarboximidamide, bis (trifluoroacetate)(salt)

EXAMPLE 112A

The above was prepared from Example 127 using method described in Example 41A
MS (DCI/$NH_3$) m/z $(M+H)^+$411.

EXAMPLE 112B (E)-6-[2-(1,2,3,4-tetrahydro-6-isoquinolinyl) ethenyl]-2-naphthalenecarboximidamide, bis (trifluoroacetate)(salt)

The desired compound was prepared by the method described in Example 40D.

MS (DCI/$NH_3$) m/z $(M+H)^+$328; $^1$H-NMR (300 MHz, DMSO-$d_6$) δ 9.36 (s, 2H), 9.25 (s, 2H), 9.10 (d, 2H), 8.41 (s, 1H), 7.99 (t, 2H), 7.89 (d, 1H), 7.78 (d, 1H), 7.71 (dd, 1H), 7.56 (m, 4H), 7.43 (s, 1H), 3.11 (br, 2H) 2.16 (br 2H), 1.78 (br, 2H); Anal. calc'd for $C_{26}H_{23}N_3O_4F_6$ 3/5 TFA: C, 52.31; H, 3.81; N, 6.72. Found: C, 52.13; H, 4.42; N, 7.23.

EXAMPLE 113

(E)-6-[2-[3-(2-hydroxyethyl)phenyl]ethenyl]-2-naphthalenecarboximidamide, mono (trifluoroacetate)(salt)

EXAMPLE 113A

The above was prepared from 2-bromo-3(hydroxyethyl) alcohol and the compound prepared in Example 98A using method described in Example 41A MS (DCI/$NH_3$) m/z $(M+NH_3)^+$317.

EXAMPLE 113B (E)-6-[2-[3-(2-hydroxyethyl)phenyl]ethenyl]-2-naphthalenecarboximidamide, mono (trifluoroacetate)(salt)

The above was prepared from Example 113A using method described in Example 40D.

MS (DCI/$NH_3$) m/z $(M+H)^+$317; $^1$H-NMR (300 MHz, DMSO-$d_6$) δ 8.9 (br, 4H), 8.46 (s, 1H), 8.17 (s, 1H), 8.13–8.03 (m, 3H), 7.82 (dd, 1H), 7.54 (s, 2H), 7.49 (s, 2H), 7.33 (t, 1H) 7.18 (d, 1H), 4.71 (t, 1H), 3.66 (m, 2H), 2.78 (t, 2H); Anal. calc'd for $C_{23}H_{21}N_2O_3F_3$ 3/10 TFA: C, 61.41; H, 4.66; N, 6.09. Found: C, 64.18; H, 4.92; N, 6.51.

EXAMPLE 114

6-(aminoiminomethyl)-4-(3-furanyl)-N-[4-(trifluoromethyl)phenyl]-2-naphthalenecarboxamide, mono(trifluoroacetate)(salt)

EXAMPLE 114A

The product from Example 152B (100 mg, 0.36 mmol), 4-(trifluoromethyl)aniline (86 mg, 0.53 mmol), and DMAP (5 mg, 0.04 mmol) were dissolved in THF (5 mL) and stirred for 24 hours. The reaction mixture was concentrated on silica gel and purified by chromatography (Biotage Flash 40) using ethyl acetate/hexanes.

MS (ESI) m/z $(M+H)^+$406.

EXAMPLE 114B 6-(aminoiminomethyl)-4-(3-furanyl)-N-[4-(trifluoromethyl)phenyl]-2-naphthalenecarboxamide, mono(trifluoroacetate)(salt)

The above was prepared from Example 114A using method described in Example 1B.

MS (CI) m/z $(M+H)^+$424; $^1$H-NMR (300 MHz, DMSO-$d_6$) δ 10.91 (s, 1H), 9.51 (s, 2H), 9.11 (s, 2H), 8.69 (s, 1H), 8.62 (s, 1H), 8.43–8.35 (m, 2H), 8.18 (d, 1H), 8.06 (d, 2H), 7.98 (t, 1H), 7.92 (dd, 1H), 7.78 (dd, 2H) 7.14 (m, 1H); Anal. calc'd for $C_{25}H_{17}N_3O_4F_6$ 1/10 TFA: C, 55.37; H, 3.15; N, 7.70. Found: C, 55.44; H, 3.15; N, 7.31.

EXAMPLE 115

6-(aminoiminomethyl)-4-(3-furanyl)-N-(4-pyridinyl)-2-naphthalenecarboxamide, dihydrochloride

EXAMPLE 115A

The above product was prepared in the manner of Example 114A.

MS (ESI) m/z (M+H)$^+$340.

EXAMPLE 115B 6-(aminoiminomethyl)-4-(3-furanyl)-N-(4-pyridinyl)-2-naphthalenecarboxamide, dihydrochloride The above was prepared from Example 115A using method described in Example 1B.

MS (AP/CI) m/z (M+H)$^+$357; $^1$H-NMR (300 MHz, DMSO-d$_6$) δ 12.43 (s, 1H), 9.69 (s, 2H), 9.40 (s, 2H), 8.94 (s, 1H), 8.81 (d, 2H), 8.65 (s, 1H), 8.58–8.56 (m, 2H), 8.49 (s, 1H), 8.42 (d, 1H), 8.30 (m, 1H) 7.97–7.95 (m, 2H), 7.27 (s, 1H); Anal. calc'd for $C_{21}H_{18}N_4O_2Cl_2$ 37/10 HCl: C, 44.65 H, 3.88 N, 9.92. Found: C, 44.72; H, 3.70; N, 9.51.

EXAMPLE 116

6-(aminoiminomethyl)-4-(3-furanyl)-N-(1H-pyrazol-3-yl)-2-naphthalenecarboxamide, dihydrochloride

EXAMPLE 116A

The above product was prepared in the manner of Example 114A.

MS (ESI) m/z (M+H)$^+$329.

EXAMPLE 116B 6-(aminoiminomethyl)-4-(3-furanyl)-N-(1H-pyrazol-3-yl)-2-naphthalenecarboxamide, dihydrochloride The above was prepared from Example 116A using method described in Example 1B.

MS (CI) m/z (M–H)$^+$344; $^1$H-NMR (300 MHz, DMSO-d$_6$) δ 11.16 (s, 1H), 9.52 (s, 2H), 9.10 (s, 2H), 8.69 (s, 1H), 8.61 (s, 1H), 8.35 (m, 2H), 8.24 (s, 1H), 7.96–7.88 (m, 3H), 7.69 (m, 1H), 7.15 (s, 1H) 6.69 (m, 1H); Anal. calc'd for $C_{19}H_{17}N_5O_2Cl_2$ 9/10 HCl: C, 50.63; H, 4.00; N, 15.54. Found: C, 51.05; H, 4.62; N, 14.26.

EXAMPLE 117

6-(aminoiminomethyl)-4-(3-furanyl)-N-(3-pyridinyl)-2-naphthalenecarboxamide, dihydrochloride

EXAMPLE 117A

The above product was prepared in the manner of Example 114A.

MS (ESI) m/z (M+H)$^+$340.

EXAMPLE 117B 6-(aminoiminomethyl)-4-(3-furanyl)-N-(3-pyridinyl)-2-naphthalenecarboxamide, dihydrochloride The above was prepared from Example 117B using method described in Example 1B.

MS (CI) m/z (M+H)$^+$357; $^1$H-NMR (300 MHz, DMSO-d$_6$) δ 10.90 (s, 1H), 9.59 (s, 2H), 9.26 (s, 2H), 9.03 (s, 2H), 8.74 (s, 1H), 8.63 (s, 1H), 8.42–8.26 (m, 3H), 8.22 (s, 1H), 7.97–7.91 (m, 2H), 7.47–7.43 (m, 2H), 7.17 (s, 1H); Anal. calc'd for $C_{21}H_{18}N_4O_2Cl_2$ 55/10 HCl: C, 40.00 H, 3.76 N, 8.89. Found: C, 40.09; H, 3.78; N, 8.44.

EXAMPLE 118

6-(aminoiminomethyl)-N-(2,3-dihydro-1H-inden-5-yl)-2-naphthalenecarboxamide, mono (trifluoroacetate)(salt)

EXAMPLE 118A

To a solution of the compound prepared in Example 8E (303 mg, 1.4 mmol) in THF (30 mL) and propylene oxide (15 mL) was added two drops of Et$_3$N followed by the 5-aminoindene (300 mg, 2.2 mmol). The reaction was stirred at room temperature overnight. The solvent was evaporated and the product was purified via crystallization from ether to yield 226 mg (56%) of the product as white solid. Mass spectrum (CI+), 313 (M+1)$^+$.

EXAMPLE 118B 6-(aminoiminomethyl)-N-(2,3-dihydro-1H-inden-5-yl)-2-naphthalenecarboxamide, mono (trifluoroacetate)(salt)

The compound prepared in Example 118A (205 mg, 0.66 mmol) in THF (20 mL) at room temperature, was added butyl lithium (1 mL, 1 mmol) followed by chlorotrimethyl silane (180 μL, 1.5 mmol). After 10 minutes the mixture was charged with additional butyl lithium (3 mL, 3 mmol). The reaction was stirred at room temperature, overnight. The reaction mixture was added a solution of 4 N HCl in dioxane stirred for an hour then added water and evaporated. The product was purified by MPLC RP C$_{18}$ with methanol-water and 0.1% TFA as eluent chromatography. The yield of the product as TFA salt with 0.25% water as white solid 51 mg (17%).

MS (ESI+) 330 (M+1)$^+$; $^1$H NMR (DMSO-d6) 10.45 (s, 1H), 9.51 (s, 2H), 9.21 (s, 2H), 8.66 (s, 1H), 8.55 (s, 1H), 8.32 (d, J=8.5 Hz, 1H), 8.20 (Abq, J=9.0 Hz, 2H), 7.90 (dd, J$_1$=9.0 Hz, J$_2$=1.5 Hz, 1H), 7.73 (s, 1H), 7.53 (dd, J$_1$=8.0 Hz, J$_2$=1.5 Hz, 1H), 7.22 (d, J=8.1 Hz, 1H), 2.91–2.82 (m, 4H), 2.04 (quintet, J=7.3 Hz, 2H); Anal. calc'd for $C_{21}H_{19}N_3O$.TFA.0.25 H$_2$O C: 61.67; H, 4.61; N, 9.38. Found: C: 61.63; H, 4.43; N, 9.25.

EXAMPLE 119 methyl 5-[7-[(aminoiminomethyl)-2-naphthalenyl] oxy]pentanoate, mono(trifluoroacetate) (salt)

EXAMPLE 119A 7-hydroxy-2-cyanonaphthalene 7-methoxy-2-cyanonaphthalene (2.79 g, 5.23 mmol) and tetrabutylammonium iodide (17 mg, 0.157 mmol) were combined in a mixture of benzene (35 mL) and cyclohexanes (17.5 mL). The resulting solution was added to a rapidly stirring, cooled (ice/water) suspension of aluminum triiodide (6.21 g, 15.23 mmol) in a mixture of benzene (35 mL) and cyclohexanes (17.5 mL) under an inert atmosphere. After the addition, the resulting suspension was heated at reflux for 2.5 hours. The heating was removed and after cooling to near room temperature, the reaction mixture was cooled in an ice bath and quenched by the addition of water (100 mL). The resulting mixture was further diluted with 2 M aqueous sodium thiosulfate solution (50 mL) and extracted with ethyl acetate (3×80 mL). The combined organic layers were dried and evaporated. The resulting solid was dissolved in a minimum of hot ethyl acetate, diluted hot with hexanes to the cloud point and placed in a refrigerator for 2 hours. The desired compound was collected by filtration, (1.99 g, 77%).

MS (DCI ($NH_3$)) m/z 187 $(M+NH_4)^+$.

EXAMPLE 119B

The resulting product from Example 119A was treated with methyl 5-bromovalerate in an analogous manner as described in Example 119A.

MS (DCI ($NH_3$)) m/z 301 $(M+NH_4)^+$.

EXAMPLE 119C methyl 5-[7-[(aminoiminomethyl)-2-naphthalenyl]oxy]pentanoate, mono(trifluoroacetate) (salt)

The resulting product from Example 119B (380 mg, 1.3412 mmol) was treated in an analogous manner as described in Example 94D to yield the desired compound (369 mg, 73%).

MS (DCI ($NH_3$)) m/z 301 $(M+H)^+$; $^1$H NMR (300 MHz, DMSO-d6) δ 1.785 (m, 4H), 2.425 (t, 2H), 3.600 (s, 3H), 4.150 (t, 2H), 7.380 (dd, 1H), 7.460 (d, 1H), 7.640 (dd, 1H), 7.980 (d, 1H), 8.070 (d, 1H), 8.322 (d, 1H), 9.230 (v br s, 3H); Anal. calc'd for $C_{17}H_{20}N_2O_3 \cdot C_2HO_2F_3$: C, 55.07; H, 5.11; N, 6.76. Found: C, 54.96; H, 5.22; N, 6.66.

EXAMPLE 120

(E)-3-[7-(aminoiminomethyl)-2-methoxy-1-naphthalenyl)-2-propenamide, mono (trifluoroacetate)(salt)

EXAMPLE 120A

The product obtained from Example 53B and acrylamide were subjected to the conditions described in Example 41A to provide the desired compound.

MS (DCI/$NH_3$) m/z 253 $(M+H)^+$.

EXAMPLE 120B (E)-3-[7-(aminoiminomethyl)-2-methoxy-1-naphthalenyl)-2-propenamide, mono (trifluoroacetate)(salt)

The product obtained from Example 120A was subjected to the conditions described in Example 94D to provide the desired compound.

MS (DCI/$NH_3$) m/z 270 $(M+H)^+$; $^1$H NMR (300 MHz, DMSO) δ 4.02 (s, 3H), 6.90 (d, 1H), 7.22 (s, 1H), 7.62–7.70 (m, 2H), 7.74 (d, 1H), 8.02 (d, 1H), 8.11 (d, 1H), 8.15 (d, 1H), 8.58 (s, 1H), 9.18 (s, 2H), 9.50 (s, 2H); Anal. calc'd for $C_{17}H_{16}F_3N_3O_4 \cdot H_2O$: C, 50.88; H, 4.52; N, 10.47. Found: C, 50.89; H, 4.32; N, 10.43.

EXAMPLE 121

6[(4aminophenyl)ethynyl]-2-naphthalenecarboximidamide, bis(trifluoroacetate) (salt)

EXAMPLE 121A

A mixture of the product obtained in Example 63B (130 mg, 0.73 mmol), 4-iodoaniline (173 mg, 0.79 mmol), dichlorobis (triphenylphosphine)palladium (II) (25 mg, 0.0325 mmol), copper (I) iodide (2.7 mg, 0.0186 mmol), DMF (0.65 mL), and triethylamine (1.95 mL) was degassed with $N_2$ and was stirred at 75°–80° for 1.5 hour. The mixture was cooled to room temperature, diluted with $CH_2Cl_2$, washed with water, dried ($MgSO_4$), filtered, and evaporated under vacuum to afford an oil which was purified by flash chromatography, eluting with 3:1 hexanes:ethyl acetate to afford the desired compound.

MS (DCI/$NH_3$) m/z 269 $(M+H)^+$.

EXAMPLE 121B

6-[(4-aminophenyl)ethynyl]-2-naphthalenecarboximidamide, bis(trifluoroacetate) (salt)

Using the product obtained in Example 121A and the procedure described in Example 40D, the desired compound was obtained.

MS (DCI/$NH_3$) m/z 286 $(M+H)^+$; $^1$H NMR (300 MHz, DMSO) δ 6.80 (d, 2H), 7.29 (d, 2H), 7.70 (dd, 1H), 7.85 (dd, 1H), 8.09 (d, 1H), 8.14 (d, 1H), 8.20 (s, 1H), 8.45 (s, 1H), 9.09 (s, 2H), 9.42 (s, 2H); Anal. calc'd for $C_{23}H_{17}F_6N_3O_4 \cdot 0.25 \ H_2O$: C, 53.34; H, 3.41; N, 8.11. Found: C, 53.45; H, 3.70; N, 7.76.

EXAMPLE 122

1,1-dimethylethyl [2-[3-[[6-(aminoiminomethyl)-2-naphathalenyl]ethynyl]-6-methoxyphenyl]ethyl] carbamate, mono(trifluoroacetate)(salt)

EXAMPLE 122A

Using 5-bromo-2-methoxyphenethylamine hydrobromide (Transworld), and the procedure described in Example 63C, the desired compound was obtained. MS (DCI/$NH_3$) m/z 330 $(M+H)^+$.

EXAMPLE 122B

Using the procedure described for Example 121A, and substituting the product obtained in Example 122A for 4-iodoaniline, the desired compound was obtained. MS (ESI) m/z 427 $(M+H)^+$.

EXAMPLE 122C 1,1-dimethylethyl [2-[3-[[6-(aminoiminomethyl)-2-naphathalenyl]ethynyl]-6-methoxyphenyl]ethyl] carbamate, mono(trifluoroacetate)(salt)

Using the product obtained in Example A-226638-B and the procedure described in Example 40-D, the desired compound was obtained.

MS (DCI/$NH_3$) m/z 444 $(M+H)^+$; $^1$H NMR (300 MHz, DMSO) δ 1.38 (s, 9H), 2.70 (t, 2H), 3.15 (q, 2H), 3.85 (s, 3H), 6.89 (t, 1H), 7.04 (d, 1H), 7.37 (d, 1H), 7.49 (dd, 1H), 7.75 (dd, 1H), 7.85 (dd, 1H), 8.11 (d, 1H), 8.16 (d, 1H), 8.30 (s, 1H), 8.48 (s, 1H), 9.07 (s, 2H), 9.42 (s, 2H) Anal. calc'd for $C_{29}H_{30}F_3N_3O_5 \cdot 0.25 \ H_2O$: C, 61.97; H, 5.47; N, 7.48. Found: C, 61.81; H, 5.14; N, 7.21.

EXAMPLE 123

1,1-dimethylethyl [[4-[[6-(aminoiminomethyl)-2-naphathalenyl]ethynyl]phenyl]methyl]carbamate, mono(trifluoroacetate)(salt)

EXAMPLE 123A

Using 4-bromobenzylamine, and the procedure described in Example 63C, the desired compound was obtained.

MS (DCI/$NH_3$) m/z 303 $(M+NH_4)^+$.

EXAMPLE 123B

Using the procedure described for Example 121A, and substituting the product obtained in Example 123 for 4-iodoaniline, the desired compound was obtained.

MS (DCI/NH$_3$) m/z 400 (M+NH$_4$)$^+$.

EXAMPLE 123C 1,1-dimethylethyl [[4-[[6-(aminoiminomethyl)-2-naphathalenyl]ethynyl]phenyl]methyl]carbamate, mono(trifluoroacetate)(salt)

Using the product obtained in Example 123B and the procedure described in Example 40D, the desired compound was obtained.

MS (DCI/NH$_3$) m/z 400 (M+H)$^+$; $^1$H NMR (300 MHz, DMSO) δ 1.40 (s, 9H), 4.18 (d, 2H), 7.34 (d, 2H), 7.45 (t, 1H), 7.58 (d, 2H), 7.78 (dd, 1H), 7.86 (dd, 1H), 8.15 (d, 1H), 8.19 (d, 1H), 8.31 (s, 1H), 8.50 (s, 1H), 9.10–9.42 (s, 4H); Anal. calc'd for C$_{27}$H$_{26}$F$_3$N$_3$O$_4$: C, 63.15; H, 5.10; N, 8.18. Found: C, 62.95; H, 4.97; N, 8.09.

EXAMPLE 124

6-[[4-(aminomethyl)phenyl]ethynyl]-2-naphthalenecarboximidamide, bis(trifluoroacetate) (salt)

Trifluoroacetic acid (0.73 mL) was added dropwise to a suspension of the product obtained in Example 123C (80 mg, 0.2 mmol) and 1.5 mL CH$_2$Cl$_2$. The reaction mixture was stirred for 0.25 hour at room temperature, then was evaporated to dryness under vacuum. Toluene was added and evaporated under vacuum several times to afford a tan solid which was purified by reverse phase chromatography, eluting with methanol/0.1% aqueous TFA to afford the desired compound.

MS (APCI) m/z 300 (M+H)$^+$; $^1$H NMR (300 MHz, DMSO) δ 4.10 (s, 2H), 7.55 (d, 2H), 7.70 (d, 2H), 7.79 (dd, 1H), 7.89 (dd, 1H), 8.16 (d, 1H), 8.19 (d, 1H), 8.20 (s, 2H), 8.36 (s, 1H), 8.53 (S, 1H), 9.20 (s, 2H), 9.44 (s, 2H); Anal. calc'd for C$_{24}$H$_{19}$F$_6$N$_3$O$_4$: C, 54.66; H, 3.63; N, 7.97. Found: C, 54.42; H, 3.57; N, 7.76.

EXAMPLE 125

6-[[3-(2-aminoethyl)-4-methoxyphenyl]ethynyl]-2-naphthalenecarboximidamide, bis(trifluoroacetate) (salt)

Using the product obtained in Example 122C and the procedure described for Example 124, the desired compound was obtained.

MS (ESI) m/z 344 (M+H)$^+$; $^1$H NMR (300 MHz, DMSO) δ 2.90 (t, 2H), 3.06 (t, 2H), 3.88 (s, 3H), 7.11 (d, 1H), 7.44 (d, 1H), 7.57 (dd, 1H), 7.75 (dd, 1H), 7.82 (s, 2H), 7.88 (dd, 1H), 8.12 (d, 1H), 8.17 (d, 1H), 8.28 (s, 1H), 8.50 (s, 1H), 9.20 (s, 2H), 9.45 (s, 2H); Anal. calc'd for C$_{26}$H$_{23}$F$_6$N$_3$O$_5$.0.5 H$_2$O: C, 53.80; H, 4.17; N, 7.24. Found: C, 53.89; H, 4.31; N, 6.83.

EXAMPLE 126

6-[[4-(hydroxymethyl)phenyl]ethynyl]-2-naphthalenecarboximidamide, mono (trifluoroacetate) (salt)

EXAMPLE 126A

Using the procedure described for Example 121A, and substituting 4-bromobenzyl alcohol for 4-iodoaniline, the desired compound was obtained.

MS (DCI/NH$_3$) m/z 301 (M+NH$_4$)$^+$.

EXAMPLE 126B

6-[[4-(hydroxymethyl)phenyl]ethynyl]-2-naphthalenecarboximidamide, mono (trifluoroacetate)(salt)

Using the product obtained in Example 126A and the procedure described in Example 94B the desired compound was obtained.

MS (ESI) m/z 301 (M+H)$^+$; $^1$H NMR (300 MHz, DMSO) δ 4.58 (d, 2H), 5.32 (t, 1H), 7.41 (d, 2H), 7.59 (d, 1H), 7.79 (dd, 1H), 7.86 (dd, 1H), 8.12 (d, 1H), 8.18 (d, 1H), 8.32 (s, 1H), 8.50 (s, 1H), 9.14 (s, 2H), 9.46 (s, 2H); Anal. calc'd for C$_{22}$H$_{17}$F$_3$N$_2$O$_3$.0.5 H$_2$O: C, 62.41; H, 4.29; N, 6.62. Found: C, 62.56; H, 4.13; N, 6.65.

EXAMPLE 127

6-[(1,2,3,4-tetrahydro-6-isoquinolinyl)ethynyl]-2-naphthalenecarboximidamide, bis(trifluoroacetate) (salt)

EXAMPLE 127A

A solution of boron tribromide (1.2 mL, 12.5 mmol) and 12.5 mL CH$_2$Cl$_2$ was added dropwise to a –78° solution of 6-methoxytetrahydroisoquinoline (1.0 g, 5.0 mole, Org. Synth., 67, 60, 1988) and 38 mL CH$_2$Cl$_2$. The reaction mixture was stirred for 1 hour at –78°, 1 hour at 0°, and 0.25 hour at room temperature. The reaction mixture was cooled to –78°, and 20 mL methanol was added dropwise. The solution was stirred for 1 hour at room temperature. Solvent was evaporated under vacuum and the residue was dried under vacuum to afford the desired compound.

MS (DCI) m/z 150 (M+H)$^+$.

EXAMPLE 127B

The product obtained in Example 127A (1.15 g, 5.0 mmol) was subjected to the conditions described in Example 63C. A 2.1 g portion of this material was stirred at reflux for 1.5 hour with 60 mL methanol and 9 mL 10% aqueous NaOH. After cooling to room temperature, methanol was evaporated under vacuum. Water was added and the solution was acidified with 6 N HCl. The mixture was extracted with CH$_2$Cl$_2$. The organic layer was washed with water, saturated aqueous sodium chloride, dried (MgSO$_4$), filtered, and solvent evaporated under vacuum to afford the desired compound.

MS (DCI/NH$_3$) m/z 267 (M+NH$_4$)$^+$.

EXAMPLE 127C

Using the product from Example 127B and the procedure described in Example 28B, the desired compound was obtained.

MS (DCI/NH$_3$) m/z 399 (M+NH$_4$)$^+$.

EXAMPLE 127D

Using the procedure described for Example 121A, and substituting the product obtained in Example 127C for 4-iodoaniline, the desired compound was obtained.

MS (DCI/NH$_3$) m/z 426 (M+NH$_4$)$^+$.

EXAMPLE 127E

Using the product obtained in Example 127D and the procedure described in Example 40D, the desired compound was obtained.

MS (ESI) m/z 426 (M+H)$^+$; $^1$H NMR (300 MHz, DMSO) δ 1.45 (s, 9H), 2.82 (t, 2H), 3.59 (t, 2H), 4.58 (s, 2H), 7.29 (d, 1H), 7.42 (d, 2H), 7.76 (dd, 1H), 7.83 (dd, 1H), 8.15 (d, 1H), 8.19 (d, 1H), 8.35 (s, 1H), 8.51 (s, (1H), 9.20 (s, 2H), 9.45 (s, 2H).

EXAMPLE 127F

6-[(1,2,3,4-tetrahydro-6-isoquinolinyl)ethynyl]-2-naphthalenecarboximidamide, bis(trifluoroacetate) (salt)

Using the product obtained in Example 127E and the procedure described in Example 124D, the desired compound was obtained.

MS (ESI) m/z 326 (M+H)$^+$; $^1$H NMR (300 MHz, DMSO) δ 3.03 (t, 2H), 3.42 (t, 2H), 4.35 (s, 2H), 7.35 (d, 1H), 7.46 (d, 2H), 7.78 (dd, 1H), 7.89 (dd, 1H), 8.15 (d, 1H), 8.19 (d, 1H), 8.35 (s, 1H), 8.52 (s, 1H), 9.17 (s, 2H), 9.31 (s, 2H), 9.48 (s, 2H); Anal. calc'd for $C_{26}H_{21}F_6N_3O_4$: C, 56.42; H, 3.82; N, 7.59. Found: C, 56.31; H, 3.81; N, 7.42.

EXAMPLE 129

5-[[6-(aminoiminomethyl)-2-naphthalenyl]oxy] pentanoic acid, mono(trifluoroacetate)(salt)

EXAMPLE 129A

The resulting product from Example 119A (250 mg, 1.477 mmol) was treated with methyl 5-bromovalerate in an analogous manner as described in Example 119B to yield the desired compound (394 mg, 94%).

MS (DCI (NH$_3$)) m/z 301 (M+NH$_4$)$^+$.

EXAMPLE 129B

5-[[6-(aminoiminomethyl)-2-naphthalenyl]oxy] pentanoic acid, mono(trifluoroacetate)(salt)

The resulting product from Example 129A (262 mg, 0.8723 mmol) was treated in an analogous manner as described in Example 94D to yield the ester amidine product. The product (140 mg, 0.542 mmol) was dissolved in methanol (11 mL). To this was added a solution of lithium hydroxide (68.2 mg, 1.626 mmol) in water (3 mL) and the resulting mixture was stirred at room temperature under an inert atmosphere for 18 hours. The reaction was evaporated and the residue purified by reverse phase chromatography to yield the desired compound (184 mg, 74%).

MS (DCI (NH$_3$)) m/z 287 (M+H)$^+$; $^1$H NMR (300 MHz, DMSO-d6) δ 1.711 (m, 2H), 1.817 (m, 2H), 2.320 (t, 2H), 4.144 (t, 2H), 7.377 (dd, 1H), 7.472 (d, 1H), 7.632 (dd, 1H), 7.980 (d, 1H), 8.081 (d, 1H), 8.329 (s 1H), 9.100 (br s, 2H), 9.390 (br s, 2H), 12.100 (br s, 1H); Anal. calc'd for $C_{16}H_{18}N_2O_3 \cdot (C_2HO_2F_3)$ 1.15.H$_2$O 0.65: C, 51.22; H, 4.80; N, 6.53. Found: C, 51.30; H, 5.07; N, 6.12.

EXAMPLE 131

7-methoxy-8-(3-oxo-1-cyclopenten-1-yl)-2-naphthalenecarboximidamide, mono (trifluoroacetate)(salt)

EXAMPLE 131A

The material prepared as described in Example 25A (0.5 g, 1.5 mmol) and the 3-tributylstannyl-2-cyclopentenone prepared as described by Labourde et al. Tet Letters 31, (13), 1837–1840 (1990) are coupled via Pd catalyst as described by the method of Stille et al. *JACS* 109, 5478–5486 (1987) yielding after flash chromatography with 3:1 hexanes/ethyl acetate a white solid. 300 mg, 72%.

MS (DCI/NH$_3$): 281 (M+NH$_4$).

EXAMPLE 131B 7-methoxy-8-(3-oxo-1-cyclopenten-1-yl)-2-naphthalenecarboximidamide, mono (trifluoroacetate)(salt)

The material prepared above (130 mg, 0.4 mmol) is prepared according to the H$_2$S/pyridine method described in Example 40D. The desired compound was obtained as an off-white solid after reverse phase chromatography. 52 mg, 45%.

MS (DCI/NH3): M+H+281 $^1$H NMR (DMSO-d6): 9.45 (bs, 2H); 9.12 (bs, 2H), 8.25–8.32 (m, 2H), 8.20 (dd, 1H), 7.86 (d, 1H), 7.75 (dd, 1H), 6.42 (m, 1H), 4.05 (s, 3H), 3.15 (m, 2H), 2.75 (m, 2H) Anal. calc'd for $C_{19}H_{17}N_2O_4F_3 \cdot 1.75$ TFA: C, 57.87; H, 4.35; N, 7.10. Found: C, 51.37; H, 4.21; N, 7.14.

EXAMPLE 132

6-(aminoiminomethyl)-N-(4-methylphenyl)-2-naphthalenecarboxamide, mono(trifluoroacetate) (salt)

EXAMPLE 132A p-Toluidine (0.11 g, 1 mmol), and the cyano ester prepared in Example 8E (0.2 g, 1 mmol) are coupled according to the procedure described in Example 8G, providing an off-white solid as the desired compound (0.16 g, 56%).

MS (ESI +, –): 287 (M+); 285 (M–).

EXAMPLE 132B 6-(aminoiminomethyl)-N-(4-methylphenyl)-2-naphthalenecarboxamide, mono(trifluoroacetate) (salt)

The desired compound is prepared according to the procedure described in Example 6B and purified as described in Example 1B, yielding a white solid (35 mg, 35%).

MS (ESI+): 304 (M+) 1HNMR (DMSO-d6): 10.55 (s, 1H); 9.45 (bs, 2H); 9.15 (bs, 2H); 8.65 (s, 1H); 8.58 (s, 1H); 8.32 (d, 1H), 8.20 (d, 1H), 8.19 (dd, 1H); 7.96 (dd, 1H), 7.75 (d, 2H), 7.12 (d, 2H), 2.35 (s, 3H); Anal. calc'd for $C_{21}H_{18}N_3O_3F_3$: C, 60.43; H, 4.35; N, 10.07 Found: C, 59.94; H, 4.06; N, 9.80.

EXAMPLE 133 methyl 4-[[[7-(aminoiminomethyl)-1-(2-pyrimidinylamino)-2-naphthalenyl]oxy]methyl] benzoate, mono(trifluoroacetate)(salt)

EXAMPLE 133A

The material described in Example 91A is treated with AlI$_3$ according to the procedure described in Example 119A and alkylated with 4-CarbomethoxyBenzylbromide according to the procedure described in Example 109B, yielding the desired compound as a white solid, 100 mg, 83%.

MS (ESI +, –): 411 (M+); 409 (M–).

EXAMPLE 133B methyl 4-[[[7-(aminoiminomethyl)-1-(2-pyrimidinylamino)-2-naphthalenyl]oxy]methyl] benzoate, mono(trifluoroacetate)(salt)

The desired compound is prepared according to the procedure described in Example 40D and purified according to the procedure described in Example 119B, yielding a light yellow solid, (49 mg, 50%).

MS (ESI +, −): 428 (M+); 426 (M−) $^1$H NMR (DMSO-d6): 9.45 (bs, 2H); 9.15 (s, 1H); 8.97 (bs, 2H); 8.45 (dd, 1H); 8.38 (d, 1H); 8.15 (d, 1H), 8.09 (d, 1H), 7.95 (d, 2H); 7.76 (d, 1H), 7.68 (dd, 1H), 7.35 (d, 2H), 6.85 (d, 2H), 5.39 (s, 2H); 3.85 (s, 3H); Anal. calc'd for $C_{26}H_{22}N_5O_5F_3$: C, 57.67; H, 4.10; N, 12.93 Found: C, 55.34; H, 3.88; N, 12.05.

EXAMPLE 134

4-[[[7-(aminoiminomethyl)-1-(2-pyrimidinylamino)-2-naphthalenyl]oxy]methyl]benzoic acid, mono (trifluoroacetate)(salt)

The material prepared in Example 134 (40 mg) is dissolved in 1:1 THF/water. To the clear solution is added LiOH.water (9 mg), the resulting clear solution is stirred 18 hours at room temperature. The reaction mixture is concentrated to a yellow solid. The solid is dissolved in distilled water, acidified to pH 2 with 3 N HCl and stirred 2 hours at room temperature. The desired compound is isolated by filtration, dried under vacuum as a yellow solid. Yield: 39 mg (46%)

MS (APCI): M+H$^+$: 414 $^1$H NMR (DMSO-d6): 9.45 (bs, 2H); 9.15 (s, 1H); 8.97 (bs, 2H); 8.45 (dd, 1H); 8.38 (d, 1H); 8.15 (d, 1H), 8.09 (d, 1H), 7.95 (d, 2H); 7.76 (d, 1H), 7.68 (dd, 1H), 7.35 (d, 2H), 6.85 (d, 2H), 5.39 (s, 2H); Anal. calc'd for $C_{25}H_{20}N_5O_5F_3Cl.3\ H_2O$: C, 48.67; H, 4.25; N, 11.35 Found: C, 49.64; H, 4.44; N, 11.69.

EXAMPLE 135

1,1-dimethylethyl [[4-[[[6-(aminoiminomethyl)-2-naphathalenyl]amino]carbonyl]-phenyl]methyl] carbamate, mono(trifluoroacetate)(salt)

EXAMPLE 135A

The material prepared in Example 8B was added to cold (0° C.) sulfuric acid (45 mL). Within 1 minutes at 0° C. bubling started to form. Allowed to bubble at 0° C. for 30 minutes than slowly warmed to room temperature. Left at room temperature for 20 minutes, then poured into ice and diluted with water (to approx. 500 mL). The suspension was placed in an ice bath and carefully added a solution of 50% aqueuos sodium hydroxide so that the temperature would not exceed 35° C. The light yellow solid was filtered than washed with water till the wash became neutral to pH paper (7.0). The product was dried under vacuum. The product was purified on silica gel column using 20% ethyl acetate 80% hexanes as eluent to yield 3.3 g (67%) of light yellow solid.

MS m/z 169 (M+1)$^+$.

EXAMPLE 135B

A solution of Example 135A (135 mg, 0.8 mmol), 4-N-Boc-aminomethylbenzoic acid (404 mg, 1.6 mmol) and EDCI (307 mg, 1.6 mmol) in methylene chloride (25 mL), at room temperature, was added DMAP (3 mg) and stirred overnight. The reaction mixture was diluted with methylene chloride (60 mL) then washed 2% aqueous hydrochloric acid (2×30 mL), water (20 mL), 0.5 M aqeuos sodium hydroxide (2×50 mL) and brine. The organic phase was dried over magnesium sulfate and evapoorated. The product was purified via on silica column usinga gradient of 25% to 60% ethyl acetate in hexanes as eluent. Yield 175 mg (54%) of white powder.

EXAMPLE 135C 1,1-dimethylethyl [[4-[[[6-(aminoiminomethyl)-2-naphathalenyl]amino]carbonyl]phenyl]methyl] carbamate, mono(trifloroacetate)(salt)

The reaction was carried out in the same manner as described in Example 40D.

Yield 110 mg (64%). MS m/z 408 (M+1)$^+$, 425 (M+18)$^+$ $^1$H NMR: 3.30 (s, 9H), 4.22 (d, 2H, J=7.1 Hz), 7.42 (d, 2H, J=8.5 Hz), 7.49 (t, 1H, J=7.1 Hz), 7.79 (dd, 1H, J1=8.2 Hz, J2=2.0 Hz), 7.95–8.00 (m, 3H), 8.09 (d, 2H, J=8.4 Hz), 8.42 (s, 1H), 8.63 (d, 1H, J=2.0 Hz), 9.18 (br s, 4H), 10.58 (s, 1H); Anal. calc'd for $C_{26}H_{27}F_3N_4O_5$: C, 58.55; H, 4.85; N, 10.41. Found: C, 58.64; H, 5.11; N, 10.52.

EXAMPLE 136

N-[6-(aminoiminomethyl)-2-naphthalenyl) benzamide, mono(trifluoroacetate)(salt)

The desired compound is prepared as described in Example 135;

$^1$H NMR (300 MHz, DMSO-d$_6$) 10.67 (s, 1H), 9.25 (br.s, 4H), 8.65 (d, J=1.5 Hz, 1H), 8.43 (d, J=1.4 Hz, 1H), 8.10 (d, J=9.2 Hz, 2H), 8.03–7.97 (m, 3H), 7.81–7.78 (m, 1H), 7.65–7.55 (m, 3H). MS (ESI/NH$_3$) m/z 290 (M+H)$^+$; Anal. calc'd for $C_{18}H_{15}N_3O.CF_3COOH$: C, 59.55; H, 4.00; F, 14.13; N, 10.42. Found: C, 50.47; H, 3.88; F, 14.42; N, 10.39.

EXAMPLE 137

1,1-dimethylethyl [[4-[[[6-(aminoiminomethyl)-2-naphathalenyl]amino]carbonyl]cyclohexyll]methyl] carbamate, mono(trifluoroacetate)(salt)

EXAMPLE 137A

To a solution of the 6-Amino-2-naphthalenecarbonitrile prepared in Example 73 (100 mg, 0.6 mmol) in methylene chloride (35 mL) at room temperature, was added 1-carboxy-4-(Boc-aminomethyl)cyclohexanes (280 mg, 1.1 mmol) followed by 1-ethyl-3-(3-dimethylaminopropyl) carbodiimide hydrochloride (EDAC, 225 mg, 1.2 mmol). After 5 minutes to the reaction mixture was added DMAP (20 mg, catalytic). The reaction was stirred at room temperature for 72 hours. The reaction mixture was diluted 7:3 ethyl acetate:hexanes then filtered through silica gel and washed with the same solvent mixture.

The organic solvent was washed by aq. Acid (2% Hcl, 2×50 mL), water and aq. Base (10% NaOH, 50 mL). The solvent was dried over magnesium sulfate filtered and evaporated. Crystalization from ether/hexanes afforded the product as white solid. Yield 166 mg (68%).

MS (DCI/NH$_3$) m/z 408 (M+H)$^+$.

EXAMPLE 137B 1,1-dimethylethyl [[4-[[[6-(aminoiminomethyl)-2-naphathalenyl]amino]carbonyl]cyclohexyll]methyl] carbamate, mono(trifluoroacetate)(salt)

A solution of the substrate (Example 137A) in Pyr: Et$_3$N (10:1, 20 mL) was bubbled H$_2$S for 5 minutes. Stirred at room temperature overnight. The reaction mixture was added ethyl acetate (100 mL) followed by 1% aq. KHSO4 (60 mL) and separated; washed organic layer with water (2×50 mL), sodium bicarb. And brine, dried over magnesium sulfate & evaporated. To a suspension of the resulting solid in acetone (25 mL) and added MeI (1.0 mL). Stirred at 50° C. for 2 hours, all dissolved. Evaporated solvent to a complete dryness and added methanol (30 mL) and ammonium acetate (150 mg). The mixture was stirred at room temperature overnight. Purification by Reverse Phase C$_{18}$ MPLC. After evaporation added toluene & evaporated (2×40 mL). The resulting oil was treated with methanol and ether and the product precipitated as white solid (72 mg, 43%).

MS (ESI/NH$_3$) m/z 425 (M+H)$^+$; $^1$H NMR (300 MHz, DMSO-d$_6$) 10.24 (s, 1H), 9.05 (br.s, 4H), 8.49 (s, 1H), 8.38 (d, J=1.7 Hz, 1H), 8.03–8.00 (m, 2H), 7.77–7.74 (m, 2H), 6.93–6.91 (m, 1H), 2.83–2.79 (m, 2H), 2.40–2.30 (ml), 1.92–1.75 (m, 4H), 1.50–1.45 (m, 1H), 1.39 (s, 9H), 0.96–0.91 (m, 4H); Anal. calc'd for C$_{24}$H$_{32}$N$_4$O$_3$.CF$_3$COOH: C, 57.98; H, 6.18; N, 10.40. Found: C, 57.63, H, 6.24; N, 10.21.

EXAMPLE 138

N-[6-(aminoiminomethyl)-2-naphthalenyl]-N'-(4-aminophenyl)urea, bis(trifluoroacetate(salt)

EXAMPLE 138A

To a solution of the compound prepared in Example 40B (194.2 mg, 1 mmol) in dioxane (10 mL) at room temperature, was added 4-phenylenediamine mono Boc (416, 5 mg, 2 mmol). The product started to precipitate within minutes. After an hour the reaction mixture was added ether (5 mL) and the white solid product was filtered and washed with ether to yield 350 mg (87%).

MS (DCI/NH$_3$) m/z 403 (M+H)$^+$.

EXAMPLE 138B

A solution of the corresponding nitrile prepared in Example 138A (105 mg, 0.36 mmol) in Pyr: Et$_3$N (10:1, 20 mL) was bubbled H$_2$S for 5 minutes and stirred at room temperature overnight. The reaction mixture was diluted with ethyl acetate (100 mL) washed with aqueous 0.25 N HCl (25 mL) followed by water (2×50 mL), saturated solution of sodium bicarbonate, and brine, dried over magnesium sulfate & evaporated. To a solution of the resulting solid in acetone (25 mL) was added MeI (1.0 mL)and stirred at 50° C. for 30 minutes—very strong precipitate was observed. Added ether and filtered the yellow precipitated. The yellow solid was added methanol (10 mL) and ammonium acetate (150 mg) and stirred at room temperature overnight. Purified as described in Example 1B. Yield of the white solid 69 mg.

MS (DCI/NH$_3$) m/z 420 (M+H)$^+$.

EXAMPLE 138C

N-[6-(aminoiminomethyl)-2-naphthalenyl]-N'-(4-aminophenyl)urea, bis(trifluoroacetate)(salt)

The Boc protected substrate (Example 138B) was dissolved in methylene chloride:TFA 1:1 (25 mL) and stirred at room temperature for 1 hour. Evaporated solvent under vacuum added toluene & evaporated again. Added water & little acetonitrile, filtered & lyophilized. 36 mg of white solid.

MS (ESI/NH$_3$) m/z 320 (M+H)$^+$; $^1$H NMR (300 MHz, DMSO-d$_6$) 9.26 (br.s, 2H), 9.21 (br.s, 1H), 8.85 (br.s, 2H), 8.31 (d, J=1.7 Hz, 1H), 8.18 (d, J=1.7 Hz, 1H), 7.95–7.91 (m, 2H), 7.68 (dd, J1=6.6 Hz, J2=2.0 Hz, 1H), 7.57 (dd, J1=9.2 Hz, J2=1.4 Hz, 1H), 7.34 (d, J=8.8 Hz, 2H), 6.91 (d, J=8.4 Hz, 2H); Anal. calc'd for C$_{18}$H$_{17}$N$_5$O.2.CF$_3$COOH.H$_2$O: C, 46.73; H, 3.74; N, 12.39. Found: C, C, 47.03; H, 3.55; N, 12.36.

EXAMPLE 139

N-[6-(aminoiminomethyl)-2-naphthalenyl]-4-4-(aminomethyl)cyclohexanescarboxamide, bis(trifluoroacetate)(salt)

A solution of the substrate prepared in Example 137 as TFA salt (45 mg) in methylene chloride: TFA 1:1 (20 mL) was stirred at room temperature for 1 hour. The solvent was evaporated under vacuum, added toluene & evaporated (20 mL×2). Dissolved in water, filtered—0.45μ frit and lyophilized. 35 mg, white solid as bis TFA salt.

MS (ESI/NH$_3$) m/z 325 (M+H)$^+$; $^1$H NMR (300 MHz, DMSO-d$_6$) 10.31 (s, 1H), 9.31 (br.s, 2H), 9.10 (br.s, 2H), 8.49 (s, 1H), 8.39 (s, 1H), 8.04–8.00 (m, 2H), 7.78–7.71 (m, 2H), 2.71 (d, J=7.0 Hz, 2H), 2.44–2.36 (m, 1H)1.96–1.85 (m, 4H), 1.61–1.42 (m, 3H), 1.09–1.02 (m, 2H); Anal. calc'd for C$_{19}$H$_{24}$N$_4$O.2.CF$_3$COOH: C, 50.00; H, 4.74; N, 10.14. Found: C, 49.95; H, 4.70; N, 09.96.

EXAMPLE 140

N-[6-(aminoiminomethyl)-2-naphthalenyl]-N'-[(4-aminomethyl)phenyl]urea, bis(trifluoroacetate)(salt)

EXAMPLE 140A

To a solution of the isocyanate prepared in Example 40B (140 mg, 0.72 mmol) in dioxane (8.0 mL) at room temperature, was added 4-N-Boc-aminomethylbenzoic acid (320 mg, 1.44 mmol) and stirred for 1 hour. The product was precipitating during the reaction. The mixture diluted with ether (15 mL), filtered and washed with ether to yield 215 mg (72%) of white solid.

MS (DCI/NH$_3$) m/z 417 (M+H)$^+$.

EXAMPLE 140B

A solution of the nitrile (Example 140A) (198 mg, 0.47 mmol) in 10:1 pyridine:triethylamine (10 mL) was treated with H$_2$S for 5 min, stirred at room temperature for 18 h and concentrated. The resulting solid was dissolved in acetone (15 mL), treated with iodomethane (0.8 mL, 12.8 mmol), stirred for 2 hours, diluted with ether (10 mL), filtered, washed with ether and dried under vacuum. The resulting solid was dissolved in methanol (4 mL) and was added NH$_4$OAc (200 mg, 2.6 mmol) at room temperature overnight. The product was purified according to the procedure described in Example 1B to provide 112 mg (54%) of the corresponding amidine.

MS (DCI/NH$_3$) m/z 434 (M+H)$^+$.

EXAMPLE 140C

N-[6-(aminoiminomethyl)-2-naphthalenyl]-N'-[(4-aminomethyl)phenyl]urea, bis(trifluoroacetate)(salt)

A solution of the substrate (Example 140B) in methylene chloride: TFA 1:1 (20 mL) was stirred at room temperature for 1 hour. The solvent was evaporated under vacuum, added toluene & evaporated (20 mL×2). Dissolved in water, filtered—0.45μ frit and lyophilized. 38.1 mg, white solid.

MS (ESI/NH$_3$) m/z 334 (M+H)$^+$; $^1$H NMR (300 MHz, DMSO-d$_6$) 9.68 (s, 1H), 9.45 (s, 1H), 9.35 (br.s, 2H), 9.08 (br. s, 2H), 8.40 (d, J=1.7 Hz, 1H), 8.31 (d, J=1.8 Hz, 1H), 8.10 (br.s, 3H), 8.04–7.99 (m, 2H), 7.76 (dd, J1=8.8 Hz, J2=1.8 Hz, 1H), 7.67 (dd, J1=8.8 Hz, J2=1.7 Hz, 1H), 7.58 (d, J=8.4 Hz, 2H), 7.39 (d, J=8.4 Hz, 2H), 3.98 (br. s, 2H); Anal. calc'd for C$_{19}$H$_{19}$N$_5$O$_1$.2.CF$_3$COOH.H$_2$O: C, 47.67; H, 4.00; F, 19.67; N, 12.09. Found: C, 47.33; H, 3.70; F, 19.59; N, 11.71.

EXAMPLE 141 methyl [7-(aminoiminomethyl)-3-[[[4-(aminomethyl)phenyl]amino]carbonyl]-1-naphathalenyl]carbamate, bis(trifluoroacetate)(salt)

EXAMPLE 141A

To a solution of the ester, prepared as described in Example 26, (747 mg, 2.63 mmol) in dioxane (10 mL) was added acetone (1 mL) and an excess of sodium hydroxide (1 N in water, 10 mL). After 1 hour the mixture was added water (40 mL) and ethyl acetate (85 mL) then was acidified with 10% aq. HCl. The ethyl acetate layer was separated washed with water (2×20 mL) then brine, dried over magnesium sulfate filtered and evaporated. The product was isolated as a light yellow solid.

MS m/z 271 (M+1)$^+$.

EXAMPLE 141B

To a suspension of naphthoic acid derivative, prepared in Example 141A (270 mg, 1.1 mmol) in methylene chloride (8.0 mL) was added diisopropylethylamine (DIEA, 485 µL, 2.8 mmol) followed by O-(azabenzotriazole-1-yl)-N, N, N', N'-tetramethyluroniumhexafluorophosphate (HATU, 527 mg, 1.39 mmol). After 10 minutes added the 4-N-Boc-aminomethylaniline (370 mg, 1.7 mmol). After an hour, added ethyl acetate (120 mL) and washed organic layer with 5% aq. citric acid (50 mL), water (2×40 mL) and brine (50 mL). The rxn was dried over magnesium sulfate filtered through small amount of silica and evaporated. Purification on silica eluting with ethyl acetate in hexanes. The product, after concentration, was added ethyl acetate and ether and filtered to yield 350.0 mg (70%) of yellow solid.

MS m/z 447 (M+1)$^+$.

EXAMPLE 141C

A suspension of the naph derivative (Example 141B) (300 mg, 0.67 mmol) in ethyl acetate (20 mL) was added 120 mg of the Pd catalysit then stirred at room temperature, under hydrogen, at atmospheric pressure and stirred for 1 hour. The crude was carried on to the next step without any purifications or analysis.

To a solution of the crude amine in dioxane (25 mL) and 10% aqeuos sodium carbonate (2.5 mL) was added the methyl chloroformate (1.0 mL, large excess). After 2 hours the rxn was quenched with methanol then diluted with ethyl acetate (80 mL) and water (50 mL). The ethyl acetate layer was separated, dried over magnesium sulfate filtered and evaporated. The product was separated on silica column using a gradient of ethyl acetate in hexanes (from 5 to 30% ethyl acetate in hexanes). Yield 140 mg of off white solid. MS m/z 492 (M+18)$^+$.

EXAMPLE 141D

The desired compound was prepared as described in Example 26.

MS m/z 492 (M+1$^+$.

EXAMPLE 141E methyl [7-(aminoiminomethyl)-3-[[[4-(aminomethyl)phenyl]amino]carbonyl]-1-naphathalenyl]carbamate, bis(trifluoroacetate)(salt)

A solution of the substrate (Example 141D) in a mixture of methylene chloride:TFA 4:1 (20 mL) was stirred at room temperature for 15 minutes. The solvent was concentrated under vacuum, and separated on RP C18 MPLC. Yield, 21 mg off white solid.

MS m/z 392 (M+18)$^+$ $^1$H NMR (DMSO): 3.783 (s, 3H), 4.03 (q, 2H, J=5.5 Hz), 7.47 (d, 2H, j=8.4 Hz), 7.85 (d, 2H, j=8.4 Hz), 7.94 (d, 1H, j=8.8 Hz), 8.15 (wide s, 2H), 8.31 (d, 1H, j=8.8 Hz), 8.33 (s, 1H), 8.47 (s, 1H), 8.74 (s, 1H), 9.29 (s, 2H), 9.47 (s, 2H), 9.90 (s, 1H), 10.68 (s, 1H). Anal. calc'd for $C_{25}H_{25}F_6N_5O_8$ (base molecule+2 TFA+1 H$_2$O): C, 47.04; H, 3.70; N, 10.52. Found: C, 47.10; H, 3.95; N, 10.99.

EXAMPLE 142

6-(aminoiminomethyl)-N-(4-ethylphenyl)-2-naphthalenecarboxamide, acetate(salt)

EXAMPLE 142A

The reaction was carried out in the same manner as described in Example 141B.

Yield 374 mg (61%) of white powder. MS DCI/NH3): m/z 301 (M+NH4+).

EXAMPLE 142B 6-(aminoiminomethyl)-N-(4-ethylphenyl)-2-naphthalenecarboxamide, acetate(salt)

The reaction was carried out in the same manner as described for the naphthyl analog prepared in Example 141D, 313 mg. The solid that precipitated during the last step was filtered and washed in ether to yield 71 mg (18%) of white solid, as acetate salt.

MS (ECI) m/z 301 (M+H)$^+$; $^1$H NMR (300 MHz, DMSO-d$_6$) δ 1.19 (t, J=7.4 Hz, 3H), 2.60 (q, J=7.4 Hz, 2H), 7.22 (d, J=8.5 Hz, 2H), 7.72 (d, J=8.5 Hz, 2H), 7.94 (dd, J$_1$=8.8 Hz, J$_2$=1.7 Hz, 1H), 8.08–8.23 (m, 3H), 8.47 (d, J=1.7 Hz, 1H), 8.63 (s, 1H), 10.43 (br. s, 1H); Anal. calc'd for $C_{20}H_{19}N_3O.AcOH.0.5$ H$_2$O: C, 68.38; H, 6.26; N, 10.87. Found: C, 68.56; H, 6.21; N, 10.67.

EXAMPLE 143

6-(aminoiminomethyl)-N-(2-naphthalenyl)-2-naphthalenecarboxamide, mono(trifluoroacetate) (salt)

EXAMPLE 143A

To a solution of the acid chloride prepared as described in Example 8B (341 mg, 1.6 mmol) in methylene chloride (20 mL) was added a solution of the 2-Amino naphthalene (249 mg, 1.74 mmol) in methylene chloride (10 mL) and propylene oxide (12 mL). The rxn was stirred at room temperature overnight. The reaction mixture was added ether and the product was filtered, washed with ether and hexanes and dried under vacuum. Yield 440 mg (86%).

MS (DCI/NH3) m/z 340 (M+NH4)$^+$.

EXAMPLE 143B 6-(aminoiminomethyl)-N-(2-naphthalenyl)-2-naphthalenecarboxamide, mono(trifluoroacetate) (salt)

The desired compound is prepared as described in Example 141B. Yield of white solid 40 mg (10%).

MS (ESI) m/z 340 (M+H)$^+$; $^1$H NMR (300 MHz, DMSO-d$_6$) 7.43–7.55 (m, 2H), 7.86–7.96 (m, 5H), 8.20–8.28 (m, 2H), 8.08–8.23 (m, 3H), 8.34 (d, J=8.8 Hz, 1H), 8.50 (d, J=1.7 Hz, 1H), 8.57 (d, J=1.3 Hz, 1H), 8.75 (s, 1H), 9.33 (br. s, 4H) 10.75 (s, 1H); Anal. calc'd for $C_{22}H_{17}N_3O.TFA.0.25$ H$_2$O: C, 62.95; H, 4.07; N, 9.18. Found: C, 63.09; H, 3.72; N, 8.99.

EXAMPLE 144

6-(5-phenyl-2-oxazolyl)-2-naphthalenecarboximidamide, mono (trifluoroacetate)(salt)

EXAMPLE 144A

To a suspension of the phenacyl amine hydrochloride (Aldrich) (415 mg, 2.42 mmol) in a mixture of methylene chloride (50 mL) and propylene oxide (15 mL) at room temperature was added a solution of the 2-nitrile-6-acidchloride (560 mg, 2.6 mmol) in methylene chloride (30 mL) followed by DMF (3.0 mL). Thje reaction was stirred at room temperature overnight. The reaction mixture was added ether (15 mL) and the product was filtered and washed with hexanes to yield 555 mg (73%) of white solid.

MS (DCI/NH$_3$) m/z 315 (M+H)$^+$.

EXAMPLE 144B

A suspension of the substrate (Example 144A) (354 mg, 1.12 mmol) in phosphorous oxychloride (3.5 mL) was boiled for 1.5 hours. The reaction mixture was poured into ice and the mixture was added ethyl acetate (80 mL) and aqeuous solution of 10% potassium carbonate (100 mL). The organic layer was separated, washed with brine dried over magnesium sulfate and evaporated. Added ether and filtered 249 mg (75%).

MS (DCI/NH$_3$) m/z 297 (M+H)$^+$.

EXAMPLE 144C 6-(5-phenyl-2-oxazolyl)-2-naphthalenecarboximidamide, mono (trifluoroacetate)(salt)

To a solution of the substrate Example 144B (132 mg, 0.44 mmol) in THF (20 mL) at room temperature was added a solution of 1 N LiHMDS in hexanes (1.5 mL, 1.5 mmol) and stirred overnight. Quenched with 4 N HCl in dioxane (1 mL). After 10 minutes added a few drops of water and stirred for additional 30 minutes. The solvent was evaporated under vacuum and the residue was purified on reverse phase chromatography. Yield 58 mg of white solid 41%).

MS (ESI/NH$_3$) m/z 314 (M+H)$^+$; $^1$H NMR (300 MHz, DMSO-d$_6$) 9.50 (s, 2H), 9.19 (s, 2H), 8.86 (s, 1H), 8.55 (s, 1H), 8.38–8.26 (m, 3H), 7.98 (s, 1H), 7.96–7.89 (m, 3H), 7.58–7.54 (m, 2H), 7.47–7.42 (m, 1H); Anal. calc'd for C$_{20}$H$_{15}$N$_3$O.1.15CF$_3$COOH: C, 60.26; H, 3.66; N, 9.45; F, 14.75. Found: C, 60.11; H, 3.81; N, 9.20; F, 14.81.

EXAMPLE 145

6-(5-phenyl-2-thiazolyl)-2-naphthalenecarboximidamide, mono (trifluoroacetate)(salt)

EXAMPLE 145A

A suspension of the substrate, prepared in Example 144A, (340 mg, 1.1 mmol) and Lawesson's reagent (600 mg, 1.48 mmol) was heated to 85° C. for 48 hours. Solvent was evaporated to dryness and the product was isolated via silica column using 10% ethyl acetate in hexanes as eluent. Yield: 200.0 mg (59%) of yellow solid.

MS (DCI/NH$_3$) m/z 313 (M+H)$^+$.

EXAMPLE 145B

6(5-phenyl-2-thiazolyl)-2-naphthalenecarboximidamide, mono (trifluoroacetate)(salt)

To a solution of the substrate, Example 145A (180 mg, 0.58 mmol) in THF (20 mL) at room temperature was added a solution of 1 N LiHMDS in hexanes (2.0 mL, 2.0 mmol) and stirred overnight. Quenched with 4 N HCl in dioxane (1 mL). After 10 minutes added a few drops of water and stirred for additional 30 minutes. The solvent was evaporated under vacuum and the residue was purified on MPLC RPC18. Yield 36 mg (19%) of white solid.

MS (ESI/NH$_3$) m/z 330 (M+H)$^+$; $^1$H NMR (300 MHz, DMSO-d$_6$) 9.49 (s, 2H), 9.14 (s, 2H), 8.71 (s, 1H), 8.52 (s, 1H), 8.47 (s, 1H), 8.35–8.22 (m, 3H), 7.90–7.78 (m, 3H), 7.55–7.50 (m, 2H), 7.46–7.43 (m, 1H); Anal. calc'd for C$_{20}$H$_{15}$N$_3$S.CF$_3$COOH.H$_2$O: C, 57.26; H, 3.93; N, 9.11. Found: C, 56.83; H, 3.55; N, 8.79.

EXAMPLE 146

6-(aminoiminomethyl)-4-(3-furanyl)-N-(2-pyridinyl)-2-naphthalenecarboxamide, dihydrochloride

EXAMPLE 146A

The above product was prepared in the manner of Example 114A.

MS (ESI) m/z (M+H)$^+$340.

EXAMPLE 146B 6-(aminoiminomethyl)-4-(3-furanyl)-N-(2-pyridinyl)-2-naphthalenecarboxamide, dihydrochloride The above was prepared from Example 146A using method described in 145B.

MS (CI) m/z (M+H)$^+$357; $^1$H-NMR (300 MHz, DMSO-d$_6$) δ 11.27 (s, 1H), 9.56 (s, 2H), 9.17 (s, 2H), 8.76 (s, 1H), 8.63 (s, 1H), 8.45–8.24 (m, 5H), 7.96–7.89 (m, 3H), 7.25 (m, 2H), 7.18 (s, 1H); Anal. calc'd for C$_{21}$H$_{18}$N$_4$O$_2$Cl$_2$ 19/10 HCl: C, 54.33 H, 4.75 N, 12.07. Found: C, 54.89; H, 5.28; N, 9.81.

EXAMPLE 147

6-(aminoiminomethyl)-N-(1,2,3,4-tetrahydro-6-quinolinyl)-2-naphthalenecarboxamide, bis (trifluoroacetate)(salt)

EXAMPLE 147A

The reaction was carried out in exactly the same manner as described for Example 118A using 6-aminoquinoline to yield the product in 72%. Mass spectrum (CI+) 324 (M+1)$^+$.

EXAMPLE 147B

The reaction was carried out in exactly the same manner as described for Example 118B to yield the product in 45% (off white solid). Mass spectrum (ESI+) 341 (M+1)$^+$.

EXAMPLE 147C 6-(aminoiminomethyl)-N-(1,2,3,4tetrahydro-6-quinolinyl)-2-naphthalenecarboxamide, bis (trifluoroacetate)(salt)

To a suspension of the substrate, Example 147B (261 mg, 0.6 mmol) in degassed methanol (15 mL) was added platinum oxide (10 mg, cat). The reaction mixture was charged with hydrogen at atmospheric pressure and stirred vigorously overnight. The next day the solution was filtered through celite to remove the catalyst, and the product was purified over mplc with RPC18 silica using methanol (+0.1% TFA) and water (+0.1% TFA) as eluent. Yield 122 mg of white solid and bis TFA salt.

MS (ESI+) 345 (M+1)⁺; ¹H NMR (DMSO-d6) 10.51 (s, 1H), 9.65 (s, 2H), 9.50 (s, 2H), 8.64 (s, 1H), 8.52 (s, 1H), 8.22 (d, J=8.0 Hz, 1H), 8.12 (Abq, J=9.0 Hz, 2H), 7.86 (d, J=9.0 Hz, 1H), 7.61 (s, 1H), 7.56 (d, J=8.0 Hz, 1H), 6.98 (d, J=8.5 Hz, 1H), 3.28 (t, J=5.5 Hz, 2H), 2.75 (t, J=6.3 Hz, 2H), 1.92–1.86 (m, 2H); Anal. calc'd for $C_{21}H_2ON_4O+2.25$ TFA+0.25 $H_2O$: C, 50.59 (50.46); H, 3.79 (3.79); N, 9.25 (9.25); F, 21.18 (20.83).

EXAMPLE 148

7-methoxy-8-(pyrazinyloxy)-2-naphthalenecarboximidamide, dimethanesulfonate (salt

EXAMPLE 148A

The product from Example 4A (125 mg, 0.627 mmol) was combined with chloropyrazine (112 mL, 1.25 mmol) and $Cs_2CO_3$ (409 mg, 1.25 mmol) in N-methylpyrrolidinone (4 mL), and the reaction was stirred at 130° C. for 1 hour. The reaction was cooled, and the crude mixture was chromatographed on $SiO_2$ using 40% ethyl acetate/hexanes as eluent, to yield 75 mg (43%) of the desired compound.

MS (DCI (NH₃) m/z 278 (M+H)⁺.

EXAMPLE 148B 7-methoxy-8-(pyrazinyloxy)-2-naphthalenecarboximidamide, dimethanesulfonate (salt)

The product from Example 148A (70 mg, 0.252 mmol) was subjected to the procedure described in Example 1B to yield the desired compound (106 mg, 71%). m.p. 155° C.

MS (DCI (NH₃) m/z 295 (M+H)⁺; ¹H NMR (300 MHz, DMSO) δ 9.42 (br s, 2H), 9.04 (br s, 2H), 8.72 (s, 1H), 8.38 (d, J=3 Hz, 1H), 8.36 (m, 1H), 8.21 (d, J=9 Hz, 1H), 8.09 (m, 1H), 8.06 (d, J=9 Hz, 1H), 7.82 (d, J=9 Hz, 1H), 7.73 (dd, J=9, 2 Hz, 1H), 3.83 (s, 3H), 2.38 (s, 3H); Anal. calc'd for $C_{18}H_{22}N_4S_2O_8 \cdot 1.1CH_4SO_3$: C, 38.74; H, 4.49; N, 9.46. Found: C, 38.68; H, 4.53; N, 9.34.

EXAMPLE 149

7-methoxy-8-(phenylthio)-2-naphthalenecarboximidamide, methanesulfonate

EXAMPLE 149A

To a solution of NaH (48 mg, 60%,1.2 mmol) in HMPA (2 mL) was added PhSH (0.133 mL, 1.3 mmol), and the reaction was stirred for 5 minutes. To this was added the product from Example 53B (309 mg, 1 mmol), and the reaction was heated at 100° C. for 3 hours. The crude reaction mixture was chromatographed on $SiO_2$ using 20% ethyl acetate/hexanes as eluent. The product was taken up in ethyl acetate (10 mL) and methanol (10 mL), and treated with a 2 M solution of TMSCHN₂ (10 mL). The reaction was stirred for 60 minutes and condensed. The crude product was chromatographed on $SiO_2$ using 15% ethyl acetate/hexanes as eluent, to yield 115 mg (39%) of the desired compound:

MS (DCI (NH₃) m/z 309 (M+NH₄)⁺.

EXAMPLE 149B 7-methoxy-8-(phenylthio)-2-naphthalenecarboximidamide,methanesulfonate The desired compound was prepared from Example 149A and the procedure of Example 55D.

MS (DCI/NH₃) m/z 309 (M+H)⁺; ¹H NMR (300 MHz, DMSO-d₆) δ 2.33 (s, 3H), 3.96 (s, 3H), 6.96 (d, 2H), 7.11 (dd, 1H), 7.20 (d, 1H), 7.22 (d, 1H), 7.69 (dd, 1H), 7.82 (d, 1H), 8.22 (d, 1H), 8.33 (d, 1H), 8.81 (s, 1H), 9.01 (br s, 2H), 9.46 (br s, 2H); Anal. calc'd for $C_{18}H_{16}N_2OS \cdot 1.15 CH_4SO_3$: C, 54.91; H, 4.96; N, 6.69. Found: C, 54.70; H, 5.15; N, 6.58.

EXAMPLE 150

7-methoxy-8-(pyrazinylamino)-2-naphthalenecarboximidamide, bis(trifluoroacetate) (salt)

The desired compound was prepared from the product prepared in Example 90D using the method described in Example 91A, then converted to the amidine as described in Example 40D.

MS (DCI/NH₃) m/z (M+H)⁺294; ¹H-NMR (300 MHz, DMSO-d₆) δ 9.39 (s, 2H), 9.02 (s, 2H), 8.95 (s, 1H), 8.40 (d, 1H), 8.14 (d, 1H), 8.03 (s, 2H), 7.92 (dd, 1H), 7.84 (d, 1H), 7.76 (d, 1H) 7.66 (dd 1H), 3.90 (s, 3H); Anal. calc'd for $C_{20}H_{17}N_5O_5F_6$ 1/2 TFA: C, 43.79; H, 3.07; N, 12.20. Found: C; 43.81; H, 3.22; N, 12.24.

EXAMPLE 152

6-(aminoiminomethyl)-4-(3-furanyl)-N-phenyl-2-naphthalenecarboxamide, monohydrochloride

EXAMPLE 152A

To a solution of the product from Example 8D (5.50 g, 26.04 mmol) in $CH_2Cl_2$ (125 mL) was added dibromodimethylhydantoin (4.47 g, 15.62 mmol) and trifluoromethanesulfonic acid (2.51 mL, 28.41 mmol), and the reaction was stirred at 23° C. in the dark for 18 hours. The mixture was poured into aqueous $NaHSO_3$, the solution was made basic with $Na_2CO_3$, and extracted with 3× ethyl acetate, and the extracts were washed with brine, dried over $Na_2SO_4$, and condensed. The product was recrystallized from ethanol/ethyl acetate, to yield 5.80 g (77%) of the desired compound.

MS (DCI (NH₃) m/z 307 (M+NH₄)⁺.

EXAMPLE 152B

To a solution of the product from Example 152A (1.40 g, 4.826 mmol) in THF (40 mL), water (10 mL), and methanol (10 mL) was added LiOH.water (405 mg, 9.65 mmol), and the reaction was stirred for 18 hours. The mixture was poured into 1 M HCl and extracted with 3× ethyl acetate, and the extracts were washed with brine, dried over $Na_2SO_4$, and condensed, to yield 1.23 g (92%) of the desired compound.

MS (DCI (NH₃)) m/z 295 (M+NH₄)⁺.

EXAMPLE 152C

To a solution of the product from Example 152B (440 mg, 1.60 mmol), in toluene (25 mL) was added oxalyl chloride (0.140 mL, 1.6 mmol), and the reaction was stirred at 80° C. for 18 hours. The toluene was boiled off until HCl evolution ceased, and the reaction was then cooled. Aniline (1 mL, 11 mmol) was added, and the reaction was stirred for 10 min, nad poured into 1 M HCl. The solution was extracted with 3× ethyl acetate, and the extracts were washed with brine, dried over $Na_2SO_4$, and condensed, to yield 560 mg (99%) of the desired compound.

MS (DCI (NH₃)) m/z 370 (M+NH₄)⁺.

EXAMPLE 152D

The desired compound was prepared from Example 152C (408 mg, 1.16 mmol), furan-3-boronic acid (182 mg, 1.62 mmol) and the procedure of Example 57B, to yield 220 mg (56%) of the desired compound.

MS (DCI (NH$_3$)) m/z 356 (M+NH$_4$)$^+$.

EXAMPLE 152E 6-(aminoiminomethyl)-4-(3-furanyl)-N-phenyl-2-naphthalenecarboxamide, monohydrochloride The desired compound was prepared from Example 152D and the procedure of Example 40D.

MS (DCI/NH$_3$) m/z 356 (M+H)$^+$; $^1$H NMR (300 MHz, DMSO-d$_6$) δ 7.15 (m, 2H), 7.41 (dd, 2H), 7.83 (d, 2H), 7.91 (d, 1H), 7.99 (dd, 1H), 8.19 (d, 1H), 8.38 (s, 1H), 8.41 (d, 1H), 8.62 (s, 1H), 8.69 (s, 1H), 9.15 (br s, 2H), 9.55 (br s, 2H); Anal. calcd for C$_{22}$H$_{17}$N$_3$O$_2$.2.75 HCl: C, 57.99; H, 4.37; N, 9.22. Found: C, 57.85; H, 4.84; N, 9.44.

EXAMPLE 153

6-(aminoiminomethyl)-4-[1-(methylsulfonyl)-1H-pyrazol-4-yl]-N-phenyl-2-naphthalenecarboxamide, monohydrochloride

EXAMPLE 153A

The desired compound was prepared from the product from Example 53D and the product from Example 152A by the procedure of Example 47A.

MS (DCI/NH$_3$) m/z 408 (M+H)$^+$.

EXAMPLE 153B

The desired compound was prepared from the product from Example 153A, by the procedure of Example 53F.

MS (DCI/NH$_3$) m/z 278 (M+H)$^+$.

EXAMPLE 153C

The desired compound was prepared from the product from Example 153B, by the procedure of Example 87A (86A).

MS (DCI/NH$_3$) m/z 373 (M+NH$_4$)$^+$.

EXAMPLE 153D

The desired compound was prepared from the product from Example 153C, by the procedures of Example s 152B and 152C MS (DCI/NH$_3$) m/z 356 (M–SO$_2$Me+NH$_4$)$^+$.

EXAMPLE 153E 6-(aminoiminomethyl)-4-[1-(methylsulfonyl)-1H-pyrazol-4-yl]-N-phenyl-2-naphthalenecarboxamide, monohydrochloride The desired compound was prepared from Example 153D and the procedure of Example 40D.

MS (DCI/NH$_3$) NONE; $^1$H NMR (300 MHz, DMSO-d$_6$) δ 3.99 (s, 3H), 7.14 (t, 1H), 7.40 (t, 2H), 7.84 (d, 2H), 7.91 (d, 1H), 8.08 (s, 1H), 8.15 (d, 1H), 8.35 (m, 2H), 8.65 (br s, 2H), 9.33 (br s, 2H), 9.61 (br s, 2H), 10.58 (s, 1H); Anal. calc'd for C$_{22}$H$_{19}$N$_5$SO$_3$.2.75 HCl: C, 49.51; H, 4.11; N, 13.12. Found: C, 49.44; H, 3.83; N, 12.09.

EXAMPLE 154

6-(aminoiminomethyl)-4-[5-(methylthio)-3-furanyl)]-N-phenyl-2-naphthalenecarboxamide, monohydrochloride

EXAMPLE 154A

To a solution of 2-trimethylsilyl-3-bromofuran (4.17 g, 19.03 mmol) in THF (40 mL) at –78° C. was added a 1.5 M solution of LDA (12.7 mL, 19.03 mmol), and the reaction was stirred at –78° C. for 1 hour. Methyl disulfide (1.89 mL, 20.93 mmol) was then added, and the reaction was allowed to warm to room temperature overnight. The reaction was poured into saturated aqueous NH$_4$Cl solution, and extracted with 3× diethyl ether. The combined extracts were washed with brine, dried over Na$_2$SO$_4$, and condensed. The crude material was chromatographed on SiO$_2$ using hexanes as eluent, to yield 3.02 g (60%) of the desired compound.

MS (DCI/NH$_3$) m/z 265, 267 (M+H)$^+$.

EXAMPLE 154B

A solution of the product from Example 154A (2.68 g, 10.1 mmol) and a 1 M solution of TBAF (20.2 mL) in THF (20 mL) was stirred for 30 minutes. The reaction was condensed and The desired compound was chromatographed on SiO$_2$ using hexanes as eluent, to yield 1.39 g (71%) of 2-methylthio-4-bromofuran. This material was taken on directly to the next step. To a solution of this product (7 mmol) in THF (25 mL) at –78° C. was added a 2.5 M solution of BuLi (2.8 mL, 7 mmol), and the reaction was stirred for 5 minutes. Bu$_3$SnCl (1.90 mL, 7 mmol) was then added, the reaction was stirred for 30 min, and then allowed to warm to room temperature. The reaction was poured into saturated aqueous NH$_4$Cl solution, and extracted with 3× diethyl ether. The combined extracts were washed with brine, dried over Na$_2$SO$_4$, and condensed. The crude material was chromatographed on SiO$_2$ using hexanes as eluent, to yield 1.24 g (30%) of the desired compound.

MS (DCI/NH$_3$) m/z 404 (M+H)$^+$.

EXAMPLE 154C

A solution of the product from Example 154B (920 mg, 2.28 mmol), the product from Example 152A (662 mg, 2.28 mmol), and PdCl$_2$ (PPh$_3$)$_2$ (161 mg, 0.23 mmol) in CH$_3$CN (15 mL) was stirred for 18 hours at 80° C. The reaction was condensed and the crude material was chromatographed on SiO$_2$ using 20% ethyl acetate/hexanes as eluent, to yield 671 mg (91%) of the desired compound.

MS (DCI/NH$_3$) m/z 324 (M+H)$^+$.

EXAMPLE 154D

The desired compound was prepared from the product from Example 154C, by the procedure of Example 152B.

MS (DCI/NH$_3$) m/z 310 (M+H)$^+$.

EXAMPLE 154E

The desired compound was prepared from the product from Example 154D, by the procedure of Example 152C.

MS (DCI/NH$_3$) m/z 402 (M+NH$_4$)$^+$.

EXAMPLE 154F 6-(aminoiminomethyl)-4-[5-(methylthio)-3-furanyl)]-N-phenyl-2-naphthalenecarboxamide, monohydrochloride The desired compound was prepared from Example 154E and the procedure of Example 144C.

MS (DCI/NH$_3$) m/z 402 (M+H)$^+$; $^1$H NMR (300 MHz, DMSO-d$_6$) δ 2.54 (s, 3H), 7.15 (t, 1H), 7.24 (s, 1H), 7.40 (t, 2H), 7.84 (d, 2H), 7.92 (dd, 1H), 8.19 (d, 1H), 8.39 (d, 1H), 8.44 (s, 1H), 8.61 (s, 1H), 8.69 (s, 1H), 9.35 (br s, 4H), 10.61 (s, 1H); Anal. calc'd for C$_{23}$H$_{19}$N$_3$SO$_2$.2.25 HCl: C, 57.14; H, 4.43; N, 8.69. Found: C, 57.13; H, 4.21; N, 8.56.

EXAMPLE 155 methyl [7-(aminoiminomethyl)-1-naphthalenyl]
methylcarbamate, mono(trifluoroacetate) salt The desired compound is prepared according to the procedures described in Example s 12 and 13. Yield: 40 mg (42%) of white solid MS m/z: 258 (M+H)$^+$ $^1$H NMR (DMSO, 300 MHz): 3.28 (s, 3H), 3.82 (br, 3H), 7.66 (dd, 1 H, J1=7.5 Hz, J2=1.4 Hz), 7.78 (m, 1H), 8. 89 (Dd, 1H, J1=8.8 Hz, J2=2.0 Hz), 8.05 (d, 1 H, 8.1 Hz), 8.24 (d, 1 H, 8.8 Hz), 8.30 (s, 1H), 9.09 (s, 2H), 9.52 (s, 2H); Anal. calc'd for $C_{14}H_{15}N_3O_2$.1.25 $C_2F_3O_2H$.0.25 $H_2O$: C, 49.02; H, 4.18; N, 10.39. Found: C, 48.81; H, 3.91; N, 10.15.

EXAMPLE 156 propyl [7-(aminoiminomethyl)-1-naphthalenyl]
carbamate, mono(trifluoroacetate)(salt)

The desired compound is prepared according to the procedures described in Example s 12 and 13. Yield: 52 mg (46%) of white solid MS m/z: 272 (M+H)$^+$ $^1$H NMR (DMSO, 300 MHz): 0.97 (t, 3H, J1=J2=7.1 Hz), 1.67 (Sextet, 2H, J=7.1 Hz), 4.19 (t, 3H, J1=J2=6.8 Hz). 7.71 (d, 1 H, 8.5 Hz), 7.83 (m, 3H), 8.14 (d, 1H, J=8.5 Hz), 8.67 (s, 1H), 9.22 (Br, 3H), 9.63 (s, 1H); Anal. calc'd for $C_{15}H_{17}N_3O_2$. 0.25 $C_2F_3O_2H$.0.75 $H_2O$: C, 49.18; H, 4.66; N, 9.83. Found: C, 49.27; H, 4.87; N, 10.02.

EXAMPLE 157

N-[7-(aminoiminomethyl)-1-naphthalenyl]-N'-
methylurea, mono(trifluoroacetate)(salt)

The desired compound is prepared according to the procedures described in Example s 12 and 13. Yield: 36 mg (54%) of white solid MS m/z: 243 (M+H)$^+$ $^1$H NMR (DMSO, 300 MHz): 2.80 (d, 1H), 6.45 (d, 1H), 7.70 (m, 2H), 7.82 (dd, J1=8.9 Hz, J2=2.1 Hz), 8.08 (dd, 7.4 Hz, J=1.3 Hz), 8.17 (d, 1H, J=8.5 Hz), 8.62 (s, 1H), 8.72 (s, 1H), 9.07 (s, 2H), 9.47 (s, 2H), (s, 2H); Anal. calc'd for $C_{13}H_{14}N_4O$. 1.5 $C_2F_3O_2H$.0.5 $H_2O$: C, 45.50; H, 3.94; N, 13.27. Found: C, 45.22; H, 3.86; N, 13.12.

EXAMPLE 158 ethyl [7-(aminoiminomethyl)-1-naphthalenyl)
carbamate, mono(trifluoroacetate)(salt)

The desired compound is prepared according to the procedures described in Example s 12 and 13. Yield: 70 mg (76%) of white solid MS m/z: 258 (M+H)$^+$ $^1$H NMR (DMSO, 300 MHz): 1.30 (t, 3H, J1=J2=7.4 Hz), 4.20 (q, 2H, J=7.0 Hz), 7.80 (m, 4H), 8.15 (d, 8.5 Hz), 8.68 (s, 1H), 9.13 (s, 2H), 9.38 (s, 2H), 9.66 (s, 1H); Anal. calc'd for $C_{14}H_{15}N_3O_2$.1.5 $C_2F_3O_2H$: C, 47.67; H, 3.88; N, 9.81. Found: C, 47.97; H, 3.85; N, 9.78.

EXAMPLE 159

N-[7-(aminoiminomethyl)-1-naphthalenyl)
propanamide, mono(trifluoroacetate)(salt)

The desired compound is prepared according to the procedures described in examples 12 and 13.

Yield: 20 mg (23%) of white solid MS m/z: 242 (M+H)$^+$ $^1$H NMR (DMSO, 300 MHz): 1.18 (t, 3H, 7.4 Hz), 3.38 (m, 2H), 7.89 (m, 3H), 7.81 (dd, 1H, J1=8.4 Hz, J2=1.9 Hz), 7.87 (d, 1H, 8.5 Hz), 8.58 (s, 1H), 9.02 (s, 2H), 9.47 (s, 2H), 9.97 (s, 1H). Anal. calc'd for $C_{14}H_{15}N_3O$. 1.15 $C_2F_3O_2H$ . 0.25 $H_2O$: C, 51.94; H, 4.45; N, 11.15; Found: C, 52.02; H, 4.24; N, 10.76.

EXAMPLE 160

N-[7-(aminoiminomethyl)-1-naphthalenyl)-2-
methoxyacetamide, mono(trifluoroacetate)(salt)

The desired compound is prepared according to the procedures described in Example s 12 and 13. Yield: 30 mg (30%) of white solid MS m/z: 258 (M+H)$^+$ $^1$H NMR (DMSO, 300 MHz): 3.49 (s, 3H), 4.18 (s, 2H), 7.80 (m, 3H), 7.93 (d, 1 H, 7.7 Hz), 8.47 (d, 1 H, 8.5 Hz), 8.47 (s, 1H), 9.10 (s, 2H), 9.46 (s, 2H), 9.99 (s, 2H); Anal. calc'd for $C_{14}H_{15}N_3O_2$.1$C_2F_3O_2H$.1.25 $H_2O$: C, 48.80; H, 4.73; N; 10.67. Found: C, 48.53; H, 4.34; N, 10.54; $^1$H NMR (DMSO, 300 MHz): 2.16 (s, 3H), 4.85 (s, 2H), 7.82 (m, 4H), 8.18 (d, 1H, J=8.18 Hz), 8.55 (s, 1H), 9.10 (s, 2H), 9.44 (s, 2H), 10.24 (s, 1H); Anal. calc'd for $C_{15}H_{15}N_3O_3$.1$C_2F_3O_2H$.1 $H_2O$: C, 48.93; H, 4.35; N, 10.07. Found: C, 48.82; H, 4.27; N, 10.00.

EXAMPLE 161

N-[7-(aminoiminomethyl)-1-naphthalenyl]urea,
mono(trifluoroacetate)(salt)

The desired compound is prepared according to the procedures described in Example s 12 and 13. Yield: 35 mg (54%) of yellownish solid MS m/z: 229 (M+H)$^+$ $^1$H NMR (DMSO, 300 MHz): 6.22 (s, 2H), 7.65 (m, 2H), 7.77 (dd, J1=8.8 Hz, J2=1.5 Hz). 8.57 (s, 1H), 8.79 (s, 1H), 9.07 (s, 2H), 9.49 (br, 2H); Anal. calc'd for $C_{12}H_{12}N_4O$. 1 $C_2F_3O_2H$.0.75 $H_2O$: C, 40.90; H, 3.33; N, 11.95. Found: C, 40.95; H, 3.64; N, 12.31.

EXAMPLE 162

N-[7-(aminoiminomethyl)-1-naphthalenyl]-2-
hydroxyacetamide, mono(trifluoroacetate)(salt)

The desired compound is prepared according to the procedures described in Examples 12 and 13. Yield: 24 mg (37%) of white solid MS m/z: 244 (M+H)$^+$ $^1$H NMR (DMSO, 300 MHz): 4.18 (s, 2H), 5.82 (br, 1H). 7.67 (m, 1H), 7.85 (m, 3H), 8.20 (d, 1H), 9.18 (s, 2H), 9.42 (s, 2H), 9.89 (s, 1H); Anal. calc'd for $C_{13}H_{13}N_3O_2$. 1 $C_2F_3O_2H$.0.75 $H_2O$: C, 48.59; H, 4.21; N, 11.33. Found: C, 48.64; H, 3.89; N, 11.25.

EXAMPLE 163

8-(2-pyrimidinylamino)-2-
naphthalenecarboximidamide, bis(trifluoroacetate)
(salt)

The desired compound is prepared according to the procedures described in Examples 91A and 13.Yield: 28 mg (28%) of pale yellow solid MS m/z: 264 (M+H)$^+$ $^1$H NMR (DMSO, 300 MHz): 6.90 (t, 1H, J1=J2=4.7 Hz), 7.69 (d, J=7.8 Hz), 7.80 (1 H, J=8.1 Hz), 7.81 (1 H, dd, J1=8.4 Hz, J2=2.1 Hz), 8.08 (1H, dd, J1=7.4 Hz, J2=0.6 Hz), 8.14 (1H, d, J=8.5 Hz), 8.49 (d, 2H), 8.75 (1H, d, J=1.7 Hz). 9.06 (s, 2H), 9.37 (s, 2H), 9.60 (s, 1H); Anal. calc'd for $C_{15}H_{13}N_5$. 2.25 $C_2F_3O_2H$.0.25 $H_2O$: C, 44.67; H, 4.283.03; N, 13.36. Found: C, 44.49; H, 2.80; N, 13.40.

EXAMPLE 164

8-amino-2-naphthalenecarboximidamide, bis (trifluoroacetate)(salt)

To a solution of crude 8-amino-2-nitrile-naphthalene prepared as described in Example 10 at room temperature in 10:1 pyridine: triethylamine (10 mL) was bubbled hydrogen sulfide for 5 minutes and stirred at room temperature overnight. The reaction mixture was added water (50 mL) and the product was extracted into ethyl acetate (3×30 mL). The combined organic solvent was dried over magnesium sulfate, filtered and evaporated. The resulting yellow substance was taken up in acetone (30 mL) then added methyl iodide (2 mL). The reaction mixture was boiled for 1 hour, then evaporated to dryness. To the resulting yellow substance in methanol (25 mL) was added ammonium acetate (100 mg) and stirred at room temperature overnight. The solvent was removed under vacuum and the product was purified via reverse phase chromatography using 0.1% TFA/water and 0.1% TFA/methanol as eluent.

MS m/z: 186 (M+H)$^+$ $^1$H NMR (DMSO, 300 MHz): 5.14 (br, 3H), 6.80 (dd, 1H, J1=7.8 Hz, J2=1 Hz), 7.17 (d, 1H, J=7.8 Hz), 7.40 (dd, 1H, J1=J2=7.8 Hz), 7.70 (dd, 1H, J1=8.9 Hz, J2=2.1 Hz), 7.91 (d, 1H, J=8.5 Hz), 8.65 (s, 1H), 8.95 (s, 2H), 9.23 (s, 2H); Anal. calc'd for $C_{11}H_{11}N_3.2.5 C_2F_3O_2H.0.75 H_2O$: C, 39.72; H, 3.13; N, 8.69. Found: C, 40.01; H, 3.19; N, 8.88.

EXAMPLE 165

6-(aminoiminomethyl)-N-[4-(aminomethyl)phenyl]-4-(2-pyrimidinylamino)-2-naphthalenecarboxamide, tris(trifluoroacetate)(salt)

EXAMPLE 165A

A suspension of 2-nitrile-6-methyester naphthalene Example 8D (5.0 g, 23 mmol) in concentrated sulfuric acid (50 mL) at −5° C. was added a solid potassium nitrate. The colour of reaction mixture was gradually changed into a dark brown. The reaction mixture was stirred for 15 minutes and was poured into ice-water. Collected the precipitate and washed with water. The crude product was recrystallized from ethyl acetate and ethanol. Yield 4.3 g (68%) of pale yellow powder.

EXAMPLE 165B

To a solution of 2-nitrile-6-methylester-8-nitro-naphthalene, Example 165A (3.5 g, 13.6 mmol) in a mixture of THF (100 mL) and ethyl acetate (120 mL) was added 10% Pd-C (350 mg). The reaction mixture was placed under hydrogen at atmospheric pressure (balloon) and stirred at room temperature for 3 5 hour. The mixture was filtered through celite and silica gel, washed with ethyl acetate and evaporated. The resulting solid was washed with ether (20 mL). Yield 2.20 g (71%) of yellow powder.

EXAMPLE 165C

A mixture containing 2-Nitrile-6-methylester-8-amino-naphthalene, Example 165B (2.8 g, 12.3 mmol), BINAP (116 mg, 0.186 mmol), Pd$_2$ (DBA)$_3$(64 mg, 0.061 mmol), NaO-t-Bu (1.667 g, 17.6 mmol), 2-Bromopyrimidine (2.363 g, 14.9 mmol) and Toluene (80 mL) in an oven-dried flask under nitrogen, was stirred at room temperature for 10 minutes. The reaction mixture was heated to 80° C. for 1 hour. At the end of the reaction (TLC, hexanes+ethyl acetate=4:1), brine 9200 mL) was added. Extracted the mixture with CH$_2$Cl$_2$. (4×250 mL). Evaporated the solvent. Yield 3.5 g (93%) of pale yellow powder.

EXAMPLE 165D

To a suspension of 2-nitrile-6-methylester-8-N-(2-pyrimidine)-naphthalene, Example 165C (5.2 g, 17.1 mmol ) in ethanol (150 mL) was added potassium carbonate (3.54 g, 33.3 mmol) in water (200 mL). The resulting suspension was heated at 120° C. for 2 hours, at that time all the suspension turned into a clear solution. The mixture is cooled down, then acidified with 2 N HCl. The resulting precipitate was collected by filtration to yield 4.5 g (90%) of pale yellow powder. No further purification was required for the next step.

EXAMPLE 165E

To a cold (0° C.) solution of 2-nitrile-8-N-(2-pyrimidine)-6-carboxylic acid-naphthalene Example 165D (5.0 g, 17.2 mmol) in DMF (150 mL) was added DIEA (7.6 mL, 42.6 mmol) and O-(7-Azabenzotriazol-1-yl)-N, N, N', N'-tetramethyluroniumhexafluorophosphate (9.8 g, 25.7 mmol) followed by tert-Butoxycarbonylamino-4-aminomethylaniline (5.74 g, 20 mmol). The resuting reaction mixture was stirred for about 1 hour. The reaction was quenched with water (200 mL) and the resulting precipitate was collected by filtration to yield 3.26 g (38%) of pale yellow powder.

EXAMPLE 165F

To a solution of the substrate, Example 165E (3.0 g, 6.07 mmol) in pyridine (150 mL) was added triethylamine (9 mL). H$_2$S was passed for 10 minutes and the resultiing mixture was stirred at room temperature for 48 hour. 100 mL of water was added to the reaction mixture and the precipitate was Collected by filtration. Yield (3.0 g (93%) of yellow solid.

EXAMPLE 165G

To a solution of the thioamide, Example 165F in acetone (200 mL) was added MeI (6 mL) and the mixture was stirred at room temperature overnight. The mixture was evaporated to dryness to yield 1.2 g (78%) of yellow solid.

EXAMPLE 165H 6-(aminoiminomethyl)-N-[4-(aminomethyl)phenyl]-4-(2-pyrimidinylamino)-2-naphthalenecarboxamide, tris(trifluoroacetate)(salt)

To a solution of the imidate ester, Example 165G, (1.5 g, 2.2 mmol) in methanol (50 mL ) was added ammonium acetate (0.5 g, 6.4 mmol) and stirred at room temperature overnight. After evaporation of the solvent the residue was treated with ether (3×25 mL) and the ether was decanterd out. The residue was dissolved in a mixture of 10:1:1 acetonitrile: water: acetic acid (50 mL). After addition of ether (100 mL), the Boc protected product precipitated as an acetate salt and was collected by filtration. The solid was added 1:1 TFA: methylene chloride (50 mL) containing thioanisole (0.5 mL). The reaction mixture was stirred at room temperature overnight. The product was purified over RPC$_{18}$ chromatography using water: methanol with 0.1% TFA as eluent. Yield after lyophilization 0.5 g (54%) of pale yellow solid.

MS m/z: 412 (M+H)$^+$ $^1$H NMR (DMSO, 300 MHz): 4.02 (q, 2H, J=5.8), 6.94 (dd, 1H, J12=J2=4.8 Hz), 7.45 (d, 2H,

J=8.5 Hz), 7.84 (d, 2H, J=8.4 Hz), 7.92 (dd, 1H, J1=8.5 Hz, J2=1.7 Hz), 8.13 (br, 3H), 8.30 (d, 1H, J=8.9 Hz), 8.41 (s, 1H), 8.52 (d., 2H), 8.55 (s, 1H), 8.81 (s, 1H), 9.19 (s, 2H), 9.43 (s, 2H), 9.75 (s, 1H), 10.62 (s, 1H); Anal. calc'd for $C_{23}H_{21}N_7O.2.5\ C_2F_3O_2H.1\ H_2O$: C, 43.49; H, 3.22; N, 11.83. Found: C, 43.54; H, 3.34; N, 11.69.

EXAMPLE 166

6-(aminoiminomethyl)-N-phenyl-4-(2-pyrimidinylamino)-2-naphthalenecarboxamide, mono(trifluoroacetate) (salt)

The same procedure as described in Examples 165 substituting aniline for 4-amino benzyl amine.

MS m/z: 383 (M+H)$^+$ $^1$H NMR (DMSO, 300 MHz): 6.93–6.96 (m, 1H), 7.14 (dd, 1H, J1=7.3 Hz, J2=7.4 Hz), 7.40 (dd, 2H, J1=J2=7.3 Hz), 7.80 (, d, 2H, J=8.1 Hz), 7.91 (d, 1H, J=8.9 Hz), 8.30 (d, 1H, J=9.0 Hz), 8.41 (s, 1H), 8.52–8.54 (m, 3H), 8.80 (s, 1H), 9.16 (s, 2H), 9.45 (s, 2H), 9.78 (s, 1H), 10.55 (s, 1H); Anal. calc'd for $C_{22}H_{18}N_6O.2\ C_2F_3O_2H.0.25\ H_2O$: C, 50.78; H, 3.28; N, 13.31. Found: C, 50.85; H, 3.28; N, 13.31.

EXAMPLE 167

N-[(4-(aminomethyl)phenyl]-6-[amino(hydroxyimino)methyl]-4-(2-pyrimidinylamino)-2-naphthalenecarboxamide, bis(trifluoroacetate)(salt)

To a suspension of compound, prepared in Example 165 E (0.20 g, 0.40 mmol) in methanol (40 mL) and water (20 mL) was added hydroxylamine hydro-chloride (112 mg, 1.75 mmol) and sodium carbonate (85 mg, 0.80 mmol), the reaction mixture was stirred for 48 hours at room temperature, TLC showed no reaction. Th reaction mixture was heated at reflux for 10 hours and removed the most of the solvents, the precipitate was collected by filtration, gave 1.2 g of pale yellow solid. The solid was disoolved in 1:1 TFA+CH$_2$Cl$_2$ (30 mL) and sitrred at room temperature for 24 hours. The solvents was removed under vaccuum and the residue was loaded to a R18 reverse phase column. The fraction was lyophilized and yielded a pale yellow powder (80 mg, 66%).

MS m/z: 428 (M+H)$^+$ $^1$H NMR (DMSO, 300 MHz): 4.02 (q, 2H, J=6.1 Hz), 6.92 (dd, 1H, J1=J2=5.1 Hz), 7.46 (d, 2H, 8.4 Hz), 7.85 (d, 2H, J=8.5 Hz), 7.88 (d, 1H, 9 Hz), 8.12 (br, 3H), 8.22 (d, 1H, J=8.9 Hz), 8.40 (s, $^1$H ), 8.48 (s, 1H), 8.51 (d, 2H, J=4.8 Hz), 8.64 (s, 1H), 9.74 (s, 2H), 10.61 (s, 2H); Anal. calc'd for $C_{23}H_{21}N_7O_2.2.9\ C_2F_3O_2H.1.25\ H_2O$: C, 44.31; H, 3.41; N, 12.56; F, 21.17 Found: C, 44.08; H, 3.30; N, 12.50, F, 21.25.

EXAMPLE 168

6-(aminoiminomethyl)-N-[4-(hydroxymethyl)phenyl]-4-(2-pyrimidinylamino)-2-naphthalenecarboxamide, mono(trifluoroacetate) (salt)

The desired compound is prepared as described in Example 165 using 4-amino benzyl alcohol instead of 4-amino benzylamine.

MS m/z: 413 (M+H)$^+$ $^1$H NMR (DMSO, 300 MHz): 4.48 (s, 2H), 6.94 (dd, 1H, 2H, J=8.8 Hz), J1=J2=4.8 Hz), 7.32 (d, 2H, J=8.8 Hz), 7.90 (dd, 1H, J1=8.5 Hz, J2=1.7 Hz), 8.28 (d, 2H, J=8.8 Hz), 8.41 (s, 1H), 8.54 (d, 2H, J=4.8 Hz), 8.55 (dd, 1H, J=1.3 Hz), 8.80 (s, 1H), 9.08 (s, 2H), 9.43 (s, 2H), 9.73 (s, 1H), 10.48 (s, 1H); Anal. calc'd for $C_{23}H_2ON_6O_2$: C, 49.06; H, 3.83; N, 12.81; F, 16.50. Found: C, 48.74; H, 3.86; N, 12.63, F, 16.54.

EXAMPLE 170 methyl [3-[[[4-(aminomethyl)phenyl]amino]carbonyl]-7-[4-amino(hydroxyimino)methyl]-1-naphthalenyl]carbamate, bis(trifluoroacetate)(salt)

EXAMPLE 170A

To a suspension of the nitrile, Example 141D (213 mg, 0.45 mmol) and hydroxylamine hydrochloride (338 mg, 4.86 mmol) in methanol (40 mL) water (5 mL) was added potassium carbonate (538 mg, 3.9 mmol) stirred at room temperature overnight. The solvent was evaporated and the resulting solid was washed with ether and hexanes to yield the product as white solid 153 mg (62%).

MS (ECI) m/z 508 (M+H)$^+$.

EXAMPLE 170B methyl [3-[[[4-(aminomethyl)phenyl]amino]carbonyl]-7-[4-amino(hydroxyimino)methyl]-1-naphthalenyl]carbamate, bis(trifluoroacetate)(salt)

The Boc protected substrate, Example 170A was added 3 mL of 4 N HCl in dioxane and stirred at room temperature for 20 minutes. The solvent was evaporated under vacuum and the product was separated on MPLC with a column of RP C$_{18}$ using methanol-water +0.1% TFA as eluent. Yield of white solid 117 mg (79%).

MS (ECI) m/z 408 (M+H)$^+$; $^1$H NMR (300 MHz, DMSO-d$_6$) δ 3.77 (S, 3H), 4.03 (s, 2H), 4.01 (q, J=5.9 2H), 7.46 (d, J=8.5 Hz, 2H), 7.86 (d, J=8.5 Hz, 2H), 7.90 (dd, J$_1$=8.5, Hz, J$_2$=1.4 Hz, 1H), 8.09–8.15 (m, 4H), 8.17 (d, J=8.4 Hz, 1H), 8.29 (s, 1H), 8.42 (s, 1H), 8.56 (s, 1H), 9.80 (s, 1H), 10.62 (s, 1H); Anal. calc'd for $C_{21}H_{21}N_5O_4.2.5\ TFA.0.5\ H_2O$: C, 44.52; H, 3.52; F, 20.31; N, 9.98. Found: C, 44.78; H, 3.57; F, 19.82; N, 9.87.

EXAMPLE 171

6-[amino(hydroxyimino)methyl]-N-phenyl-2-naphthalenecarboxamide

The title compound is prepared as described by Judkins et al., Synthetic Communications 26 (23), 4351–4367 (1996). The compound prepared in Example 55C (0.1 g, 0.36 mmole) is dissolved in a 10:1 mixture of Toluene:methanol to which is added hydroxylamine hydrochloride (3.6 mmole) and potassium tert-butoxide (3.6 mmole). The resulting slurry is refluxed for 17 hr., cooled, solvents removed under vacuum. The residue is taken up in distilled water (30 ml) extracted with ethyl acetate (2×100 ml). The combined organic extracts are washed with 10% NaCl (50 ml), dried over anhydrous Na$_2$SO$_4$. The sample is filtered of drying agent and the solvent removed under vacuum leaving a white solid (65 mg). The material is purified by medium pressure reverse phase chromatography as described in Example 1. The title compound is obtained as white solid (45 mg)

MS (m/z) M+H$^+$: 306 $^1$H NMR (DMSO-d$_6$): 10.51 (s, 1H), 9.32 (s, OH), 8.70 (s, 1H), 8.57 (s, 1H), 8.34 (d, 1H), 8.25 (d, 1H), 8.17 (dd, 1H), 7.90 (dd, 1H), 7.83 (d, 2H), 7.40 (dd, 2H), 7.15 (dd, 1H), 6.25 (bs, 2H). Analysis: calc'd for $C_{20}H_{16}N_3O_4F_3$: C, 57.28, H, 3.85, N, 10.02; Found C, 56.89, H, 3.65, N, 9.90.

EXAMPLE 174

8-(2-pyridinylamino)-2-naphthalenecarboximidamide, bis(trifluoroacetate) salt

EXAMPLE 174A

To a solution of the product from 11D (168 mg, 1.00 mmol) in 5 mL toluene was added 2-bromopyridine (0.105 mL, 1.1 mmol), NaOtBu (135 mg, 1.4 mmol), Pd$_2$dba$_3$ (92 mg, 0.1 mmol), and P(o-tolyl)$_3$ (122 mg, 0.4 mmol), and the reaction was stirred for 24 hours at 100° C. The reaction was cooled, and the crude reaction mixture was chromatographed on SiO$_2$ using 50% ethyl acetate/hexanes as eluent to yield 80 mg (33%) of the desired compound.

MS (DCI (NH$_3$)) m/z 246 (M+H)$^+$.

EXAMPLE 174B 8-(2-pyridinylamino)-2-naphthalenecarboximidamide, bis(trifluoroacetate) salt The product from Example 174A (121 mg, 0.493 mmol) was dissolved in THF (2 mL) and 0.543 mL of a 1 M solution of LiN (TMS)$_2$ in THF was added. The reaction was stirred for 5 min, and TMSCl (0.069 mL, 0.543 mmol) was added. After stirring for 30 min, another 1.09 mL of the 1 M solution of LiN (TMS)$_2$ was added. The reaction was stirred for 18 hours, and 10 mL of a 2 M aq. HCl solution was added. The reaction was stirred for another 24 hours, and was basicified with saturated aq. Na$_2$CO$_3$. The mixture was extracted with 3× ethyl acetate, and the extracts were washed with brine, dried over Na$_2$SO$_4$, and condensed. The crude product was purified by reverse-phase HPLC to yield the desired compound (21 mg, 7%): m.p. 137–147° C.

MS (DCI (NH$_3$) m/z 263 (M+H)$^+$; $^1$H NMR (300 MHz, DMSO) δ 9.98 (br s, 1H), 9.46 (br s, 2H), 9.27 (br s, 2H), 8.74 (s, 1H), 8.21 (d, J=9 Hz, 1H), 8.11 (d, J=6 Hz, 1H), 8.02 (d, J=9 Hz, 1H), 7.81–7.95 (m, 3H), 7.75 (dd, J=9, 9 Hz, 1H), 7.16 (m, 1H), 6.95 (m, 1H), 2.55 (s, 3H); Anal. calc'd for C$_{16}$H$_{14}$N$_4$·3.1C$_2$HF$_3$O$_2$: C, 43.30; H, 2.80; N, 9.10. Found: C, 43.14; H, 3.04; N, 9.90.

EXAMPLE 176

6-[4-[(hydroxymethyl)phenyl]methoxy]-2-naphthalenecarboximidamide,methanesulfonate(salt)

EXAMPLE 176A

To a solution of NaH (60% in mineral oil, 1.17 g, 29.3 mmol) in THF (50 mL) was added 4-bromobenzyl alcohol (5.22 g, 27.9 mmol) in THF (50 mL), and the reaction was stirred at room temperature for 20 minutes. p-Methoxybenzyl chloride (4.07 mL, 30 mmol) was then added, and the reaction was stirred at 50° C. for 2 hours. The mixture was poured into water and extracted with 3× diethyl ether, and the extracts were washed with brine, dried over Na$_2$SO$_4$, and condensed. The crude reaction mixture was chromatographed on SiO$_2$ using hexanes as eluent, to yield 7.39 g (86%) of the desired compound.

MS (DCI (NH$_3$)) m/z 326 (M+NH$_4$)$^+$; $^1$H NMR (300 MHz, CDCl$_3$) δ 7.47 (d, 2H), 7.28 (d, 2H), 7.23 (d, 2H), 6.90 (d, 2H), 4.48 (s, 3H), 4.47 (s, 2H), 3.91 (s, 3H).

EXAMPLE 176B

To a solution of the product from Example 176A (6.80 g, 22.13 mmol) in THF (100 mL) and hexanes (20 mL) at −100° C. was added a 2.5 M solution of BuLi (8.85 mL, 22.13 mmol), and the reaction was stirred for 2 minutes. DMF (3.43 mL, 44.3 mmol) was then added, and the reaction was warmed to room temperature. The mixture was poured into water and extracted with 3× diethyl ether, and the extracts were washed with brine, dried over Na$_2$SO$_4$, and condensed. The crude reaction mixture was taken up in methanol (100 mL) and NaBH$_4$ (1.0 g, 26.2 mmol) was added in portions. A few drops of water were added, and the mixture condensed. The residue was chromatographed on SiO$_2$ using 20% ethyl acetate/hexanes as eluent, to yield 3.32 g (58%) of the desired compound.

MS (DCI (NH$_3$)) m/z 276 (M+NH$_4$)$^+$; $^1$H NMR (300 MHz, CDCl$_3$) δ 7.38 (s, 4H), 7.29 (d, 2H), 6.90 (d, 2H), 4.70 (s, 2H), 4.54 (s, 2H), 4.49 (s, 2H), 3.81 (s, 3H), 1.62 (s, 1H).

EXAMPLE 176C

To a solution of the product from Example 176B (193 mg, 0.747 mmol), the product from Example 28A (139 mg, 0.822 mmol), and Ph$_3$P (216 mg, 0.822 mmol) in THF (10 mL) at 0° C. was added diethylazodicarboxylate (0.129 mL, 0.822 mmol), and the reaction was stirred for 90 minutes at room temperature. The crude reaction mixture was condensed, and the residue was chromatographed on SiO$_2$ using 10% ethyl acetate/hexanes as eluent, to yield 225 mg (74%) of the desired compound.

MS (DCI (NH$_3$)) m/z 427 (M+NH$_4$)$^+$; $^1$H NMR (300 MHz, CDCl$_3$) δ 8.15 (s, 1H), 7.81 (d, 1H), 7.77 (d, 1H), 7.58 (dd, 1H), 7.48 (d, 2H), 7.42 (d, 2H), 7.02–7.15 (m, 4H), 6.90 (d, 2H), 5.21 (s, 2H), 4.56 (s, 2H), 4.51 (s, 2H), 3.91 (s, 3H).

EXAMPLE 176D

To a solution of the product from Example 176C (220 mg, 0.537 mmol) in CH$_2$Cl$_2$ (40 mL) and water (7 mL) was added DDQ (244 mg, 1.07 mmol), and the reaction was stirred for 90 minutes. The crude reaction mixture was taken up in CH$_2$Cl$_2$, washed with 2× aqueous NaHCO$_3$ and brine, dried over Na$_2$SO$_4$, and condensed. The residue was chromatographed on SiO$_2$ using 50% ethyl acetate/hexanes as eluent, to yield 89 mg (57%) of the desired compound.

MS (DCI (NH$_3$)) m/z 307 (M+NH$_4$)$^+$; $^1$H NMR (300 MHz, CDCl$_3$) δ 8.15 (s, 1H), 7.81 (d, 1H), 7.77 (d, 1H), 7.57 (dd, 1H), 7.49 (d, 2H), 7.41 (d, 2H), 7.33 (dd, 1H), 7.21 (d, 1H), 5.21 (s, 2H), 4.74 (s, 2H), 1.63 (br s, 1H);

EXAMPLE 176E

6-[4-[(hydroxymethyl)phenyl]methoxy]-2-naphthalenecarboximidamide,methanesulfonate(salt)

The desired compound was prepared from Example 176D and the procedure of Example 55D.

MS (DCI/NH$_3$) m/z 307 (M+H)$^+$; $^1$H NMR (300 MHz, DMSO-d$_6$) δ 2.31 (s, 3H), 4.52 (s, 2H), 5.25 (s, 2H), 7.37 (d, 2H), 7.39 (dd, 1H), 7.47 (d, 2H), 7.59 (d, 1H), 7.79 (dd, 1H), 8.00 (d, 1H), 8.03 (d, 1H), 8.41 (s, 1H), 8.89 (br s, 2H), 9.34 (br s, 2H); Anal. calc'd for C$_{19}$H$_{18}$N$_2$O$_2$·1.15 CH$_4$SO$_3$: C, 58.06; H, 5.46; N, 6.72. Found: C, 58.24; H, 5.62; N, 6.59.

EXAMPLE 177

N-hydroxy-8-(2-pyrimidinylamino)-2-naphthalenecarboximidamide, mono (trifluoroacetate)(salt)

The desired compound is prepared from the nitrile described in Example 163 and utilizing the procedure described in Example 167. Yield as a white powder: 50 mg MS m/z: 280 (M+H)$^+$ $^1$H NMR (DMSO, 300 MHz): 6.90 (dd, 1H, J1=J2=5.2 Hz), 7.45 (m, 3H), 8.0 (d, 1H, J=8.5 Hz), 8.14 (d, 1H, J=8.4 Hz), 8.49 (d, J=5.3 Hz), 8.61 (s, 1H), 9.58 (s, 1H); Anal. calc'd for C$_{15}$H$_{13}$N$_5$O.2.0 C$_2$F$_3$O$_2$H.0.5 H$_2$O: C, 44.20; H, 3.12; N, 13.56. Found: C, 44.24; H, 2.94; N, 13.49.

EXAMPLE 179

6-(2-pyridinylethynyl)-2-naphthalenecarboximidamide, mono (trifluoroacetate)(salt)

EXAMPLE 179A

Using the product obtained in Example 28B, 2-ethynylpyridine (Lancaster Chemical Corp.) and the procedure described in Example 121A, the desired compound was obtained.

MS (DCI/NH$_3$) m/z 255 (M+H)$^+$.

EXAMPLE 179B

Using the product obtained in Example 179A and the procedure described in Example 94D the desired compound was obtained.

MS (DCI) m/z 272 (M+H)$^+$; $^1$H NMR (300 MHz, DMSO) δ 7.45–7.50 (m, 1H), 7.72 (d, 1H), 7.82 (dd, 1H), 7.86–7.92 (m, 2H), 8.18 (d, 1H), 8.22 (d, 1H), 8.42 (s, 1H), 8.54 (s, 1H), 8.68 (m, 1H), 9.25 (s, 2H), 9.49 (s, 2H); Anal. calc'd for $C_{20}H_{14}F_3N_3O_2 \cdot 0.25 H_2O$: C, 61.62; H, 3.75; N, 10.78. Found: C, 61.72; H, 3.64; N, 10.66.

EXAMPLE 180

6-(aminoiminomethyl)-N-phenyl-4-(tetrahydro-3-furanyl)-2-naphthalenecarboxamide, monohydrochloride

EXAMPLE 180A

The desired compound was prepared from the product from Example 152 by the procedure of Example 62A.

MS (DCI/NH$_3$) m/z 340 (M–H$_2$O)$^+$.

EXAMPLE 180B

The desired compound was prepared from the product from Example 180A by the procedure of Example 62B.

MS (DCI/NH$_3$) m/z 343 (M+H)$^+$.

EXAMPLE 180C

The desired compound was prepared from Example 180B and the procedure of Example 55D.

MS (DCI/NH$_3$) m/z 360 (M+H)$^+$; $^1$H NMR (300 MHz, DMSO-d$_6$) δ 2.20 (m, 1H), 2.52 (m, 1H), 3.85 (dd, 1H), 3.94 (ddd, 1H), 4.08 (ddd, 1h), 4.26 (dddd, 1H), 4.39 (dd, 1H), 7.14 (t, 1H), 7.40 (t, 2H), 7.81 (d, 2H), 7.95 (d, 1H), 8.08 (s, 1H), 8.32 (d, 1H), 8.59 (s, 1H), 8.79 (s, 1H), 9.25 (br s, 2H), 9.61 (br s, 2H); Anal. calc'd for $C_{22}H_{21}N_3O_2 \cdot 2.6$ HCl: C, 58.18; H, 5.24; N, 9.25. Found: C, 58.21; H, 4.91; N, 9.13.

EXAMPLE 181

6-[amino(hydroxyimino)methyl]-N-phenyl-4-(2-pyrimidinylamino)-2-naphthalenecarboxamide Prepared in a similar manner as described in Example 177 using the material prepared in Example 166.

MS m/z: 399 (M+H)$^+$ $^1$H NMR (DMSO, 300 MHz): 6.88 (dd, 1H, 4.7 Hz), 7.11 (dd, 1H, J1=J2=7.5 Hz), 7.37 (dd, 2H, J1=J2=7.5 Hz), 7.82 (d, 2H, J=8.8 Hz), 7.94 (dd, 1H, J1=8.5 Hz, J2=1.4 Hz), 8.04 (d, 1H, J=8.8 Hz), 8.31 (s, 1H), 8.43 (dd, 1H, J=14 Hz), 8.74 (d, 2H, J=4.7 Hz), 8.52 (s, 1H), 9.55 (s, 1H), 9.85 (s, 2H), 10.41 (s, 1H); Anal. calc'd for $C_{22}H_{18}N_6O_2 \cdot 0.4 H_2O$: C, 65.14; H, 4.67; N, 20.72. Found: C, 65.57; H, 4.45; N, 20.18.

EXAMPLE 182 methyl 4-[[[7-amino(hydroxyimino)methyl]-2-naphthalenyl]oxy]methyl]benzoate

The resulting product from Example 213A (110 mg, 0.347 mmol), hydroxylamine hydrochloride (26.5 mg, 0.381 mmol), triethylamine (53 μl, 0.381 mmol) and N,N-dimethylformamide (12 mL) were combined in a four inch glass pressure tube. The tube was sealed and heated for 24 hours at 80° C. The tube was cooled to room temperature and additional hydroxylamine hydrochloride (48.1 mg, 0.693 mmol) and triethylamine (96.6 μl, 0.693 mmol) in N,N-dimethylformamide (2 mL) was added. The tube was resealed and heated for 24 hours at 80° C. The addition, as above, was repeated a second time, the tube was resealed and heated for 72 hours at 80° C. The reaction mixture was concentrated to a solide residue which was purified by column chromatography on silica gel (60 g) eluted with 15% acetone in methylene chloride to yield the target compound as a white solid (43 mg, 50% based on recovered starting material).

MS (DCI (NH$_3$)) m/z 351 (M+H)$^+$; $^1$H NMR NMR (300 MHz, DMSO-d6) δ 3.860 (s, 3H), 5.349 (s, 2H), 5.860 (s, 2H), 7.280 (dd, 1H), 7.381 (d, 1H), 7.660 (d, 2H), 7.688 (dd, 1H), 7.805 (d, 1H), 7.850 (d, 1H), 8.010 (d, 2H), 8.070 (s, 1H), 9.724 (s, 1H); Anal. calc'd for $C_{20}H_{18}N_2O_4 \cdot 0.15 H_2O$: C, 68.04; H, 5.22; N, 7.93. Found: C, 68.06; H, 5.05; N, 7.87.

EXAMPLE 184

N-[4-(aminocarbonyl)phenyl]-6-(aminoiminomethyl)-2-naphthalenecarboxamide, mono(trifluoroacetate) salt

EXAMPLE 184A

A suspension of the product obtained in Example 8A (300 mg, 1.39 mmol) and 5 mL dichloromethane was added dropwise to a 0° solution of 4-aminobenzamide (207 mg, 1.52 mmol), triethylamine (0.44 mL, 3.2 mmol), and 10 mL dichloromethane. The reaction mixture was stirred for 0.5 hour at 0° and for 18 hours at room temperature. Excess ether was added with stirring and the resultant solid was filtered, washed with 1 N HCl, water, and was dried under vacuum to afford the desired compound.

MS (DCI) m/z 333 (M+NH$_3$)$^+$.

EXAMPLE 184B

N-[4-(aminocarbonyl)phenyl]-6-(aminoiminomethyl)-2-naphthalenecarboxamide, mono(trifluoroacetate) salt Using the product obtained in Example 184A and the procedure described in Example 4C the desired compound was obtained.

MS (DCI) m/z 333 (M+H)$^+$; $^1$H NMR (300 MHz, DMSO) δ 10.76 (S, 1H), 9.51 (S, 2H), 9.14 (S, 2H), 8.74 (S, 1H), 8.56 (S, 1H), 8.33 (D, 1H, J=8.8 Hz), 8.26 (D, 1H, J=8.8 HZ Hz), 8.16 (DD, 1H, J=8.46, 1.11 Hz), 7.91 (M, 6H), 7.31 (S, 1H); Anal. calc'd for $C_{20}H_{17}F_3N_4O_4 \cdot 1.5 H_2O$: C, 53.28; H, 4.26; N, 11.83. Found: C, 53.47; H, 3.86; N, 11.96.

EXAMPLE 185 methyl 2-[[6-(aminoiminomethyl)-2-naphthalenyl]oxy]acetate, mono(trifluoroacetate)(salt)

EXAMPLE 185A 7-methoxy-2-cyanonaphthalene, (2.79 g, 5.23 mmol) and tetrabutylammonium iodide (17 mg, 0.157 mmol) were combined in a mixture of benzene (35 mL) and cyclohexanes (17.5 mL). The resulting solution was added to a rapidly stirring, cooled (ice/water) suspension of aluminum triiodide (6.21 g, 15.23 mmol) in a mixture of benzene (35 mL) and cyclohexanes (17.5 mL) under an inert atmosphere.

After the addition, the resulting suspension was heated at reflux for 2.5 hours. The heating was removed and after cooling to near room temperature, the reaction mixture was cooled in an ice bath and quenched by the addition of water (100 mL). The resulting mixture was further diluted with 2 M aqueous sodium thiosulfate solution (50 mL) and extracted with ethyl acetate (3×80 mL). The combined organic layers were dried and evaporated. The resulting solid was dissolved in a minimum of hot ethyl acetate, diluted hot with hexanes to the cloud point and placed in a refrigerator for 2 hours. The desired compound was collected by filtration, (1.99 g, 77%).

MS (DCI (NH$_3$)) m/z 187 (M+NH$_4$)$^+$.

EXAMPLE 185B

The resulting product from Example 185A (217 mg, 1.283 mmol) was combined with cesium carbonate (460 mg, 1.411 mmol) and tetrabuthylammonium iodide (catalytic) in DMF (7 mL). To this was added t-butyl bromoacetate (193 μL, 1.283 mmol) and the resulting mixture was stirred 2 hours under an inert atmosphere. The reaction mixture was diluted with water (100 mL) and extracted with ethyl acetate (2×50 mL). The combined organic layers were dried and evaporated. The residue was purified by column chromatography to yield the desired compound as an oil (332 mg, 91%): MS (DCI (NH$_3$)) m/z 284 (M+H)$^+$, 301 (M+NH$_4$)$^+$.

EXAMPLE 185C methyl 2-[[6-(aminoiminomethyl)-2-naphthalenyl]oxy]acetate, mono(trifluoroacetate)(salt)

The product from Example 185B (323 mg, 1.140 mmol) was dissolved in anhydrous methanol (32 mL) under an inert atmosphere and cooled to 0° C. Anhydrous hydrogen chloride was bubbled into the solution until it became saturated. The reaction was stirred for 15 minutes at 0° C. and saturated again with anhydrous hydrogen chloride. After stirring for an additional 20 minutes at 0° C. the solution was saturated one final time with anhydrous hydrogen chloride and stirred 18 hours while warming to room temperature. The reaction was evaporated to a solid and dried under high vacuum for 2 hours. The solid was slurried in methanol (64 mL), ammonium acetate (220 mg, 2.850 mmol) was added, and the mixture was heated at reflux 2 hours. The reaction was evaporated and purified by reverse phase chromatography to give the desired compound (265 mg, 90%).

MS (DCI (NH$_3$)) m/z 259 (M+H)$^+$; $^1$H NMR (300 MHz, DMSO-d6) δ 3.735 (s, 3H), 4.995 (s, 2H), 7.430 (dd, 1H), 7.458 (s, 1H), 7.669 (dd, 1H), 8.025 (d, 1H), 8.095 (d, 1H), 8.325 (d, 1H), 9.090 (br s, 1H), 9.410 (br s, 1H; Anal. calc'd for C$_{14}$H$_{14}$N$_2$O$_3$. (C$_2$HO$_2$F$_3$) 1.05: C, 51.16; H, 4.01; N, 7.41. Found: C, 51.35; H, 3.98; N, 7.48.

EXAMPLE 186

6-(aminoiminomethyl)-N-(2-thiazolyl)-2-naphthalenecarboxamide, monohydrochloride

EXAMPLE 186A

The above product was prepared in the manner of Example 8A using 2-aminothiazole.

MS (APCI) m/z (M+H)$^+$280.

EXAMPLE 186B 6-(aminoiminomethyl)-N-(2-thiazolyl)-2-naphthalenecarboxamide, monohydrochloride The above was prepared from Example 1B.

MS (APCI) m/z (M+H)$^+$297; 1H-NMR (300 MHz, DMSO-d$_6$) δ 12.88 (s, 1H), 9.59 (s, 2H), 9.30 (s, 2H), 8.87 (s, 1H), 8.59 (s, 1H), 8.32–8.22 (m, 4H), 7.93 (dd, J=1.8, 8.4 Hz, 1H), 7.61 (d, J=3.3 Hz, 1H), 7.33 (d, J=3.3 Hz, 1H); Anal. calc'd for C$_{15}$H$_{13}$N$_4$OClS 2/5 HCl: C, 52.03; H, 3.89; N, 16.18. Found: C, 52.01; H, 3.88; N, 16.12.

EXAMPLE 187

6-(aminoiminomethyl)-N-(6-methoxy-3-pyridinyl)-2-naphthalenecarboxamide, monohydrochloride

EXAMPLE 187A

The above product was prepared in the manner of Example 8A using 5-amino-2-methoxypyridine.

MS (APCI) m/z (M+H)$^+$304.

EXAMPLE 187B 6-(aminoiminomethyl)-N-(6-methoxy-3-pyridinyl)-2-naphthalenecarboxamide, monohydrochloride The above was prepared as described Example 1B (144D).

MS (CI) m/z (M+H)$^+$321; 1H-NMR (300 MHz, DMSO-d$_6$) δ 10.71 (s, 1H), 9/60 (s, 2H), 9.41 (s, 2H), 8.76 (s, 1H), 8.60 (s, 2H), 8.30 (d, J=9, 1H), 8.25–8.12 (m, 4H), 7.93 (dd, J=1.8, 8.7 Hz, 1H), 6.89 (d, J=9.0 Hz, 1H), 3.87 (s, 3H); Anal. calc'd for C$_{20}$H$_{17}$N$_4$O$_4$F$_3$ 1/2 TFA: C, 51.47; H, 3.60; N, 11.45. Found: C, 51.39; H, 3.88; N, 11.65.

EXAMPLE 188

6-(aminoiminomethyl)-N-(1,3-benzodioxol-5-yl)-2-naphthalenecarboxamide, mono(trifluoroacetate) (salt)

EXAMPLE 188A

The above product was prepared in the manner of Example 8A using 3,4-methylenedioxyaniline.

MS (APCI) m/z (M+H)$^+$317.

EXAMPLE 188B

The above was prepared as described Example 1B.

MS (CI) m/z (M+H)$^+$334; 1H-NMR (300 MHz, DMSO-d$_6$) δ 9.70 (s, 1H), 8.20 (s, 2H), 9.96 (s, 1H), 7.81–87.63 (m, 3H), 7.31 (dd, J=1.8, 8.4 Hz, 1H), 7.11 (d, J=4.2 Hz, 1H), 6.91 (dd, J=4.5, 10.8 Hz), 6.4 (d, J=8.4 Hz, 1H), 5.59 (s, 2H); Anal. calc'd for C$_{21}$H$_{16}$N$_3$O$_3$F$_3$ 3/5 TFA: C, 55.44; H, 3.48; N, 8.77. Found: C, 55.44; H, 3.52; N, 8.85.

EXAMPLE 189

6-(aminoiminomethyl)-N-(1,2,3,4-tetrahydro-2,4-dioxo5-pyrimidinyl)-2-naphthalenecarboxamide, monohydrochloride

EXAMPLE 189A

The above product was prepared in the manner of Example 8A using 5-aminouracil.

MS (APCI) m/z (M−H)$^+$305.

EXAMPLE 189B 6-(aminoiminomethyl)-N-(1,2,3,4-tetrahydro-2,4-dioxo5-pyrimidinyl)-2-naphthalenecarboxamide, monohydrochloride The above was prepared as described in Example 1B.

MS (CI) m/z (M+H)+324; $^1$H-NMR (300 MHz, DMSO-$d_6$) δ 11.50 (s, 1H), 10.90 (m, 1H), 9.53 (s, 3H), 9.21 (s, 2H), 8.70 (s, 1H), 8.55 (s, 1H), 8.33 (d, J=8.4 Hz, 1H), 8.20 (d, J=8.7 Hz, 1H), 8.13–8.09 (m, 2H), 8.00 (s, 1H), 7.88 (dd, J=1.8, 8.4 Hz, 1H); Anal. calc'd for $C_{16}H_{14}N_5O_3Cl$ 2/5 HCl: C, 51.49; H, 3.88; N, 18.76. Found: C, 51.87; H, 4.01; N, 17.68.

EXAMPLE 190

6-(aminoiminomethyl)-N-(3,5-difluorophenyl)-2-naphthalenecarboxamide, mono(trifluoroacetate) (salt)

EXAMPLE 190A

The above product was prepared in the manner of Example 8A using 3,5-difluoroaniline.

MS (APCI) m/z (M–H)+ 307.

EXAMPLE 190B 6-(aminoiminomethyl)-N-(3,5-difluorophenyl)-2-naphthalenecarboxamide, mono(trifluoroacetate) (salt)

The above was prepared as described in Example 1B.

MS (CI) m/z (M+H)+ 326; $^1$H-NMR (300 MHz, DMSO-$d_6$) δ 10.93 (s, 1H), 9.53 (s, 2H), 9.34 (s, 2H), 8.71 (s, 1H), 8.58 (s, 1H), 8.33 (d, J=8.4 Hz, 1H), 8.26 (d, J=8.7 Hz, 1H), 8.14 (m, 1H), 7.92 (dd, J=0.9, 8.1 Hz, 1H), 7.61 (d, J=7.8 Hz, 2H), 7.04–6.97 (m, 1H); Anal. calc'd for $C_{20}H_{14}N_3O_2F_5$ 2/5 TFA: C, 54.92; H, 3.21; N, 9.42. Found: C, 54.96; H, 3.36; N, 9.37.

EXAMPLE 191

6-(aminoiminomethyl)-N-(1H-pyrazol-3-yl)-2-naphthalenecarboxamide, mono(trifluoroacetate) (salt)

EXAMPLE 191A

The above product was prepared in the manner of Example 8A using 3-aminopyrazole.

MS (APCI) m/z (M+H)+ 263.

EXAMPLE 191B 6-(aminoiminomethyl)-N-(1H-pyrazol-3-yl)-2-naphthalenecarboxamide, mono(trifluoroacetate) (salt)

The above was prepared as desribed in Example 1B.

MS (CI) m/z (M+H)+ 280; $^1$H-NMR (300 MHz, DMSO-$d_6$) δ 11.13 (s, 1H), 9.55 (s, 2H), 9.37 (s, 2H), 8.75 (s, 1H), 8.55 (s, 1H), 8.23 (d, J=8.4 Hz, 1H), 8.12 (s, 2H), 7.90 (d, J=8.4 Hz, 1H), 7.70 (s, 1H), 6.69 (s, 1H); Anal. calc'd for $C_{17}H_{14}N_5O_3F_3$ 7/10 TFA: C, 46.53; H, 3.12; N, 14.70. Found: C, 46.47; H, 3.16; N, 14.85.

EXAMPLE 192

6-(aminoiminomethyl)-N-(5-methyl-3-isoxazolyll)-2-naphthalenecarboxamide, mono(trifluoroacetate) (salt)

EXAMPLE 192A

The above product was prepared in the manner of Example 8A using 3-amino-5-methylisoxazole.

MS (APCI) m/z (M+H)+ 278.

EXAMPLE 192B 6-(aminoiminomethyl)-N-(5-methyl-3-isoxazolyll)-2-naphthalenecarboxamide, mono(trifluoroacetate) (salt)

The above was prepared as described in Example 1B.

MS (CI) m/z (M+H)+ 295; $^1$H-NMR (300 MHz, $d_6$-DMSO) δ 11.62 (s, 1H), 9.52 (s, 2H), 9.33 (s, 2H), 8.78 (s, 1H), 8.55 (dd, 1H), 8.31–8.16 (m, 3H), 7.90 (dd, 1H), 6.81 (s, 1H), 2.44 (s, 3H) Anal. calc'd for $C_{18}H_{15}N_4O_4F_3$: C, 52.95; H, 3.70; N, 13.72. Found: C, 52.73; H, 3.64; N, 13.24.

EXAMPLE 193

6-(aminoiminomethyl)-N-(pyrazinyl)-2-naphthalenecarboxamide, mono(trifluoroacetate) (salt)

EXAMPLE 193A

The above product was prepared in the manner of Example 8A using 2-aminopyrazine.

MS (APCI) m/z (M–H)+ 275.

EXAMPLE 193B 6-(aminoiminomethyl)-N-(pyrazinyl)-2-naphthalenecarboxamide, mono(trifluoroacetate) (salt)

The above was prepared as described in Example 1B.

MS (CI) m/z (M+H)+ 292; $^1$H-NMR (300 MHz, $d_6$-DMSO) δ 11.41 (s, 1H), 9.52 (s, 2H), 9.49 (s, 1H), 9.27 (s, 2H), 8.83 (s, 1H), 8.56 (s, 1H), 8.53–8.46 (m, 2H), 8.30 (d, 1H), 8.23 (s, 2H), 7.90 (dd, 1H); Anal. calc'd for $C_{18}H_{14}N_5O_3F_3$: C, 49.36; H, 3.16; N, 15.15 1/2 TFA. Found: C, 49.53; H, 3.22; N, 14.87.

EXAMPLE 194

6-(aminoiminomethyl)-N-(6-methyl-2-pyridinyl)-2-naphthalenecarboxamide, mono(trifluoroacetate) (salt)

EXAMPLE 194A

The above product was prepared in the manner of Example 8A using 2-amino-6-methylpyridine.

MS (APCI) m/z (M+H)+ 288.

EXAMPLE 194B 6-(aminoiminomethyl)-N-(6-methyl-2-pyridinyl)-2-naphthalenecarboxamide, mono(trifluoroacetate) (salt)

The above was prepared as described in Example 1B.

MS (CI) m/z (M+H)+ 305; $^1$H-NMR (300 MHz, $d_6$-DMSO) δ 11.02 (s, 1H), 9.53 (s, 2H), 9.37 (s, 2H), 8.80 (s, 1H), 8.55 (s, 1H), 8.29 (d, 1H), 8.20 (s, 2H), 8.07 (d, 1H), 7.89 (d, 1H), 7.78 (t, 1H), 7.08 (d, 1H), 2.48 (s, 3H); Anal. calc'd for $C_{20}H_{17}N_4O_3F_3$: C, 48.74; H, 3.33; N, 10.20 7/5 TFA. Found: C, 48.74; H, 3.59; N, 10.11.

EXAMPLE 195

6-(aminoiminomethyl)-N-(3,4,5-trimethoxyphenyl)-2-naphthalenecarboxamide, monohydrochloride

EXAMPLE 195A

The above product was prepared in the manner of Example 8A using 3,4,5-trimethoxyaniline.

MS (APCI) m/z (M+H)+ 363.

EXAMPLE 195B 6-(aminoiminomethyl)-N-(3,4,5-trimethoxyphenyl)-2-naphthalenecarboxamide, monohydrochloride The above was prepared as described in Example 1B.
MS (CI) m/z (M+H)+ 380; $^1$H-NMR (300 MHz, $d_6$-DMSO) δ 10.54 (s, 1H), 9.61 (s, 2H), 9.34 (s, 2H), 8.72 (s, 1H), 8.59 (s, 1H), 8.33–8.15 (m, 3H), 7.91 (dd, 1H), 7.30 (s, 2H), 3.80 (s, 9H) Anal. calc'd for $C_{21}H_{22}N_3O_4Cl$ 63/10 HCl: C, 39.09; H, 4.42; N, 6.51. Found: C, 38.94; H, 4.60; N, 7.61.

EXAMPLE 196

6-(aminoiminomethyl)-N-(3-methyl-2-pyridinyl)-2-naphthalenecarboxamide, bis(trifluoroacetate)(salt)

EXAMPLE 196A

Using the procedure described for Example 184A and substituting 2-amino-3-picolene for 4-aminobenzamide, the desired compound was obtained.
MS (DCI) m/z 288 (M+H)+.

EXAMPLE 196B 6-(aminoiminomethyl)-N-(3-methyl-2-pyridinyl)-2-naphthalenecarboxamide, bis(trifluoroacetate)(salt)

Using the procedure described in Example 1B and the product obtained in Example 196A, the desired compound was obtained.
MS (DCI) m/z 305 (M+H)+; $^1$H NMR (300 MHz, DMSO) δ 10.85 (s, 1H), 9.52 (s, 2H), 9.22 (s, 2H), 8.76 (s, 1H), 8.56 (s, 1H), 8.35 (dd, 1H, J=4.41, 1.10), 8.32 (d, 1H, J=8.80), 8.22 (m, 2H), 7.90 (dd, 1H, J=8.83, 1.84), 7.80 (dd, 1H, J=7.73, 1.11), 7.31 (dd, 1H, J=7.72, 4.78), 2.26 (s, 1H); Anal. calc'd for $C_{22}H_{18}F_6N_4O_3 \cdot 0.75\ H_2O$: C, 48.40; H, 3.60; N, 10.26. Found: C, 48.81; H, 3.66; N, 10.43.

EXAMPLE 197

6-(aminoiminomethyl)-N-(5-bromo-2-thiazolyll)-2-napthalenecarboxamide, mono(trifluoroacetate)(salt)

EXAMPLE 197A

Using the procedure described for Example 184A and substituting 2-amino-5-bromothiazole for 4-aminobenzamide, the desired compound was obtained.
MS (DCI) m/z 358 (M+H)+.

EXAMPLE 197B 6-(aminoiminomethyl)-N-(5-bromo-2-thiazolyll)-2-naphthalenecarboxamide, mono(trifluoroacetate)(salt)

Using the procedure described in Example 1B and the product obtained in Example 197A, the desired compound was obtained.
MS (ESI+) m/z 375 (M+H)+; $^1$H NMR (300 MHz, DMSO) δ 10.85 (s, 1H), 9.55 (s, 2H), 9.24 (s, 2H), 8.87 (s, 1H), 8.57 (d, 1H, J=1.69), 8.31 (d, 1H, J=8.47), 8.25 (d, 2H, J=1.01), 7.92 (dd, 1H, J=8.48, 2.04), 7.71 (s, 1H); Anal. calc'd for $C_{17}H_{12}BrF_3SN_4O_3 \cdot 1.25\ H_2O \cdot 0.25$ TFA: C, 38.90; H, 2.75; N, 10.37. Found: C, 38.97; H, 3.24; N, 10.66.

EXAMPLE 198

6-(aminoiminomethyl)-N-(5-methyl-2-pyridinyl)-2-naphthalenecarboxamide, mono(trifluoroacetate) (salt)

EXAMPLE 198A

Using the procedure described for Example 184A and substituting 2-amino-5-picolene for 4-aminobenzamide, the desired compound was obtained.
MS (ESI+) m/z 288 (M+H)+.

EXAMPLE 198B 6-(aminoiminomethyl)-N-(5-methyl-2-pyridinyl)-2-naphthalenecarboxamide, mono(trifluoroacetate) (salt)

Using the procedure described in Example 1B and the product obtained in Example 198A, the desired compound was obtained.

MS (DCI) m/z 305 (M+H)+; $^1$H NMR (300 MHz, DMSO) δ 11.01 (s, 1 H), 9.50 (s, 2H), 9.16 (s, 2H), 8.79 (s, 1H), 8.54 (s, 1H), 8.30 (d, 1H, J=9.19), 8.27 (d, 1H, J=1.47), 8.20 (s, 2H), 8.15 (d, 1H, J=8.83), 7.89 (dd, 1H, J=8.46, 1.48), 7.72 (dd, 1H, J=8.46, 1.84), 2.31 (s, 3H); Anal. calc'd for $C_{20}H_{17}F_3N_4O_3 \cdot 0.25\ H_2O \cdot 0.2$ TFA: C, 54.98; H, 4.00; N, 12.57. Found: C, 54.99; H, 3.59; N, 12.43.

EXAMPLE 199

6-(aminoiminomethyl)-N-(4-methyl-2-thiazolyl)-2-naphthalenecarboxamide, mono(trifluoroacetate) (salt)

EXAMPLE 199A

Using the procedure described for Example 184A and substituting 2-amino-5-methyl benzothiazole for 4-aminobenzamide, the desired compound was obtained.

MS (ESI−) m/z 293 (M+H)−.

EXAMPLE 199B 6-(aminoiminomethyl)-N-(4-methyl-2-thiazolyl)-2-naphthalenecarboxamide, mono(trifluoroacetate) (salt)

Using the procedure described in Example 1B and the product obtained in Example 199A, the desired compound was obtained.

MS (ESI+) m/z 311 (M+H)+; $^1$H NMR (300 MHz, DMSO) δ 9.51 (s, 2H), 9.25 (s, 2H), 8.86 (s, 1H), 8.55 (s, 1H), 8.30 (d, 1H, J=8.48), 8.25 (d, 1H, J=2.03), 7.91 (dd, 1H, J=8.48, 1.70), 6.87 (s, 1H), 2.34 (s, 3H); Anal. calc'd for $C_{18}H_{15}F_3N_4SO_3 \cdot 0.5$ TFA: C, 47.40; H, 3.25; N, 11.64. Found: C, 47.90; H, 3.36; N, 11.71.

EXAMPLE 200

6-(aminoiminomethyl)-4-[5-(ethylthio)-3-furanyl]-N-phenyl-2-naphthalenecarboxamide, monohydrochloride

EXAMPLE 200A

The desired compound was prepared from 2-trimethylsilyl-3-bromofuran and diethyldisulfide by the procedure of Example 154A.

MS (DCI/NH$_3$) m/z 279, 281 (M+H)+.

EXAMPLE 200B

A solution of the product from Example 200A (8.60 g, 30.8 mmol) in THF (20 mL) and a 1 M solution of TBAF (61.6 mL) was stirred for 24 hours. The reaction was condensed and chromatographed on SiO$_2$ using hexanes as eluent, to yield 3.32 g (52%) of 2-ethylthio-4-bromofuran. The desired compound was prepared from this material by the procedure of Example 57A.

MS (DCI/NH$_3$) m/z 127 (M−B (OH)$_2$)$^+$.

EXAMPLE 200C

The desired compound was prepared from the product from Example 200B and the product from Example 152C by the procedure of Example 57B.

MS (DCI/NH$_3$) m/z 416 (M+NH$_4$)$^+$.

EXAMPLE 200D 6-(aminoiminomethyl)-4-[5-(ethylthio)-3-furanyl]-N-phenyl-2-naphthalenecarboxamide, monohydrochloride The desired compound was prepared from Example 200C and the procedure of Example 144C.

MS (DCI/NH$_3$) m/z 416 (M+H)$^+$; $^1$H NMR (300 MHz, DMSO-d$_6$) δ 1.30 (t, 3H), 2.92 (q, 2H), 7.15 (t, 1H), 7.34 (s, 1H), 7.40 (t, 2H), 7.83 (d, 2H), 7.92 (dd, 1H), 8.20 (d, 1H), 8.40 (d, 1H), 8.47 (s, 1H), 8.60 (s, 1H), 8.69 (s, 1H), 9.21 (br s, 2H), 9.58 (br s, 2H), 10.61 (s, 1H); Anal. calc'd for C$_{24}$H$_{21}$N$_3$SO$_2$.1.5 HCl: C, 61.31; H, 4.82; N, 8.94. Found: C, 61.39; H, 4.89; N, 9.03.

EXAMPLE 201

6-(aminoiminomethyl)-4-[5-(propylthio)-3-furanyl]-N-phenyl-2-naphthalenecarboxamide, monohydrochloride

EXAMPLE 201A

The desired compound was prepared from 2-trimethylsilyl-3-bromofuran and dipropyldisulfide by the procedure of Example 154A.

MS (DCI/NH$_3$) m/z 293, 295 (M+H)$^+$.

EXAMPLE 201B

The desired compound was prepared from the product from Example 201A by the procedure of 154B.

MS (DCI/NH$_3$) m/z 432 (M+H)$^+$.

EXAMPLE 201C

The desired compound was prepared from the product from Example 201B and the product from Example 152C by the procedure of Example 154C.

MS (DCI/NH$_3$) m/z 430 (M+NH$_4$)$^+$.

EXAMPLE 201D 6-(aminoiminomethyl)-[5-(propylthio)-3-furanyl]-N-phenyl-2-naphthalenecarboxamide, monohydrochloride The desired compound was prepared from Example 201C and the procedure of Example 144C.

MS (DCI/NH$_3$) m/z 430 (M+H)$^+$; $^1$H NMR (300 MHz, DMSO-d$_6$) δ 1.01 (t, 3H), 1.66 (qt, 2H), 2.89 (t, 2H), 7.15 (t, 1H), 7.34 (s, 1H), 7.40 (t, 2H), 7.84 (d, 2H), 7.92 (dd, 1H), 8.20 (d, 1H), 8.40 (d, 1H), 8.47 (s, 1H), 8.60 (s, 1H), 8.69 (s, 1H), 9.22 (br s, 2H), 9.58 (br s, 2H), 10.61 (s, 1H); Anal. calc'd for C$_{25}$H$_{23}$N$_3$SO$_2$.1.25 HCl: C, 63.20; H, 5.14; N, 8.84. Found: C, 63.24; H, 5.16; N, 8.93.

EXAMPLE 202

6-(aminoiminomethyl)-N-(6-quinolinyl)-2-naphthalenecarboxamide, bis(trifluoroacetate)(salt)

EXAMPLE 202A

To a solution of the acid chloride, Example 8B, (331 mg, 1.5 mmol) in THF (15 mL), at room temperature, was added propylene oxide (10 mL), DMAP (5 mg), a drop of triethylamine and finally 6-aminoquinoline (288 mg, 2.0 mmol). After 4 hours at room temperature, added ethyl acetate (10 mL) and ether (20 mL) and filtered the off-white solid product. Yield 357 mg (72%).

MS (DCI/NH$_3$) m/z 324 (M+H)$^+$.

EXAMPLE 202B 6-(aminoiminomethyl)-N-(6-quinolinyl)-2-naphthalenecarboxamide, bis(trifluoroacetate)(salt)

The desired compound was prepared as described in Example 1B.

MS (ESI$^+$) m/z 341 (M+H)$^+$, (ESI$^-$) 339 (M−1)$^-$; $^1$H NMR (300 MHz, DMSO-d$_6$) δ 10.98 (s, 1H), 9.53 (s, 2H), 9.25 (s, 2H), 8.93–8.91 (m, 1H), 8.77 (s, 1H), 8.67 (d, J=1.8 Hz, 1H), 8.58 (s, 1H), 8.53 (d, J=8.5 Hz, 1H), 8.37–8.09 (m, 5H), 7.93 (dd, J1=8.5 Hz, J2=1.8 Hz, 1H), 7.65–7.62 (m, 1H); Anal. calc'd for C$_{21}$H$_{16}$N$_4$O.2TFA: C, 52.83; H, 3.19; N, 9.86. Found: C, 52.62; H, 2.94; N, 9.74.

EXAMPLE 203

6-(aminoiminomethyl)-N-(1H-indazol-6-yl)-2-naphthalenecarboxamide, bis(trifluoroacetate)(salt)

EXAMPLE 203A

The desired compound was prepared as described for Example 202A but substituting 6-aminoquinoline for 6-aminoindazole to provide 285 mg of the desired compound.

MS: ESI+: 313 (M+1); ESI-311 (M−1).

EXAMPLE 203B 6-(aminoiminomethyl)-N-(1H-indazol-6-yl)-2-naphthalenecarboxamide, bis(trifluoroacetate)(salt)

To a suspension of the ammonium chloride (140 mg, 2.6 mmol) in Toluene (2 mL) at 0° C. was slowly added a solution of 2 N trimethylaluminium in toluene (871 μL, 1.74 mmol). After 5 minute the reaction mixture was allowed to warm to room temperature for 30 minutes. To the solution of the aluminium reagent at room temperature was added the nitrile, Example 203A from section (a) and the reaction mixture was heated to 100° C. for 48 hours. The reaction mixture was cooled down then was poured into a suspension of silica in chloroform and stirred for an hour. The silica was filtered then washed with methanol. The solvent was concentrated and purified by medium pressure liquid chromatography on a 30 cm×2 cm C-18 column (40 micron, J. T Baker) with UV detection at 250 nM with solvent mixtures in a gradient ranging from 90%A (0.1% aq TFA)/10%B (methanol) to 10%A/90%B over 160 minutes at a flow rate of 5 mL/min (fractions were collected every 2 minutes for 100 min, to provide 42 mg of the desired compound.

MS (ESI$^+$) m/z 330 (M+H)$^+$, (ESI–) 328 (M–1)$^-$; $^1$H NMR (300 MHz, DMSO-d$_6$) δ 10.65 (s, 1H), 9.47 (m, 4H), 8.65 (s, 2H), 8.50 (s, 2H), 8.25–8.23 (m, 2H), 8.17–8.10 (m, 2H), 7.94 (s, 1H), 7.86–7.84 (dd, J1=8.8 Hz, J2=1.6 Hz, 1H), 7.66 (d, J=8.5 Hz, 1H), 7.37 (d, J=8.4 Hz, 1H); Anal. calc'd for C$_{19}$H$_{15}$N$_5$ O.2 TFA: C, 49.56; H, 3.07; N. 12.56. Found: C, 49.68; H, 3.10; N, 12.47.

EXAMPLE 204

6-(aminoiminomethyl)-N-(1H-indazol-5-yl)-2-naphthalenecarboxamide, bis(trifluoroacetate)(salt)

EXAMPLE 204A

The desired compound was prepared as described for Example 202A but substituting 6-aminoquinoline for 5-aminoindazole to provide 362 mg of the desired compound.

MS: ESI+: 313 (M+1); ESI–311 (M–1).

EXAMPLE 204B 6-(aminoiminomethyl)-N-(1H-indazol-5-yl)-2-naphthalenecarboxamide, bis(trifluoroacetate)(salt)

The desired compound was prepared as described for Example 203B to provide 55 mg of the desired compound.

MS (ESI$^+$) m/z 330 (M+H)$^+$, (ESI$^-$) 328 (M–1)$^-$; $^1$H NMR (300 MHz, DMSO-d$_6$) δ 13.06 (s, 1H), 10.58 (s, 1H), 9.51 (s, 2H), 9.15 (s, 2H), 8.71 (d, j=1.9 Hz, 1H), 8.56 (d, j=1.9 Hz, 1H), 8.34–8.17 (m, 4H), 8.10 (s, 1H), 7.90 (dd, J1=8.5 Hz, J2=1.7 Hz, 1H), 7.63 (dd, J1=8.9 Hz, J2=1.7 Hz, 1H), 7.56 (d, J=8.8 Hz, 1H); Anal. calc'd for C$_{19}$H$_{15}$N$_5$ O.TFA.1.75 H$_2$O: C, 53.11; H, 4.14; N, 14.75. Found: C, 53.20; H, 3.99; N, 14.42.

EXAMPLE 205

6-(aminoiminomethyl)-N-(1H-indol-5-yl)-2-naphthalenecarboxamide, mono(trifluoroacetate) (salt)

EXAMPLE 205A

The desired compound was prepared as described for Example 202A but substituting 6-aminoquinoline for 6-aminoindole to provide 744 mg of the desired compound.

MS: (ESI)$^+$: 329 (M+1)$^+$ and (ESI)$^-$: 327 (M–1)$^-$.

EXAMPLE 205B 6-(aminoiminomethyl)-N-(1H-indol-5-yl)-2-naphthalenecarboxamide, mono(trifluoroacetate) (salt)

The desired compound was prepared as described for Example 203B to provide 90 mg of the desired compound.

MS (ESI$^+$) m/z 329 (M+H)$^+$, (ESI$^-$) 327 (M–1)$^-$; $^1$H NMR (300 MHz, DMSO-d$_6$) δ 11.09 (s, 1H), 10.40 (s, 1H), 9.51 (s, 2H), 9.15 (s, 2H), 8.71 (s, 1H), 8.55 (s, 1H), 8.32 (d, J=8.4 Hz, 1H), 8.26–8.17 (m, 2H), 8.05 (d, J=2.6 Hz, 1H), 7.90 (dd, J1=8.4 Hz, J2=1.8 Hz, 1H), 7.46–7.35 (m, 3H), 6.45–6.43 (m, 1H); Anal. calc'd for C$_{20}$H$_{16}$N$_4$ O.TFA: C, 59.73; H, 3.87; N, 12.66. Found: C, 59.27; H, 4.17; N, 12.74.

EXAMPLE 206

7-[2-(4-morpholinyl)ethoxy]-2-naphthalenecarboximidamide, bis(trifluoroacetate) (salt)

EXAMPLE 206A

The nitrile was prepared as described in Example 119A using 2-chloroethylmorpholine.

MS (DCI (NH$_3$)) m/z 283 (M+H)$^+$.

EXAMPLE 206B

7-[2-(4-morpholinyl)ethoxy]-2-naphthalenecarboximidamide, bis(trifluoroacetate) (salt)

The desired compound was prepared as described in Example 119B, as an off-white, solid (50% yield).

MS (DCI (NH$_3$)) m/z 300 (M+H)$^+$; $^1$H NMR (300 MHz, DMSO-d$_6$) δ 3.500 (br m, 4H), 3.700 (br m, 2H), 3.990 (br m, 4H), 4.490 (br m, 2H), 7.435 (dd, 1H), 7.530 (d, 1H), 7.680 (dd, 1H), 8.035 (d, 1H), 8.100 (d, 1H), 8.345 (d 1H), 9.165 (br s, 2H), 9.420 (br s, 2H); Anal. calc'd for C$_{17}$H$_{21}$N$_3$O$_2$.(C$_2$HO$_2$F$_3$) 2.15: C, 46.98; H, 4.29; N, 7.72. Found: C, 47.00; H, 4.32; N, 7.77.

EXAMPLE 207

6-(aminoiminomethyl)-N-phenyl-4-(2-pyrrolidinyl)-2-naphthalenecarboxamide, mono(trifluoroacetate) (salt)

EXAMPLE 207A

The desired compound was prepared from the product from Example 152A, by the procedure of Example 68A.

MS (DCI/NH$_3$) m/z 281 (M+H)$^+$.

EXAMPLE 207B

The desired compound was prepared from the product from Example 207A by the procedure of Example 152B.

MS (DCI/NH$_3$) m/z 267 (M+H)$^+$.

EXAMPLE 207C

A solution of the product from Example 207B (220 mg, 0.826 mmol), diisopropylethyl amine (0.288 mL, 1.65 mmol), and O-(7-azabenzotriazol-1-yl)-N,N,N',N'-tetramethyluronium hexafluorophosphate (314 mg, 0.826 mmol) in DMF (10 mL) was stirred for 30 minutes at 0° C. Aniline (0.083 mL, 0.909 mmol) was added, and the reaction was stirred at room temperature for 4 hours. The reaction was poured into saturated aqueous Na$_2$CO$_3$ solution, and extracted with 3× ethyl acetate. The combined extracts were washed with water and brine, dried over Na$_2$SO$_4$, and condensed. The crude material was recrystallized from ethanol/hexanes to yield 212 mg (75%) of the desired compound.

MS (DCI/NH$_3$) m/z 342 (M+H)$^+$.

EXAMPLE 207D 6-(aminoiminomethyl)-N-phenyl-4-(2-pyrrolidinyl)-2-naphthalenecarboxmide, mono(trifluoroacetate) (salt)

The desired compound was prepared from Example 207C and the procedure of Example 1B.

MS (DCI/NH$_3$) m/z 359 (M+H)$^+$; $^1$H NMR (300 MHz, DMSO-d$_6$) δ 2.02 (t, 4H), 3.55 (t, 4H), 7.13 (t, 1H), 7.38 (t, 2H), 7.41 (s, 1H), 7.80 (m, 3H), 8.08 (s, 1H), 8.18 (d, 1H), 8.67 (s, 1H), 9.10 (br s, 2H), 9.43 (br s, 2H), 10.41 (br s, 1H); Anal. calc'd for C$_{22}$H$_{22}$N$_4$O.1.0 C$_2$HF$_3$O$_2$: C, 61.01; H, 4.91; N, 11.86. Found: C, 60.47; H, 5.36; N, 7.39.

EXAMPLE 208

6-(aminoiminomethyl)-N-(5-pyrimidinyl)-2-naphthalenecarboxamide, mono(trifluoroacetate) (salt)

EXAMPLE 208A

The above product was prepared in the manner of Example 8A using 5-aminopyrimidne.
MS (APCI) m/z (M+H)$^+$ 275.

EXAMPLE 208B 6-(aminoiminomethyl)-N-(5-pyrimidinyl)-2-naphthalenecarboxamide, mono(trifluoroacetate) (salt)

The above was prepared as described in Example 1B.
MS (CI) m/z (M+H)$^+$ 292; $^1$H-NMR (300 MHz, DMSO-d$_6$) δ 10.99 (s, 1H), 9.52 (s, 2H), 9.27 (s, 2H), 9.24 (s, 2H), 8.98 (s, 1H), 8.76 (s, 1H), 8.58 (s, 1H), 8.36–8.18 (m, 3H), 7.92 (dd, J=1.5, 8.4 Hz, 1H); Anal. calc'd for C$_{18}$H$_{14}$N$_5$O$_3$F$_3$ 7/10 TFA: C, 47.97; H, 3.05; N, 14.40. Found: C, 47.78; H, 3.05; N, 14.67.

EXAMPLE 209

6-(aminoiminomethyl)-N-(3-pyridazinyl)-2-naphthalenecarboxamide, mono(trifluoroacetate) (salt)

EXAMPLE 209A

3-Amino-6-chloropyridazine (1.05 g, 8.2 mmol) was dissolved in 10 mL methanol with 2 mL ammonia/methanol. Palladium/carbon (200 mg, 10%) was added and stirred under 1 atm hydrogen for 4 hours. The reaction was filtered, concentrated, and used without further purification.
MS (CI) m/z (M+H)$^+$ 96.

EXAMPLE 209B

The above product was prepared in the manner of Example 12 using the product from Example 209A.
MS (APCI) m/z (M+H)$^+$ 275.

EXAMPLE 209C 6-(aminoiminomethyl)-N-(3-pyridazinyl)-2-naphthalenecarboxamide, mono(trifluoroacetate) (salt)

The above was prepared from Example 209B as described in Example 1B.
MS (CI) m/z (M+H)$^+$ 292; $^1$H-NMR (300 MHz, d$_6$-DMSO) δ 11.72 (s, 1H), 9.51 (s, 2H), 9.22 (s, 2H), 9.06 (m, 1H), 8.86 (s, 1H), 8.56 (s, 1H), 8.45 (d, 1H), 8.31 (d, 1H), 8.23 (s, 2H), 7.90 (dd, 1H), 7.78 (dd, 1H) Anal. calc'd for C$_{18}$H$_{14}$N$_5$O$_3$F$_3$ 1/2 TFA: C, 49.29; H, 3.16; N, 14.73. Found: C, 49.56; H, 3.23; N, 14.73.

EXAMPLE 210

6-(aminoiminomethyl)-N-(5-bromo-2-pyridinyl)-2-naphthalenecarboxamide, mono(trifluoroacetate) (salt)

EXAMPLE 210A

Using the product obtained in Example 8E, 2-amino-5-bromopyridine, and the procedure described for Example 8G the desired compound was obtained.
MS (APCI+) m/z 352 (M+H)$^+$.

EXAMPLE 210B 6-(aminoiminomethyl)-N-(5-bromo-2-pyridinyl)-2-naphthalenecarboxamide, mono(trifluoroacetate) (salt)

Using the procedure described in Example 1B and the product obtained in Example 210A, the desired compound was obtained.
MS (DCI) m/z 369 (M+H)$^+$; $^1$H NMR (300 MHz, DMSO) δ 11.30 (s, 1H), 9.51 (s, 2H), 9.17 (s, 2H), 8.80 (s, 1H), 8.57 (d, 1H, J=2.57), 8.55 (s, 1H), 8.31 (d, 1H, J=8.45), 8.26 (d, 1H, J=8.82), 8.19–8.24 (m, 2H, ), 8.14 (dd, 1H, J=2.57, 9.19), 7.90 (dd, 1H, J=1.83, 8.82; Anal. calc'd for C$_{19}$H$_{14}$BrF$_3$N$_4$O$_3$: C, 47.22; H, 2.92; N, 11.59. Found: C, 47.60; H, 3.01; N, 11.30.

EXAMPLE 211

6-(aminoiminomethyl)-N-[3-(1-methylethoxy)phenyl]-2-naphthalenecarboxamide, mono(trifluoroacetate)(salt)

EXAMPLE 211A

The above product was prepared in the manner of Example 12 using 3-isopropoxyaniline.
MS (APCI) m/z (M+H)$^+$ 331.

EXAMPLE 211B 6-(aminoiminomethyl)-N-[3-(1-methylethoxy)phenyl]-2-naphthalenecarboxamide, mono(trifluoroacetate)(salt)

The above was prepared from Example 211A using method 1B.
MS (CI) m/z (M+H)$^+$ 348; $^1$H-NMR (300 MHz, d$_6$-DMSO) δ 10.50 (s, 1H), 9.50 (s, 2H), 9.22 (s, 2H), 8.67 (s, 1H), 8.56 (s, 1H), 8.31 (d, 1H), 8.25–8.13 (m, 2H), 7.90 (dd, 1H), 7.51 (m, 1H), 7.36 (m, 1H), 7.26 (t, 1H), 6.68 (dd, 1H), 4.59 (m, 1H), 1.30 (d, 6H) Anal. calc'd for C$_{23}$H$_{22}$N$_3$O$_4$F$_3$ 1/5 TFA: C, 57.96; H, 4.61; N, 8.66. Found: C, 57.99; H, 4.90; N, 8.68.

EXAMPLE 212

2-[[6-(aminoiminomethyl)-2-naphthalenyl]oxy]acetic acid, mono(trifluoroacetate)(salt)

The product from Example 185C (140 mg, 0.542 mmol) was dissolved in methanol (11 mL). To this was added a solution of lithium hydroxide (68.2 mg, 1.626 mmol) in water (3 mL) and the resulting mixture was stirred at room temperature under an inert atmosphere for 18 hours. The reaction was evaporated and the residue purified by reverse phase chromatography to yield the desired compound (102 mg, 52%).
MS (DCI (NH$_3$)) m/z 245 (M+H)$^+$; $^1$H NMR (300 MHz, DMSO-d$_6$) δ 4.875 (s, 2H), 7.420 (s, 1H), 7.435 (dd, 1H), 7.660 (dd, 1H), 8.015 (d, 1H), 8.100 (d, 1H), 8.340 (d, 1H), 9.125 (br s, 1H), 9.420 (br s, 1H; Anal. calc'd for C$_{13}$H$_{12}$N$_2$O$_3$.(C$_2$HO$_2$F$_3$)$_{1.30}$: C, 47.74; H, 3.42; N, 7.14. Found: C, 47.93; H, 3.36; N, 7.17.

EXAMPLE 213 methyl 4-[6-(aminoiminomethyl)-2-naphthalenyl]oxy]methyl benzoate, mono(trifluoroacetate)(salt)

EXAMPLE 213A

The resulting product from Example 185A was treated with methyl 4-(bromomethyl)benzoate in an analogous manner as described in Example 119B.
MS (DCI (NH$_3$)) m/z 335 (M+NH$_4$)$^+$.

EXAMPLE 213B methyl 4-[6-(aminoiminomethyl)-2-naphthalenyl]oxy]methyl]benzoate, mono(trifluoroacetate)(salt)

The resulting product from Example 213A (250 mg, 0.788 mmol) was treated in an analogous manner as described in Example 119C to yield the desired compound (130 mg, 79%).

MS (DCI (NH$_3$)) m/z 335 (M+H)$^+$; $^1$H NMR (300 MHz, DMSO-d$_6$) δ 3.870 (s, 3H), 5.400 (s, 2H), 7.500 (dd, 1H), 7.540 (d, 1H), 7.619 (dd, 1H), 7.620 (d, 2H), 8.025 (d, 2H), 8.026 (d, 1H), 8.090 (d, 1H), 8.410 (d, 1H), 9.260 (v br s, 3H); Anal. calc'd for $C_{14}H_{14}N_2O_3 \cdot C_2HO_2F_3 \cdot H_2O$ 0.70: C, 57.32; H, 4.46; N, 6.08. Found: C, 57.33; H, 4.70; N, 5.95.

EXAMPLE 214

6-(aminoiminomethyl)-N-(1H-imidazolyl)-2-naphthalenecarboxamide, bis(trifluoroacetate)(salt)

EXAMPLE 214A

Using the product obtained in Example 8E, 2-aminoimidazole, and the procedure described for Example 8G the desired compound was obtained.

MS (ESI$^-$) m/z 261 (M+H)$^-$.

EXAMPLE 214B

Using the procedure described in Example 1B and the product obtained in Example 214A, the desired compound was obtained.

MS (ESI+) m/z 280 (M+H)$^+$; $^1$H NMR (300 MHz, DMSO) δ 9.50 (s, 2H), 9.16 (s, 2H), 8.78 (s, 1H), 8.53 (s, 1H), 8.26–8.31 (m, 2H), 8.20 (d, 1H, J=8.46), 7.88 (dd, 1H, J=1.84, 8.83), 6.95 (s, 2H); Anal. calc'd for $C_{17}H_{14}F_3N_5O_3 \cdot 0.2$ TFA·H$_2$O: C, 48.14; H, 3.76; N, 16.13. Found: C, 48.54; H, 3.40; N, 16.02.

EXAMPLE 215

6-[2-[4-(hydroxymethyl)phenyl]-1-cyclopropyl]-2-naphthalenecarboximidamide, mono(trifluoroacetate)(salt)

EXAMPLE 215A

The material prepared as described in Example 104 (210 mg, 0.52 mmol) is dissolved in THF (6 mL) and added dropwise to 10 mL diazomethane cooled to 0° C. then added Pd (OAc)$_2$ (9.8 mg). Vigorous bubbling occurs for 5 minutes. the resulting black slurry is stirred 20 min, filtered and solvent removed under vacuum leaving 0.1 g clear oil.

MS (DCI/NH$_3$): m/z (M+NH$_4^+$): 316.

EXAMPLE 215B

6-[2-[4-(hydroxymethyl)phenyl]-1-cyclopropyl]-2-naphthalenecarboximidamide, mono(trifluoroacetate)(salt)

The desired compound is prepared as described in Example 1, purified by reverse phase chromatography to give 19.9 mg of white solid.

MS (DCI/NH$_3$) m/z (M+H)$^+$ 316; $^1$H-NMR (300 MHz, DMSO-d$_6$) δ 9.41 (s, 2H), 9.16 (s, 2H), 8.46 (s, 1H), 8.08 (d, 2H), 8.03 (d, 1H), 7.85 (s, 1H), 7.75 (dd, 1H), 7.58 (dd, 1H), 7.3–7.1 (m, 4H), 4.49 (s, 2H), 2.38–2.48 (m, 2H), 1.61–1.70 (m, 2H); Anal. calc'd for $C_{23}H_{21}N_2O_2F_3$ 1 H$_2$O: C, 62.10; H, 4.80; N, 6.29. Found: C, 62.00; H, 4, 75; N, 6.25.

EXAMPLE 216

N-(ethoxycarbonyl)-6-(2-phenyl-1-cyclopropyl)-2-naphthalenecarboximidamide

The sample described in Example 97 (130 mg, 0.45 mmol) is dissolved in DMF (3 mL) cooled to 0° C. and treated with triethylamine (0.01 mL) and ethyl chloroformate (0.05 mL). The resulting solution is stirred three days at room temperature then diluted with 100 mL ethyl acetate washed with distilled water (20 mL), dried over anhydrous sodium sulfate, filtered and solvent removed under vacuum leaving a clear oil. The oil is purified by silica gel chromatography eluting with 2:1 hexanes/ethyl acetate, lyophilized and the desired compound is isolated as a white powder (55 mg).

MS (DCI/NH$_3$) m/z (M+H)$^+$ 359; $^1$H-NMR (300 MHz, DMSO-d$_6$) δ 9.21 (s, 2H), 8.46 (s, 1H), 7.83 (d, 2H), 7.62 (s, 1H), 7.58 (dd, 1H), 7.34 (dd, 1H), 7.35–7.29 (m, 3H), 7.25–7.17 (m, 2H) 4.1 (q, 2H), 2.38–2.28 (m, 2H), 1.61 (t, 2H), 1.25 (t, 3H); Anal. calc'd for $C_{23}H_{22}N_2O_2$ C, 77.07; H, 6.19; N, 7.82. Found: C, 76.63; H, 6.05; N, 7.45.

EXAMPLE 217

6-(aminoiminomethyl)-N-(2-methyl-6-quinolinyl)-2-naphthalenecarboxamide, bis(trifluoroacetate)(salt)

The desired compound is prepared in a similar manner as described in Example 8E and 144C.

MS m/z: 355 (M+H)$^+$ $^1$H NMR (DMSO, 300 MHz): 10.95 (s, 1H), 9.51 (s, 2H), 9.14 (s, 2H), 8.75 (s, 1H), 8.65 (s, 1H), 8.57 (s, 1H), 8.35 (dd, 1H, J1=J2=8.5 Hz), 8.28 (dd, 1H, J1=J2=8.5 Hz), 8.19 (dd, 1H, J1=J2=8.8 Hz), 8.15 (dd, 1H, J1=J2=8.3 Hz), 8.04 (dd, 1H, J1=J2=8.8 Hz), 7.91 (dd, 1H, J1=8.4 Hz, J2=8.8 Hz), 7.60 (dd, 1H, J1=J2=8.1 Hz). 5.99 (S, 3H); Anal. calc'd for $C_{22}H_{18}N_4O \cdot 2.25\ C_2F_3O_2H \cdot 2\ H_2O$: C, 49.20; H, 3.78; N, 8.66; F, 19.82. Found: C, 49.02; H, 3.36; N, 8.66.

EXAMPLE 218

6-(aminoiminomethyl)-N-(3-propoxyphenyl)-2-naphthalenecarboxamide, mono(trifluoroacetate)(salt)

EXAMPLE 218A

3-Aminophenol (1 g, 7.2 mmol), triphenylphosphine (2.25 g, 8.6 mmol), and 1-propanol (0.517 g, 8.6 mmol) were dissolved in 25 mL anhydrous THF. Diethylazodicarboxylate (1.5 g, 8.6 mmol) was added dropwise over 1 minute. The solution was allowed to stir 15 minutes and poured slowly into hexanes while stirring. Filtration through silica gel/celite afforded the product as a viscous yellow oil.

MS (APCI) m/z (M+H)$^+$ 152.

EXAMPLE 218B

The above product was prepared in the manner of Example 12 using the product from Example 218A.

MS (APCI) m/z (M+H)$^+$ 331.

EXAMPLE 218C 6-(aminoiminomethyl)-N-(3-propoxyphenyl)-2-naphthalenecarboxamide, mono(trifluoroacetate)(salt)

The above was prepared from Example 218 as described in Example 1B.

MS (CI) m/z (M+H)⁺ 348; ¹H-NMR (300 MHz, d₆-DMSO) δ 10.51 (s, 1H), 9.50 (s, 2H), 9.18 (s, 2H), 8.68 (s, 1H), 8.55 (s, 1H), 8.32 (d, 1H), 8.25–8.13 (m, 2H), 7.90 (dd, 1H), 7.52–7.33 (m, 2H), 7.27 (t, 1H), 6.73 (dd, 1H), 3.94 (t, 2H), 1.75 m, 2H), 1.00 (t, 3H) Anal. calc'd for $C_{23}H_{22}N_3O_4F_3$: 1/20 TFA: C, 59.49; H, 4.77; N, 9.02. Found: C, 59.43; H, 4.94; N, 9.10.

EXAMPLE 219

6-(aminoiminomethyl)-N-[3-(1-ethylpropoxy) phenyl]-2-naphthalenecarboxamide, mono (trifluoroacetate)(salt)

EXAMPLE 219A

The above product was prepared in the manner of Example 218A using 3-pentanol.
MS (APCI) m/z (M+H)⁺ 180.

EXAMPLE 219B

The above product was prepared in the manner of Example 12 using the product from Example 219A.
MS (APCI) m/z (M+H)⁺ 359.

EXAMPLE 219C 6-(aminoiminomethyl)-N-[3-(1-ethylpropoxy) phenyl]-2-naphthalenecarboxamide, mono (trifluoroacetate)(salt)

The above was prepared from Example 219B as described in Example 1B.
MS (CI) m/z (M+H)⁺ 376; ¹H-NMR (300 MHz, d₆-DMSO) δ 10.47 (s, 1H), 9.49 (s, 2H), 9.14 (s, 2H), 8.67 (s, 1H), 8.55 (s, 1H), 8.31 (d, 1H), 8.25–8.16 (m, 2H), 7.90 (dd, 1H), 7.51 (s, 1H), 7.38 (m, 1H), 7.26 (t, 1H), 6.72 (dd, 1H), 4.18 (m, 1H), 1.65 (m, 4H), 0.93 (t, 6H) Anal. calc'd for $C_{25}H_{26}N_3O_4F_3$: C, 61.34; H, 5.35; N, 8.58. Found: C, 61.05; H, 5.42; N, 8.22.

EXAMPLE 220

6-(aminoiminomethyl)-N-[3-(cyclopentyloxy) phenyl]-2-naphthalenecarboxamide, mono (trifluoroacetate)(salt)

EXAMPLE 220A

The above product was prepared in the manner of Example 218A using cyclopentanol.
MS (APCI) m/z (M+H)⁺ 86.

EXAMPLE 220B

The above product was prepared in the manner of Example 12 using the product from Example 220A.
MS (APCI) m/z (M+H)⁺ 357.

EXAMPLE 220C 6-(aminoiminomethyl)-N-[3-(cycopentyloxy) phenyl]-2-naphthalenecarboxamide, mono (trifluoroacetate)(salt)

The above was prepared from Example 220B as described in Example 1B.
MS (CI) m/z (M+H)⁺ 374; ¹H-NMR (300 MHz, d₆-DMSO) δ 10.50 (s, 1H), 9.51 (s, 2H), 9.30 (s, 2H), 8.68 (s, 1H), 8.56 (s, 1H), 8.32 (d, 1H), 8.25–8.13 (m, 2H), 7.90 (dd, 1H), 7.49 (m, 1H), 7.38 (m, 1H), 7.26 (t, 1H), 6.72 (dd, 1H), 4.79 (m, 1H), 1.96–1.08 (m, 8H). Anal. calc'd for $C_{25}H_{24}N_3O_4F_3$ 2/5 TFA: C, 60.68; H, 5.06; N, 8.49. Found: C, 60.68; H, 5.33; N, 8.65.

EXAMPLE 221

6-(aminoiminomethyl)-N-(3-phenoxyphenyl)-2-naphthalenecarboxamide, mono(trifluoroacetate) (salt)

EXAMPLE 221A

The above product was prepared in the manner of Example 218A using 3-phenoxyanline.
MS (APCI) m/z (M+H)⁺ 365.

EXAMPLE 221B

6(aminoiminomethyl)-N-(3-phenoxyphenyl)-2-naphthalenecarboxamide, mono(trifluoroacetate) (salt)

The above was prepared from Example 221A as described in Example 1B.
¹H-NMR (300 MHz, d₆-DMSO) δ 10.61 (s, 1H), 9.50 (s, 2H), 9.20 (s, 2H), 8.66 (s, 1H), 8.54 (s, 1H), 8.30 (d, 1H), 8.22 (d, 1H), 8.12 (dd, 1H), 7.90 (dd, 1H), 7.64–7.57 (m, 2H), 7.46–7.37 (m, 3H), 7.17 (m, 1H), 7.06 (m, 2H), 6.79 (dd, 1H), MS (CI) m/z (M+H)⁺ 382; Anal. calc'd for $C_{26}H_{20}N_3O_4F_3$: C, 63.03; H, 4.07; N, 8.48. Found: C, 62.87; H, 4.24; N, 8.08.

EXAMPLE 222

6-(aminoiminomethyl)-N-[3-(phenylmethoxy) phenyl]-2-naphthalenecarboxamide, mono (trifluoroacetate)(salt)

EXAMPLE 222A

The above product was prepared in the manner of Example 218A using 3-benzyloxyaniline.
MS (APCI) m/z (M+H)⁺ 379.

EXAMPLE 222B 6-(aminoiminomethyl)-N-[3-(phenylmethoxy) phenyl]-2-naphthalenecarboxamide, mono (trifluoroacetate)(salt)

The above was prepared from Example 222A as described in 1B.
MS (CI) m/z (M+H)⁺ 396; ¹H-NMR (300 MHz, d₆-DMSO) δ 10.53 (s, 1H), 9.50 (s, 2H), 9.22 (s, 2H), 8.68 (s, 1H), 8.55 (s, 1H), 8.31 (d, 1H), 8.23 (d, 1H), 8.14 (dd, 1H), 7.90 (dd, 1H), 7.61–7.27 (m, 8H), 6.80 (dd, 1H), 5.13 (s, 2H) Anal. calc'd for $C_{27}H_{22}N_3O_4F_3$: C, 63.65; H, 435; N, 8.25. Found: C, 63.48; H, 4.27; N, 8.07.

EXAMPLE 223

6-(aminoiminomethyl)-N-(3-ethoxyphenyl)-2-naphthalenecarboxamide, mono(trifluoroacetate) (salt)

EXAMPLE 223A

The above product was prepared in the manner of Example 218A using 3-ethoxyaniline.
MS (APCI) m/z (M+H)⁺ 317.

EXAMPLE 223B 6-(aminoiminomethyl)-N-(3-ethoxyphenyl)-2-naphthalenecarboxamide, mono(trifluoroacetate) (salt)

The above was prepared from Example 223A as described in Example 1B.

MS (CI) m/z (M+H)$^+$ 334; $^1$H-NMR (300 MHz, d$_6$-DMSO) δ 10.52 (s, 1H), 9.50 (s, 2H), 9.24 (s, 2H), 8.68 (s, 1H), 8.55 (s, 1H), 8.32 (d, 1H), 8.25–8.13 (m, 2H), 7.90 (dd, 1H), 7.51 (m, 1H), 7.38 (m, 1H), 7.26 (t, 1H), 6.72 (dd, 1H), 4.04 (q, 2H), 1.34 (t, 3H) Anal. calc'd for C$_{22}$H$_{20}$N$_3$O$_4$F$_3$: C, 59.06; H, 4.51; N, 9.39. Found: C, 58.69; H, 4.54; N, 9.82.

EXAMPLE 224

6-(aminoiminomethyl)-N-(4-nitrophenyl)-2-naphthalenecarboxamide, mono(trifluoroacetate) (salt)

EXAMPLE 224A

The above product was prepared in the manner of Example 218A using 4-nitroaniline.

MS (APCI) m/z (M+H)$^+$ 318.

EXAMPLE 224B 6-(aminoiminomethyl)-N-(4-nitrophenyl)-2-naphthalenecarboxamide, mono(trifluoroacetate) (salt)

The above was prepared from Example 224A as described in Example 1B.

MS (CI) m/z (M+H)$^+$ 335; $^1$H-NMR (300 MHz, d$_6$-DMSO) δ 11.15 (s, 1H), 9.55 (s, 2H), 9.22 (s, 2H), 8.77 (s, 1H), 8.58 (s, 1H), 8.36–8.12 (m, 7H) Anal. calc'd for C$_{20}$H$_{15}$N$_4$O$_5$F$_3$ 1/10 TFA: C, 52.54; H, 3.29; N, 12.10. Found: C, 53.58; H, 3.37; N, 12.50.

EXAMPLE 225

6-(aminoiminomethyl)-N-[3-(cyclobutylmethoxy)phenyl]-2-naphthalenecarboxamide, mono(trifluoroacetate)(salt)

EXAMPLE 225A

The above product was prepared in the manner of Example 218A using cyclobutylmethanol.

MS (APCI) m/z (M+H)$^+$ 177.

EXAMPLE 225B

The above product was prepared in the manner of Example 225A using the product from Example 11

MS (APCI) m/z (M+H)$^+$ 357.

EXAMPLE 225C 6-(aminoiminomethyl)-N-[3-(cyclobutylmethoxy)phenyl]-2-naphthalenecarboxamide, mono(trifluoroacetate)(salt)

The above was prepared from Example 225B as described in Example 1B.

MS (CI) m/z (M+H)$^+$ 374; $^1$H-NMR (300 MHz, d$_6$-DMSO) δ 10.50 (s, 1H), 9.50 (s, 2H), 9.20 (s, 2H), 8.68 (s, 1H), 8.55 (s, 1H), 8.32 (d, 1H), 8.25–8.13 (m, 2H), 7.90 (dd, 1H), 7.51 (m, 1H), 7.38 (m, 1H), 7.26 (t, 1H), 6.72 (dd, 1H), 3.95 (d, 2H), 2.11–1.81 (m, 7H); Anal. calc'd for C$_{25}$H$_{24}$N$_3$O$_4$F$_3$ 7/5 TFA: C, 59.09; H, 5.22; N, 8.27. Found: C, 59.02; H, 5.20; N, 8.55.

EXAMPLE 226

6-[amino(ethoxycarbonyl)imino]-N-[3-(1-methylethoxy)phenyl]-2-naphthalenecarboxamide The above was prepared from Example 211A using method described in Example 216.

MS (CI) m/z (M+H)$^+$ 420; $^1$H-NMR (300 MHz, d$_6$-DMSO) δ 10.41 (s, 1H), 9.24 (br, 2H), 8.67 (s, 1H), 8.59 (s, 1H), 8.12–7.96 (m, 4H), 7.47 (s, 1H), 7.36 (m, 1H), 7.25 (t, 1H), 6.67 (dd, 1H), 4.58 (m, 1H), 4.11 (q, 2H), 1.30 (m, 9H) Anal. calc'd for C$_{24}$H$_{25}$N$_3$O$_4$ 1/4 H$_2$O: C, 67.99; H, 6.06 N, 9.91. Found: C, 67.99; H, 6.07; N, 9.64.

EXAMPLE 227

6-(aminoiminomethyl)-4-[5-(ethylsulfonyl)-3-furanyl]-N-phenyl-2-naphthalenecarboxamide, monohydrochloride

EXAMPLE 227A

A solution of the product from Example 200C (670 mg, 1.68 mmol) and mCPBA (725 mg, 3.36 mmol) in CH$_2$Cl$_2$ (25 mL) was stirred for 1 hour. The reaction was condensed and chromatographed on SiO$_2$ using 50% ethyl acetate/hexanes as eluent, to yield 585 mg (81%) of the desired compound.

MS (DCI/NH$_3$) m/z 448 (M+NH$_4$)$^+$.

EXAMPLE 227B 6-(aminoiminomethyl)-4-[5-(ethylsulfonyl)-3-furanyl]-N-phenyl-2-naphthalenecarboxamide, monohydrochloride The desired compound was prepared from Example 227A and the procedure of Example 13.

MS (DCI/NH$_3$) m/z 448 (M+H)$^+$; $^1$H NMR (300 MHz, DMSO-d$_6$) δ 1.29 (t, 3H), 3.50 (q, 2H), 7.16 (t, 1H), 7.42 (t, 2H), 7.83 (d, 2H), 7.95 (dd, 1H), 8.05 (s, 1H), 8.28 (s, 1H), 8.43 (d, 1H), 8.57 (s, 1H), 8.74 (s, 1H), 8.79 (s, 1H), 9.19 (br s, 2H), 9.59 (br s, 2H), 10.61 (s, 1H); Anal. calc'd for C$_{24}$H$_{22}$N$_3$SO$_4$·1.0 HCl·1.0 H$_2$O: C, 57.43; H, 4.82; N, 8.37. Found: C, 57.21; H, 5.04; N, 8.34.

EXAMPLE 228

6-(aminoiminomethyl)-4-[5-(propylsulfonyl)-3-furanyl]-N-phenyl-2-naphthalenecarboxamide, monohydrochloride

EXAMPLE 228A

The desired compound was prepared from the product from Example 201C by the procedure of Example 227A.

MS (DCI/NH$_3$) m/z 462 (M+NH$_4$)$^+$.

EXAMPLE 228B 6-(aminoiminomethyl)-4-[5-(propylsulfonyl)-3-furanyl]-N-phenyl-2-naphthalenecarboxamide, monohydrochloride The desired compound was prepared from Example 228A and the procedure of Example 13.

MS (DCNH$_3$) m/z 462 (M+H)$^+$; $^1$H NMR (300 MHz, DMSO-d$_6$) δ 1.03 (t, 3H), 1.75 (qt, 2H), 3.48 (q, 2H), 7.16 (t, 1H), 7.41 (t, 2H), 7.84 (d, 2H), 7.95 (dd, 1H), 8.05 (s, 1H), 8.28 (d, 1H), 8.42 (d, 1H), 8.58 (s, 1H), 8.77 (s, 1H), 8.82 (s, 1H), 9.28 (br s, 2H), 9.63 (br s, 2H), 10.66 (s, 1H); Anal. calc'd for C$_{25}$H$_{24}$N$_3$SO$_4$.1.0 HCl.1.5 H$_2$O: C, 57.20; H, 5.18; N, 8.00. Found: C, 56.86; H, 5.08; N, 8.28.

EXAMPLE 229

6-(aminoiminomethyl)-4-[5-[methylthio)methyl]-3-furanyl]-N-phenyl-2-naphthalenecarboxamide, monohydrochloride

EXAMPLE 229A

To a solution of 2-trimethylsilyl-3-bromofuran (10.41 g, 47.5 mmol) in THF (100 mL) at −78° C. was added a 1.5 M solution of LDA (34.8 mL, 52.25 mmol), and the reaction was stirred at −78° C. for 1 hour. DMF (4.41 mL, 57.0 mmol) was then added, and the reaction was allowed to warm to room temperature and stirred for 1 hour. The reaction was poured into saturated aqueous NH$_4$Cl solution, and extracted with 3x diethyl ether. The combined extracts were washed with brine, dried over Na$_2$SO$_4$, and condensed. The crude material was taken up in methanol (200 mL) and NaBH$_4$ (1.15 g, 24.0 mmol) was added in portions to the stirred solution. After 30 min, the solution was consensed, taken up in pH7 buffer, and extracted with 3x ethyl acetate. The combined extracts were washed with brine, dried over Na$_2$SO$_4$, and condensed. The crude product was chromatographed on SiO$_2$ using 30% ethyl acetate/hexanes as eluent, to yield 5.52 g (47%) of the desired compound.

MS (DCI/NH$_3$) m/z 250 (M+H)$^+$.

EXAMPLE 229B

To a solution of the product from Example 229A (5.52 g, 22.15 mmol) and LiCl (1.03 g, 24.36 mmol) in DMF (60 mL) at 0° C. was added PCl$_3$ (2.12 mL, 24.36 mmol), and the reaction was stirred at room temperature for 1 hour. The reaction was poured into saturated aqueous NH$_4$Cl solution, and extracted with 3x diethyl ether/hexanes. The combined extracts were washed with 2x water, 2x brine, dried over Na$_2$SO$_4$, and condensed to yield 4.70 g (79%) of the desired compound.

EXAMPLE 229C

A solution of the product from Example 229B (4.70 g, 17.56 mmol) and MeSNa (1.35 g, 19.3 mmol) in DMF (40 mL) was stirred at room temperature for 3 hours. The reaction was poured into saturated aqueous NaHCO$_3$ solution, and extracted with 3x Diethyl ether. The combined extracts were washed with brine, dried over Na$_2$SO$_4$, and condensed. The crude product was chromatographed on SiO$_2$ using 30% ethyl acetate/hexanes as eluent, to yield 4.00 g (82%) of the desired compound.

EXAMPLE 229D

The desired compound was prepared from the product from Example 229C by the procedure of Example 154B.

MS (DCI/NH$_3$) m/z 308 (Bu$_3$Sn+NH$_4$)$^+$.

EXAMPLE 229E

The desired compound was prepared from the product from Example D and the product from Example 152C by the procedure of Example 154C.

MS (DCI/NH$_3$) m/z 416 (M+NH$_4$)$^+$.

EXAMPLE 229F 6-(aminoiminomethyl)-4-[5-[methylthio)methyl]-3-furanyl]-N-phenyl-2-naphthalenecarboxamide, monohydrochloride The desired compound was prepared from Example 229E and the procedure of Example 144C.

MS (DCI/NH$_3$) m/z 416 (M+H)$^+$; $^1$H NMR (300 MHz, DMSO-d$_6$) δ 2.15 (s, 3H), 3.87 (s, 2H), 7.14 (t, 1H), 7.40 (t, 2H), 7.84 (d, 2H), 7.92 (dd, 1H), 8.19 (d, 1H), 8.32 (s, 1H), 8.39 (d, 1H), 8.64 (s, 1H), 8.69 (s, 1H), 9.31 (br s, 2H), 9.61 (br s, 2H), 10.62 (s, 1H); Anal. calc'd for C$_{24}$H$_{21}$N$_3$SO$_2$.1.4 HCl: C, 61.79; H, 4.84; N, 9.01. Found: C, 61.83; H, 4.82; N, 9.13.

EXAMPLE 230

6-(aminoiminomethyl)-4-[5-(methoxymethyl)-3-furanyl]-N-phenyl-2-naphthalenecarboxamide, monohydrochloride

EXAMPLE 230A

The desired compound was prepared from 2-trimethylsilyl-3-bromofuran and chloromethyl methyl ether by the procedure of Example 154A.

EXAMPLE 230B

The desired compound was prepared from the product from Example 230A by the procedure of Example 154B.

MS (DCI/NH$_3$) m/z 308 (Bu$_3$Sn+NH$_4$)$^+$.

EXAMPLE 230C

The desired compound was prepared from the product from Example 230B and the product from Example 152C by the procedure of Example 154C.

MS (DCI/NH$_3$) m/z 400 (M+NH$_4$)$^+$.

EXAMPLE 230D 6-(aminoiminomethyl)-4-[5-(methoxymethyl)-3-furanyl]-N-phenyl-2-naphthalenecarboxamide, monohydrochloride The desired compound was prepared from Example 230C and the procedure of Example 144C.

MS (DCI/NH$_3$) m/z 400 (M+H)$^+$; $^1$H NMR (300 MHz, DMSO-d$_6$) δ 3.38 (s, 3H), 4.49 (s, 2H), 7.14 (t, 1H), 7.18 (t, 1H), 7.40 (t, 2H), 7.84 (d, 2H), 7.92 (dd, 1H), 8.19 (d, 1H), 8.38 (d, 1H), 8.42 (s, 1H), 8.64 (s, 1H), 8.70 (s, 1H), 9.32 (br s, 2H), 9.62 (br s, 2H), 10.68 (s, 1H); Anal. calc'd for C$_{24}$H$_{21}$N$_3$O$_3$.2.8 HCl: C, 57.48; H, 4.78; N, 8.38. Found: C, 57.40; H, 4.44; N, 8.38.

EXAMPLE 231

6-(aminoiminomethyl)-4-[5-(methylsulfonyl)-3-furanyl]-N-phenyl-2-naphthalenecarboxamide, mono(trifluoroacetate)(salt)

EXAMPLE 231A

The desired compound was prepared from the product from Example 152C by the procedure of Example 227A.

MS (DCI/NH$_3$) m/z 434 (M+NH$_4$)$^+$.

EXAMPLE 231B 6-(aminoiminomethyl)-4-[5-(methylsulfonyl)-3-furanyl]-N-phenyl-2-naphthalenecarboxamide, mono(trifluoroacetate)(salt)

The desired compound was prepared from Example 231A and the procedure of Example 13.

MS (DCI/NH$_3$) m/z 434 (M+H)$^+$; $^1$H NMR (300 MHz, DMSO-d$_6$) δ 3.44 (s, 3H), 7.16 (t, 1H), 7.40 (t, 2H), 7.82 (d, 2H), 7.91 (s, 1H), 7.95 (dd, 1H), 8.00 (s, 1H), 8.36 (s, 1H), 8.43 (d, 1H), 8.57 (s, 1H), 8.75 (s, 2H), 9.18 (br s, 2H), 9.53 (br s, 2H); Anal. calc'd for C$_{23}$H$_{19}$N$_3$SO$_4$·1.0 C$_2$HF$_3$O$_2$: C, 54.84; H, 3.68; N, 7.67. Found: C, 55.05; H, 3.74; N, 7.75.

EXAMPLE 232

6-(aminoiminomethyl)-4-[5-(ethythio)tetrahydro-3-furanyl]-N-phenyl-2-naphthalenecarboxamide, monohydrochloride

EXAMPLE 232A

The desired compound was prepared from the product from Example 152A by the procedure of Example 62A.

MS (DCI/NH$_3$) m/z 315 (M+NH$_4$)$^+$.

EXAMPLE 232B

A solution of the product from Example 232A (1.62 g, 5.45 mmol), ethanethiol (2.2 mL), and concentrated HCl (0.80 mL) in CHCl$_3$ (22 mL) was stirred at room temperature for 3 hours and condensed. The crude product was chromatographed on SiO$_2$ using 15% ethyl acetate/hexanes as eluent, to yield 1.20 g (65%) of the desired compound.

MS (DCI/NH$_3$) m/z 359 (M+NH$_4$)$^+$.

EXAMPLE 232C

The desired compound was prepared from the product from Example 232B by the procedure of Example 152B.

MS (DCI/NH$_3$) m/z 345 (M+NH$_4$)$^+$.

EXAMPLE 232D

The desired compound was prepared from the product from Example 232C by the procedure of Example 207C.

MS (DCI/NH$_3$) m/z 420 (M+NH$_4$)$^+$.

EXAMPLE 232E 6-(aminoiminomethyl)-4-[5-(ethythio)tetrahydro-3-furanyl]-N-phenyl-2-naphthalenecarboxamide, monohydrochloride The desired compound was prepared from Example 232D and the procedure of Example 144C.

MS (DCI/NH$_3$) m/z 420 (M+H)$^+$; $^1$H NMR (300 MHz, DMSO-d$_6$) δ 1.18 (dt, 3H), 2.42 (m, 1H), 3.50 (dq, 2H), 3.74 (m, 1H), 3.93 (m, 1h), 4.39 (m, 1H), 4.54 (m, 1H), 5.38 (dd, 0.5H), 5.42 (dd, 0.5H), 7.14 (t, 1H), 7.40 (t, 2H), 7.82 (d, 2H), 7.95 (d, 1H), 8.06 (s, 0.5H), 8.20 (s, 0.5H), 8.32 (d, 1H), 8.60 (s, 1H), 8.71 (s, 0.5H), 8.80 (s, 0.5H), 9.32 (br s, 2H), 9.62 (br s, 2H), 10.59 (br s, 1H); Anal. calc'd for C$_{24}$H$_{25}$N$_3$O$_2$S·1.0 HCl: C, 63.22; H, 5.75; N, 9.21. Found: C, 62.93; H, 5.58; N, 9.01.

EXAMPLE 233

N-[4-(aminocarbonyl)-3-(cyclopentyloxy)phenyl]-6-(aminoiminomethyl)-2-naphthalenecarboxamide, mono(trifluoroacetate) (salt)

EXAMPLE 233A

A mixture of 2-chloro-4-nitrobenzoic acid (2.0 g, 10 mmol), CaO (1.2 g), Cu powder (0.1 g), and 6 mL water was heated in a Parr shaker at 155° C. at 1400 psi hydrogen pressure for 6 hours. The mixture was cooled to room temperature, triturated with 6 N HCl, and the solid filtered. The solid was added to 100 mL boiling water. The pH was adjusted to pH 5 (25% NaOH), and the insoluble material was removed by filtration. The pH of the filtrate was adjusted to pH2 (6 N HCl), and the resultant solid was filtered, washed with water, and dried (in-vacuo), to afford the title compound.

MS (ESI)$^-$ m/z 182 (M–H)$^-$; $^1$H NMR (300 MHz, DMSO-d$_6$) δ 8.00 (d, J=9.15 Hz, 1H), 7.71 (m, 2H).

EXAMPLE 233B

A solution of the compound obtained in Example 233A (2.1 g, 11.5 mmol), 42 mL methanol, and 2.1 mL concentrated H$_2$SO$_4$ was stirred at reflux for 20 hours. After cooling to room temperature, the solution was concentrated to ½ volume, then was cooled to 0° C. and the resultant solid was filtered. The solid was dissolved in methylene chloride, washed with water, brine, dried (MgSO$_4$), filtered and evaporated to afford the title compound.

MS (ESI)$^-$ m/z 196 (M–H)$^-$; $^1$H NMR (300 MHz, CDCl$_3$) δ 10.98 (s, 1H), 8.03 (d, J=8.82 Hz, 1H), 7.82 (d, J=2.38 Hz, 1H), 7.71 (dd, J=8.81, 2.37 Hz, 1H), 4.02 (s, 3H).

EXAMPLE 233C

Diethylazodicarboxylate (1.2 mL, 7.6 mmol) was added droopwise to a 0° C. solution of the product obtained in Example 233B (1.25 g, 6.3 mmol), triphenylphosphine (2.0 g, 7.6 mmol), cyclopentanol (0.69 mL, 7.6 mmol), and 24 mL THF. The reaction mixture was stirred for 0.25 hour at 0° C. and for 1 Hour at room temperature. The reaction mixture was poured slowly onto 150 mL hexane with rapid stirring. The mixture was filtered through a pad of Silica Gel and was evaporated to afford the title compound.

MS (DCI) m/z 266 (M+H)$^+$; $^1$H NMR (300 MHz, CDCl$_3$) δ 7.85 (dd, J=6.62, 2.21 Hz, 1H), 7.79 (m, 2H), 4.94 (m, 1H), 3.91 (s, 3H), 1.90–2.03 (m, 6H), 1.81–1.89 (m, 2H).

EXAMPLE 233D

A solution of the product obtained in Example 233C (0.84 g, 3.2 mmol) and 25 mL ammonia was heated in a Parr shaker at 120° C. for 24 hours. The ammonia was evaporated to afford the title compound.

MS (ESI)$^-$ m/z 250 (M–H)$^-$; $^1$H NMR (300 MHz, DMSO-d$_6$) δ 7.84 (s, 2H), 7.78 (s, 1H), 7.64 (s, 1H), 5.42 (s, 1H), 5.12 (s, 1H), 1.97 (m, 2H), 1.78–1.84 (m, 2H), 1.62–1.72 (m, 4).

EXAMPLE 233E

A mixture of the product obtained in Example 233D (0.83 g, 3.3 mmol), 10% Pd on carbon (166 mg), 10 mL THF, 25 mL iso-propyl alcohol, and 50 mL ethyl acetate was hydrogenated in a Parr shaker at 4 atmospheres for 18 hours. The mixture was filtered, evaporated, and the crude product was purified by flash chromatography, eluting with 1-Hexane-ethyl acetate/2% HOAc to afford the title compound.

MS (DCI) m/z 221 (M+H)$^+$; $^1$H NMR (300 MHz, DMSO-d$_6$) δ 7.63 (d, J=8.46 Hz, 1H), 7.25 (s, 1H), 7.04 (s, 1H), 6.23 (d, J=1.84 Hz, 1H), 6.16 (dd, J=8.46, 1.84 Hz, 1H), 5.70 (s, 2H), 1.91–1.97 (m, 2H), 1.62–1.81 (m, 6H).

EXAMPLE 233F

The product obtained in Example 8 and the product obtained in Example 233E were subjected to the conditions described in Example 8 to afford the title compound.

MS (DCI) m/z 221 (M+H)+; 1H NMR (300 MHz, DMSO-d6) δ 10.75 (s, 1H), 8.70 (d, J=5.15 Hz, 2H), 8.31 (d, J=8.83 Hz, 1H), 8.23 (d, J=8.82 Hz, 1H), 8.15 (dd, J=8.45, 1.47 Hz, 1H), 7.92 (dd, J=8.46, 1.47 Hz, 1H), 7.91 (d, J=8.46 Hz, 1H), 7.76 (d, J=1.57 Hz, 1H), 7.52 (dd, J=8.46, 1.84 Hz, 2H), 7.46 (s, 1H), 4.95 (m, 1H), 2.00–2.07 (m, 2H), 1.84–1.89 (m, 2H), 1.63–1.77 (m, 4H).

EXAMPLE 233G

Using the product obtained in Example 233F and the procedure described in Example 40C, the title compound was obtained.

MS (ESI)+ m/z 417 (M+H)+; 1H NMR (300 MHz, DMSO-d6) δ 10.76 (s, 1H), 9.52 (s, 2H), 9.18 (s, 2H), 8.71 (s, 1H), 8.57 (s, 1H), 8.35 (d, J=8.82 Hz, 1H), 8.27 (d, J=8.83 Hz, 1H), 8.17 (d, J=8.46 Hz, 1H), 7.92 (d, J=8.46 Hz, 2H), 7.77 (d, J=1.47 Hz, 1H), 7.53 (dd, J=8.46, 1.47 Hz, 2H), 7.46 (d, J=2.21 Hz, 1H), 4.95 (m, 1H), 2.03 (m, 2H), 1.83–1.90 (m, 2H), 1.64–1.76 (m, 4H); Anal. calcd for $C_{26}H_{25}F_3N_4O_5 \cdot .25H_2O$: C, 56.47; H, 5.01; N, 10.13. Found: C, 56.40; H, 4.84; N, 9.94.

EXAMPLE 234 ethyl 7-[[[6-(aminoiminomethyl)-2-naphthalenyl]carbonyl]amino]-1,2,3,4-tetrahydro-1-(hydroxymethyl)-2-isoquinolinecarboxylate, mono (trifluoroacetate) (salt)

EXAMPLE 234A

Potassium nitrate (0.49 g, 4.8 mmol) was added to a 0° C. solution of 3,4-dihydro-1H-isoquinoline-1,2-dicarboxylic acid-2-ethyl ester (1.1 g, 4.4 mmol, *Tetrahedron* 43 (2), 439, 1987), and 8 mL c $H_2SO_4$. The reaction mixture was stirred at 0° C. for 25 minutes, then water was added. The mixture was extracted with methylene chloride. The combined extracts were washed with water, brine, dried (MgSO4), filtered, and evaporated to afford the title compound.

MS (DCI) m/z 312 (M+NH4)+; 1H NMR (300 MHz, CDCl3) δ 8.43 (s, 1H), 8.12 (dd, J=8.09, 2.21 Hz, 1H), 7.35 (d, J=8.46 Hz, 1H), 4.23 (q, J=6.99 Hz, 2H), 3.91–4.11 (m, 1H), 3.62–3.79 (m, 1H), 3.00–3.34 (m, 1H), 3.00 (t, J=5.88 Hz, 2H), 1.30 (m, 3H).

EXAMPLE 234B

Diborane methylsulfide complex (1.0 m in THF, 0.33 mL) was added dropwise to at solution of the product from Example 234A (0.77 g, 2.6 mmol) and 10 mL THF. The reaction mixture was stirred at reflux for 1.5 hours. After cooling to 0°, 0.1 M dibasic sodium phosphate was added slowly. The mixture was extracted with ether. Extracts were washed with brine, dried (MgSO4), filtered, and evaporated to afford the title compound.

MS (ESI)− m/z 279 (M−H)−; 1H NMR (300 MHz, CDCl3) δ 8.12 (d, J=2.21 Hz, 1H), 8.07 (dd, J=8.45, 2.20 Hz, 1H), 7.33 (d, J=8.46 Hz, 1H), 7.25 (d, J=8.82 Hz, 1H), 7.18 (d, J=6.99 Hz, 1H), 5.39 (m, 1H), 4.22 (q, J=6.98 Hz, 2H), 4.10 (m, 1H), 3.90 (m, 2H), 3.50 (m, 2H), 3.00 (m, 1H), 1.31 (t, J=6.99 Hz, 3H).

EXAMPLE 234C

Using the product obtained in Example 234B and the procedure described in *J. Org. Chem.* 44, 3772, 1979, the title compound was obtained.

MS (DCI) m/z 365 (M+H)+; 1H NMR (300 MHz, CDCl3) δ 8.19–8.26 (m, 1H), 8.05 (dd, J=8.46 Hz, 1H), 5.30–5.46 (m, 1H), 4.60 (m, 1H), 4.20 (q, J=6.99 Hz, 2H), 3.96–4.06 (m, 1H), 3.65–3.73 (m, 1H), 3.36–3.60 (m, 3H), 2.89–3.08 (m, 1H), 1.49–1.69 (m, 8H), 1.30 (t, J=7.36 Hz, 3H).

EXAMPLE 234D

The product obtained in Example 234C (0.41 g, 1.13 mmol), 5% Pt on carbon (41 mg), and 50 mL ethyl acetate was hydrogenated in a Parr shaker at 4 atmospheres for 5 hours. The mixture was filtered, solvent evaporated, and the crude product was purified by flash chromatography, eluting with 1-1Hexane-Ethyl acetate, to afford the title compound.

MS (DCI) m/z 335 (M+H)+; 1H NMR (300 MHz, CDCl3) δ 6.91 (t, J=7.35 Hz, 1H), 6.53–6.60 (m, 2H), 5.30 (m, 0.5H), 5.20 (m, 0.5H), 4.70 (m, 0.5H), 4.55 (m, 0.5H), 4.11–4.20 (m, 3H), 3.86–4.00 (m, 1H), 3.62–3.76 (m, 2H), 3.28–3.48 (m, 2H), 2.63–2.92 (m, 2H), 1.51–1.79 (m, 8H), 1.28 (t, J=7.35 Hz, 3H).

EXAMPLE 234E

Using the product obtained in Example 234E, the product obtained in Example 8, and the procedure described in Example 8 the title compound was obtained.

MS (ESI)− m/z 512 (M−H)−. 1H NMR (300 MHz, CDCl3) δ 8.42 (s, 1H), 8.30 (s, 1H), 7.99–8.07 (m, 4H), 7.71 (dd, J=8.46, 1.47 Hz, 1H), 7.66 (m, 1H), 7.43 (m, 1H), 7.17 (d, J=8.46 Hz, 1H), 5.41 (m, 0.5H), 5.33 (m, 0.5H), 4.70 (m, 0.5H), 4.57 (m, 0.5H), 4.17–4.30 (m, 3H), 3.96–4.04 (m, 1H), 3.66–3.82 (m, 2H), 3.45–3.52 (m, 2H), 2.77–2.96 (m, 2H), 1.43–1.76 (m, 8H), 1.30 (t, J=6.98 Hz, 3H).

EXAMPLE 234F

Using the product obtained in Example 234E and the procedure described for Example 40D the title compound was obtained.

MS (ESI)+ m/z 531 (M+H)+.

EXAMPLE 234G

Using the product obtained in Example 234F and the procedure described in *J.Am. Chem. Soc.* 100, 8031, 1978, the title compound was obtained.

MS (ESI)+ m/z 447 (M+H)+; 1H NMR (300 MHz, DMSO-d6) d 10.51 (s, 1H), 9.50 (s, 2H), 9.20 (s, 2H), 8.69 (s, 1H), 8.55 (s, 1H), 8.32 (d, J=8.82 Hz, 1H), 8.24 (d, J=9.15 Hz, 1H), 8.16 (dd, J=8.48, 1.70 Hz, 1H), 7.90 (dd, J=8.48, 1.70 Hz, 1H), 7.60–7.68 (m, 2H), 7.17 (d, J=8.47 Hz, 1H), 5.01 (m, 2H), 4.09 (q, J=7.12 Hz, 2H), 3.66 (m, 2H), 2.76 (m, 2H), 1.22 (t, J=7.12 Hz, 3H); Anal. calcd for $C_{27}H_{27}F_3N_4O_6 \cdot 2.00H_2O$: C, 54.36; H, 5.24; N, 9.39. Found: C, 54.67; H, 4.86; N, 9.02.

EXAMPLE 235

6-(aminoiminomethyl)-N-[3,4-dihydro-1-(2-methylpropyl)-6-isoquinolinyl]-2-naphthalenecarboxamide, bis(trifluoroacetate) (salt)

EXAMPLE 235A

Using 1-isobutyl-3,4-dihydroisoquinoline (*J.Med.Chem.* 32 (6), 1242, 1989) and the procedure described for Example 72, the title compound was obtained.

MS (DCI/NH3) m/z 233 (M+H)+; 1H NMR (300 MHz, CDCl3) δ 8.32 (d, J=2.3 Hz, 1H), 8.22 (dd, J=8.1, 2.3 Hz, 1H), 7.38 (d, J=8.1 Hz, 1H), 3.74 (dt, J=6.0, 1.2 Hz, 2H), 2.79 (t, J=7.5 Hz, 2H), 2.68 (dd, J=5.8, 1.1 Hz, 2H), 2.08–2.11 (m, 1H), 0.98 (d, J=6.4 Hz, 6H).

EXAMPLE 235B

Using the product obtained in Example 235A and the procedure described for Example 72B, the title compound was obtained.

MS (DCI/NH$_3$) m/z 203 (M+H)$^+$; $^1$H NMR (300 MHz, CDCl$_3$) δ 6.99 (d, J=8.14 Hz, 1H), 6.81 (d, J=2.04 Hz, 1H), 6.69 (dd, J=8.14, 2.38 Hz, 1H), 3.62 (t, J=7.12 Hz, 4H), 2.56 (t, J=4.74 Hz, 4H), 2.02–2.11 (m, 1H), 0.94 (d, J=6.78 Hz, 6H).

EXAMPLE 235C

Using the product obtained in Example 8, and the product obtained in Example 235B and the procedure described for Example 8G, the title compound was obtained.

MS (DCI) m/z 382 (M+H)$^+$; $^1$H NMR (300 MHz, DMSO-d$_6$) δ 10.84 (s, 1H), 8.71 (d, J=1.84 Hz, 2H), 8.45 (d, J=1.1 Hz, 1H), 8.33 (d, J=8.45 Hz, 1H), 8.25 (d, J=8.46 Hz, 1H), 8.18 (dd, J=8.46, 1.11 Hz, 1H), 8.12 (dd, J=8.45, 1.83 Hz, 1H), 7.93 (dd, J=8.46, 1.10 Hz, 1H), 7.56 (d, J=8.09 Hz, 1H), 3.87 (t, J=7.35 Hz, 2H), 3.07 (t, J=7.73 Hz, 2H), 2.93 (d, J=7.35 Hz, 2H), 2.08–2.18 (m, 1H), 0.99 (d, J=6.25 Hz, 6H).

EXAMPLE 235D

Using the compound obtained in Example 235C and the procedure described for Example 40C, the title compound was obtained.

MS (ESI)$^+$ m/z 399 (M+H)$^+$; $^1$H NMR (300 MHz, DMSO-d$_6$) δ 10.91 (s, 1H), 9.51 (S, 2H), 9.28 (s, 2H), 8.74 (s, 1H), 8.57 (s, 1H), 8.49 (d, J=1.7 Hz, 1H), 8.35 (d, J=8.81 Hz, 1H), 8.27 (d, J=8.48 Hz, 1H), 8.20 (dd, J=4.41, 1.69 Hz, 1H), 8.18 (dd, J=6.78, 2.04 Hz, 1H), 7.92 (dd, J=8.81, 1.69 Hz, 1H), 7.58 (d, J=8.48 Hz, 1H), 3.93 (t, J=8.14 Hz, 2H), 3.11 (t, J=7.79 Hz, 2H), 2.97 (d, 2H, 6.45), 2.09–2.18 (m, 1H), 1.00 (d, J=6.78 Hz, 6H); Anal. calcd for C$_{29}$H$_{28}$F$_6$N$_4$O$_5$1.50H$_2$O: C, 53.29; H, 4.78; N, 8.57. Found: C, 53.32; H, 4.72; N, 8.35.

EXAMPLE 236

1,1-dimethylethyl 6-[[[6-(aminoiminomethyl)-2-naphthalenyl]carbonyl]amino]-1,2,3,4-tetrahydro-1-(2-methylpropyl)-2-isoquinolinecarboxylate, mono (trifluoroacetate) (salt)

EXAMPLE 236A

Using the product obtained from Example 235B and the procedure described in Example 70A, the title compound was obtained.

MS (DCI/NH$_3$) m/z 205 (M+H)$^+$; $^1$H NMR (300 MHz, CDCl$_3$) δ 8.87 (d, J=8.09 Hz, 1H), 6.50 (dd, J=8.09, 2.57 Hz, 1H), 6.45 (d, J=2.20 Hz, 1H), 3.91 (dd, J=10.67 Hz, 1H), 3.68), 3.52 (s, 2H), 3.19 (m, 1H), 2.94 (m, 1H), 2.67 (q, 2H, 5.52), 1.75–1.97 (m, 2H), 1.62–1.71 (m, 1H), 1.48–1.57 (m, 1H), 1.01 (d, J=6.62 Hz, 3H), 0.97 (d, J=6.62 Hz, 1H).

EXAMPLE 236B

Using the compound obtained in Example 236A and the procedure described for Example 70B, the title compound was obtained.

MS (DCI/NH$_3$) m/z 305 (M+H)$^+$; $^1$H NMR (300 MHz, CDCl$_3$) δ 6.92–7.01 (m, 2H), 6.62–6.72 (m, 1H), 6.57 (s, 1H), 4.12–4.22 (m, 1H), 3.06–3.22 (m, 1H), 2.75–2.92 (m, 1H), 2.55–2.65 (m, 1H), 1.59–1.85 (m, 4H), 1.49 (s, 9H), 1.05 (d, J=6.62 Hz, 3H), 0.93 (d, J=6.62 Hz, 3H).

EXAMPLE 236C

Using the product obtained in Example 8E and the product obtained in Example 236B and the procedure described for Example 18G, the title compound was obtained.

MS (ESI)$^-$ m/z 482 (M+H)$^-$. $^1$H NMR (300 MHz, CDCl$_3$) δ 8.43 (s, 1I), 8.30 (s, 1H), 8.00–8.07 (m, 3H), 7.95 (s, 1H), 7.71 (dd, J=8.47, 1.01 Hz, 1H), 7.49–7.58 (m, 1H), 7.31–7.36 (m, 1H), 7.09–7.15 (m, 1H), 4.18–4.27 (m, 1H), 3.98–4.15 (m, 1H), 3.12–3.28 (m, 1H), 2.85–3.00 (m, 1H), 2.65–2.75 (m, 1H), 1.78–1.86 (m, 1H), 1.70 (m, 1H), 1.50 (s, 9H), 1.26 (t, J=7.12 Hz, 1H), 1.08 (d, J=6.10 Hz, 3H), 0.96 (t, J=6.44 Hz, 3H).

EXAMPLE 236D

Using the product obtained in Example 236C and the procedure described in Example 40D the title compound was obtained.

MS (ESI)$^+$ m/z 501 (M+H)$^+$; $^1$H NMR (300 MHz, DMSO-d$_6$) δ 10.50 (s, 1H), 9.51 (s, 2H), 9.22 (s, 2H), 8.70 (s, 1H), 8.55 (s, 1H), 8.33 (d, J=8.82 Hz, 1H), 8.25 (d, J=8.82 Hz, 1H), 8.17 (d, J=8.09 Hz, 1H), 7.91 (d, J=8.45 Hz, 1H), 7.64 (d, J=7.72 Hz, 1H), 7.58 (s, 1H), 7.15 (d, J=8.46 Hz, 1H), 5.00–5.15 (m, 1H), 3.90–4.05 (m, 1H), 2.31–2.27 (m, 1H), 2.56–2.82 (m, 3H), 1.81 (m, 1H), 1.60 (m, 1H), 1.43 (s, 9H), 1.06 (dd, J=7.73, 2.21 Hz, 3H), 0.95 (t, J=5.51 Hz, 3H); Anal. calcd for C$_{32}$H$_{37}$F$_3$N$_4$O$_5$.1.00H$_2$O: C, 60.75; H, 6.21; N, 8.86. Found: C, 60.88; H, 6.23; N, 8.80.

EXAMPLE 237

6-(aminoiminomethyl)-N-[1,2,3,4-tetrahydro-1-(2-methylpropyl)-6-isoquinolinyl]-2-naphthalenecarboxamide, bis(trifluoroacetate) (salt)

Using the product obtained in Example 236D and the procedure described for Example 71, the title compound was obtained.

MS (DCI)$^+$ m/z 401 (M+H)$^+$; $^1$H NMR (300 MHz, DMSO-d$_6$) δ 10.53 (s, 1H), 9.51 (s, 2H), 9.26 (s, 2H), 8.82 (s, 1H), 8.70 (s, 1H), 8.56 (s, 1H), 8.33 (d, J=8.82 Hz, 1H), 8.25 (d, J=8.83 Hz, 1H), 8.16 (dd, J=1.10, 8.45 Hz, 1H), 7.91 (dd, J=1.47, 8.45 Hz, 1H), 7.74 (d, J=7.35 Hz, 2H), 7.27 (d, J=8.82 Hz, 1H), 4.55 (s, 1H), 3.35 (m, 2H), 3.00 (m, 2H), 1.70–1.92 (m, 3H), 1.03 (dd, J=6.62 Hz, 1H); Anal. calcd for C$_{29}$H$_{30}$F$_6$N$_4$O$_5$.0.5TFA: C, 52.56; H, 4.48; N, 8.17. Found: C, 52.30; H, 4.40; N, 8.29.

EXAMPLE 238

6-(aminoiminomethyl)-N-[1,2,3,4-tetrahydro-2-[(4-methylphenyl)mehtyl]-6-isoquinolinyl]-2-naphthalenecarboxamide, bis(trifluoroacetate) (salt)

EXAMPLE 238A

To a cooled (0° C.) solution of the 2-[2-(hydroxymethyl)-5-nitrophenyl]ethanol [J. Org. Chem. vol. 63 (12), 4116–4119 (1998)] (386 mg) in THF (30 mL) was added TEA (500 µL) and DMAP (2 mg) followed by methanesulfonyl chloride (345 µL). After 15 minutes at 0° C., the 4-aminomethyltoluene (600 µL) was added and the reaction mixture was allowed to warm up to room temperature. The reaction mixture was heated at 70° C. overnight. The solvent was concentrated under vacuum and ethyl acetate (100 mL) and water (70 mL) were added to the reaction mixture. The organic phase was washed with water (2×50 mL) and brine (50 mL), dried over magnesium sulfate, filtered and evaporated. The product was was purified over silica gel using a gradient of 5 to 10% ethyl acetate in hexane to afford 300 mg of white semisolid.

MS (DCI$^+$) m/z 283 (M+H)$^+$.

EXAMPLE 238B

To a solution of the nitro derivative from part (238A) (200 mg) in methylene chloride (10 mL) at room temperature, was successively added, water (1 mL), 1,1'-di-n-octyl-4,4'-bipyridinium dibromide (5 mg), and a solution of potassium carbonate (489 mg) and sodium dithionate (555 mg) in water (3.0 mL) . A very strong blue color developed and the mixture was heated using in a 35° C. oil bath for 24 hours. An additional portion of sodium dithionate (200 mg) was added to the reaction mixture and the resulting mixture was allowed to stir for an additional hour. Water (30 mL) wsa added to the mixture and the aqueous layer was extracted with methylene chloride (3×40 mL) The combined methylene chloride layers were dried over magnesium sulfate and filtered through a small silica column. The column was eluted sequentially with methylene chloride, ethyl acetate, and finally with 5% methanol in ethyl acetate to afford 145 mg of a white solid.

EXAMPLE 238C

To a solution of the amine from part (238B) (140 mg), in methylene chloride (15 mL) was added DIEA (1.2 mL), 6-nitrile-2-naphthoyl chloride (130 mg) and catalytic amount of DMAP (2 mg). After 2 hours the reaction mixture was quenched with methanol and the solvent was evaporated under vacuum. The mixture was diluted with ethyl acetate (60 mL) and the ethyl acetate phase was washed with an aqueous solution of 0.5N NaOH, followed by brine. The organic layer was dried over magnesium sulfate, filtered and evaporated. The product was purified on silica column using a gradient of 25% to 50% ethyl acetate in hexane to afford 70 mg of white solid.

EXAMPLE 238D

The title compound was prepared as described in Example 55B.

MS (ESI$^+$) m/z 449 (M+H)$^+$, (ESI$^-$) 447 (M-1)$^-$. $^1$H NMR (300 MHz, DMSO-d$_6$) δ 10.6 (s, 1H), 10.1 (br. s, 1H), 9.51 (s, 2H), 9.16 (s, 2H), 8.68 (s, 1H), 8.56 (s, 1H) 8.33–8.16 (m, 3H), 7.92–7.88 (m, 1H), 7.78 (s, 1H), 7.67–7.64 (m, 1H), 7.47–7.31 (m, 4H), 7.25–7.22 (m, 1H), 4.45 (s, 2H), 4.32 (s, 2H), 3.72–3.50 (m, 4H), 2.30 (s, 3H); Anal. calcd for (C29H$_{28}$N$_4$O.2×TFA.2× H$_2$O: C, 55.62; H, 4.81; F, 16.00; N, 7.86. Found: C, 55.60; H, 4.77; F. 15.50; N, 7.62.

EXAMPLE 239

6-(aminoiminomethyl)-N-[1,2,3,4-tetrahydro-2-[(3-methylphenyl)mehtyl]-6-isoquinolinyl]-2-naphthalenecarboxamide, bis(trifluoroacetate) (salt)

The title compound was prepared as described in Example 238 substituting 4-aminomethyltoluene for 3-aminomethyltoluene to afford 150 mg of the title compound.

MS (ESI$^+$) m/z 449 (M+H)$^+$; $^1$H NMR (300 MHz, DMSO-d$_6$) δ 10.62 (s, 1H), 10.2 (br. s, 1H), 9.51 (s, 2H), 9.21 (s, 2H), 8.68 (s, 1H), 8.56 (s, 1H) 8.33–8.13 (m, 3H), 7.92–7.89 (m, 1H), 7.78 (s, 1H), 7.67–7.64 (m, 1H), 7.39–7.34 (m, 4H), 7.26–7.23 (m, 1H), 4.46 (br. s, 2H), 4.33 (br. s, 2H), 3.75–3.65 (m, 2H), 3.20–3.12 (m, 2H), 2.37 (s, 3H); Anal. calcd for (C$_{29}$H$_{28}$N$_4$O.2×TFA.1.5×H$_2$O) C, 56.33; H, 4.73; F, 16.20; N, 7.96. Found: C, 56.27; H, 4.81; F, 16.21; N, 7.96.

EXAMPLE 240 phenylmethyl 6-[[[6-(aminoiminomethyl)-2-naphthalenyl]carbonyl]amino]-1,2,3,4-tetrahydro-2-isoquinolinecarboxylate, mono(trifluoroacetate) (salt)

To a solution of the amine prepared as described in Example 238 (620 mg), in methylene chloride (80 mL) was added DIEA (1.0 mL), 6-nitrile-2-naphthoyl chloride (Example 40) (750 mg) and catalytic amount of DMAP (2 mg). The reaction mixture was stirred at room temperature overnight then quenched with methanol and the solvent was evaporated under vacuum. The mixture was diluted with ethyl acetate (60 mL) and the ethyl acetate phase was washed with water and brine. The organic layer was dried over magnesium sulfate, filtered and evaporated. The resulting material was treated with ethyl acetate:hexane and the product crystalyzed to afford 1.0 g of a light yellow solid.

MS (ESI$^+$) m/z 368 (M+H)$^+$, (ESI$^-$) 366 (M-1)$^-$.

EXAMPLE 240B

To a solution of Pd (dba)$_2$ (36.4 mg) in THF (3 mL) was added DPPB (16.9 mg) and the mixture was allowed to stir at room temperature under nitrogen and thiosalicilic acid (147 mg) was added. This mixture was transfered via cannula into a solution of the substrate (from 240A) in THF (3.0 mL), at room temperature under nitrogen. After 20 minutes, the mixture was heated using a 40° C. oil bath for 1 hour. The reaction mixture was cooled to room temperature and triethylamine (3.0 mL) was added followed by Cbz-Cl (800 mg) and a catalytic amount of DMAP (2 mg). The reaction mixture was stirreed at room temperature overnight, and the reaction was quenched with N, N-dimethylethylenediamine (1 mL) and stirred for an hour. The mixture was diluted with ethyl acetate (150 mL) and washed with aqueous 10% citric acid followed by brine. The reaction mixture was dried over magnesium sulfate, filtered, and evaporated. The product was purified over silica using 25% to 50% ethyl acetate in hexane to afford 156 mg of a white solid.

MS (ESI+) m/z 462 (M+H)$^+$, (ESI$^-$) 460 (M-1)$^-$.

EXAMPLE 240C

The title compound was prepared as described in Example 55B.

MS (ESI$^+$) m/z 479 (M+H)$^+$, (ESI$^-$) 477 (M-1)$^-$; $^1$H NMR (300 MHz, DMSO-d$_6$) δ 10.50 (s, 1H), 10.2 (br. s, 1H), 9.49 (s, 2H), 9.14 (s, 2H), 8.68 (s, 1H), 8.55 (s, 1H) 8.33–8.13 (m, 3H), 7.91–7.88 (m, 1H), 7.68 (s, 1H), 7.63–7.59 (m, 2H), 3.66–3.62 (m, 2H), 2.84 (t, J=6.1 Hz, 2H); Anal. calcd for (C$_{29}$H$_{26}$N$_4$O$_3$.TFA0.5H$_2$O) C, 61.89; H, 4.69; N, 9.31. Found: C, 61.49; H, 4.69; N, 9.19.

EXAMPLE 241

6-(aminoiminomethyl)-N-[4ethyl-1,2,3,4-tetrahydro-2-(2-propenyl)-6-isoquinolinyl]-2-naphthalenecarboxamide, bis(trifluoroacetate) (salt)

EXAMPLE 241A 2-(ethylcarboxylate-5-nitrophenyl)-1'-ethylmalonic acid diethyl ester To a solution of 2-(carboxy-5-nitrophenyl)malonic acid diethyl ester (1.79 g) J. Org. Chem. vol. 63 (12), 4116–4119

(1998). in acetone (150 mL) was added potassium carbonate (4.2 g) followed by ethyl iodide (6.0 mL) and and the mixture was heated to reflux for 14 hours. Ethyl acetate (200 mL) was added to the reaction mixture and the organic phase was washed with water and brine. Organic phase was dried over magnesium sulfate, filtered, and evaporated to afford the 2.0 g of the product as light reddish oil.

MS (ESI)$^+$, (M+1)$^+$382, (M+118)$^+$399.

EXAMPLE 241B

To a suspension of Example 241A (1.8 g) in a mixture water (150 mL) and ethanol (50 mL), was added 50% aqueous MaOH (10.0 mL, ), and the mixture was heated to reflex for 2.5 hours. The mixture was cooled and acidified with 2N HCl, and heated to reflux for 2 hours and then concentrated to a volume of approximately 100 mL. The product, which precipitated upon cooling, was filtered, washed with water, and dried under vacuum to afford 4.36 g of a light baige solid.

MS (ESI$^+$) m/z, (ESI$^-$) 252 (M–1)$^-$.

EXAMPLE 241C

To a solution of Example 241B (1.04 g) in THF (80 mL) at room temperature was added a solution of 1N borane in THF (12.3 mL) and the mixture was allowed to stir at room temperature overnight. The reaction mixture was quenched with acetone followed by a solution of 10% KHSO$_4$. The solvent was partially concentrated and ethyl acetate (100 mL) and the mixture was washed with water, followed by an aqueous solution of 0.5 M NaOH and brine. The organic layer was dried over magnesium sulfate, filtered, and evaporated. The resulting brown oil was treated with hot hexane to afford 1.43 g of light brown waxy-solid.

MS (DCI)$^+$, 243 (M+18)$^+$.

EXAMPLE 241D

To a solution of the Example 241C (900 mg) in THF (10.0 mL) at 0° C. was added TEA (2.0 mL) and DMAP (2 mg) followed by MsCl (710 μL). After 18 minutes, allyl amine (899 μL) was added and the mixture was allowed stir at 0° C. for 15 minutes, room temperature for 12 hours, and finally 70° C. for 4 hours. Ethyl acetate (120 mL) and water (70 mL) were added to the reaction mixture and the organic phase was washed with water (2×50 mL) and brine (50 mL), dried over magnesium sulfate, filtered and evaporated. The product purified on a silica column using 5% to 15% ethyl acetate in hexane to afford 690 mg of a light orange solid.

MS (ESI)$^+$, 247 (M+1)$^+$.

EXAMPLE 241E

The title compound was prepared as described for Example 238B using 90D to provide 450 mg of the title compound as a crude material which was carried on to the next step without further purification.

MS (ESI)$^+$, 217 (M+1)$^+$.

EXAMPLE 241F

The title compound was prepared as described in Example 238 using 241E to provide 255 mg of the title compound.

MS (ESI)$^+$, 396 (M+1)$^+$, 394 (M–1)$^-$.

EXAMPLE 241G

The title compound was prepared as described in Example 55B using the compound prepared in Example 242F.

MS (ESI$^+$) m/z 413 (M+H)$^+$, (ESI$^-$) 411 (M–1)$^-$. $^1$H NMR (300 MHz, DMSO-d$_6$) δ 10.6 (s, 1H), 101 (br. s, 1H), 9.52 (s, 2H), 9.16 (s, 2H), 8.70 (s, 1H), 8.57 (s, 1H), 8.34–8.14 (m, 3H), 7.93–7.87 (m, 2H), 7.77–7.725 (m, 1H), 7.27 (d, J=8.5 Hz, 1H), 6.07–5.98 (m, 1H), 5.65–5.60 (m, 2H), 4.45–4.29 (m, 2H), 3.80–3.76 (m, 2H), 3.13–3.09 (m, 1H), 2.08–1.74 (m, 2H), 0.91 (t, J=8.7 Hz, 3H); Anal. calcd for (C$_{26}$H$_{28}$N$_4$O.2.5TFA.H$_2$O) C, 52.03; H, 4.58; F, 19.91; N, 7.83. Found: C, 52.11; H, 4.37; F, 20.38; N, 8.10.

EXAMPLE 242

6-(aminoiminomethyl)-N-(4-ethyl-1,2,3,4-tetrahydro-6-isoquinolinyl)-2-naphthalenecarboxamide, bis(trifluoroacetate) (salt)

EXAMPLE 242A

To a solution of Pd (dba)$_2$ (17.1 mg) in THF (3 mL) was added DPPB (7.9 mg) and the compound prepared in Example 241G the mixture was allowed to stir at room temperature under nitrogen. After 20 minutes, thiosalicylic acid (87 mg) was added and the resulting mixture was transfered via cannula to a solution of Example 242 (100 mg in DMF, 3.0 mL), at room temperature under nitrogen. After 2.5 hours the reaction mixture was quenched with 1N HCl and diluted with water and ethyl acetate. After removal of the volatile organic phase, the aqueous phase was concentrated and loaded on RP18 MPLC to yield 72 mg of white solid.

MS (ESI$^+$) m/z 373 (M+H)$^+$, (ESI$^-$) 371 (M–1)$^-$. $^1$H NMR (300 MHz, DMSO-d$_6$) δ 10.60 (s, 1H), 10.1 (br. s, 1H), 9.50 (s, 2H), 9.25 (s, 2H), 9.05 (br. s, 1H), 9.00 (br. s, 1H), 8.70 (s, 1H), 8.56 (s, 1H), 8.33–8.17 (m, 3H), 7.92–7.85 (m, 2H), 7.73–7.71 (m, 1H), 7.25 (d, J=9.5 Hz, 1H), 4.26 br. s, 2H), 3.25–3.03 (m, 3H), 3.13–3.09 (m, 1H), 1.92–1.71 (m, 2H), 0.98 (t, J=8.5 Hz, 3H); Anal. calcd for (C$_{23}$H$_{24}$N$_4$O.2.1TFA.2H$_2$O) C, 50.42; H, 4.68; N, 8.65; F, 18.47. Found: C, 50.13; H, 4.34; N, 8.31; F, 18.46.

EXAMPLE 243

6-(aminoiminomethyl)-N-(3,5-dimethoxyphenyl)-2-naphthalenecarboxamide

EXAMPLE 243A

A solution of the product from Example 40A (150 mg, 0.696 mmol), 3,5-dimethoxyaniline (106 mg, 0.697 mmol), and Et$_3$N (0.107 mL, 0.77 mmol) in THF (20 mL) were stirred for 30 minutes The reaction was poured into 1 M HCl, and extracted with diethyl ether (2×). The extracts were washed with brine, dried over Na$_2$SO$_4$, filtered, and concentrated. The crude product was triturated with a small amount of ethyl acetate and hexanes to afford 225 mg (97%) of the title compound.

MS (DCI/NH$_3$) m/z 350 (M+NH$_4$)$^+$.

EXAMPLE 243B

The title compound was prepared from Example 243A by the procedure of Example 55D.

MS (DCI/NH$_3$) m/z 350 (M+H)$^+$; $^1$H NMR (300 MHz, DMSO-d$_6$) δ 2.33 (s, 3H), 3.77 (s, 6H), 6.31 (dd, 1H), 7.12 (d, 2H), 7.90 (dd, 1H), 8.13 (dd, 1H), 8.25 (d, 1H), 8.33 (d, 1H), 8.56 (s, 1H), 8.68 (s, 1H), 9.12 (br s, 2H), 9.51 (br s, 2H), 10.50 (s, 1H); Anal. calcd for C$_{20}$H$_{19}$N$_3$O$_3$.0.5 CH$_4$SO$_3$: C, 52.32; H, 5.11; N, 8.51. Found: C, 52.29; H, 5.26; N, 8.53.

EXAMPLE 244

6-(aminoiminomethyl)-N-3-((2-methylpropyl)
phenyl)-2-naphthalenecarboxamide,
monohydrochloride, mono(trifluoroacetate) (salt)

EXAMPLE 244A

Propyl-2-(triphenylphosphonium) bromide (1.06 g, 7 mmol) was suspended in 45 mL anhydrous THF and cooled under nitrogen to −78° C. Butyllithium (3.5 mL, 8.75 mmol) was added dropwise over 10 minutes. After complete addition, the slurry was warmed to −20° C. and maintained at that temperature for 0.25 hours and then cooled to −78° C. A solution of 3-nitrobenzaldehyde (1.06 g, 7 mmol) in 14 mL THF was cooled to −78° C. and was added to the above solution dropwise over 5 minutes. After complete addition, the solution was allowed to warm to room temperature. The reaction mixture was poured into diethyl ether and filtered through silica gel, concentrated, dissolved in ether a second time, and poured through silica gel, and concentrated to a clear oil. The crude olefin was dissolved in 10 mL methanol with 250 uL acetic acid and stirred with 10% Pd/C under 1 atm hydrogen for 18 hours. The reaction was filtered through celite and concentrated to afford the title compound.

MS (APCI) m/z (M+H)$^+$178.

EXAMPLE 244B

The above product was prepared in the manner of Example 8 using the product from Example 245A.

MS (APCI) m/z (M+H)$^+$329.

EXAMPLE 244C

The above was prepared from Example 244B using method described in Example 55.

MS (CI) m/z (M+H)$^+$346; $^1$H NMR (300 MHz, DMSO-d$_6$) δ 10.50 (s, 1H), 9.55 (s, 2H), 9.22 (s, 2H), 8.70 (s, 1H), 8.57 (s, 1H), 8.31 (d, J=9 Hz, 1H), 8.23 (d, J=9 Hz, 1H), 8.16 (dd, J=1.5, 8.1 Hz, 1H), 7.91 (dd, J=1.8, 8.4 Hz, 1H), 7.66 (m, 1H), 7.29 (t, J=7.5 Hz, 1H), 6.94 (d, J=9.2 Hz, 1H, ), 2.46 (d, J=6.9 Hz, 2H, ), 1.85 (m, 1H), 0.90 (d, J=5.4 Hz, 6H); Anal. calcd for C$_{22}$H$_{24}$N$_3$OCl: C: 69.19; H: 6.33; N: 11.00. Found: C: 66.89; H: 6.50; N: 10.64.

EXAMPLE 245

6-(aminoiminomethyl)-N-(3-(cyclopentylmethyl)
phenyl)-2-naphthalenecarboxamide,
monohydrochloride, mono(trifluoroacetate) (salt)

EXAMPLE 245A

The above product was prepared in the manner of Example 244 using cyclopentyl (triphenylphosphonium) bromide.

MS (APCI) m/z (M+H)$^+$176.

EXAMPLE 245B

The above product was prepared in the manner of Example 8 using the product from Example 245A.

MS (APCI) m/z (M+H)$^+$355.

EXAMPLE 245C

The above was prepared from Example 245B using the method described in Example 55.

MS (CI) m/z (M+H)$^+$372; $^1$H NMR (300 MHz, DMSO-d$_6$) δ 10.48 (s, 1H), 9.55 (s, 2H), 9.22 (s, 2H), 8.70 (s, 1H), 8.56 (s, 1H), 8.31 (d, J=9 Hz, 1H), 8.23 (d, J=9 Hz, 1H), 8.15 (dd, J=1.5, 8.1 Hz, 1H), 7.91 (dd, J=1.8, 8.4 Hz, 1H), 7.66 (m, 1H), 7.28 (t, J=7.5 Hz, 1H), 6.97 (d, J=9.2 Hz, 1H), 2.59 (d, J=6.9 Hz, 2H), 2.09 (m, 1H), 1.71–1.17 (m, 8H); Anal. calcd for C$_{24}$H$_{26}$N$_3$O$_1$Cl; C: 70.66; H: 6.42;N:10.30. Found: C: 67.76; H: 6.62; N: 9.88.

EXAMPLE 246

6-(aminoiminomethyl)-N-[1,2,3,4-tetrahydro-1-[4-methyl-2-(2-propenyl)-6-isoquinolinyl]-2-naphthalenecarboxamide, bis(trifluoroacetate) (salt)

The title compound was prepared as described in Example 241.

MS (ESI$^+$) m/z 399 (M+H)$^+$, (ESI$^-$) 397 (M−1)$^-$; $^1$H NMR (300 MHz, DMSO-d$_6$) δ 10.6 (s, 1H), 10.1 (br. s, 1H), 9.51 (s, 2H), 9.16 (s, 2H), 8.68 (s, 1H), 8.56 (s, 1H) 8.33–8.16 (m, 3H), 7.92–7.88 (m, 1H), 7.78 (s, 1H), 7.67–7.64 (m, 1H), 7.25–7.22 (m, 1H), 6.07–5.98 (m, 1H), 5.65–5.60 (m, 2H), 4.45 (s, 2H), 4.32 (s, 2H), 3.72–3.50 (m, 4H), 0.98 (t, 3H); Anal. calcd for (C$_{25}$H$_{26}$N$_4$O.2×TFA.2×H$_2$O: C, 54.04; H, 4.69; N, 8.69. Found: C, 54.10; H, 4.77; N, 8.62.

EXAMPLE 247

6-(aminoiminomethyl)-N-(4-methyl-1,2,3,4-tetrahydroisoquinolin-6yl)-2-naphthalenecarboxamide The title compound was prepared as described in Example 242 using the compound prepared as described in Example 246.

MS (ESI$^+$) m/z 358 (M+H)$^+$, (ESI$^-$) 356 (M−1)$^-$; $^1$H NMR (300 MHz, DMSO-d$_6$) δ 10.6 (s, 1H), 10.1 (br. s, 1H), 9.51 (s, 2H), 9.16 (s, 2H), 8.68 (s, 1H), 8.56 (s, 1H) 8.33–8.16 (m, 3H), 7.92–7.88 (m, 1H), 7.78 (s, 1H), 7.67–7.64 (m, 1H), 7.25–7.22 (m, 1H), 4.45 (s, 2H), 4.32 (s, 2H), 3.72–3.50 (m, 4H), 0.98 (t, 3H); Anal. calcd for (C$_{22}$H$_{21}$N$_4$O.2×TFA.2×H$_2$O: C, 50.07; H, 7.27; N, 8.98. Found: C, 49.87; H, 7.12; N, 8.62.

EXAMPLE 248

6-(aminoiminomethyl)-N-(2,4-difluorophenyl)-2-naphthalenecarboxamide

EXAMPLE 248A

6-Chlorocarbonyl-2-naphthonitrile was reacted with 2,4-difluoroaniline to give the title compound as a slightly purple tinted white powder in 76% yield:

MS (DCI/NH$_3$) m/z 309 (M+H)$^+$, 326 (M+NH$_4$)$^+$; $^1$H NMR (300 MHz, DMSO-d$_6$) δ 7.161 (m, 1H), 7.410 (m, 1H), 7.655 (m, 1H), 7.910 (dd, 1H), 8.155 (dd, 1H), 8.216 (d, 1H), 8.296 (d, 1H), 8.700 (br s, 2H), 10.450 (br s, 1H).

EXAMPLE 248B

The title compound from Example 248A above, was treated as described in Example 40, to give the title compound, after reverse phase medium pressure liquid chromatography, as a white powder in 60% yield:

MS (ESI+) m/z 326 (M+H)$^+$, (ESI$^-$) 324 (M−H)$^-$; $^1$H NMR (300 MHz, DMSO-d$_6$) δ 7.165 (m, 1H), 7.400 (m, 1H), 7.652 (m, 1H), 7.900 (dd, 1H), 8.169 (dd, 1H), 8.250 (d, 1H), 8.329 (d, 1H), 8.555 (br s, 1H), 8.723 (br s, 1H), 9.200 (v br s, 2H), 9.500 (v br s, 2H), 10.450 (br s, 1H);

Anal. calcd for $C_{18}H_{13}N_3OF_2$ $(C_2HO_2F_3)_{1.1}$: C, 53.83; H, 3.15; N, 9.32. Found: C, 53.93; H, 3.09; N, 9.42.

EXAMPLE 249

6-(6-fluoro-1,3-benzoxazol-2-yl)-2-naphthalenecarboximidamide

EXAMPLE 249A

The difluorophenyl amide intermediate from Example 248A was treated with lithium bis(trimethylsilyl)amide as described in Example 55 to give the title compound as an off-white powder after purification by reverse phase medium pressure liquid chromatography in 25% yield.

MS (DCI/NH$_3$) m/z 306 (M+H)$^+$; $^1$H NMR (300 MHz, DMSO-d$_6$) δ 7.363 (m, 1H), 7.895 (m, 2H), 7.935 (d, 1H), 8.370 (d, 1H), 8.420 (m, 2H), 8.580 (s, 1H), 8.960 (s, 1H), 9.212 (v br s, 2H), 9.520 (v br s, 2H); Anal. calcd for $C_{18}H_{12}N_3OF$ $(C_2HO_2F_3)_{1.02}$: C, 57.09; H, 3.11; N, 9.97. Found: C, 56.89; H, 3.26; N, 9.95.

EXAMPLE 250

6-(amino(hydroxyimino)methyl)-N-(2,4-difluorophenyl)-2-naphthalenecarboxamide

The difluorophenyl amide intermediate from Example 248A was treated as described in Example 78 using hydroxyamine hydrochloride instead of O-ethyl hydroxylamine to give the desired compound as an off-white solid after flash chromatography in 49% yield.

MS (DCI/NH$_3$) m/z 342 (M+H)$^+$; $^1$H NMR (300 MHz, DMSO-d$_6$) δ 5.991 (br s, 2H), 7.151 (m, 1H), 7.390 (m, 1H), 7.646 (m, 1H), 7.950 (dd, 1H), 8.040 (m, 3H), 8.300 (s, 1H), 8.590 (s, 1H), 9.890 (s, 1H), 10.310 (s, 1H);

Anal. calcd for $C_{18}H_{13}N_3O_2F_2$: C, 63.34; H, 3.84; N, 12.31; F, 11.13. Found: C, 63.17; H, 4.15; N, 12.18; F, 11.23.

EXAMPLE 251

4-[[6-(aminoiminomethyl)-2-naphthalenyl]ethynyl]-N-[(1,1-dimethylethoxy)carbonyl]-L-phenylalanine, mono(trifluoroacetate) (salt)

EXAMPLE 251A

Using the procedure described for Example 121, and substituting N-BOC-p-iodophenylalanine (BACHEM Bioscience Inc.) for 4-iodoaniline, the title compound was obtained.

MS (DCI/NH$_3$) m/z 458 (M+NH$_4$)$^+$;
$^1$H NMR (300 MHz, CDCl$_3$) δ 1.35 (s, 9H), 2.90 (t, 1H), 3.09 (dd, 1H), 4.15 (m, 1H), 7.20 (d, 1H), 7.36 (d, 2H), 7.56 (d, 2H), 7.78 (d, 1H), 7.85 (d, 1H), 8.12 (d, 1H), 8.17 (d, 1H), 8.32 (s, 1H), 8.62 (s, 1H).

EXAMPLE 251B

Using the product obtained in Example 251A and the procedure described in Example 40D the title compound was obtained.

MS (ESI) m/z 458 M+H)$^+$; $^1$H NMR (300 MHz, DMSO-d$_6$) δ 1.35 (s, 9H), 2.90 (dd, 1H), 3.10 (dd, 1H), 4.13 (m, 1H), 7.10 (d, 1H), 7.36 (d, 2H), 7.55 (d, 2H), 7.78 (dd, 1H), 7.85 (dd, 1H), 8.13 (d, 1H), 8.19 (d, 1H), 8.30 (s, 1H), 8.50 (s, 1H), 9.22 (s, 2H), 9.42 (s, 2H).

EXAMPLE 252

6-phenyl-2-naphthalenecarboximidamide

EXAMPLE 252A 6-(phenyl)-2-naphthalenecarbonitrile

A solution of Example 121B (300 mg, 1 mmol), palladium (II) acetate (22 mg, 0.1 mmol) and 1-1'-bis (diphenyphosphino)ferrocene (111 mg, 0.2 mmol) was stirred in DMF (3 mL) for 15 minutes, treated with Cs$_2$CO$_3$ (813 mg, 2.5 mmol) and phenylboronic acid (228 mg, 1.5 mmol), stirred for 20 minutes at 80° C., cooled, treated with pH 7 buffer (10 mL), and extracted with diethyl ether. The ether extracts were dried (MgSO$_4$), concentrated, filtered, and purified on silica gel with 10% ethyl acetate/hexane to provide 140 mg of the title compound as a white solid.

MS (DCI/NH$_3$) m/z 247 (M+NH$_4$)$^+$.

EXAMPLE 252B 6-(phenyl)-2-naphthalenecarboximidamide mono (trifluoroacetate) salt The title compound was prepared from Example 252A and the procedure of Example 55B.

$^1$H NMR (300 MHz, DMSO-d$_6$) 7.03 (m, 1H), 7.44 (m, 3H), 7.84 (dd, 1H), 8.05 (dd, 1H), 8.19 (d, 1H), 8.21 (d, 1H), 0.41 (s, 1H), 8.51 (s, 1H), 9.11 (s, 2H), 9.45 (s, 2H); Anal. calcd for $C_{17}H_{14}N_2$.TFA.0.2H$_2$O: C, 63.33; H, 4.20; N, 7.77. Found: C; 62.93; H, 4.19; N, 7.57.

EXAMPLE 253

(Z)-6-[2-chloro-2-phenylethenyl]naphthalene-2-carboximidamide

EXAMPLE 253A

Preparation of 6-(2,2-dichloroethyl-1-ene)-2-methoxynaphthalene

Following the method of Lee, K. S., et. al. (*Synthetic Comun.* 1991, 21 (15–16), 1657–61) 2-methoxynaphthalene-6-carboxaldehyde (2.0 g, 10.7 mmol) was converted to the title compound. Purification on silica gel with 5% ethyl acetate/hexanes afforded 1.55 g (57%) of the title compound as a colorless solid.

MS (DCI/NH$_3$) m/z 234/236 (M+NH$_4$–HCl)$^+$.

EXAMPLE 253B

Preparation of 6-(cis-2-chloro-2-(phenyl)ethyl-1-ene)-2-methoxynaphthalene

Following the method of Minato, A., et. al. (*J. Am. Chem. Soc.* 1987, 109, 1257–58) a 3.0 M solution of phenylmagnesium bromide in ether (2.23 mL, 6.68 mmol) was added to a solution of 6-(2,2-dichloroethyl-1-ene)-2-methoxynaphthalene (1.30 g, 5.14 mmol) and 1,1'-bis (diphenylphosphino)ferrocene)dichloropalladium (II) (42 mg, 0.051 mmol) in dry toluene (21 mL). The resulting solution was flushed with argon and heated at 35° C. for 0.5 hours. The reaction solution was partitioned between ethyl acetate and saturated aqueous ammonium chloride, and the organic layer was washed with brine (2×), dried (Na$_2$SO$_4$), filtered, and concentrated under vacuum. Purification on silica gel with 5% ether/hexanes gave the title compound (1.03 g, 68%) as an off-white solid.

MS (DCI/NH$_3$) m/z 295 (M+H)$^+$, 312 (M+NH$_4$)$^+$, 329 (M+NH$_4$+NH$_3$)$^+$.

EXAMPLE 253C

Preparation of 6-(cis-2-chloro-2-(phenylethyl-1-ene)-2-hydroxynaphthalene

A solution of 6(cis-2-chloro-2-(phenylethyl-1-ene)-2-methoxynaphthalene (0.90 g, 3.05 mmol) in dry dichloromethane (12 mL) was cooled to −23° C. under a flow of nitrogen and borontribromide was added (6.11 mL of a 1.0 m solution in dichloromethane, 6.11 mmol). The resulting solution was stirred 0.5 hours at −23° C., the cooling bath was removed, and the reaction was stirred at ambient temperature for 2 hours. The reaction was quenched by adding methanol (1.23 mL, 30.5 mmol), and the resulting solution was heated to reflux for 0.5 hours, cooled, concentrated under vacuum, and purified on silica gel with 20% ethyl acetate/hexanes to give the title compound (0.81 g, 94%) as a colorless solid.

MS (DCI/NH$_3$) m/z 280 (M)$^+$, 298 (M+NH$_4$)$^+$.

EXAMPLE 253D

Preparation of 6-(cis-2-chloro-2-(phenyl)ethyl-1-ene)-2-trifluoromethanesulfonyloxynaphthalene To a solution of 6-(cis-2-chloro-2-(phenyl)ethyl-1-ene)-2-hydroxynaphthalene (0.74 g, 2.64 mmol) and triethylamine (0.55 mL, 3.96 mL) in dry THF (11 mL) was added N-phenyltrifluoromethanesulfonimide (1.11 g, 3.16 mmol). The reaction was heated to refluxe for 2 hours and partitioned between ethyl acetate and brine. The organic layer was washed with 10% aqueous HCl (2×), saturated sodium carbonate (2×), brine (2×), dried (Na$_2$SO$_4$), filtered, and concentrated under vacuum. Purification on silica gel with 2% ether/hexanes gave the title compound (0.84 g, 77%) as a thick pale gold oil.

MS (DC/NH$_3$) m/z 412 (M)$^+$, 430 (M+NH$_4$)$^+$.

EXAMPLE 253E

Preparation of 6-(cis-2-chloro-2-(phenyl)ethyl-1-ene)-2-cyanonaphthalene

A solution of 6-(cis-(2-chloro-2-phenyl)ethyl-1-ene)-2-trifluoromethanesulfonyloxynaphthalene (0.75, 1.82 mmol) in dry DMF (18 mL) was stirred vigorously under a flow of nitrogen for 10 minutes. To the resulting solution was added tetrakis (triphenylphosphine)palladium (0) (63.3 mg, 0.055 mmol) and dicyanozinc (113 mg, 0.596 mmol). The reaction was heated at 90° C. for 1 hour after flushing with nitrogen. The reaction mixture was partitioned between ethyl acetate and brine. The organic layer was diluted with an equal volume of hexanes and washed with water (3×), saturated sodium bicarbonate (1×), brine (2×), dried (Na$_2$SO$_4$), filtered, and concentrated under vacuum. Purification on silica gel with 3% ether/hexanes gave the title compound (0.35 g, 66%) as a waxy solid.

MS (DCI/NH$_3$) m/z 289 (M)$^+$, 307 (M+NH$_4$)$^+$, 324 (M+NH$_4$+NH$_3$)$^+$.

EXAMPLE 253F

Preparation of 6-(cis-2-chloro-2-(phenyl)ethyl-1-ene)-naphthalene-2-carboximidamide bis (hydrochloric acid) salt To a slurry of ammonium chloride (0.25 g, 4.75 mmol) in dry toluene (1.5 mL) at 0° C. under nitrogen was added trimethylaluminum (2.0 m in toluene; 2.37 mL, 4.75 mmol) in a dropwise fashion. The cooling bath was removed and the reaction was stirred until gas evolution ceased (approximately 10 minutes). To the resulting solution was added 6-(cis-(2-chloro-2-phenyl)ethyl-1-ene)-2-cyanonaphthalene (343.8 mg, 1.19 mmol) in dry THF (3 mL). The reaction was heated incrementally to reflux (a noticeable exotherm usually occured between 85–100° C.) and maintained there for 2.5 hours. The reaction was cooled and quenched by slowly adding excess methanol to give a fine powdery suspension. The solid was removed by suction filtration through a paper filter on a buchner funnel. The filtrate was concentrated under vacuum and purified on silica gel with 30% methanol/chloroform to give a powdery solid. The solid was dissolved in the minimum volume of hot methanol and purified on silica gel with 15% methanol/chloroform to provide the title compound as a light yellow solid (26.8 mg, 6%).

MS (DCI/NH$_3$) m/z 307 (neutral M+H)$^+$; $^1$H NMR (300 MHz, DMSO-d$_6$) δ =9.32 (br s, 4H), 8.51 (br d, J=7.5 Hz, 2H), 8.20 (d, J=9 Hz, 1H), 8.16 (d, J=9 Hz, 1H), 8.07 (dd, J=9, 2 Hz, 1H), 7.83–7.90 (m, 3H), 7.67 (2, 1H), 7.46–7.55 (m, 3H); Anal. calcd for C$_{19}$H$_{15}$ClN$_2$ (HCl)$_2$: C, 60.09; H, 4.51; N, 7.37. Found: C, 59.64; H, 4.83; N, 7.99.

EXAMPLE 254

(Z)-6-(2-chloro-2-(3-(2-methyl-1-propenyl)phenyl) ethenyl)-2-naphthalenecarboximidamide

EXAMPLE 254A

Preparation of 3-(iso-buten-1-yl)-phenylbromide

To a suspension of iso-propyltriphenylphosphonium iodide in dry THF (150 mL) under nitrogen at −23° C. was added 2.5 M n-butyl lithium in hexanes (13.4 mL, 33.6 mmol). The resulting solution was stirred 0.5 hours at −23° C., the cooling bath was removed, and the reaction was stirred 0.5 hours at ambient temperature to give a dark red homogeneous solution which was cooled to −23° C. To the solution was added neat 3-bromobenzaldehyde (3.73 mL, 32 mmol). The cooling bath was removed, the reaction was stirred at ambient temperature for 1 hour, quenched by adding excess saturated ammonium chloride, and partitioned between ether and brine. The organic layer was washed with saturated aqueous Na$_2$S$_2$O$_5$, brine, dried (Na$_2$SO$_4$), filtered, and concentrated under vacuum. Purification on silica gel with hexanes gave the title compound (5.34 g, 79%) as a colorless oil.

MS (DCI/NH$_3$) m/z 210/212 (M)$^+$.

EXAMPLE 254B

Preparation of 3-(iso-buten-1-yl)phenylmagnesium bromide

To a suspension of Rieke magnesium (0.12 g, 4.74 mmol; commercially available suspension) in dry THF (4.61 mL) was added neat 3-(iso-buten-1-yl)-phenylbromide (1.0 g, 4.74 mmol) at such a rate as to maintain a steady reflux. After the arylbromide was completely added, the reaction was refluxed under nitrogen for 0.5 hours. The solution was allowed to settle for 18 hours and the supernatant was determined to have a 0.56 m titer for active grignard by tritrating a known quantity of 2-methoxynaphthalene-6-carboxaldehyde.

EXAMPLE 254C

Preparation of 6-(cis-2-chloro-2-(3-(iso-buten-1-yl) phenyl)ethyl-1-ene)-2-methoxynaphthalene Following the method of Example 253B but employing 3-(iso-buten-1-yl)phenylmagnesium bromide in lieu of phenylmagnesium bromide afforded the title compound after purification on silica gel with hexanes and 1% ether/hexanes as a thick oil.

MS (DCI/NH$_3$) m/z 349 (M+H)$^+$, 366 (M+NH$_4$)$^+$, 383 (M+NH$_4$+NH$_3$)$^+$.

EXAMPLE 254D

Preparation of 6-(2-cis-chloro-2-trans-(3-(iso-buten-1-yl)phenyl)ethyl-1-ene)-naphthalene-2-carboximidamide bis(hydrochloric acid) salt Following the methods of Examples 160 C, D, E and F but employing 6-(cis-2-chloro-2-(3-(iso-buten-1-yl)phenyl) ethyl-1-ene)-2-methoxynaphthalene in lieu of 6-(cis-2-chloro-2-(phenyl)ethyl-1-ene)-2-methoxynaphthalene the title compound was prepared.

EXAMPLE 255

(Z)-6-(2-chloro-2-(3-(1-methylethoxy)phenyl) ethenyl)-2-naphthalenecarboximidamide

EXAMPLE 255A

Preparation of 6-bromo-2-t-butyloxynaphthalene

To a solution of 6-bromo-2-hydroxynaphthalene (1.5 g, 6.72 mmol) and liquefied iso-butylene (6 mL) in dry dichloromethane (6 mL) at −78° C. was added triflic acid (6 drops). The resulting solution was stirred for 4 hours as it warmed from −78 to 0° C. The reaction was quenched by adding excess saturated aqueous sodium bicarbonate and partitioned between ethyl acetate and brine. The organic layer was washed with brine, dried (Na$_2$SO$_4$), filtered, and concentrated under vacuum. Purification on silica gel with 25% ether/hexanes gave the title compound (1.64 g, 80%) as a colorless oil.

MS (DCI/NH$_3$) m/z 279/291 (M+H)$^+$, 296/298 (M+NH$_4$)$^+$.

EXAMPLE 255B

Preparation of 2-t-butyloxynaphthalene-6-carboxaldehyde

To a −78° C. solution of 6-bromo-2-t-butyloxynaphthalene (2.00 g, 7.16 mmol) in dry THF (30 mL) under nitrogen was added 2.5 m n-butyl lithium in hexanes (3.16 mL, 7.88 mmol). The resulting solution was stirred 0.5 hours at −78° C. and dry DMF (1.66 mL, 21.56 mL) was added neat. The cooling bath was removed, the reaction was allowed to stir for 1 h, and quenched with excess saturated ammonium chloride. The reaction was partitioned between ethyl acetate and brine. The organic layer was washed with brine, dried (Na$_2$SO$_4$), filtered, and concentrated under vacuum. Purification on silica gel with 10% ethyl acetate/hexanes gave the title compound (1.47 g, 90%) as a colorless oil. mp 51–52° C.;

MS (DCI/NH$_3$) m/z 229 (M+H)$^+$, 246 (M+NH$_4$)$^+$.

EXAMPLE 255C

Preparation of 6-(2,2-dichloroethyl-1-ene)-2-t-butyloxynaphthalene

Following the procedure in Example 253A but employing 2-t-butyloxynaphthalene-6-carboxaldehyde in lieu of 2-methoxynaphthalene-6-carboxaldehyde afforded the title compound (0.81 g, 28%), after purification on silica gel with 2% ether/hexanes, as a waxy colorless solid.

MS (DCI/NH$_3$) m/z 295 (M+H)$^+$, 312 (M+NH$_4$)$^+$, 329 (M+NH$_3$).

EXAMPLE 255D

Preparation of 3-(iso-propyloxy)phenylmagnesium bromide

Following the method of Example 255B but employing 3-(isopropyloxy)phenylbromide in lieu of 3-(iso-buten-1-yl)-phenylbromide afforded a THF solution of the title compound.

EXAMPLE 255E

Preparation of 6(cis-2-chloro-2-(3-(iso-propyloxy) phenyl)ethyl-1-ene)-2-t-butyloxynaphthalene Following the method of Example 253B but employing 3-(iso-propyloxy)phenylmagnesium bromide in lieu of phenylmagnesium bromide and 6-(2,2-dichloroethyl-1-ene)-2-t-butyloxynaphthalene in lieu of 6-(2,2-dichloroethyl-1-ene)-2-methoxynaphthalene afforded the title compound, after purification on silica gel with hexanes and 1% ether/hexanes, as a thick oil.

MS (DCI/NH$_3$) m/z (M+H)$^+$, (M+NH$_4$)$^+$, (M+NH$_4$+NH$_3$)$^+$.

EXAMPLE 256

(Z)-6-[1-chloro-2-phenylethenyl]-2-naphthalenecarboximidamide, mono (trifluoroacetate) (salt)

EXAMPLE 256A

Preparation of (2,2-dichloroethyl-1-ene)benzene

The title compound was prepared as in Example 253A but employing benzylaldehyde in lieu of 2-methoxynaphthalene-6-carboxaldehyde. Purification on silica gel with hexane afforded the title compound (42%).

$^1$H NMR (300 MHz, CDCl$_3$) δ 7.53 (d, J=7.5 Hz, 2H), 7.35 (br m, 4H, 6.87 (s, 1H.

EXAMPLE 256B

Preparation of 6-(cis-1-chloro-2-(phenyl)ethyl-1-ene)-2-methoxynaphthalene

The title compound was prepared as in Example 253B but employing (2,2-dichloroethyl-1-ene)benzene and 2-methoxynaphthalenyl-6-magnesium bromide in lieu of 6-(2,2-dichloroethyl-1-ene)-2-methoxynaphthalene and phenylmagnesium bromide. Purification on silica gel with 10% ether/hexanes afforded 0.75 g (21%) of the title compound.

MS (DCI/NH$_3$) m/z 295 (M+H)$^+$, 312 (M+NH$_4$)$^+$.

EXAMPLE 256C

Preparation of 6-(cis-1-chloro-2-(phenyl)ethyl-1-ene)-2-hydroxynaphthalene

The title compound was prepared as in Example 253 but employing 6-(cis-1-chloro-2-(phenyl)ethyl-1-ene)-2-methoxynaphthalene in lieu of 6-(cis-(2-chloro-2-phenyl) ethyl-1-ene)-2-methoxynaphthalene. Purification on silica gel with 25% ethyl acetate/hexane afforded 0.62 g (93%) of the title compound.

MS (DCI/NH$_3$) m/z 281 (M+H)$^+$, 298 (M+NH$_4$)$^+$.

EXAMPLE 256D

Preparation of 6-(cis-1-chloro-2-(phenyl)ethyl-1-ene)-2-trifluoromethanesulfonyloxynaphthalene The title compound was prepared as in Example 253D but employing 6-(cis-1-chloro-2-(phenyl)ethyl-1-ene)-2- hydroxynaphthalene in lieu of 6-(cis-(2-chloro-2-phenyl) ethyl-1-ene)-2-hydroxynaphthalene. Purification on silica gel with 20% ethyl acetate/hexane afforded 0.71 g (74%) of the title compound.

MS (DCI/NH$_3$) m/z 412 (M)$^+$.

EXAMPLE 256E

Preparation of 6-(cis-1-chloro-2-(phenyl)ethyl-1-ene)-2-cyanonaphthalene

The title compound was prepared as in Example 253E but employing 6-(cis-1-chloro-2-(phenyl)ethyl-1-ene)-2-trifluoromethanesulfonyloxynaphthalene in lieu of 6-(cis (2-chloro-2-phenyl)ethyl-1-ene)-2-trifluoromethanesulfonyloxynaphthalene. Purification on silica gel with 25% ethyl acetate/hexane afforded 0.35 g (71%) of the title compound.

MS (DCI/NH$_3$) m/z 289 (M)$^+$, 307 (M+NH$_4$)$^+$.

EXAMPLE 256F

Preparation of 6-(cis-1-chloro-2-(phenyl)ethyl-1-ene)-naphthalene-2-carboximidamide hydrochloric Acid salt The title compound was prepared as in Example 253F but employing 6-(cis-1-chloro-2-(phenyl)ethyl-1-ene)-2-cyanonaphthalene in lieu of 6-(cis-(2-chloro-2-phenyl) ethyl-1-ene)-2-cyanonaphthalene. Purification on silica gel with 25% methol/chloroform afforded 0.13 g (62%) of the title compound.

MS (DCI/NH$_3$) m/z 289 (M)$^+$, 307 (M+H)$^+$, 324 (M+NH$_4$+NH$_3$)$^+$; $^1$H NMR (300 MHz, DMSO-D$_6$) δ 9.38 (br s, 3H, 8.54 (s, 1H, 8.50 (s, 1H, 8.28 (d; 1H, J=8.5 Hz), 8.17 (s, 2H), 7.88 (dd; 1H, J=8.5 Hz), 7.86 (d; 2H, J=6.6), 7.73 (s, 1H, 7.47 (t; 2H, J=6.6 Hz), 7.41 (t; 1H, J=6.6 Hz); Anal. calcd for C$_{19}$H$_{15}$ClN$_2$ (HCl) C, 66.48; H, 4.69; N8.16. Found: C, 64.16; H, 4.69; N, 7.70.

EXAMPLE 257

(Z)-6-(1-chloro-2-(3-(1-methylethoxy)phenyl) ethenyl)-2-naphthalenecarboximidamide, monohydrochloride

EXAMPLE 257A

Preparation of 3-iso-propyloxybenzaldehyde

A solution of 1-bromo-3-iso-propyloxybenzene (2.16 g, 10 mmol) in dry THF (30 mL) was cooled to −78° C. and n-BuLi (4.8 mL of a 2.5 m solution in hexane, 12 mmol) was added. The resulting solution was stirred 0.5 hours and DMF (7.3 g, 10 mmol) was added at −78° C. The reaction solution was partitioned between ethyl acetate and water. The organic layer was washed with brine, dried (Na$_2$SO$_4$), filtered and concentrated under vacuum. Purification on silica gel with 25% ethyl acetate/hexane afforded the title compound (1.64 g, 100%).

MS (DCI/NH$_3$) m/z 182 (M+NH$_4$)$^+$.

EXAMPLE 257B

Preparation of 1-(2,2-dichloroethyl-1-ene)-3-iso-propyloxy-benzene

The title compound was prepared as in Example 253A but employing 3-isopropyloxybenzaldehyde in lieu of 2-methoxynaphthalene-6-carboxaldehyde. Purification on silica gel with 10% ether/hexane afforded the title compound (1.71 g, 83%).

MS (DCI/NH$_3$) m/z 231 (M)$^+$.

EXAMPLE 257C

Preparation of 2-t-butyloxynaphthalenylmagnesium bromide

The title compound was prepared as in Example 254B but employing 6-bromo-2-t-butyloxynaphthalene in lieu of 3-(isobuten-1-yl)-phenylbromide.

EXAMPLE 257D

Preparation of 6-(cis-1-chloro-2-((3-iso-propyloxy) phenyl)ethyl-1-ene)-2-t-butyloxynaphthalene The title compound was prepared as in Example 253B but employing 1-(2, 2-dichloroethyl-1-ene)-3-iso-propyloxy-benzene and 2-t-butyloxynaphthalenylmagnesium bromide in lieu of 6-(2,2-dichloroethyl-1-ene)-2-methoxynaphthalene and phenylmagnesium bromide. Purification on silica gel with 10% ether/hexane afforded 0.35 g (44%) of the title compound.

MS (DCI/NH$_3$) m/z 395 (M+H)$^+$, 412 (M+NH$_4$)$^+$, 429 (M+NH$_3$+NH$_4$)$^+$.

EXAMPLE 257E

Preparation of 6-(cis-1-chloro-2-((3-iso-propyloxy) phenyl)ethyl-1-ene)-2-hydroxynaphthalene To a solution of 6-(cis-1-chloro-2-((3-iso-propyloxy) phenyl)ethyl-1-ene)-2-t-butyloxynaphthalene (0.33 g, 0.84 mmol) in ethanol (5 mL) and dichloromethane (2 mL) was added trifluoromethanesulfonic acid (0.01 g, 0.08 mmol). The reaction was stirred at ambient temperature for 10 minutes. The reaction solution was partitioned between ethyl acetate and water. The organic layer was washed brine, dried (Na2SO4), filtered and concentrated under vacuum. Purification on silica gel with 25% ether/hexane afforded the title compound (0.28 g, 97%).

MS (DCI/NH$_3$) m/z 339 (M+H)$^+$, 356 (M+NH$_4$)$^+$, 373 (M+NH$_3$+NH$_4$)$^+$.

EXAMPLE 257F

Preparation of 6-(cis-1-chloro-2-((3-iso-propyloxy) phenyl)ethyl-1-ene)-naphthalene-2-carboximidamide hydrochloric acid salt The title compound was processed according to the procedure in Example 253D, E and F and employing 6-(cis-1-chloro-2-((3-iso-propyloxy)phenyl)ethyl-1-ene)-2-hydroxynaphthalene in lieu of 6-(cis-(2-chloro-2-phenyl) ethyl-1-ene)-2-hydroxynaphthalene. Purification on silica gel with 25% methanol/chloroform afforded the title compound (0.27 g, 52%).

MS (DCI/NH$_3$) m/z 365 (M+H)$^+$; $^1$H NMR (300 MHz, DMSO-D$_6$) δ 9.38 (br s, 3H, 8.54 (s, 1H, 8.48 (s, 1H, 8.28 (d; 1H, J=8.5 Hz), 8.18 (d, J=8.5 Hz, 1H), 8.14 (d; 1H, J=8.5 Hz), 7.88 (dd; 1H, J=8.5 Hz), 7.70 (s, 1H, 7.42 (br s, 1H, 7.38 (t; 1H, J=10.2 Hz), 6.96 (dd; 1H, J=10.2 Hz); Anal. calcd for C$_{22}$H$_{21}$ClON$_2$ (HCl) C, 68.57; H, 5.75; N, 7.26. Found: C, 65.33; H, 5.94; N, 6.62.

EXAMPLE 258

(Z)-6-(1-chloro-2-(2-(1-methylethoxy)phenyl) ethenyl)-2-naphthalenecarboximidamidemonohydrochloride

EXAMPLE 258A

Preparation of 2-iso-propyloxybenzaldehyde

The title compound was prepared as in Example 257A but employing 2-iso-propyloxybromobenzene in lieu of 1-bromo-3-isopropoxybenzene. Purification on silica, gel with 10% ether/hexane afforded the title compound (2.3 g, 70%).

MS (DCI/NH$_3$) m/z 165 (M+H)$^+$, 182 (M+NH$_4$)$^+$.

EXAMPLE 258B

Preparation of 1-(2,2-dichloroethyl-1-ene)-2-iso-propyloxybenzene

The title compound was prepared as in Example 253A but employing 2-iso-propyloxybenzaldehyde in lieu of 2-methoxynaphthalene-6-carboxaldehyde. Purification on silica gel with 10% ether/hexane afforded the title compound (2.2 g, 88%).

$^1$H NMR (300 MHz, DMSO-D$_6$) δ 7.62 (d; 1H, J=8.6 Hz), 7.34 (t; 1H, J=8.6 Hz), 7.09 (s, 1H, 7.08 (d; 1H, J=7.5 Hz), 6.96 (t; 1H, J=7.5 Hz), 4.65 (sep; 1H, J=6.0 Hz), 1.28 (d; 6H, J=6.0 Hz).

EXAMPLE 258C

Preparation of 6-(cis-1-chloro-2-((2-iso-propyloxy)phenyl)ethyl-1-ene)-2-t-butyloxynaphthalene The title compound was prepared as in Example 253B but employing 1-(2,2-dichloroethyl-1-ene)-2-iso-propyloxy-benzene and 2-t-butyloxynaphthalenylmagnesium bromide in lieu of 6-(2,2-dichloroethyl-1-ene)-2-methoxynaphthalene and phenylmagnesium bromide. Purification on silica gel with 10% ether/hexane afforded 0.36 g (11%) of the title compound.

MS (DCI/NH$_3$) m/z 395 (M+H)$^+$, 412 (M+NH$_4$)$^+$, 429 (M+NH$_3$+NH$_4$)$^+$.

EXAMPLE 258D

Preparation of 6-(cis-1-chloro-2-((2-iso-propyloxy)phenyl)ethyl-1-ene)-2-hydroxynaphthalene The title compound was prepared as in 257E but employing 6-(cis-1-chloro-2-((2-iso-propyloxy)phenyl)ethyl-1-ene)-2-t-butyloxynaphthalene in lieu of 6-(cis-1-chloro-2-((3-iso-propyloxy)phenyl)ethyl-1-ene)-2-t-butyloxynaphthalene. Purification on silica gel with 10% ether/hexane afforded 0.3 g (100%) of the title compound.

MS (DCI/NH$_3$) m/z 339 (M+H)$^+$, 356 (M+NH$_4$)$^+$, 373 (M+NH$_3$+NH$_4$)$^+$.

EXAMPLE 258E

Preparation of 6-(cis-1-chloro-2-((2iso-propyloxy)phenylethyl-1-ene)-naphthalene-2-carboximidamide hydrochloric acid salt The title compound was processed according to the procedure in Example 253D, E and F but employing 6-(cis-1-chloro-2-(2-iso-propyloxy)phenyl)ethyl-1-ene)-2-hydroxynaphthalene in lieu of 6-(cis-(2-chloro-2-phenyl)ethyl-1-ene)-2-hydroxynaphthalene. Purification on silica gel with 25% methanol/chloroform afforded the title compound (0.16 g, 65%).

MS (DCI/NH$_3$) m/z 365 (M+H)$^+$; $^1$H NMR (300 MHz, DMSO-D$_6$) δ 9.32 (br s, 3H, 8.54 (s, 1H, 8.44 (s, 1H, 8.28 (d; 1H, J=8.5 Hz), 8.18 (d, J=8.5 Hz, 1H), 8.05 (d; 1H, J=8.5 Hz), 7.88 (d; 1H, J=10.2 Hz), 7.61 (s, 1H, 7.38 (t; 1H, J=10.2 Hz), 7.15 (t; 1H, J=10.2 Hz), 7.03 (t; 1H, J=10.2 Hz); Anal. calcd for C$_{22}$H$_{21}$ClON$_2$ (HCl) C, 68.57; H, 5.75; N, 7.26. Found: C, 63.49; H, 5.78; N, 6.60.

EXAMPLE 259

(Z)-6-(1-chloro-2-(4-(1-methylethoxy)phenyl)ethenyl)-2-naphthalenecarboximidamide

EXAMPLE 259A

Preparation of 4-iso-propyloxybenzaldehyde

To a solution of 4-hydoxybenzaldehyde (4.0 g, 32.8 mmol) in dry DMF (100 mL) was added 2-bromopropane (6.0 g, 49.2 mmol) and potassium carbonate (6.8 g, 49.2 mmol). The resulting reaction was heated to 100° C. and stirred for 3 hours. The reaction was quenched by adding excess water and partitioned between ethyl acetate and brine. The organic layer was washed with brine, dried (Na2SO4), filtered, and concentrated under vacuum. Purification on silica gel with 15% ether/hexane afforded the title compound (5.0 g, 93%).

MS (DCI/NH$_3$) m/z 165 (M+H)$^+$, 182 (M+NH$_4$)$^+$, 198 (M+NH$_3$+NH$_4$)$^+$.

EXAMPLE 259B

Preparation of 1-(2,2-dichloroethyl-1-ene)-4-iso-propyloxybenzene

The title compound was prepared as in Example 253A but employing 4-iso-propyloxybenzaldehyde in lieu of 2-methoxynaphthalene-6-carboxaldehyde. Purification on silica gel with 15% ether/hexane afforded the title compound (5.0 g, 88%).

MS (DCI/NH$_3$) m/z 165 (M+H)$^+$, 182 (M+NH$_4$)$^+$, 198 (M+NH$_3$+NH$_4$)$^+$.

EXAMPLE 259C

Preparation of 6-(cis-1-chloro-2-((4-iso-propyloxy)phenyl)ethyl-1-ene)-2-t-butyloxynaphthalene The title compound was prepared as in Example 253B but employing 1-(2,2-dichloroethyl-1-ene)-4-is(propyloxy-benzene and 2-t-butyloxynaphthalenylmagnesium bromide in lieu of 6-(2,2-dichloroethyl-1-ene)-2-methoxynaphthalene and phenylmagnesium bromide. Purification on silica gel with 10% ether/hexane afforded 0.48 g (56%) of the title compound.

MS (DCI/NH$_3$) m/z 395 (M+H)$^+$, 412 (M+NH$_4$)$^+$, 429 (M+NH$_3$+NH$_4$)$^+$.

EXAMPLE 259D

Preparation of 6-(cis-1-chloro-2-((4-iso-propyloxy)phenyl)ethyl-1-ene)-2-hydroxynaphthalene The title compound was prepared as in Example 258E but employing 6(cis-1-chloro-2-(4-iso-propyloxy)phenyl)ethyl-1-ene)-2-t-butyloxynaphthalene in lieu of 6-(cis-1-chloro-2-(3-iso-propyloxy)phenyl)ethyl-1-ene)-2-t-butyloxynaphthalene. Purification on silica gel with 10% ether/hexane afforded 0.35 g (86%) of the title compound.

MS (DCI/NH$_3$) m/z 339 (M+H)$^+$, 356 (M+NH$_4$)$^+$, 373 (M+NH$_3$+NH$_4$)$^+$.

EXAMPLE 259E

Preparation of 6-(cis-1-chloro-2-((4-iso-propyloxyphenyl)ethyl-1-ene)-naphthalene-2-carboximidamide hydrochloric acid salt The title compound was processed according to the procedure in Example 253D, E and F but employing 6-(cis-1- chloro-2-(4-iso-propyloxy)phenyl)ethyl-1-ene)-2-hydroxynaphthalene in lieu of 6-(cis-2-chloro-2-(phenyl)ethyl-1-ene)-2-hydroxynaphthalene. Purification on silica gel with 1–4% methanol/chloroform afforded the title compound.

EXAMPLE 260

(E)-6-[2-[3,4-dihydro-1-(1-methyethyl)-7-isoquinolinyl]ethenyl]-2-naphthalenecarboximidamide, bis(trifluoroacetate) (salt)

EXAMPLE 260A

Tributyltinhydride was added dropwise to a suspension of the product obtained in Example 63B (130 mg, 0.73 mmol), 2,2'-azobisisobutyronitrile (3.3 mg, 0.02 mmol), and 3.5 mL toluene. The reaction mixture was stirred at 85° C. for 1 hour. After cooling to room temperature, solvent was evaporated, and the residue was purified by flash chromatography, eluting with 97 Hexanes: 2 ethyl acetate: 1 triethylamine to afford the title compound.

MS (APCI)+ m/z 468 (M+H)+; $^1$H NMR (300 MHz, CDCl$_3$) δ 8.20 (s, 1H), 7.76–7.90 (m, 4H), 7.55–7.62 (m, 2H), 7.10 (d, J=12.87 Hz, 1H), 1.36 (q, J=7.35 Hz, 8H), 1.01 (t, J=8.09 Hz, 2H), 0.92 (t, J=7.36 Hz, 9H), 0.82 (t, J=7.35 Hz, 8H).

EXAMPLE 260B

A solution of sodium nitrite (200 mg, 2.9 mmol) and 4.9 mL H$_2$O was added dropwise, over 8 minutes to a 0° C. solution of the product obtained in Example 72B and 5 mL 2N HCl. After 10 minutes at 0°, a solution of KI (13.5 g, 81.3 mmol) and 9.8 mL H$_2$O were added dropwise. The reaction mixture was stirred at room temperature for 1.5 hour and at 80° C. for 10 minutes. After cooling to 0°, the reaction mixture was basified with 28% NH$_4$OH and was extracted with methylene chloride. The organic extracts were combined, washed with 10% aqueous Na$_2$S$_2$O$_3$, H$_2$O, brine, dried (MgSO$_4$), filtered, and evaporated to afford the title compound.

MS (DCI) m/z 300 (M+H)+; $^1$H NMR (300 MHz, CDCl$_3$) δ 8.20 (s, 1H), 7.83 (d, J=1.47 Hz, 1H), 7.66 (dd, 1HJ=7.72, 1.47 Hz, 1H), 6.97 (d, J=8.09 Hz, 1H), 3.67 (t, J=6.98 Hz, 2H), 3.20 (m, 1H), 2.60 (t, J=7.72 Hz, 2H), 1.21 (d, J=6.99 Hz, 6H).

EXAMPLE 260C

A solution of the compound obtained in Example 260A (120 mg, 0.26 mmol), and 0.2 mL DMF was added dropwise to a solution of the compound obtained in Example 260B (70 mg, 0.23 mmol), dichlorobis (triphenylphosphine)palladium (II) (7.0 mg, 0.01 mmol), LiCl (31 mg, 0.73 mmol), and 1.7 mL DMF. The reaction was stirred at 80° C. for 1.75 hours, cooled to room temperature, diluted with ethyl acetate, washed with H$_2$O (4x), saturated aqueous NaCl, dried (MgSO$_4$), filtered, evaporated, and purified by flash chromatography, eluting with hexane/30% ethyl acetate to afford the title compound.

MS (DCI) m/z 351 (M+H)+; $^1$H NMR (300 MHz, CDCl$_3$) δ 8.19 (s, 1H), 7.89 (d, J=10.50 Hz, 4H), 7.59 (t, J=8.47 Hz, 2H), 7.22–7.31 (m, 4H), 3.71 (t, J=6.78 Hz, 2H), 3.37 (m, 1H), 2.69 (t, J=7.46 Hz, 2H), 1.27 (d, J=6.78 Hz, 6H).

EXAMPLE 260D

Using the compound obtained in Example 260C and the procedure described for Example 55B, the title compound was obtained.

MS (DCI) m/z 368 (M+H)+; $^1$H NMR (300 MHz, DMSO-d$_6$) δ 9.55 9 (s, 2H), 9.29 (s, 2H), 8.52 (s, 1H), 8.42 (s, 1H), 8.07–8.19 (m, 6H), 7.87 (dd, J=8.46, 1.47 Hz, 1H), 7.69 (d, J=9.92 Hz, 1H), 7.60 (d, J=8.09 Hz, 1H), 3.95 (m, 1H), 3.86 (t, J=7.35 Hz, 2H), 3.11 (t, J=7.72 Hz, 2H), 1.42 (d, J=6.98 Hz, 6H); Anal. calcd for C$_{25}$H$_{27}$Cl$_2$N$_3$·1.25H$_2$O: C, 64.86; H, 6.42; N, 9.08. Found: C, 64.83; H, 6.29; N, 9.08.

EXAMPLE 261

6-((3-(cyclopentyloxy)phenyl)ethynyl)-2-naphthalenecarboximidamide

EXAMPLE 261A

To a solution of 3-hydroxybenzaldehyde (6.11 g, 50 mmol), PPh$_3$ (14.42 g, 55 mmol), and cyclopentanol (5.00 mL, 55 mmol) in THF (125 mL) at 0° C. was added DEAD (8.66 mL, 55 mmol) and the reaction was stirred for 20 minutes The reaction was condensed and chromatographed on SiO$_2$ using 10% ethyl acetate/hexanes as eluent, to yield 5.35 g (56%) of the title compound.

MS (DCI/NH$_3$) m/z 208 (M+NH$_4$)+.

EXAMPLE 261B

To a solution of CBr$_4$ (13.95 g, 42.05 mmol) and PPh$_3$ (22.06 g, 84.1 mmol) in CH$_2$Cl$_2$ (300 mL) at 0° C. was added the product prepared in example 261A (4.00 g, 21.0 mmol) and the reaction was stirred for 30 minutes The reaction was diluted with ether and filtered through a plug of SiO$_2$. The liquid was condensed and chromatographed on SiO$_2$ using hexanes as eluent, to yield 4.87 g (67%) of the title compound.

MS (DCI/NH$_3$) m/z 347 (M+H)+.

EXAMPLE 261C

To a solution of the product from Example 261B (3.02 g, 8.73 mmol), Example 41 (1.72 g, 8.73 mmol), and Pd (PPh$_3$)$_4$ (1.00 g, 0.87 mmol) in THF (300 mL) and water (10 mL) was added Ba (OH)$_2$ (1.80 g, 10.5 mmol) and the reaction was refluxed for 24 hours. The reaction was condensed and chromatographed on SiO$_2$ using 10% ethyl acetate/hexanes as eluent, to yield 1.48 g (41%) of the title compound.

MS (DCI/NH$_3$) m/z 435, 437 (M+NH$_4$)+.

EXAMPLE 261D

To a solution of the product from Example 261 (202 mg, 0.483 mmol) in THF (7 mL) was added a 1 M solution of LiN(TMS)$_2$ (2 mL), and the reaction was stirred overnight. To this was added 2 M aq. HCl (7 mL), and the reaction was stirred overnight. The mixture was poured into aq. Na$_2$CO$_3$ and extracted with ethyl acetate. The extracts were washed with brine, dried over Na$_2$SO$_4$, filtered, and concentrated. The residue was taken up in EtOH and methanesulfonic acid was added (0.2 mL). The mixture was triturated with ether and filtered to yield the title compound.

$^1$H NMR (300 MHz, DMSO-d$_6$) δ 1.55–1.67 (m, 2H), 1.65–1.79 (m, 4H), 1.89–2.00 (m, 2H), 2.31 (s, 3H), 4.90 (m, 1H), 7.01 (dd, 2H), 7.11 (br s, 1H), 7.17 (d, 1H), 7.36 (dd, 1H), 7.79 (dd, 1H), 7.86 (dd, 1H), 8.14 (d, 1H), 8.18 (d, 1H), 8.32 (s, 1H), 8.50 (s, 1H), 9.08 (br s, 2H), 9.45 (br s, 2H); MS (DCI/NH$_3$) m/z 355 (M+H)+; Anal. calcd for C$_{24}$H$_{22}$N$_2$O·1.2 CH$_4$SO$_3$: C, 64.43; H, 5.75; N, 5.96. Found: C, 64.23; H, 5.76; N, 6.00.

EXAMPLE 262

(Z)-6-[1-bromo-2-[3-(cyclopentyloxy)phenyl]ethenyl]-2-naphthalenecarboximidamide, mono (trifluoroacetate) (salt)

EXAMPLE 262A

To a solution of NH$_4$Cl (174 mg, 3.25 mmol) in toluene (10 mL) was added a 2 M solution of AlMe$_3$ (0.812 mL, 1.62 mmol), and the reaction mixture was stirred for 30 minutes. To this mixture was added the product from Example 261 (170 mg, 0.406 mmol), and the reaction was heated to 90° C. for 7 days. The reaction was then cooled to room temperature and poured into a suspension of $SiO_2$ in $CHCl_3$ (100 mL), and the mixture was stirred for 30 minutes. The mixture was filtered through a plug of $SiO_2$ and rinsed with $CHCl_3$, and the liquid was discarded. The $SiO_2$ was then rinsed with $CH_3OH$/ethyl acetate and this solution was concentrated. The solid was taken up in aq. $Na_2CO_3$ solution, and extracted with ethyl acetate (3×). The extracts were washed with brine, dried over $Na_2SO_4$, filtered, and concentrated. The residue was taken up in EtOH, and methanesulfonic acid was added (0.2 mL). The mixture was triturated with ether and filtered to yield the title compound.

MS (DCI/$NH_3$) m/z 435, 437 (M+H)$^+$; $^1$H NMR (300 MHz, DMSO-$d_6$) δ 1.55–1.67 (m, 2H), 1.65–1.80 (m, 4H), 1.89–2.01 (m, 2H), 2.31 (s, 3H), 4.86 (m, 1H), 6.84 (dd, 2H), 6.97 (d, 1H), 7.02 (d, 1H), 7.18 (s, 1H), 7.31 (dd, 1H), 7.83 (dd, 1H), 8.01 (dd, 1H), 8.10 (d, 1H), 8.18 (d, 1H), 8.21 (s, 1H), 8.48 (s, 1H), 9.07 (br s, 2H), 9.42 (br s, 2H); Anal. calcd for $C24H_{23}BrN_2O.2.05\ CH_4SO_3$: C, 49.48; H, 4.97; N, 4.43. Found: C, 49.39; H, 5.38; N, 4.16.

EXAMPLE 263

(Z)-6-[1-fluoro-2-[3-(cyclopentyloxy)phenyl] ethenyl]-2-naphthalenecarboximidamide, mono (trifluoroacetate (salt)

EXAMPLE 263A

To a solution of $CFBr_3$ (1.08 mL, 11 mmol) and the product from Example 55A, (1.90 g, 10 mmol) in $CH_2Cl_2$ (25 mL) at −78° C. was added HMPT (4.00 mL, 22 mmol) and the reaction was stirred for 30 minutes at −78° C., and then allowed to warm to room temperature overnight. The reaction was poured into water/hexane, and separated. The extracts were washed with water, 1 m HCl, water, brine, and dried over $Na_2SO_4$. The extracts were condensed and chromatographed on $SiO_2$ using 3% ethyl acetate/hexanes as eluent, to yield 880 mg (81%) of the title compound as a ~60:40 mixture of isomers, with the E-isomer predominating.

MS (DCI/$NH_3$) m/z 285, 287 (M+H)$^+$.

EXAMPLE 263B

To the product mixture from Example 263A (990 mg, 3.47 mmol), Example 41 (342 mg, 1.74 mmol), and Pd (PPh$_3$)$_4$ (401 mg, 0.347 mmol) in THF (25 mL) and water (3 mL) was added TlOEt (0.173 mL, 2.44 mmol) and the reaction was stirred for 30 minutes The reaction was diluted with $Et_2O$ and filtered through a plug of Celite® and $SiO_2$. The filtered liquid was condensed and chromatographed on $SiO_2$ using 5% ethyl acetate/hexanes as eluent, to yield 250 mg (20%) of the title compound.

MS (DCI/$NH_3$) m/z 375 (M+$NH_4$)$^+$.

EXAMPLE 263C

The title compound was prepared from Example 263B by the procedure of Example 55D.

MS (DCI/$NH_3$) m/z 375 (M+H)$^+$; $^1$H NMR (300 MHz, DMSO-$d_6$) δ 1.55–1.67 (m, 2H), 1.65–1.80 (m, 4H), 1.89–2.02 (m, 2H), 2.36 (s, 3H), 4.86 (m, 1H), 6.90 (dd, 2H), 7.06 (d, J=40 Hz, 1H), 7.27 (d, 1H), 7.32 (dd, 1H), 7.35 (dd, 1H), 7.87 (dd, 1H), 8.09 (d, 1H), 8.19 (d, 1H), 8.26 (d, 1H), 8.39 (s, 1H), 8.51 (s, 1H), 9.12 (br s, 2H), 9.48 (br s, 2H); Anal. calcd for $C_{24}H_{23}FN_2O.1.25\ CH_4SO_3$: C, 61.32; H, 5.71; N, 5.66. Found: C, 61.38; H, 5.78; N, 5.57.

EXAMPLE 264

(Z)-6-[2-bromo-2-[3-(cyclopentyloxy)phenyl] ethenyl]-2-naphthalenecarboximidamide, mono (trifluoroacetate) (salt)

EXAMPLE 264A

The title compound was prepared from 3-bromophenol by the procedure of Example 261A.

MS (DCI/$NH_3$) m/z 241, 243 (M+H)$^+$.

EXAMPLE 264B

To a solution of the product from Example 264A (6.00 g, 24.9 mmol) in THF (125; mL) at −78° C. was added a 2.5 M solution of BuLi (9.95 mL, 24.9 mmol), and the reaction was stirred for 5 minutes Triisopropylborate (6.32 mL, 27.4 mmol) was then added, and the reaction was warmed to room temperature, stirred for 30 minutes, and then poured into 3 M HCl (250 mL). The layers were separated and the aqueous layer extracted with ethyl acetate. The extracts were condensed, and the crude product was taken up in 1 M NaOH (400 mL). This was extracted with $Et_2O$, and these extracts were discarded. The aqueous layer was made acidic with concentrated HCl, and extracted with ethyl acetate. The extracts were washed with brine, dried over $Na_2SO_4$, filtered, and condensed. This product was taken up in a minimal amount of $Et_2O$, and triturated with hexanes to yield 2.10 g (41%) of the title compound.

MS (DCI/$NH_3$) m/z 224 (M+$NH_4$)$^+$.

EXAMPLE 264C

To a solution of 6-bromo-2-naphthol (2.23 g, 10 mmol) in THF (40 mL) at −78° C. was added 2.5 M BuLi (8 mL, 20 mmol) and the reaction was stirred for 5 minutes DMF (0.852 mL, 11 mmol) was added, the reaction was stirred for 5 minutes, and then warmed to room temperature. The reaction was poured into 1 M HCl, and extracted with $Et_2O$. The extracts were washed with brine, dried over $Na_2SO_4$, filtered, condensed and chromatographed on $SiO_2$ using 25% ethyl acetate/hexanes as eluent to yield 1.35 g (78%) of the title compound.

MS (DCI/$NH_3$) m/z 173 (M+H)$^+$.

EXAMPLE 264D

A solution of the product from Example 264C (19.1 g, 111 mmol), N-phenyl trifluoromethanesulfonamide (39.7 g, 111 mmol), and $Et_3N$ (30.9 mL, 222 mmol) in $CH_2Cl_2$ (100 mL) and DMF (100 mL) was stirred for 18 hours. The reaction was poured into water, and extracted with $Et_2O$/hexane The extracts were washed with water, brine, dried over $Na_2SO_4$, filtered, condensed and chromatographed on $SiO_2$ using 10% ethyl acetate/hexanes as eluent to yield 16.7 g (50%) of the title compound.

MS (DCI/$NH_3$) m/z 305 (M+H)$^+$.

EXAMPLE 264E

A solution of the product from Example 264D (16.7 g, 55 mmol), zinc cyanide (3.88 g, 33 mmol), and Pd (PPh$_3$)$_4$ (2 g, 1.7 mmol) in DMF (150 mL) was stirred at 90° C. for 1 hour. The reaction was poured into aq. $NaHCO_3$, and extracted with Et$_2$O. The extracts were washed with brine, dried over Na$_2$SO$_4$, filtered, and condensed. The crude product was triturated with a small amount of ethyl acetate, and hexanes to yield 10.0 g (99%) of the title compound.

MS (DCI/NH$_3$) m/z 199 (M+NH$_4$)$^+$.

EXAMPLE 264F

The title compound was prepared from the product from Example 264E by the procedure of Example 261B.

MS (DCI/NH$_3$) m/z 353, 355, 357 (M+NH$_4$)$^+$.

EXAMPLE 264G

The title compound was prepared from the product from Example 264F and the product from Example 264B by the procedure of Example 263B.

MS (DCI/NH$_3$) m/z 435, 437 (M+NH$_4$)$^+$.

EXAMPLE 264H

The title compound was prepared from the product from Example 264G and the procedure of Example 262.

MS (DCI/NH$_3$) m/z 435, 437 (M+H)$^+$; $^1$H NMR (300 MHz, DMSO-d$_6$) δ 1.55–1.67 (m, 2H), 1.65–1.80 (m, 4H), 1.89–2.01 (m, 2H), 2.31 (s, 3H), 4.92 (m, 1H), 6.99 (dd, 2H), 7.26 (d, 1H), 7.33 (d, 1H), 7.37 (dd, 1H), 7.78 (s, 1H), 7.83 (dd, 1H), 8.03 (dd, 1H), 8.14 (d, 1H), 8.20 (d, 1H), 8.42 (s, 1H), 8.49 (s, 1H), 9.03 (br s, 2H), 9.44 (br s, 2H); Anal. calcd for C$_{24}$H$_{23}$BrN$_2$O.1.25 CH$_4$SO$_3$: C, 54.60; H, 5.08; N, 5.04. Found: C, 54.37; H, 4.99; N, 5.20.

EXAMPLE 265

A-6-((methylphenylamino)methyl)-2-naphthalenecarboximidamide

EXAMPLE 265A

A solution of the product from Example 264C (80 mg, 0.442 mmol), N-methylaniline (50 μL, 0.464 mmol), NaBH (OAc)$_3$ (131 mg, 0.618 mmol) and AcOH (2:5 μL, 0.442 mmol) in 1,2-dichloroethane (3 mL) was stirred for 2 hours. The reaction was chromatographed on SiO$_2$ using 5% ethyl acetate/hexanes to yield 69 mg (57%) of the title compound.

MS (DCI/NH$_3$) m/z 273 (M+H)$^+$.

EXAMPLE 265B

To a solution of the product from Example 265A (202 mg, 0.483 mmol) in THF (7 mL) was added a 1 M solution of LiN (TMS)$_2$ (2 mL), and the reaction was stirred overnight. To this was added 2 M aq. HCl (7 mL), and the reaction was stirred overnight. The mixture was poured into aq. Na$_2$CO$_3$ and extracted with ethyl acetate. The extracts were washed with brine, dried over Na$_2$SO$_4$, filtered, and condensed. The residue was chromatographed by HPLC to yield the title compound as a trifluoroacetic acid salt.

MS (DCI/NH$_3$) m/z 290 (M+H)$^+$; $^1$H NMR (300 MHz, DMSO-d$_6$) δ 1.55–1.67 (m, 2H), 1.65–1.79 (m, 4H), 1.89–2.00 (m, 2H), 2.31 (s, 3H), 4.90 (m, 1H), 7.01 (dd, 2H), 7.11 (br s, 1H), 7.17 (d, 1H), 7.36 (dd, 1H), 7.79 (dd, 1H), 7.86 (dd, 1H), 8.14 (d, 1H), 8.18 (d, 1H), 8.32 (s, 1H), 8.50 (s, 1H), 9.08 (br s, 2H), 9.45 (br s, 2H); Anal. calcd for C$_{19}$H$_{19}$N$_3$.2.15 C$_2$HF$_3$O$_2$: C, 52.36; H, 3.99; N, 7.86. Found: C, 52.15; H, 3.98; N, 7.59.

EXAMPLE 266

N-(6-(aminoiminomethyl)-2-naphthaleny)lurea

EXAMPLE 266A

A solution of the 2-cyano-6-naphthalene carboxylic acid azide (2.22 g, 10 mmol), from Example 40B in toluene (200 mL) was heated at 85° C. for 1 hour then 95° C. for 1.5 hours. The solvent was evaporated under vacuum and the solid was suspended in ether:hexane 1:1 (100 mL). Filtration of the solid afforded pure product as a white solid. Yield, 1.84g (95%).

EXAMPLE 266B

To a solution of the 6-isocyanate-2-cyanonaphthalene (227 mg, 1.17 mmol) in toluene (20 mL), at room temperature was bubbled dry ammonia for 5 minutes. After 10 minutes diethyl ether (30 mL) was added to the reaction mixture and the product was filtered and washed with diethyl ether to yield 130 mg (53%) of a white solid.

MS m/z DCI$^+$212 (M+1)$^+$, 229 (M+18)$^+$.

EXAMPLE 266C

The title compound was prepared from 2-urea-2-cyanonaphthalene and the procedure of Example 40.

MS (ESI$^+$) m/z 229 (M+H)$^+$, (ESI$^-$) m/z 227 (M–H)$^-$; $^1$H NMR (300 MHz, DMSO-d$_6$) 9.1–9.0 (br. s, 5H). 8.35 (s, 1H), 8.21 (d, J=1.5 Hz, 1H), 7.96 (d, J=8.5 Hz, 1H), 7.97–7.94 (m, 2H), 7.72 (dd, J=8.8 Hz, J=1.8 Hz, 1H), 7.58 (dd, J=8.8 Hz, J=1.8 Hz, 1H), 6.11 (s, 2H); Anal. calcd for C$_{12}$H$_{12}$N$_4$O$_1$.TFA.0.25H$_2$O: C, 48.49; H, 3.92; N, 16.16. Found: C; 48.40; H, 3.80; N, 15.96.

EXAMPLE 267

6-(2-(4-methoxyphenyl)cyclopropyl)-2-naphthalenecarboximidamide

The material prepared from 4-methoxystyrene as described in Example 43 (210 mg, 0.52 mmol) was dissolved in THF (6 mL) and added dropwise to 10 mL diazomethane cooled to 0° C. and then Pd (OAc)$_2$ (9.8 mg) was added. Vigorous bubbling occurs for 5 minutes and the resulting black slurry was stirred 20 minutes, filtered and concentrated in-vacuo affording 0.1 g clear oil.

MS (DCI/NH$_3$) m/z 316 (M+NH$_4$)$^+$.

The title compound is prepared as described in Example 55, purified by reverse phase chromatography to give 19.9 mg of white solid.

MS (DCI/NH$_3$) m/z 316 (M+H)$^+$; $^1$H NMR (300 MHz, DMSO-d$_6$) δ 9.41 (s, 2H), 9.16 (s, 2H), 8.46 (s, 1H), 8.08 (d, 2]H, 8.03 (d, 1H), 7.85 (s, 1H), 7.75 (dd, 1H), 7.58 (dd, 1H), 7.3–7.1 (m, 4H), 3.68 (s, 3H), 2.38–2.48 (m, 2H), 1.61–1.70 (m, 2H); Anal. calcd for C$_{23}$H$_{21}$N$_2$O$_2$F$_3$ 1H$_2$O: C, 62.10; H, 4.80; N, 6.29. Found: C, 62.00; H, 4, 75; N, 6.25.

EXAMPLE 268

6-(2-(4-(1-methylethyl)phenyl-1-cyclopropyl)-2-naphthalenecarboximidamide, monohydrochloride Material prepared from 4-isopropylstyrene, as described in Example 43 (210 mg, 0.52 mmol) was dissolved in THF (6 mL) and added dropwise to 10 mL diazomethane cooled to 0° C. followed by addition of Pd (OAc)$_2$ (9.8 mg). Vigorous bubbling occurs for 5 minutes and the resulting black slurry was stirred 20 minutes, filtered, and solvent removed in-vacuo leaving 0.1 g clear oil.

MS (DCI/NH$_3$) m/z (M+NH$_4$$^+$) 329

The title compound was prepared as described in Example 55, purified by reverse phase chromatography to give 19.9 mg of white solid.

MS (DCI/NH$_3$) m/z (M+H)$^+$329; $^1$H NMR (300 MHz, DMSO-d$_6$) d 9.41 (s, 2H), 9.16 (s, 2H), 8.46 (s, 1H), 8.08 (d,

2H), 8.03 (d, 1H), 7.85 (s, 1H), 7.75 (dd, 1H), 7.58 (dd, 1H), 7.3–7.1 (m, 4H), 2.38–2.48 (m, 2H), 1.61–1.70 (m, 2H); 1.5 (m, 1H), 0.9 (d, 6H); Anal. calcd for $C_{23}H_{21}N_2O_2F_3$ $1H_2O$: C, 62.10; H, 4.80; N, 6.29. Found: C, 62.00; H, 4, 75; N, 6.25.

EXAMPLE 269

6-Aminonaphthalene-2-carboximidamide mono (trifluoroacetate) salt

EXAMPLE 269A

6Phenylcarbamoyl-2-naphthalenecarbonitrile

The title compound was prepared from Example 40A, phenol and the procedure from Example 40B.
MS (DCI/NH$_3$) m/z 289 (M+H)$^+$.

EXAMPLE 269B

6-Aminonaphthalene-2-carboximidamide mono (trifluoroacetate) salt

The title compound was prepared from Example 269A and the procedure of Example 40D.
MS (DCI/NH$_3$) m/z 196 (M+H)$^+$; $^1$H NMR (300 MHz, DMSO-d$_6$) δ 6.01 (br s, 2H), 6.86 (d, 1H), 7.06 (dd, 1H), 7.58–7.67 (m, 2H), 7.74 (d, 1H), 8.21 (d, 1H), 8.74 (br s, 2H), 9.16 (br s, 2H); Anal. calcd for $C_{12}H_{10}N_3$·TFA: C, 52.18; H, 4.04; N, 14.04. Found: C, 51.92; H, 3.87; N, 13.80.

EXAMPLE 270

(E)-6-(2-(phenylsulfinyl)ethenyl)-2-naphthalenecarboximidamide

EXAMPLE 270A

The above product was prepared in the manner of Example 43B using phenylvinyl sulfoxide.
MS (APCI) m/z 304 (M+H)$^+$.

EXAMPLE 270B

The above was prepared from Example 270A as described in Example 55B.
MS (CI) m/z 378 (M+H)$^+$; $^1$H NMR (300 MHz, DMSO-d$_6$) δ 10.37 (s, 1H), 9.49 (s, 2H), 9.15 (s, 2H), 8.67 (s, 1H), 8.54 (s, 1H), 8.30 (d, 1H), 8.23 (d, 1H), 8.15 (dd, 1H), 7.90 (dd, 1H), 7.49 (s, 1H), 6.98 (dd, 1H), 4.49 (m, 1H), 3.76 (s, 3H), 1.30 (d, 6H); Anal. calcd for $C_{24}H_{24}N_3O_5F_3$ 1/5 TFA: C, 56.99; H, 4.74; N, 8.17. Found: C, 57.12; H, 4.96; N, 7.37.

EXAMPLE 271

6-((3-propoxyphenyl)amino)methyl)-2-naphthalenecarboximidamide

EXAMPLE 271A

The product from Example 218 (163 mg, 0.5 mmol) and PCl$_5$ were heated in toluene for 4 hours. A slurry of sodium borohydride (285 mg, 7.5 mmol) in 2 mL of ethanol was added and the mixture was allowed to stir 18 hours. The reaction was cooled, diluted with ethyl acetate, washed with water (1×), brine (1×), dried over sodium sulfate, and purified using silica gel chromatography.
MS (APCI) m/z 317 (M+H)$^+$.

EXAMPLE 271B

The above was prepared from Example 271A as described in Example 55B.
MS (CI) m/z 378 (M+H)$^+$; $^1$H NMR (300 MHz, DMSO-d$_6$) δ 10.37 (s, 1H), 9.49 (s, 2H), 9.15 (s, 2H), 8.67 (s, 1H), 8.54 (s, 1H), 8.30 (d, 1H), 8.23 (d, 1H), 8.15 (dd, 1H), 7.90 (dd, 1H), 7.49 (s, 1H), 6.98 (dd, 1H), 4.49 (m, 1H), 3.76 (s, 3H), 1.30 (d, 6H); Anal. calcd for $C_{24}H_{24}N_3O_5F_3$ 1/5 TFA: C, 56.99; H, 4.74; N, 8.17. Found: C, 57.12; H, 4.96; N, 7.37.

EXAMPLE 272

2-(aminoiminomethyl)-N-((1-methylethoxy)phenyl)-6-quinolinecarboxamide

EXAMPLE 272A

Methyl 1-N-oxo-6-quinolinecarboxylate

A solution of methyl 6-quinoline carboxylate (13.02 g, 70 mmol), methyl trioxorhenium (100 mg) and hydrogen peroxide (20 mL of 30% solution in water) in dichloromethane (50 mL) was vigorously stirred overnight at room temperature. The precipitated product was filtered off, washed with small amount of dichloromethane and dried in vacuum oven providing 13.1 g (93%) of the white crystalline material.
MS m/z 204 (M+H)$^+$; $^1$H NMR (300 MHz, DMSO-d$_6$) δ 3.95 (s, 3H), 7.58 (dd, 1H), 8.16 (d, 1H), 8.25 (dd, 1H), 8.63 (d, 1H), 8.71 (d, 1H), 8.79 (d, 1H).

EXAMPLE 272B

Methyl 2-cyano-6-quinolinecarboxylate

Trimetylsilyl cyanide (4.96 g, 6.67 mL, 50 mmol) was added to a solution of methyl 1-N-oxo-6-quinoline carboxylate (7.52 g, 37 mmol) in dichloromethane (50 mL) at room temperature. The reaction mixture was stirred for 15 minutes when N,N-dimethylcarbamoyl chloride (5.38 g, 4.60 mL, 50 mmol) was slowly added. The mixture was allowed to stir overnight and the reaction was quenched with 10% solution of potassium carbonate (20 mL). The organic layer was separated and the water layer extracted with dichloromethane (2×40 mL). The combined organic extracts were washed with brine, dried over potassium carbonate and filtered through a short pad of silica gel providing, after evaporating of the solvent, 6.36 g (81%) of the white crystalline product.
MS m/z 213 (M+H)$^+$; $^1$H NMR (300 MHz, DMSO-d$_6$) δ 3.97 (s, 3H), 8.15 (d, 1H), 8.22 (d, 1H), 8.33 (d, 1H), 8.83 (s, 1H), 8.90 (d, 1H); $^{13}$C-NMR (300 MHz, DMSO-d$_6$) δ 52.7, 117.4, 124.7, 128.0, 129.8, 130.1, 131, 135.1, 140.1, 148.8, 165.4; IR (mic) v 2233, 1717;

EXAMPLE 272C 6-(3-Isopropoxybenzeneaminocarbonyl)-2-quinolinylnitrile

A solution of 3-isopropoxyaniline (0.332 g, 2.2 mmol) in dry dichloromethane (5 mL) was treated with trimethylaluminum (1.1 mL of 2 M solution in hexanes) under N$_2$ at room temperature. After 20 minutes, methyl 2-cyano-6-quinolinecarboxylate (0.414 g, 2 mmol) was added in one portion and the reaction mixture was allowed to stir at room temperature for three days. The reaction mixture was quenched with 2 M HCl (vigorous reaction) and allowed to stir for 10 minutes. The precipitated product was filtered off, washed with dichloromethane and water, and dried in a vacuum oven to afford 0.23 g (35%) of product sufficiently pure for the next step.

MS m/z 332 (M+H)$^+$, m/z 349 (M+NH$_4$)$^+$; $^1$H NMR (300 MHz, DMSO-d$_6$) δ 1.30 (d, 6H), 4.58 (septet, 1H), 6.68–6.72 (m, 1H), 7.29 (t, 1H), 7.34–7.39 (m, 1H), 7.47–7.49 (m, 1H), 8.15 (d, 1H), 8.27 (d, 1H), 8.38 (dd, 1H), 8.73 (d, 1H), 8.84 (d, 1H), 10.56 (s, 1H, NH); IR (mic) ν 3434, 2233, 1677;

EXAMPLE 272D 6-(3-Isopropoxybenzeneaminocarbonyl)-2-quinolinylcarboxamidine hydrochloride A suspension of nitrile (from Example 272C) (0.107 g, 0.325 mmol) in tetrahydrofuran (5 mL) was treated with lithium hexamethyldisilazide (1.626 mL, 5 eq., 1 M solution in hexanes) at room temperature. The reaction mixture was stirred overnight and then was quenched with 10% HCl (1 mL). The solvents were evaporated in-vacuo and the residue was purified over 2 g silica gel eluenting with dichloromethane-20% methanol/dichloromethane).

MS m/z 349 (M+H)$^+$; $^1$H NMR (300 MHz, DMSO-d$_6$) δ 1.30 (d, 6H), 4.57 (septet, 1H), 6.68–6.72 (m, 1H), 7.27 (t, 1H), 7.36–7.40 (m, 1H), 7.48–7.50 (m, 1H), 8.30 (d, 1H), 8.35 (d, 1H), 8.41 (dd, 1H), 8.77 (d, 1H), 8.91 (d, 1H), 9.6 (bs, 4H); Anal. calcd for C$_{20}$H$_{21}$N$_4$O$_2$·HCl 0.25 H$_2$O: C, 61.69; H, 5.56; N, 14.38. Found: C, 61.58; H, 5.58; N, 14.15.

EXAMPLE 273

2-(aminoiminomethyl)-N-(3,5-bis(trifluoromethyl)phenyl)-6-quinolinecarboxamide

EXAMPLE 273A 6-(3,5-Bistrifluoromethylbenzeneaminocarbonyl)-2-quinolinylnitrile

The title compound was prepared according to the process described in Example 272C but substituting 3,5-bistrifluoromethylaniline for 3-isopropoxyaniline. The product was purified by over silica gel eluenting with dichloromethane-2% methanol/dichloromethane)

MS m/z 410 (M+H)$^+$; $^1$H NMR (300 MHz, DMSO-d$_6$) δ 7.90 (s, 1H), 8.17 (d, 1H), 8.31 (d, 1H), 8.42 (dd, 1H), 8.54 (s, 2H), 8.80 (d, 1H), 8.85 (d, 1H); IR (mic) ν 3335, 2243, 1662; Anal. calcd for C$_{19}$H$_9$F$_6$N$_3$O: C, 55.76; H, 2.22; N, 10.27. Found: C, 55.54; H, 2.29; N, 10.13.

EXAMPLE 273B 6-(3,5-Bistrifluoromethylbenzeneaminocarbonyl)-2-quinolinylcarboxamidine hydrochloride The title compound was prepared according to the process described in Example 272D but substituting 6-(3,5-bistrifluoromethylbenzeneaminocarbonyl)-2-quinolinylnitrile for 6-(3-isopropoxybenzeneaminocarbonyl)-2-quinolinylnitrile.

MS m/z 427 (M+H)$^+$; $^1$H NMR (300 MHz, DMSO-d$_6$) δ 7.89 (s, 1H), 8.34 (d, 1H), 8.41 (d, 1H), 8.44 (dd, 1H), 8.62 (s, 2H), 8.91 (d, 1H), 8.93 (d, 1H), 9.72 (bs, 4H), 11.41 (s, 1H, NH).

What is claimed is:
1. A compound having the formula

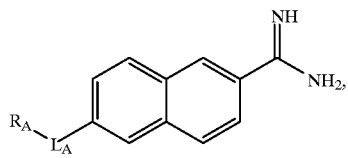

or a pharmaceutically acceptable salt or prodrug thereof, wherein L$_A$ is —NR$_2$C(X)—, wherein X is O or S, and R$_2$ is selected from the group consisting of
(a) hydrogen
(b) alkyl of one to six carbon atoms,
(c) alkenyl of two to six carbon atoms,
(d) alkynyl of two to six carbon atoms,
(e) aryl,
(f) arylalkyl, wherein the alkylene group is of one to six carbon atoms,
(g) cycloalkyl of three to eight carbon atoms, and
(h) cycloalkylalkyl, wherein the cycloalkyl group is of three to eight carbon atoms, and the alkylene group is of one to ten carbon atoms,
wherein L$_A$ is depicted with the right end being the end which is attached to the naphthyl ring and the left end being the end which is attached to R$_A$, and R$_A$ is aryl, wherein the aryl is optionally substituted with one or two substituents independently selected from the group consisting of
(a) alkyl of one to six carbon atoms,
(b) alkoxy of one to six carbon atoms,
(c) aminoalkyl of one to six carbon atoms, and
(d) cycloalkylalkyl wherein the cycloalkyl group is of three to eight carbon atoms and the alkyl group is of one to ten carbon atoms.
2. A compound selected from the group consisting of
N-[4-(aminomethyl)phenyl]-6-aminoiminomethyl-2-naphthalenecarboxamide bis(trifluoroacetate);
6-(aminoiminomethyl)-N-[4-(hydroxymethyl)phenyl]-2-naphthalenecarboxamide; mono(trifluoroacetate);
6-(aminoiminomethyl)-N-[3-(1-methylethoxy)phenyl]-2-naphthalenecarboxamide, mono(trifluoroacetate);
6-(aminoiminomethyl)-N-(3-propoxyphenyl)-2-naphthalenecarboxamide, mono(trifluoroacetate);
6-(aminoiminomethyl)-N-[3-(1-ethylpropoxy)phenyl]-2-naphthalenecarboxamide, mono(trifluoroacetate);
6-(aminoiminomethyl)-N-[3-(cyclopentyloxy)phenyl]-2-naphthalenecarboxamide, mono(trifluoroacetate);
6-(aminoiminomethyl)-N-(3-ethoxyphenyl)-2-naphthalenecarboxamide, mono(trifluoroacetate);
6-(aminoiminomethyl)-N-(3,5-dimethoxyphenyl)-2-naphthalenecarboxamide;
6-(aminoiminomethyl)-N-3-((2-methylpropyl)phenyl)-2-naphthalenecarboxamide, monohydrochloride mono(trifluoroacetate); and
6-(aminoiminomethyl)-N-(3-(cyclopentylmethyl)phenyl)-2-naphthalenecarboxamide, monohydrochloride mono(trifluoroacetate).
3. A method for inhibiting urokinase in a mammal in need of such treatment, comprising administering to the mammal a therapeutically effective amount of a compound of claim 1.
4. A composition for inhibiting urokinase comprising both a pharmaceutical carrier and a therapeutically effective amount of a compound of claim 1.

5. A compound according to claim 1, wherein X is O.

6. A compound according to claim 1, wherein $R_2$ is hydrogen.

7. A compound according to claim 1, wherein $R_A$ is phenyl, wherein the phenyl is monosubstituted as set forth therein.

8. A compound according to claim 1, wherein $R_A$ is phenyl, wherein the phenyl is disubstituted as set forth therein.

9. A compound according to claim 1, wherein $R_A$ is 4-(aminoalkyl)phenyl, wherein the 4-(aminoalkyl)phenyl is optionally substituted with one substituent selected from the group consisting of (a) alkyl of one to six carbon atoms, (b) alkoxy of one to six carbon atoms, (c) aminoalkyl of one to six carbon atoms, and (d) cycloalkylalkyl, wherein the cycloalkyl group is of three to eight carbon atoms and the alkyl group is of one to ten carbon atoms.

10. A compound according to claim 1, wherein $R_A$ is 4-(aminomethyl)phenyl, wherein the 4-(aminomethyl)phenyl is optionally substituted with one substituent selected from the group consisting of (a) alkyl of one to six carbon atoms, (b) alkoxy of one to six carbon atoms, (c) aminoalkyl of one to six carbon atoms, and (d) cycloalkylalkyl, wherein the cycloalkyl group is of three to eight carbon atoms and the alkyl group is of one to ten carbon atoms.

11. A compound according to claim 7, wherein $R_A$ is unsubstituted 4-(aminoalkyl)phenyl.

12. A compound according to claim 7, wherein $R_A$ is selected from the group consisting of 4-(aminomethyl)phenyl, 4-(hydroxymethyl)phenyl, 3-(1-methylethoxy)phenyl, 3-propoxyphenyl, 3-(1-ethylpropoxy)phenyl, 3-(cyclopentyloxy)phenyl, 3-ethoxyphenyl, 3-(1-methylethoxy)phenyl, 3-(2-methylpropyl)phenyl, and 3-(cyclopentylmethyl)phenyl.

13. A compound according to claim 8, wherein $R_A$ is 3,5-dimethoxyphenyl.

14. The compound N-[4-(aminomethyl)phenyl]-6-aminoiminomethyl-2-naphthalenecarboxamide, or a pharmaceutically acceptable salt or prodrug thereof.

* * * * *

UNITED STATES PATENT AND TRADEMARK OFFICE
CERTIFICATE OF CORRECTION

PATENT NO.    : 6,284,796 B1
DATED         : September 4, 2001
INVENTOR(S)   : Andrew G. Geyer et al.

It is certified that error appears in the above-identified patent and that said Letters Patent is hereby corrected as shown below:

<u>Title page,</u>
Item [75] Inventors, replace "Michael D. Wendt, Deerfields," with -- Michael D. Wendt, Chicago, --.

<u>Column 178,</u>
Line 14, replace "(a) hydrosen" with -- (a) hydrogen, --.

Signed and Sealed this

Twenty-eighth Day of May, 2002

Attest:

Attesting Officer

JAMES E. ROGAN
Director of the United States Patent and Trademark Office